(12) United States Patent
Grawunder et al.

(10) Patent No.: US 9,346,874 B2
(45) Date of Patent: May 24, 2016

(54) BINDING MEMBERS FOR HUMAN CYTOMEGALOVIRUS

(75) Inventors: Ulf Grawunder, Basel (CH); Michael Mach, Erlangen (DE); Luis Martin-Parras, Jena (DE); Sonja Potzsch, Hersbruck (DE); Nadja Spindler, Erlangen (DE); Heinrich Sticht, Furth (DE); Anna-Katharina Wiegers, Nuremberg (DE); Thomas Winkler, Erlangen (DE)

(73) Assignee: 4-Antibody AG, Jena (DE)

( * ) Notice: Subject to any disclaimer, the term of this patent is extended or adjusted under 35 U.S.C. 154(b) by 144 days.

(21) Appl. No.: 13/530,891

(22) Filed: Jun. 22, 2012

(65) Prior Publication Data

US 2013/0089559 A1    Apr. 11, 2013

Related U.S. Application Data

(63) Continuation-in-part of application No. PCT/EP2010/070568, filed on Dec. 22, 2010.

(60) Provisional application No. 61/289,835, filed on Dec. 23, 2009, provisional application No. 61/320,057, filed on Apr. 1, 2010.

(30) Foreign Application Priority Data

Dec. 23, 2009 (EP) .................................. 09015951
Apr. 1, 2010 (EP) .................................. 10003669

(51) Int. Cl.
*A61K 39/42* (2006.01)
*A61K 39/00* (2006.01)
*C07K 16/08* (2006.01)

(52) U.S. Cl.
CPC ............ *C07K 16/088* (2013.01); *C07K 2317/21* (2013.01); *C07K 2317/34* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| 4,618,578 A | 10/1986 | Burke et al. |
| 4,716,104 A | 12/1987 | Harris et al. |
| 4,743,562 A | 5/1988 | Rasmussen et al. |
| 4,950,595 A | 8/1990 | Masuho et al. |

(Continued)

FOREIGN PATENT DOCUMENTS

| EP | 0 122 841 A1 | 10/1984 |
| EP | 0 277 071 A2 | 8/1988 |

(Continued)

OTHER PUBLICATIONS

Rudikoff et al. ("Single amino acid substitution altering antigen-binding specificity," Proc Natl Acad Sci USA 79: 1979-1983 (1982)).*

(Continued)

*Primary Examiner* — Benjamin P Blumel
*Assistant Examiner* — M. Franco Salvoza
(74) *Attorney, Agent, or Firm* — Sterne, Kessler, Goldstein & Fox P.L.L.C.

(57) ABSTRACT

The invention relates to binding members, especially antibody molecules, which may neutralize the biological effects of human cytomegalovirus (hCMV). The binding members may be useful for the treatment and prophylaxis of hCMV infection.

25 Claims, 13 Drawing Sheets

(56) References Cited

U.S. PATENT DOCUMENTS

| | | | |
|---|---|---|---|
| 5,043,281 A | 8/1991 | Masuho et al. |
| 5,124,440 A | 6/1992 | Gehrz et al. |
| 5,126,130 A | 6/1992 | Lussenhop et al. |
| 5,153,311 A | 10/1992 | Kari et al. |
| 5,171,568 A | 12/1992 | Burke et al. |
| 5,180,813 A | 1/1993 | Stinski |
| 5,194,256 A | 3/1993 | Rasmussen et al. |
| 5,244,792 A | 9/1993 | Burke et al. |
| 5,248,768 A | 9/1993 | Lussenhop et al. |
| 5,314,800 A | 5/1994 | Rasmussen et al. |
| 5,547,834 A | 8/1996 | Spaete et al. |
| 5,567,582 A | 10/1996 | Grundy et al. |
| 5,612,041 A | 3/1997 | Burke et al. |
| 5,648,079 A | 7/1997 | Burke et al. |
| 5,728,578 A | 3/1998 | Jahn et al. |
| 5,744,298 A | 4/1998 | Stuber et al. |
| 5,747,039 A | 5/1998 | Burke et al. |
| 5,750,106 A | 5/1998 | Ostberg et al. |
| 5,750,114 A | 5/1998 | Burke et al. |
| 5,759,814 A | 6/1998 | Burke et al. |
| 5,783,383 A | 7/1998 | Kondo et al. |
| 5,800,981 A | 9/1998 | Bruggeman et al. |
| 5,834,307 A | 11/1998 | Spaete et al. |
| 5,846,733 A | 12/1998 | Jahn et al. |
| 5,883,225 A | 3/1999 | Grundy et al. |
| 6,100,064 A | 8/2000 | Burke et al. |
| 6,162,620 A | 12/2000 | Smith et al. |
| 6,183,752 B1 | 2/2001 | Epstein et al. |
| 6,183,754 B1 | 2/2001 | Horaud et al. |
| 6,190,860 B1 | 2/2001 | Spaete et al. |
| 6,194,542 B1 | 2/2001 | Kondo et al. |
| 6,248,513 B1 | 6/2001 | Horaud et al. |
| 6,569,616 B1 | 5/2003 | Compton et al. |
| 6,610,295 B1 | 8/2003 | Smith et al. |
| 6,733,989 B1 | 5/2004 | Mach et al. |
| 6,949,628 B2 | 9/2005 | Horaud et al. |
| 7,025,968 B2 | 4/2006 | Schall et al. |
| 7,147,861 B2 | 12/2006 | Compton et al. |
| 7,700,350 B2 | 4/2010 | Hahn |
| 7,704,510 B2 | 4/2010 | Shenk et al. |
| 7,763,261 B2 | 7/2010 | Lai et al. |
| 7,947,274 B2 | 5/2011 | Lanzavecchia et al. |
| 7,955,599 B2 | 6/2011 | Lanzavecchia et al. |
| 7,976,845 B2 | 7/2011 | Khanna |
| 7,982,012 B2 | 7/2011 | Olsen |
| 8,071,371 B2 | 12/2011 | Lanzavecchia |
| 8,124,093 B2 | 2/2012 | Lanzavecchia et al. |
| 8,153,129 B2 | 4/2012 | Funaro et al. |
| 8,173,362 B2 | 5/2012 | Shenk et al. |
| 8,202,518 B2 | 6/2012 | Funaro et al. |
| 8,268,309 B2 | 9/2012 | Olsen |
| 8,287,870 B2 | 10/2012 | Lanzavecchia et al. |
| 8,298,538 B2 | 10/2012 | Lanzavecchia et al. |
| 8,298,539 B2 | 10/2012 | Lanzavecchia et al. |
| 8,309,089 B2 | 11/2012 | Lanzavecchia et al. |
| 8,338,172 B2 | 12/2012 | Funaro et al. |
| 8,361,473 B2 | 1/2013 | Makler et al. |
| 8,435,524 B2 | 5/2013 | Lanzavecchia et al. |
| 8,492,529 B2 | 7/2013 | Takada et al. |
| 8,545,848 B2 | 10/2013 | Lanzavecchia et al. |
| 8,603,480 B2 | 12/2013 | Lanzavecchia et al. |
| 8,765,132 B2 | 7/2014 | Lanzavecchia et al. |
| 8,828,399 B2 | 9/2014 | Shenk et al. |
| 8,852,594 B2 | 10/2014 | Olsen |
| 2001/0029251 A1 | 10/2001 | Gonczol et al. |
| 2001/0039008 A1 | 11/2001 | Horaud et al. |
| 2002/0102562 A1 | 8/2002 | Spaete et al. |
| 2004/0082033 A1 | 4/2004 | Smith et al. |
| 2004/0087001 A1 | 5/2004 | Hahn |
| 2004/0228842 A1 | 11/2004 | Lu et al. |
| 2009/0004198 A1 | 1/2009 | Nakajima et al. |
| 2010/0068229 A1 | 3/2010 | Gargano et al. |
| 2010/0111957 A1 | 5/2010 | Makler et al. |
| 2010/0158927 A1 | 6/2010 | Reiter et al. |
| 2010/0267121 A1 | 10/2010 | Hahn |
| 2011/0171233 A1 | 7/2011 | Funaro et al. |
| 2012/0020980 A1 | 1/2012 | Kauvar et al. |
| 2012/0027768 A1 | 2/2012 | Lanzavecchia |
| 2013/0101594 A1 | 4/2013 | Makler et al. |
| 2013/0171169 A1 | 7/2013 | Lanzavecchia et al. |
| 2014/0004123 A1 | 1/2014 | Lanzavecchia |
| 2014/0056914 A1 | 2/2014 | Lanzavecchia et al. |
| 2014/0193428 A1 | 7/2014 | Lanzavecchia et al. |
| 2014/0205615 A1 | 7/2014 | Lanzavecchia et al. |
| 2014/0363440 A1 | 12/2014 | Makler et al. |
| 2014/0370026 A1 | 12/2014 | Shenk et al. |

FOREIGN PATENT DOCUMENTS

| | | |
|---|---|---|
| EP | 0 248 909 B1 | 8/1994 |
| EP | 0 926 155 BI | 2/2006 |
| JP | 5-3794 A | 1/1993 |
| JP | 5-260961 A | 10/1993 |
| JP | 6-157349 A | 6/1994 |
| JP | 8-59508 A | 3/1996 |
| JP | 8-59509 A | 3/1996 |
| JP | 2538536 B2 | 7/1996 |
| JP | 2538537 B2 | 7/1996 |
| JP | 2535455 B2 | 9/1996 |
| WO | WO 89/05855 A1 | 6/1989 |
| WO | WO 89/10966 A1 | 11/1989 |
| WO | WO 90/06771 A1 | 6/1990 |
| WO | WO 91/02004 A1 | 2/1991 |
| WO | WO 91/04277 A1 | 4/1991 |
| WO | WO 91/05876 A1 | 5/1991 |
| WO | WO 93/21952 A1 | 11/1993 |
| WO | WO 94/09136 A1 | 4/1994 |
| WO | WO 94/25490 A1 | 11/1994 |
| WO | WO 2007/068758 A1 | 6/2007 |
| WO | WO 2008/084410 | 7/2008 |
| WO | WO 2010/007463 A1 | 1/2010 |

OTHER PUBLICATIONS

Schreiber et al., "Antiviral treatment of cytomegalovirus infection and resistant strains," Expert Opin. Pharmacother. 10(2): 191-209 (2009).*

Wirtz et al., "Polyclonal cytomegalovirus-specific antibodies not only prevent virus dissemination from the portal of entry but also inhibit focal virus spread within target tissues," Med Microbiol Immuno 197: 151-158 (2008).*

Ohlin et al., "Human antibody technology and the development of antibodies against cytomegalovirus," Molecular Immunology (2015).*

Kranz, "T cell receptor CDRs: starring versus supporting roles," Nature Immunology vol. 6, No. 2: 130-132 (2005).*

Manning et al., "Effects of Complementary Determining Region Mutations on the Affinity of an T Cell Receptor: Measuring the Energy Associated with CD4/CD8 Repertoire Skewing," J. Exp. Med vol. 189, No. 3: 461-470 (1999).*

William Britt, et al., Cell Surface Expression of Human Cytomegalovirus (HCMV) gp55-116 (gB): Use of HCMV-Recombinant Vaccinia Virus-Infected Cells in Analysis of the Human Neutralizing Antibody Response, Journal of Virology (1990) vol. 64, No. 3, p. 1079-1085.

P.A. Christensen, et al., Modifying Antibody Specificity by Chain Shuffling of $V_H/V_L$ Between Antibodies With Related Specificities, Scandinavian Journal of Immunology (2009) vol. 69, p. 1-10.

Ada Funaro, et al., Generation of Potent Neutralizing Human Monoclonal Antibodies Against Cytomegalovirus Infection From Immune B Cells, BMC Biotechnology (2008) vol. 8:85.

Michael A. Jarvis, et al., Phosphorylation of Human Cytomegalovirus Glycoprotein B (gB) at the Acidic cluster Casein Kinase 2 Site ($Ser_{900}$) Is Required for Localization of gB to the Trans-Golgi Network and Efficient Virus Replication, Journal of Virology (2004) vol. 78, No. 1, p. 285-293.

Nancy O. Lussenhop, et al., Epitope Analysis of Human Cytomegalovirus Glycoprotein Complexes Using Murine Monoclonal Antibodies, Virology (1988) vol. 164, p. 362-372.

(56) References Cited

OTHER PUBLICATIONS

Philippe Mondon, et al., Method for Generation of Human Hyperdiversified Antibody Fragment Library, Biotechnology (2007) vol. 2, p. 76-82.
U. Utz, et al., Identification of a Neutralizing Epitope on Glycoprotein gp58 of Human Cytomegalovirus, Journal of Virology (1989) vol. 63, No. 5, p. 1995-2001.
Axelsson, F., et al., "Novel antibody specificities targeting glycoprotein B of cytomegalovirus identified by molecular library technology," *New Biotechnol.* 25:429-436, Elsevier B.V., Netherlands (Sep. 2009).
Babcook, J. S., et al., "A novel strategy for generating monoclonal antibodies from single, isolated lymphocytes producing antibodies of defined specificities," *Proc. Nat. Acad. Sci.* 93:7843-7848, National Academy of Sciences, United States (1996).
Backovic, M., et al., "Structure of a trimeric variant of the Epstein-Barr virus glycoprotein B," *Proc. Natl. Acad. Sci.* 106:2880-2885, National Academy of Sciences, Untied States (Feb. 2009).
Böldicke, T., et al., "Human monoclonal antibodies to cytomegalovirus: Characterization and recombinant expression of a glycoprotein-B-specific antibody," *Eur. J Biochem.* 234:397-405, Blackwell Science Ltd., England (1995).
Cranage, M.P., et al., "Identification of the human cytomegalovirus glycoprotein B gene and induction of neutralizing antibodies via its expression in recombinant vaccinia virus," *EMBO J.* 5:3057-3063, Oxford Press, England (1986).
Gupta, P., et al., "Comparison of the polypeptides of several strains of human cytomegalovirus," *J. Gen. Virol.* 34:447-454, Society for General Microbiology, England (1977).
Heldwein, E.E., et al., "Crystal structure of glycoprotein B from herpes simplex virus 1," *Science 313*:217-220, American Association for the Advancement of Science, United States (2006).
Kari, B., et al., "Biochemical and immunological analysis of discontinuous epitopes in the family of human cytomegalovirus glycoprotein complexes designated gC-I," *J Gen. Virol.* 72:1975-1983, Society for General Microbiology, England (1991).
Kniess, N., et al., "Distribution of linear antigenic sites on glycoprotein gp55 of human cytomegalovirus," *J. Virol.* 65:138-146, American Society for Microbiology, United States (1991).
Lantto, J., et al., "Non-germ-line encoded residues are critical for effective antibody recognition of a poorly immunogenic neutralization epitope on glycoprotein B of human cytomegalovirus," *Eur. J Inununol.* 32:1659-1669, Verlag Chemie GmbH, Germany (2002).
MacAgno, A., et al., "Isolation of human monoclonal antibodies that potently neutralize human cytomegalovirus infection by targeting different epitopes on the gH/gL/UL128-131A complex," *J. Virol.* 84:1005-1013, American Society for Microbiology, United States (Jan. 2010).
McLean, G.R., et al., "Recognition of human cytomegalovirus by human primary.immunoglobulins identifies an innate foundation to an adaptive immune response," *J. Immunol.* 174:4768-4778, The American Association of Immunologists, United States (2005).
Nejatollahi, F., et al., "Neutralising human recombinant antibodies to human cytomegalovirus glycoproteins gB and gH," *FEMS Imm. Med. Microbiol.* 34:237-244, Elsevier Science B.V., Netherlands (2002).

Newkirk, M.M., et al., "Complete protein sequences of the variable regions of the cloned heavy and light chains of a human anti-cytomegalovirus antibody reveal a striking similarity to human monoclonal rheumatoid factors of the Wa idiotypic family," *J. Clin. Invest.* 81:1511-1518, The American Society for Clinical Investigation, Inc., United States (1988).
Ohizumi, Y., et al., "Neutralizing mechanisms of two human monoclonal antibodies against human cytomegalovirus glycoprotein 130/55," *J Gen. Virol.* 73:2705-2707, Society for General Microbiology, England (1992).
Ohlin, M., et al., "Fine specificity of the human immune response to the major neutralization epitopes expressed on cytomegalovirus gp58/116 (gB), as determined with human monoclonal antibodies," *J. Virol.* 67:703-710, American Society for Microbiology, United States (1993).
Ohlin, M., et al., "Light chain shuffling of a high affinity antibody results in a drift in epitope recognition," *Mol. Immunol.* 33:47-56, Elsevier Science Ltd., England (1996).
Pötzsch, S., et al., "B cell repertoire analysis identifies new antigenic domains on glycoprotein B of human cytomegalovirus which are target of neutralizing antibodies," *PLoS Pathogens 7*: e1002172. doi:10.1371/journal.ppat.1002172 (Aug. 2011).
Rasmussen, L., et al., "Viral polypeptides detected by a complement-dependent neutralizing murine monoclonal antibody to human cytomegalovirus," *J. Virol.* 55:274-280, American Society for Microbiology, United States (1985).
Roche, S., et al., "Crystal structure of the low-pH form of the vesicular stomatitis virus glycoprotein G," *Science 313*:187-191, American Association for the Advancement of Science, United States (2006).
Roche, S., et al., "Structure of the prefusion form of the vesicular stomatitis virus glycoprotein G," *Science 315*:843-848, American Association for the Advancement of Science, United States (2007).
Rudikoff, S., et al., "Single amino acid substitution altering antigen-binding specificity," *Proc. Natl., Acad. Sci. U.S.A.* 79:1979-1983, National Academy of Sciences, United States (1982).
Spindler, N., et al., "Structural basis for the recognition of human cytomegalovirus glycoprotein B by a neutralizing human antibody," *PLoS Pathogens 10*: e1004377. doi:10.1371/joumal.ppat.1004377 (2014).
Stinski, M. F., "Human cytomegalovirus: glycoproteins associated with virions and dense bodies," *J. Virol.* 19:594-609, American Society for Microbiology, United States (1976).
Heimberger, A.B., and Sampson, J.H., "The Pep-3-KLH (CDX-110) vaccine in glioblastoma multiforme patients," *Expert Opin Biol Ther 9(8)*:1087-1098, Informa Healthcare, England (Aug. 2009).
Kravitz, R.H., et al., "Cloning and characterization of rhesus cytomegalovirus glycoprotein B," *J. Virol.* 78:2009-2013, Society for General Microbiology, England (1997).
Kropff, B. And Mach, M., "Identification of the gene coding for rhesus cytomegalovirus glycoprotein B and immunological analysis of the protein," *J. Virol.* 78:1999-2007, Society for General Microbiology, England (1997).
Powers, C. And Früh, K., "Rhesus CMV: an emerging animal model for human CMV," *Med Microb Immunol 197(2)*:109-115, Springer-Verlag, Germany (Jun. 2008).
Spindler, N., et al., "Characterization of a Discontinuous Neutralizing Epitoe on Glycoprotein B of Human Cytomegalovirus," *J. Virol.* 87:8927-8939, American Society for Microbiology (2013).

\* cited by examiner

BINDING MEMBERS FOR HUMAN CYTOMEGALOVIRUS

RELATED APPLICATIONS AND INCORPORATION BY REFERENCE

This application is a continuation-in-part application of international patent application Serial No. PCT/EP2010/070568 filed Dec. 22, 2010, which published as PCT Publication No. WO 2011/076883 on Jun. 30, 2011, which claims benefit of U.S. provisional Application Nos. 61/289,835 filed Dec. 23, 2009 and 61/320,057 filed Apr. 1, 2010 and European patent application Serial Nos. EP 09015951.8 filed Dec. 23, 2009 and EP 10003669.8 filed Apr. 1, 2010.

The foregoing applications, and all documents cited therein or during their prosecution ("appin cited documents") and all documents cited or referenced in the appin cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

This invention relates to binding members, especially antibody molecules, which neutralise the biological effects of human cytomegalovirus (hCMV). The binding members are useful for the treatment and prophylaxis of hCMV infection.

BACKGROUND

Human cytomegalovirus (hCMV) is a widely distributed pathogen that usually establishes asymptomatic, life-long persistence in 40-80% of the human population depending on geographical and socioeconomic origin. However, in immunocompromised patients, such as transplant recipients and HIV infected individuals, and also in newborns, hCMV infection is a major cause of morbidity and mortality and puts a significant economic burden on health care systems.

hCMV is the most significant infection impacting on the outcome of solid organ transplantation (SOT) and hematopoietic stem cell transplantation (SCT) (Razonable & Paya, 2003). After transplantation, an active hCMV infection occurs in approximately 60-70% of hCMV-seropositive patients or seronegative patients who receive organ transplants from a seropositive donor (Razonable & Paya, ibid). If no preventative measures are taken, the risk of developing hCMV disease is 20-30%. Considering the fact that approximately 26,000 allogenic SCTs were performed worldwide in 2008, the success of this therapy and the reduction of post-transplant morbidity and mortality have considerable financial implications. hCMV related complications can result in additional costs of EUR 25,000 to 50,000 per patient.

In addition, HCMV infection in transplant patients is associated with transplant related atherosclerosis and accelerated graft loss (Streblow et al., 2007).

As mentioned before, hCMV is relevant as a perinatal pathogen. Each year, approximately 1% of susceptible women seroconvert during pregnancy. Approximately 40% of these transmit hCMV to their children resulting in 40,000 infected newborns annually in the USA (Kenneson & Cannon, 2007). 10-20% of the infected children have acute symptoms at birth. Of these, up to 20% die and the remainder typically have moderate-to-severe complications, including CNS related conditions, like blindness, deafness and mental retardation. Apart from the devastating consequences for affected patients and their families, the healthcare costs for those patients are significant, in particular, if the perinatal infection results in severe and permanent disabilities.

To date, five antiviral agents are approved for use in hCMV infection: Ganciclovir/Valganciclovir, Cidofovir, Foscarnet and Fomivirsen. All compounds suffer from dose dependent side effects and the development of resistant virus strains (Schreiber et al., 2009). None of the drugs are licensed for use in children or in pregnant women. In addition, intravenous immunoglobulin preparations (IVIG) e.g. CYTOGAM® (Cytomegalovirus Immune Globulin Intravenous (Human), CSL Behring) and CYTOTECT® (Human immunoglobulin anti-cytomegalovirus, Biotest) are used for prophylaxis and treatment of patients at risk of hCMV infection. However, uncertainty about benefits of this treatment in the transplant situation is evident (Sokos et al., 2002; Raanani et al., 2009). The adoptive transfer of hCMV-specific cytotoxic T-cells has been used with success in hematopoetic SCT patients (Moss & Rickinson, 2005), but this treatment is extremely expensive and will be limited to a few transplant centres having the necessary expertise. Moreover, this type of treatment is restricted to transplant recipients who are seropositive for hCMV. In contrast, IVIG has been reported to be effective in the treatment and prevention of congenital CMV infection (Nigro et al., 2005). However, IVIG for hCMV treatment is isolated and purified from hCMV seropositive donors, resulting in variable titers and therefore batch-to-batch variation for hCMV specific antibodies in these preparations. In addition, human blood-derived drug products always bear the risk for transmission of human pathogens. As a consequence, a recombinant antibody product, allowing the efficient neutralisation of hCMV for the prophylaxis and treatment of diseases caused by hCMV infection is desired.

Targets for antibody therapy of hCMV infections are proteins expressed in the surface of the hCMV virion. The composition of the hCMV virion envelope is very complex and whilst many structural proteins that comprise the envelope have been identified, it is still not fully defined. During the development of antibodies for the therapy of hCMV, antigenic determinants have been identified in surface glycoprotein complexes gp58/116 (gB or gC-1), gp 47-52 (gC-II; gM and gN) (Shimamura et al., 2006) and gp 86 (gH or gC-III) (Urban et al., 1996). The majority of neutralising antibodies identified to date bind to gB protein, which has been shown to contain the majority of neutralising epitopes (Britt et al., 1990). The gB complex is synthesised as a 130 kD precursor, which is cleaved into two covalently linked molecules, named gp58 and gp116. The N-terminal fragment (gp116) contains one linear, neutralising epitope, called antigenic domain-2 (AD-2) of 20 amino acids (amino acids 67-86), which does not require complement for antibody-mediated biological activity (Meyer et al., 1990). The gp58 moiety of gB carries the neutralising domain AD-1, which may comprise 74 amino acids (amino acids 557-630) and most likely represents a conformational epitope (Ohlin et al., 1993; Wagner et al., 1992).

The advent of monoclonal antibodies initially gave rise to the identification of a variety of neutralising mouse monoclonal antibodies against hCMV. However, mouse monoclonal antibodies are unsuitable for use in human therapy since these proteins are recognised by the human immune system as being foreign, and are consequently eliminated after a very short period of time, resulting in low or no clinical efficacy. Chimeric antibodies have been developed against hCMV proteins and EP664834B (Harris et al) relates to a chimeric antibody targeted to the 86 kD glycoprotein of hCMV termed gH; however such antibodies have not been successful in clinical settings.

Technologies using heteromyelomas for the generation of hybridomas have been used to generate a variety of human monoclonal antibodies recognising various hCMV glycoproteins, which are found both in the viral envelope. U.S. Pat. No. 5,043,281 (Masuho et al) relates to a neutralising human monoclonal antibody that recognises a CMV antigen protein having a molecular weight of between 130,000 and 55,000. U.S. Pat. No. 5,750,106 (Ostberg) relates to a human monoclonal antibody to CMV termed SDZ MSL 109, which recognises the gH glycoprotein, as well as a hybridoma cell line for the production of this antibody. One of the virus-neutralising human monoclonal antibodies, SDZ MSL-109 has been evaluated in Phase I/II clinical trials for hCMV induced retinitis in immunocompromised patients, but due to lack of efficacy the clinical trials were not continued (Borucki et al., 2004; Hamilton et al., 1997; Boeckh et al., 2001). One plausible explanation for the failure of these trials is the antigenic variability of hCMV. hCMV is unique among the human herpes viruses in that it is antigenic variable and most human monoclonal antibodies, reacting with the envelope antigens, show strain-specific neutralisation capacity. This is especially true for the gH-specific human monoclonal antibodies, like SDZ MSL-109. This obstacle can only be overcome by the use of monoclonal antibodies directed against epitopes on hCMV that are conserved between different isolates.

In the past, progress in the isolation of hCMV neutralising monoclonal antibodies was slow, due to the fact that high-throughput screens of antibodies for neutralising capacity were not available. In addition, the method of Epstein Barr virus (EBV) immortalisation has been used frequently to generate immortalised B cells producing an antibody of interest, for a number of years. This technique has been successful for the generation of antibody-secreting cells from different sources of human B cells such as the peripheral blood of healthy subjects using antigen-specific selection (Casali et al., 1986), lymph nodes, spleen or peripheral blood from patients (Yamaguchi et al., 1987; Posner et al., 1991; Raff et al., 1988; Steenbakkers et al 1993 and 1994). This technique was used for the immortalisation of peripheral blood mononuclear cells isolated from CMV-seropositive blood donors and the subsequent isolation of three antibodies: ITC52, ITC63b and ITC88 (WO 93/021952 A1). ITC52 and ITC63b are reactive with the conformational AD-1 epitope of CMV consisting of amino acid sequence 557-630 of CMV gp58 and ITC88 is reactive against AD-2 comprising the amino acid sequence 67-86 (AD-2) of CMV gp116 (WO 93/021952 A1).

Improvements on the method of EBV transformation have been published by Lanzavecchia (WO 04/076677 A2) and Funaro et al (WO 07/068,758 A1) and these methods have been used for the generation of antibodies to hCMV. WO 08/084,410 A2 (Lanzavecchia & Macagno) relates to antibodies produced from EBV cell lines 1F11, 2F4, 5A2 and 9A11 that neutralise hCMV infection of endothelial cells, epithelial cells, retinal cells and dendritic cells and are directed towards a conformational epitope formed by gpUL130 and gpUL131A. However, the antibodies from these EBV lines do not have any detectable hCMV neutralising capacity, if fibroblasts are used as target cells for infection. WO 08/084,410 A2 also mentions EBV lines 1006, 5F1, 6B4 and 7H3, producing antibodies that neutralise hCMV infection of fibroblasts and endothelial cells at half-maximal inhibitory concentrations ($IC_{50}$) ranging between 0.3 and 2.0 µg/ml. The antibodies produced from these EBV lines are described to bind to a functional epitope of gB. However, although antibody heavy and light chain sequences have been deducted from some of the above mentioned EBV cell lines, this data has not been confirmed for recombinantly expressed and purified antibodies encoded by the published sequences. A more recent patent application from Lanzavecchia & Macagno (WO 10/007,463 A1) relates to the antibody 6G4, which binds to an epitope determined by a combination of the UL128, UL130 and UL131A proteins and which neutralises hCMV infection of endothelial, retinal and dendritic cells. Furthermore, WO 10/007,533 A1 (Lanzavecchia & Macagno) relates to hCMV neutralising antibodies that bind to an epitope in the hCMV UL128 protein, an epitope formed by gH, gL, UL128 and UL130 proteins, an epitope formed by UL128, UL130 and UL131A proteins or an epitope formed by UL130 and UL131A proteins.

WO 08/071,806 A1 (Funaro et al) relates to the antibody 26A1, which binds to and neutralises hCMV but does not show significant binding to either antigens gB or gH when tested by ELISA. A half-maximal inhibitory concentration ($IC_{50}$) of the antibody 26A1 is reported to be in the range of 1 µg/ml for both primary fibroblasts and endothelial cells, and therefore in a range that has been reached by antibodies described in the prior art. A further patent application by Funaro and colleagues, relates to the antibody 1F7, which recognises gH (WO 09/003,975 A1). Similar to antibody 26A1, as described in WO 08/071,806 A1, the half-maximal inhibitory concentration ($IC_{50}$) of the antibody 1F7 is reported to be in the range of 1 µg/ml for both primary fibroblasts and endothelial cells, and therefore in a range that has been reached by antibodies described in the prior art. Yet another patent application by Funaro and colleagues (WO 09/024,445 A1) relates to the antibodies 8C10, 37B7, 8A11 and 10B7, which either recognise the AD-2 domain of gB (clones 8C10, 8A11, 10B7), or a protein unrelated to gB or gH (clone 37B7). As in the patent applications of Funaro and colleagues (WO 08/071,806 A1 and WO 09/003,975 A1), the antibodies described in WO 09/024,445 A1 also exhibit a half-maximal inhibitory concentration ($IC_{50}$) in the range of 1 µg/ml for both primary fibroblasts and endothelial cells (10B7, 8A11, 37B7) or higher at about 10 µg/ml (8C10), and therefore in the range of previously published hCMV neutralising antibodies.

Additional recent patent applications, describe hCMV neutralising antibodies with similar features. For instance, WO 09/114,560 A2 (Olsen) relates to antibody clones 2F10, 2M16, 2N9, 3C21, 3G7, 4P12, 5P9, 9C16, which all bind to the AD-2 epitope of gB and display half-maximal inhibitory concentration ($IC_{50}$) of hCMV infection of fibroblasts in the range of 1 µg/ml. US20090004198 (Nakajima et al) relates to a high affine antibody for the gB AD-1 domain, with apparent pM binding affinity, and 80% hCMV neutralising activity on fibroblasts, if used at concentrations of 1 µg/ml and higher (10 µm/ml and 100 µg/ml). Two recent applications WO 10/114, 105 A1 and WO 10/114,106 A1, both from Evec Inc., describe antibodies that bind to AD-2 and a discontinuous epitope in AD-1, respectively.

Citation or identification of any document in this application is not an admission that such document is available as prior art to the present invention.

SUMMARY OF THE INVENTION

As disclosed in the present invention, Applicants have developed hCMV neutralising human antibodies, which bind with high affinity to the gB protein of hCMV. In addition, these antibodies display similar high potency ($IC_{50}$s below 0.5 μg/ml) in hCMV neutralisation using a broad range of hCMV susceptible cell types (fibroblasts, endothelial, epithelial and dendritic cells) and high potency not only on laboratory strain AD-169, but also on all clinical isolates tested so far. In addition, the antibodies disclosed herein recognise and define a novel neutralising epitope of the gB protein that has not been described previously. Owing to their high affinity and potency, and their novel epitope binding characteristics determined by functional studies as described herein, the binding members of the invention are particularly suitable for use in the therapeutic treatment, prophylaxis and/or diagnosis of hCMV infections in human patients. The binding members are useful for treating various disorders associated with CMV infection, as described in detail elsewhere herein.

Several, highly potent, gB specific and hCMV neutralising human antibodies are described herein, which also recognise a completely new hCMV neutralising epitope and therefore act by a different therapeutic principle in comparison to all other known antibodies specific for hCMV. Their discovery and functional characterization are disclosed further below. As described in more detail in the Examples, 50 fully human, hCMV neutralising antibodies have been identified. They have been isolated from EBV transformed human peripheral blood derived B cells derived from hCMV-infected donors. CDR sequences of the antibodies 1 to 50 are as detailed in Tables 19 and 20. $V_H$ domain and $V_L$ domain combinations for a panel of antibodies 1 to 46 are as detailed in Table 7. All sequences referred to in Tables 7 and 19 are also shown in the appended sequence listing that forms part of the present disclosure.

As described in more detail below, binding members according to the invention have been shown to neutralise hCMV infection of target cells at therapeutically relevant concentrations, i.e. with $IC_{50}$ below 1 μg/ml. The most active binding members neutralise hCMV even at $IC_{50}$s below 0.5 μg/ml. The neutralising capacity has also been observed with different clinical isolates (e.g. Towne and Altu; Table 16), representing different gB genotypes. Binding members of the invention may neutralise one or more activities of hCMV. For example, the inhibited biological activity may be prevention of infection of fibroblasts, endothelial cells, epithelial cells, retinal cells and/or dendritic cells. The prevention of infection of fibroblasts has been demonstrated in an in vitro neutralisation assay utilising a recombinant strain of hCMV, AD169 that expresses the reporter gene luciferase. Upon infection with this genetically modified hCMV strain, target cells become positive for luciferase enzyme expression, which can be detected by appropriate substrate-conversion in a standard luminometer. The binding members described in this invention were shown to neutralise the infection of hCMV strain AD169 when first incubated with the recombinant, luciferase positive virus strain and then seeded onto monolayers of primary human foreskin fibroblasts (HFFs). Following further incubation, luminescence was detected using a luminometer and the relative light units (RLU) detected. The percentage neutralisation was then calculated, wherein the neutralising titre is indicated as the concentration of binding member (μg/ml) that gives a 50% or 100% reduction of hCMV infection of target cells. Binding members may give a 50% reduction of hCMV infection at concentrations of 0.1 to 5.0 μg/ml, preferably 0.1 to 2.0 μg/ml, more preferably from 0.3 to 1.3 μg/ml or more preferably from 0.1 to 0.6 μg/ml. The binding members have been shown to result in a 50% reduction of hCMV infection at therapeutically relevant concentrations of 0.1, 0.5, 1.0, 1.1, 1.2, 1.3, 1.5 or 2.0 μg/ml.

Other methods that may be used for determining the neutralisation of infectivity of hCMV include ELISA, FACS, Western blotting, immunoprecipitation, and visual inspection based on plaque forming and counting.

The binding members described herein were shown to neutralise human hCMV not only in fibroblasts, but with similar efficacy also in endothelial, epithelial and dendritic cells (as shown in an assay using primary foreskin fibroblasts, Example 4 and in an assay using human umbilical vein endothelial cells (HUVEC), human ARPE-19 retinal pigment epithelial cells and primary dendritic cells, as shown in Example 7).

The invention relates to high affinity binding members for hCMV and specific for the hCMV gB protein. Binding members of the invention may bind hCMV gB protein with a $K_D$ of not more than 50 nM, e.g. not more than 25 nM, 15 nM, 10 nM, 5 nM, 3 nM, 1.5 nM, 1 nM, 0.5 nM, 0.1 nM, 75 pM or 57 pM. Preferably the binding member has a $K_D$ of 1 nM or less, preferably less than 0.5 nM, preferably less than 0.1 nM and more preferably less than 75 pM. The $K_D$ may be determined by surface plasmon resonance, e.g. BIACORE®. BIACORE® (surface plasmon resonance) measurements of affinity are described herein in Example 5.

As described elsewhere herein, surface plasmon resonance involves passing an analyte in fluid phase over a ligand attached to a solid support, and determining association rates ($k_a$) and dissociation rates ($k_d$) between analyte and ligand. Surface plasmon resonance may for example be performed whereby a binding member is passed in fluid phase over gB protein attached to a support. Surface plasmon resonance data may be fitted to a monovalent analyte data model. The affinity may be expressed as the dissociation constant, $K_D$, which is calculated from the ratio of the dissociation and the association rate constants $k_d/k_a$ as determined by surface plasmon resonance using a monovalent analyte data model.

The binding members described herein are shown to bind to a specific region of hCMV gB protein. Known epitopes of hCMV gB protein lie within the antigenic domain 1 (AD-1; between amino acids 552-635) and/or antigenic domain 2 (AD-2; between amino acids 67-86) of gB strain AD169, SEQ ID No: 239. In the present invention Applicants describe binding members that bind to two new antigenic domains of hCMV gB protein, antigenic domain 4 (AD-4; a discontinuous region between amino acids 121-132 and 344-438 of gB strain AD169; SEQ ID No: 239) and antigenic domain 5 (AD-5; between amino acids 133 to 343 of gB strain AD169; SEQ ID No: 239). In initial experiments, the ability of six of the binding members described herein, monoclonal, recombinant antibodies Ab-04, Ab-11, Ab-14, Ab-19, Ab-28 and Ab-42, to bind to specific regions of hCMV gB protein was investigated. In particular, the epitope binding specificity of these six binding members was first investigated in a BIACORE® (surface plasmon resonance) competition assay with a selection of anti-hCMV antibodies known in the art, which bind either to the AD-1 or to the AD-2 epitope of gB protein. As the binding members of the present invention specifically bound to gB protein with high affinity, but could not compete for gB binding with AD-1 and AD-2 specific antibodies, it was clear that the binding members of the present invention recognise a novel neutralising epitope of the gB protein. Further support for this finding was obtained by expressing a truncated version of gB protein which may comprise amino acid residues 100 to 447 (gB strain AD169; SEQ ID No: 239), which upon expression in COS cells was recognised by binding members of the invention.

Following the generation of a molecular model of HCMV gB (strain AD169; SEQ ID No: 239), surface exposed protein domains were identified and a discontinuous amino acid sequence between amino acid residues 121-132 and 344-438 was predicted to be a likely epitope, to which binding members of the invention could bind. When this predicted epitope was expressed as amino acids 116 to 132 and 344 to 440 (gB strain AD169; SEQ ID No: 239), which were coupled by a synthetic amino acid linker, it was found that this recombinant protein was specifically recognised by binding members Ab-11, Ab-14 or Ab-28 of the invention. This new epitope has been termed AD-4. Therefore the binding members of the invention do not bind to the region AD-1 of hCMV gB protein. Also, the binding members of the invention do not bind to the region AD-2 of hCMV gB protein. In contrast, binding members Ab-01 to Ab-46 of the invention bind to a new conformational epitope termed AD-4 (also termed Domain II (Dom II)), between amino acid residues 100 to 447, and preferably between amino acid residues 121 to 438. More preferably, binding members of the invention bind to discontinuous amino acid stretches 116-132 and 344-440 of gB strain AD169 (SEQ ID No: 239) and most preferably stretches 121-132 and 344-438 of gB strain AD169 (SEQ ID No: 239). In this regard it has to be understood in accordance with the invention that the discontinuous epitope generated by amino acids stretches 121-132 and 344-438 of gB strain AD169 (SEQ ID No: 239) constitutes the same epitope as the discontinuous epitope generated by amino acids stretches 116-132 and 344-440 of gB strain AD169 (SEQ ID No: 239).

Since Antibodies Ab-01 to Ab-46 all have structurally related CDRs (in particular HCDR3 of identical length and related sequence), and are derived from a single donor, these antibody molecules are most likely somatic mutants of an original gB-reactive clones, and are therefore expected to bind the same or very similar overlapping epitope on the hCMV gB protein. Accordingly, the epitope characterisation results obtained with recombinant antibodies Ab-11, Ab-14 or Ab-28 are also expected to be representative for all of the antibodies Ab-01 to Ab-46 disclosed herein. The present invention therefore relates to a binding member, preferably an antibody, that binds to a conformational epitope of the gB protein recognised by antibodies Ab-11, Ab-14 or Ab-28 and also to a binding member that competes with any of antibodies Ab-11, Ab-14 or Ab-28 for binding to a conformational epitope of the gB protein recognised by these antibodies.

Therefore in a first embodiment, a binding member of the invention may bind hCMV gB protein at a region which may comprise amino acids 116 to 132 or amino acids 121 to 132 as predicted from the structural model (Example 9). A binding member of the invention may also bind hCMV gB protein at a region which may comprise amino acids 344 to 440 or amino acids 344 to 438 as predicted from the structural model (Example 9). Optionally a binding member may bind flanking residues or structurally neighbouring residues in the hCMV gB amino acid sequence, in addition to binding amino acids 116 to 132 and/or amino acids 344 to 440. By convention, residue numbering corresponds to hCMV gB strain AD169 (SEQ ID No: 239).

In further experiments, the ability of four of the binding members described herein, monoclonal, recombinant antibodies Ab-47, Ab-48, Ab-49, Ab-50, to bind to specific regions of hCMV gB protein was also investigated. In particular, the epitope binding specificity of these four binding members was first investigated in an ELISA competition assay (Example 8.3) and then using a capture ELISA (Example 10.2). It was clear that these four binding members recognise a further novel neutralising epitope of the gB protein.

Following the generation of a molecular model of HCMV gB (strain AD169; SEQ ID No: 239), surface exposed protein domains were identified and an amino acid sequence between amino acid residues 133 and 343 was predicted to be a likely epitope, to which binding members of the invention could bind. This predicted epitope was subdivided and expressed as two subdomains: Subdomain 1 (amino acids 133-144 and 251-343) and Subdomain 2 (amino acids 140 to 255) (gB strain AD169; SEQ ID No: 239). When tested in a capture ELISA, Subdomain 1 was recognised by binding members Ab-47, Ab-49 or Ab-50 of the invention. The new epitope region of amino acids 134 to 344 (gB strain AD169; SEQ ID No: 239) has been termed AD-5. Therefore binding members Ab-47, Ab-48, Ab-49 or Ab-50 of the invention do not bind to the region AD-1 of hCMV gB protein. Also, the binding members of the invention do not bind to the region AD-2 of hCMV gB protein. In contrast, binding members Ab-47 to Ab-50 of the invention bind to a new conformational epitope termed AD-5 (also termed Domain I (Dom I)), between amino acid residues 133 to 343 of gB strain AD169 (SEQ ID No: 239).

The present invention therefore relates to a binding member, preferably an antibody, that binds to an epitope of the gB protein recognised by antibodies Ab-47, Ab-48, Ab-49 or Ab-50 and also to a binding member that competes with any of these four antibodies for binding to a conformational epitope of the gB protein recognised by these antibodies.

Therefore in a second embodiment, a binding member of the invention may bind hCMV gB protein at a region which may comprise amino acids 133 to 343, as predicted from the structural model (Example 9). Optionally a binding member may bind flanking residues or structurally neighbouring residues in the hCMV gB amino acid sequence, in addition to binding amino acids 133 to 343. By convention, residue numbering corresponds to hCMV gB strain AD169 (SEQ ID No: 239).

A binding member of the invention may comprise an antibody molecule, e.g. an antibody molecule with fully human amino acid sequence. The binding member normally may comprise an antibody $V_H$ and/or $V_L$ domain. $V_H$ and $V_L$ domains of binding members are also disclosed as part of the invention. Each of the $V_H$ and $V_L$ domains may comprise complementarity determining regions, (CDRs), and framework regions, (FRs). An antibody $V_H$ domain may comprise three HCDR regions, designated HCDR1, HCDR2, and HCDR3. An antibody $V_L$ domain may comprise three LCDR regions, designated LCDR1, LCDR2, and LCDR3. A $V_H$ or $V_L$ domain framework may comprise four framework regions, FWR1, FWR2, FWR3 and FWR4, interspersed with CDRs in the following structure: FWR1-CDR1-FWR2-CDR2-FWR3-CDR3-FWR4.

Examples of antibody $V_H$ and $V_L$ domains and CDRs according to the present invention are as listed in the appended sequence listing that forms part of the present disclosure. Further CDRs are disclosed below and in Table 19. All $V_H$ and $V_L$ sequences, CDR sequences, sets of CDRs and sets of HCDRs and sets of LCDRs disclosed herein represent aspects and embodiments of the invention. As described herein, a 'set of CDRs' may comprise CDR1, CDR2 and CDR3. Thus, a set of heavy chain CDRs refers to HCDR1, HCDR2 and HCDR3, and a set of light chain CDRs refers to LCDR1, LCDR2 and LCDR3. Unless otherwise stated, a 'set of CDRs' includes HCDRs and LCDRs.

Typically, binding members of the invention are monoclonal antibodies.

A binding member of the invention may comprise an antigen-binding site within a non-antibody molecule, normally provided by one or more CDRs e.g. a set of CDRs in a non-antibody protein scaffold, as discussed further below.

Binding members Ab-01 to Ab-46, according to the invention, were initially isolated from an hCMV infected donor and were isolated from EBV immortalised B cell lines, referred to as SM1, SM3, SM4, SM5, SM6, SM7, SM9, SM10 or SM11. From these nine cell lines 37 different $V_H$ and 62 different $V_L$ coding sequences of human antibodies could be identified (Table 6). The combination of all identified $V_H$ and $V_L$ coding sequences from each cell line as IgH and IgL chains can theoretically generate 295 different antibodies. Of these, 46 different recombinant antibodies have been identified, which were hCMV neutralising in a first-line biological screening assay using luciferase-expressing, hCMV laboratory-strain AD-169 and primary human foreskin fibroblasts. Six of these recombinant antibodies were found to neutralise hCMV with high potency ($IC_{50}$s below 1 μg/ml) and to bind gB protein with high affinity of $K_D$ of 15 nM or less (Tables 13 & 15 below).

The structures and locations of binding member variable domains may be determined by reference to Kabat et al., (1991) and updates thereof. Described herein is a panel of binding members each which may comprise the set of CDRs as specified in Tables 19 and 20, in which HCDR1 has Kabat residues 31-35; HCDR2 has Kabat residues 50-65; HCDR3 has Kabat residues 95-102. LCDR1 has Kabat residues 24-34; LCDR2 has Kabat residues 50-56 and LCDR3 has Kabat residues 89-97.

A binding member of a first embodiment of the invention may comprise one or more CDRs as described herein, e.g. a CDR3, and optionally also a CDR1 and CDR2 to form a set of CDRs. The CDR or set of CDRs may be a CDR or set of CDRs of any of antibodies Ab-01 to Ab-46, or may be a variant thereof as described herein.

A binding member may comprise a set of H and/or L CDRs of any of antibodies Ab-01 to Ab-46 with one or more amino acid mutations within the disclosed set of H and/or L CDRs. Amino acid mutations are substitutions, deletions or insertions of one amino acid. Based on the examples provided and the disclosed sequences, there may be, e.g., up to 22, 21, 20, 19, 18, 17, 16, 15, 14, 13, 12, 11, 10, 9, 8, 7, 6, 5, 4, 3, 2 or 1 mutations e.g. substitutions, within the set of H and/or L CDRs. Furthermore, there may be up to 9, 8, 7, 6, 5, 4, 3, 2 or 1 mutations, in HCDR3 and/or there may be up to 6, 5, 4, 3, 2 or 1 mutations, in HCDR2 and/or there may be up to 3, 2 or 1 mutations in HCDR1 and/or there maybe up to 6, 5, 4, 3, 2 or 1 mutations in LCDR3 and/or there maybe 1 mutation in LCDR2 and/or LCRD1. The mutation may be a substitution or the H and/or L CDRs may optionally contain an insertion or deletion of one amino acid as compared with the disclosed set of H and/or L CDRs.

Substitutions, insertions or deletions may be made at any point in the CDRs. For example, in HCDR1 substitutions may be of any of Kabat residues 31-35, e.g. any of Kabat residues 31, 32, 34 and/or 35, in HCDR2 substitutions may be of any of Kabat residues 50-65, e.g. any of Kabat residues 50, 53, 54, 58, 60, and/or 64, and in HCDR3 substitutions may be of any of Kabat residues 99-102, e.g. any of Kabat residues 99-100C, 100E, 100F and/or 100K-102. For example, in LCDR1 a substitution may be of any of Kabat residues 24-34, e.g. Kabat residues 26 or 27, in LCDR2 substitutions may be of any of Kabat residues 50-56, e.g. Kabat residue 56 and in LCDR3 substitutions may be of any of Kabat residues 89 to 97, e.g. any of Kabat residues 89 and there may be an insertion at position 95B. Details of specific amino acid mutations compared with the sequence of antibody Ab-28 can be found in Tables 20a and 20b for the HCDRs and LCDRs respectively, e.g. amino acid substitutions or insertions.

For example, the present invention provides an isolated binding member for hCMV, which may comprise a set of CDRs: HCDR1, HCDR2, HCDR3, LCDR1, LCDR2 and LCDR3, wherein the set of CDRs has 22 or fewer amino acid alterations from a set of CDRs in which:

HCDR1 has amino acid sequence SEQ ID No: 3;
HCDR2 has amino acid sequence SEQ ID No: 4;
HCDR3 has amino acid sequence SEQ ID No: 5;
LCDR1 has amino acid sequence SEQ ID No: 93;
LCDR2 has amino acid sequence SEQ ID No: 94; and
LCDR3 has amino acid sequence SEQ ID No: 95

For example a binding member or $V_H$ domain according to the invention may comprise the HCDR1 of antibody Ab-28 with one or more of the following mutations:

Kabat residue Asp 31 replaced by Gly;
Kabat residue His 32 replaced by Phe or Tyr;
Kabat residue Met 34 replaced by Ile or Leu; and
Kabat residue Val 35 replaced by Asn.

A binding member or $V_H$ domain according to the invention may comprise the HCDR2 of antibody Ab-28 with one or more of the following mutations:

Kabat residue Trp 50 replaced by Ser or Cys;
Kabat residue Gln 53 replaced by Asn or His;
Kabat residue Ser 54 replaced by Thr;
Kabat residue Gly 58 replaced by Lys, Asn or His;
Kabat residue Gly 60 replaced by Ala; and
Kabat residue Gln 64 replaced by Arg.

A binding member or $V_H$ domain according to the invention may comprise the HCDR3 of antibody Ab-28 with one or more of the following mutations:

Kabat residue Thr 99 replaced by Ala;
Kabat residue Val 100 replaced by Met;
Kabat residue Ser 100A replaced by Thr;
Kabat residue Asn 100B replaced by Thr;
Kabat residue Ser 100C replaced by Phe;
Kabat residue Leu 100E replaced by Met or Ala;
Kabat residue Ser 100F replaced by Gly;
Kabat residue His 100K replaced by Tyr;
Kabat residue Asn 100L replaced by Ser or Asp;
Kabat residue Arg 100M replaced by Val or Ile;
Kabat residue Leu 100N replaced by Met;
Kabat residue Asp 101 replaced by Gly; and
Kabat residue Ala 102 replaced by Val or Ile.

A binding member or $V_L$ domain according to the invention may comprise the LCDR1 of antibody Ab-28 in which Kabat residue Ser 26 is replaced by Asn or Kabat residue Ser 27 is replaced by Arg.

A binding member or $V_L$ domain according to the invention may comprise the LCDR2 of antibody Ab-28 in which Kabat residue Ser 56 is replaced by Pro.

A binding member or $V_L$ domain according to the invention may comprise the LCDR3 of antibody Ab-28 with one or more of the following mutations:

Kabat residue Gly 89 replaced by Ala;
Kabat residue Pro 91 replaced by Trp;
Kabat residue Arg 93 replaced by Ser;
Kabat residue Ser 94 replaced by Asp;
Kabat residue Ser 95a replaced by Gly or Ala;
Ala inserted at Kabat residue 95b;
Kabat residue Val 96 replaced by Tyr; and
Kabat residue Ile 97 replaced by Val.

Thus a binding member of the invention may comprise a LCDR3 wherein Kabat residue 95b is Ala or wherein Kabat residue 95b is absent.

The invention provides binding members which may comprise an HCDR1, HCDR2 and/or HCDR3 of any of antibodies Ab-01 to Ab-46, and/or an LCDR1, LCDR2 and/or LCDR3 of any of antibodies 1 to 46 e.g. a set of CDRs of any of antibodies Ab-01 to Ab-46 shown in Table 19 or 20.

For example, a binding member of the invention may comprise a set of CDRs: HCDR1, HCDR2, HCDR3, LCDR1, LCDR2 and LCDR3, wherein: HCDR1 is SEQ ID No: 8; HCDR2 is SEQ ID No: 9; HCDR3 is SEQ ID No: 10; LCDR1 is SEQ ID No: 98; LCDR2 is SEQ ID No: 99; and LCDR3 is SEQ ID No: 100, representing the CDRs of antibody Ab-02.

For example, a binding member of the invention may comprise a set of CDRs: HCDR1, HCDR2, HCDR3, LCDR1, LCDR2 and LCDR3, wherein: HCDR1 is SEQ ID No: 13; HCDR2 is SEQ ID No: 14; HCDR3 is SEQ ID No: 15; LCDR1 is SEQ ID No: 103; LCDR2 is SEQ ID No: 104; and LCDR3 is SEQ ID No: 105, representing the CDRs of antibody Ab-04.

For example, a binding member of the invention may comprise a set of CDRs: HCDR1, HCDR2, HCDR3, LCDR1, LCDR2 and LCDR3, wherein: HCDR1 is SEQ ID No: 18; HCDR2 is SEQ ID No: 19; HCDR3 is SEQ ID No: 20; LCDR1 is SEQ ID No: 108; LCDR2 is SEQ ID No: 109; and LCDR3 is SEQ ID No: 110, representing the CDRs of antibody Ab-11.

For example, a binding member of the invention may comprise a set of CDRs: HCDR1, HCDR2, HCDR3, LCDR1, LCDR2 and LCDR3, wherein: HCDR1 is SEQ ID No: 23; HCDR2 is SEQ ID No: 24; HCDR3 is SEQ ID No: 25; LCDR1 is SEQ ID No: 113; LCDR2 is SEQ ID No: 114; and LCDR3 is SEQ ID No: 115, representing the CDRs of antibody Ab-14.

For example, a binding member of the invention may comprise a set of CDRs: HCDR1, HCDR2, HCDR3, LCDR1, LCDR2 and LCDR3, wherein: HCDR1 is SEQ ID No: 3; HCDR2 is SEQ ID No: 4; HCDR3 is SEQ ID No: 5; LCDR1 is SEQ ID No: 93; LCDR2 is SEQ ID No: 94; and LCDR3 is SEQ ID No: 95, representing the CDRs of antibody Ab-28.

For example, a binding member of the invention may comprise a set of CDRs: HCDR1, HCDR2, HCDR3, LCDR1, LCDR2 and LCDR3, wherein: HCDR1 is SEQ ID No: 28; HCDR2 is SEQ ID No: 29; HCDR3 is SEQ ID No: 30; LCDR1 is SEQ ID No: 108; LCDR2 is SEQ ID No: 109; and LCDR3 is SEQ ID No: 110, representing the CDRs of antibody Ab-42.

The binding member may comprise a set of $V_H$ CDRs of one of these antibodies. Optionally it may also comprise a set of $V_L$ CDRs of one of these antibodies, and the $V_L$ CDRs may be from the same or a different antibody as the $V_H$ CDRs.

A $V_H$ domain which may comprise a set of HCDRs of any of antibodies Ab-01 to Ab-46, and/or a $V_L$ domain which may comprise a set of LCDRs of any of antibodies Ab-01 to Ab-46 are also provided by the invention.

Typically, a $V_H$ domain is paired with a $V_L$ domain to provide an antibody antigen-binding site, although as discussed further below a $V_H$ or $V_L$ domain alone may be used to bind antigen. The $V_H$ domain of antibody Ab-28 may be paired with the $V_L$ domain of antibody Ab-28, so that an antibody antigen-binding site is formed which may comprise both the antibody Ab-28 $V_H$ and $V_L$ domains. Analogous embodiments are provided for the other $V_H$ and $V_L$ domains disclosed herein. In other embodiments, the antibody Ab-28 $V_H$ is paired with a $V_L$ domain other than the antibody $V_L$. Light-chain promiscuity is well established in the art (Kang et al., 1991). Again, analogous embodiments are provided by the invention for the other $V_H$ and $V_L$ domains disclosed herein.

Thus, an IgH chain containing the $V_H$ of any of antibodies 1 to 46 may be paired with the IgL chain containing $V_L$ of any of antibodies Ab-01 to Ab-46 to generate a gB specific binding member.

A binding member may comprise an antibody molecule having one or more CDRs, e.g. a set of CDRs, within an antibody framework. The framework regions may be of human germline gene segment sequences. Human germline gene segment sequences are known to those skilled in the art and can be accessed for example from the VBase compilation or the IMGT online database.

A binding member of the invention may be an isolated human antibody molecule having a $V_H$ domain which may comprise a set of HCDRs in a human germline framework, e.g. IGHV1-2. Thus, the VH domain framework regions FWR1, FWR2 and/or FWR3 may comprise framework regions of human germline gene segment IGHV1-2. FWR4 may comprise a framework region of human germline J segments selected from, for example, SEQ ID Nos: 188 to 191. The amino acid sequence of $V_H$ FWR1 may be SEQ ID No: 181. The amino acid sequence of $V_H$ FWR2 may be SEQ ID No: 182. The amino acid sequence of $V_H$ FWR3 may be SEQ ID No: 183 or 184.

An antibody molecule or a $V_H$ domain of the invention may comprise the following set of heavy chain framework regions: FWR1 SEQ ID No: 181; FWR2 SEQ ID No: 182; FWR3 SEQ ID No: 183 or 184; or may comprise the said set of heavy chain framework regions with 1, 2, 3, 4, 5, 6, 7, 8, 9, 10, 11, 12, 13, 14, 15, 16, 17, 18, 19 or 20 amino acid alterations, such as a substitution, an insertion or a deletion.

Furthermore, an antibody of the invention may include a $V_H$ domain that is encoded by a nucleic acid sequence that is at least 80% homologous to the IGHV1-2 germline gene sequence, Preferably the nucleic acid sequence is at least 90%, 95%, 96%, 97% homologous to the IGHV1-2 germline gene sequence, and more preferably, at least 98%, 99% homologous to the IGHV1-2 germline gene sequence. The $V_H$ domain of an antibody of the invention may be at least 80% homologous to the amino acid sequence of the $V_H$ domain encoded by the IGHV1-2 germline gene sequence. Preferably the amino acid sequence of the $V_H$ domain is at least 90%, 95%, 96%, 97% homologous to the amino acid sequence encoded by the IGHV1-2 germline gene sequence, and more preferably, at least 98%, 99% homologous to the amino acid sequence encoded by IGHV1-2 germline gene sequence.

Normally the binding member also has a $V_L$ domain which may comprise a set of LCDRs, e.g. in a human germline framework, e.g. IGLV1-51. Thus, the $V_L$ domain framework regions may comprise framework regions FWR1, FWR2 and/or FWR3 of human germline gene segment IGLV1-51. FWR4 may comprise a framework region of human germline J segment IGLJ2 (SEQ ID No: 193). The amino acid sequence of $V_L$ FWR1 may be SEQ ID No: 185. The amino acid sequence of $V_L$ FWR2 may be SEQ ID No: 186. The amino acid sequence of $V_L$ FWR3 may be SEQ ID No: 187.

An antibody molecule or a $V_L$ domain of the invention may comprise the following set of light chain framework regions: FWR1 SEQ ID No: 185; FWR2 SEQ ID No: 186; FWR3 SEQ ID No: 187; or may comprise the said set of light chain framework regions with 1, 2, 3, 4, 5, 6, 7, 8, 9, 10, 11, 12, 13 or 14 amino acid alterations, such as a substitution, an insertion or a deletion.

Furthermore, an antibody of the invention may include a $V_L$ domain that is encoded by a nucleic acid sequence that is at least 80% homologous to the IGLV1-51 germline gene sequence. Preferably the nucleic acid sequence is at least 90%, 95%, 96%, 97% homologous to the IGLV1-51 germline gene sequence, and more preferably, at least 98%, 99% homologous to the IGLV1-51 germline gene sequence. The $V_L$ domain of an antibody of the invention may be at least 80% homologous to the amino acid sequence of the $V_L$ domain encoded by the IGLV1-51 germline gene sequence. Preferably the amino acid sequence of the $V_L$ domain is at least 90%, 95%, 96%, 97% homologous to the amino acid sequence encoded by the IGLV1-51 germline gene sequence, and more preferably, at least 98%, 99% homologous to the amino acid sequence encoded by IGLV1-51 germline gene sequence.

For example, an antibody molecule of the invention may comprise a set of heavy and light chain framework regions, wherein heavy chain FWR1 is SEQ ID No: 181; heavy chain FWR2 is SEQ ID No: 182; heavy chain FWR3 is SEQ ID No: 183; light chain FWR1 is SEQ ID No: 185; light chain FWR2 is SEQ ID No: 186; light chain FWR3 is SEQ ID No: 187; or may comprise the said set of heavy and light chain framework regions with 10 or fewer, e.g. five or fewer, amino acid alterations, e.g. substitutions.

Binding members Ab-47 to Ab-50, according to the invention, were initially isolated from three hCMV infected donors and were isolated from EBV immortalised B cell lines, referred to as SM10, SM12, 2C2 or 1G2. From these four cell lines, four different $V_H$ and five different $V_L$ coding sequences of human antibodies could be identified (Table 12). The combination of all identified $V_H$ and $V_L$ coding sequences from each cell line as IgH and IgL chains can theoretically generate 20 different antibodies. Of these, four different recombinant antibodies have been identified, which were hCMV neutralising in a first-line biological screening assay using luciferase-expressing, hCMV laboratory-strain AD-169 and primary human foreskin fibroblasts. All of these recombinant antibodies were found to neutralise hCMV with high potency ($IC_{50}$s below 0.6 μg/ml; Table 14 below).

The structures and locations of binding member variable domains may be determined by reference to Kabat et al., (1991) and updates thereof. Described herein are binding members Ab-46, Ab-47, Ab-48 and Ab-50 each which may comprise the set of CDRs as specified in Table 19, in which the CDRs were identified by the Kabat numbering system (Kabat & Wu, 1991).

A binding member of a second embodiment of the invention may comprise one or more CDRs as described herein, e.g. a CDR3, and optionally also a CDR1 and CDR2 to form a set of CDRs. The CDR or set of CDRs may be a CDR or set of CDRs of any of antibodies Ab-47 to Ab-50, or may be a variant thereof as described herein.

A binding member may comprise a set of H and/or L CDRs of any of antibodies Ab-47 to Ab-50 with one or more amino acid mutations within the disclosed set of H and/or L CDRs. Amino acid mutations are substitutions, deletions or insertions of one amino acid. Based on the examples provided and the disclosed sequences, there may be, e.g., up to 10, 9, 8, 7, 6, 5, 4, 3, 2 or 1 mutations within the set of H and/or L CDRs. The mutation may be a substitution or the H and/or L CDRs may optionally contain an insertion or deletion of one amino acid as compared with the disclosed set of H and/or L CDRs. Substitutions, insertions or deletions may be made at any point in the CDRs.

The invention provides binding members which may comprise an HCDR1, HCDR2 and/or HCDR3 of any of antibodies Ab-47 to Ab-50, and/or an LCDR1, LCDR2 and/or LCDR3 of any of antibodies Ab-47 to Ab-50, e.g. a set of CDRs of any of antibodies Ab-47 to Ab-50 shown in Table 19.

For example, a binding member of the invention may comprise a set of CDRs: HCDR1, HCDR2, HCDR3, LCDR1, LCDR2 and LCDR3, wherein: HCDR1 is SEQ ID No: 243; HCDR2 is SEQ ID No: 244; HCDR3 is SEQ ID No: 245; LCDR1 is SEQ ID No: 263; LCDR2 is SEQ ID No: 264; and LCDR3 is SEQ ID No: 265, representing the CDRs of antibody Ab-47.

For example, a binding member of the invention may comprise a set of CDRs: HCDR1, HCDR2, HCDR3, LCDR1, LCDR2 and LCDR3, wherein: HCDR1 is SEQ ID No: 248; HCDR2 is SEQ ID No: 249; HCDR3 is SEQ ID No: 250; LCDR1 is SEQ ID No: 268; LCDR2 is SEQ ID No: 269; and LCDR3 is SEQ ID No: 270, representing the CDRs of antibody Ab-48.

For example, a binding member of the invention may comprise a set of CDRs: HCDR1, HCDR2, HCDR3, LCDR1, LCDR2 and LCDR3, wherein: HCDR1 is SEQ ID No: 253; HCDR2 is SEQ ID No: 254; HCDR3 is SEQ ID No: 255; LCDR1 is SEQ ID No: 273; LCDR2 is SEQ ID No: 274; and LCDR3 is SEQ ID No: 275, representing the CDRs of antibody Ab-49.

For example, a binding member of the invention may comprise a set of CDRs: HCDR1, HCDR2, HCDR3, LCDR1, LCDR2 and LCDR3, wherein: HCDR1 is SEQ ID No: 258; HCDR2 is SEQ ID No: 259; HCDR3 is SEQ ID No: 260; LCDR1 is SEQ ID No: 278; LCDR2 is SEQ ID No: 279; and LCDR3 is SEQ ID No: 280, representing the CDRs of antibody Ab-50.

A binding member of the invention may be an isolated human antibody molecule having a $V_H$ domain which may comprise a set of HCDRs in a human germline framework, e.g. IGHV4-39 or IGHV4-59. Thus, the VH domain framework regions FWR1, FWR2 and/or FWR3 may comprise framework regions of human germline gene segment IGHV4-39 or IGHV4-59. FWR4 may comprise a framework region of human germline J segments selected from any of the six heavy chain J segments (see Ravetch et al., 1981).

The amino acid sequence of Ab-47 or Ab-50 $V_H$ domain may comprise the following set of heavy chain framework regions of IGHV4-39: FWR1 SEQ ID No: 281, FWR2 SEQ ID No: 282; FWR3 SEQ ID No: 283; or may comprise the said set of heavy chain framework regions with 1, 2, 3, 4, 5, 6, 7, 8, 9, 10 or 11 amino acid alterations, such as a substitution, an insertion or a deletion.

The amino acid sequence of Ab-48 or Ab-48 $V_H$ domain may comprise the following set of heavy chain framework regions of IGHV4-59: FWR1 SEQ ID No: 284, FWR2 SEQ ID No: 285; FWR3 SEQ ID No: 286; or may comprise the said set of heavy chain framework regions with 1, 2, 3, 4, 5, 6, 7, 8, 9, 10, 11, 12 or 13 amino acid alterations, such as a substitution, an insertion or a deletion.

Furthermore, an antibody of the invention may include a $V_H$ domain that is encoded by a nucleic acid sequence that is at least 75% homologous to the IGHV4-39 or IGHV4-59 germline gene sequence. Preferably the nucleic acid sequence is at least 80%, 85%, 90%, 95%, 96%, 97% homologous to the IGHV4-39 or IGHV4-59 germline gene sequence, and more preferably, at least 98%, 99% homologous to the IGHV4-39 or IGHV4-59 germline gene sequence. The $V_H$ domain of an antibody of the invention may be at least 75% homologous to the amino acid sequence of the $V_H$ domain encoded by the IGHV4-39 or IGHV4-59 germline gene sequence. Preferably the amino acid sequence of the $V_H$ domain is at least 80%, 85%, 90%, 95%, 96%, 97% homologous to the amino acid sequence encoded by the IGHV4-39 or IGHV4-59 germline gene sequence, and more preferably, at least 98%, 99% homologous to the amino acid sequence encoded by IGHV1-2 germline gene sequence.

A binding member of the invention may also comprise a $V_L$ domain which may comprise a set of kappa light chain CDRs in a human germline framework, e.g. IGKV2D-28 or IGKV1D-33. Thus, the VL domain framework regions FWR1, FWR2 and/or FWR3 may comprise framework regions of human germline gene segment IGKV2D-28 or IGKV1D-33. FWR4 may comprise a framework region of human germline J segments selected from any of the five kappa J segments (see Hieter et al., 1982).

The amino acid sequence of Ab-47 or Ab-48 $V_L$ domain may comprise the following set of kappa light chain framework regions of IGKV2D-28: FWR1 SEQ ID No: 287, FWR2 SEQ ID No: 288; FWR3 SEQ ID No: 289; or may comprise the said set of light chain framework regions with 1 or 2 amino acid alterations, such as a substitution, an insertion or a deletion.

The amino acid sequence of Ab-49 $V_L$ domain may comprise the following set of light chain framework regions of IGKV1D-33: FWR1 SEQ ID No: 290, FWR2 SEQ ID No: 291; FWR3 SEQ ID No: 292; or may comprise the said set of light chain framework regions with 1, 2, 3, 4, 5, 6, 7, or 8 amino acid alterations, such as a substitution, an insertion or a deletion.

A binding member of the invention may also comprise a $V_L$ domain which may comprise a set of lambda light chain CDRs in a human germline framework, e.g. IGLV1-47. Thus, the VL domain framework regions FWR1, FWR2 and/or FWR3 may comprise framework regions of human germline gene segment IGLV1-47. FWR4 may comprise a framework region of human germline J segments selected from any of the four lambda J segments (see Udey & Blomberg 1987; Vasicek & Leder, 1990).

The amino acid sequence of Ab-50 $V_L$ domain may comprise the following set of lambda light chain framework regions of IGLV1-47: FWR1 SEQ ID No: 293, FWR2 SEQ ID No: 294; FWR3 SEQ ID No: 295; or may comprise the said set of light chain framework regions with 1 or 2 amino acid alterations, such as a substitution, an insertion or a deletion.

Furthermore, an antibody of the invention may include a $V_L$ domain that is encoded by a nucleic acid sequence that is at least 90% homologous to the IGKV2D-28, IGKV1D-33 or IGLV1-47 germline gene sequence. Preferably the nucleic acid sequence is at least 95%, 96%, 97% homologous to the IGKV2D-28, IGKV1D-33 or IGLV1-47 germline gene sequence, and more preferably, at least 98%, 99% homologous to the IGKV2D-28, IGKV1D-33 or IGLV1-47 germline gene sequence. The $V_L$ domain of an antibody of the invention may be at least 90% homologous to the amino acid sequence of the $V_L$ domain encoded by the IGKV2D-28, IGKV1D-33 or IGLV1-47 germline gene sequence. Preferably the amino acid sequence of the $V_L$ domain is at least 95%, 96%, 97% homologous to the amino acid sequence encoded by the IGKV2D-28, IGKV1D-33 or IGLV1-47 germline gene sequence, and more preferably, at least 98%, 99% homologous to the amino acid sequence encoded by IGKV2D-28, IGKV1D-33 or IGLV1-47 germline gene sequence.

A binding member of the invention may be one which competes for binding to hCMV with any binding member that (i) binds hCMV and (ii) may comprise a binding member, $V_H$ and/or $V_L$ domain, CDR e.g. HCDR3, and/or set of CDRs disclosed herein.

Competition between binding members may be assayed in vitro, for example using binding assays, like ELISA, surface plasmon resonance, and/or by tagging a specific reporter molecule to one binding member which can be detected in the presence of one or more other untagged binding members, to enable identification of binding members which bind the same epitope or an overlapping epitope. Such methods are readily known to one of ordinary skill in the art, and are described in more detail herein (see the Examples). Thus, a further aspect of the present invention provides a binding member which may comprise an antibody antigen-binding site that competes with an antibody molecule, for example an antibody molecule which may comprise a $V_H$ and/or $V_L$ domain, CDR e.g. HCDR3 or set of CDRs of any of antibodies Ab-01 to Ab-50, for binding to hCMV.

In further aspects, the invention provides an isolated nucleic acid which may comprise a sequence encoding a binding member, which may comprise a $V_H$ domain and/or $V_L$ domain according to the present invention, and methods of preparing a binding member, which may comprise a $V_H$ domain and/or a $V_L$ domain of the invention, encoded by said nucleic acid under conditions to bring about production of said binding member, which may comprise $V_H$ domain and/or $V_L$ domain, and recovering it.

Another aspect of the present invention provides isolated nucleic acids encoding any of the $V_H$ CDR or $V_L$ CDR sequences disclosed herein.

A further aspect provides a host cell containing or transfected with nucleic acid of the invention.

Further aspects of the present invention describe compositions containing binding members of the invention, and their use in methods of binding, inhibiting and/or neutralising hCMV infection, including methods of treatment of the human or animal body by therapy.

Binding members according to the invention may be used in a method of treatment or diagnosis, such as a method of treatment (which may include prophylactic treatment) of a disease or disorder in the human or animal body (e.g. in a human patient), which may comprise administering to said human or animal body an effective amount of a binding member of the invention or a combination of several binding members of the invention. Conditions treatable in accordance with the present invention include any in which hCMV plays a role, as discussed in detail elsewhere herein.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

FIG. 4. Competition ELISA between anti-hCMV antibodies and Ab-50.

FIG. 9. Recognition of AD-4 and AD-4 mutant proteins by human monoclonal antibodies (Ab-28, Ab-11, Ab-14) and affinity purified IgG from hCMV seropositive donors. ELISA plates were coated with the indicated AD-4 fusion proteins and used to analyse binding of human monoclonal antibodies (Ab-28, Ab-11, Ab-14.

FIG. 14 shows ITC52 titrated in the absence (●) or presence (■) of ITC88, which was added to the titrated antibody at a constant concentration of 3 µg/ml (A). All results represent triplicate analysis.

Figure 1:
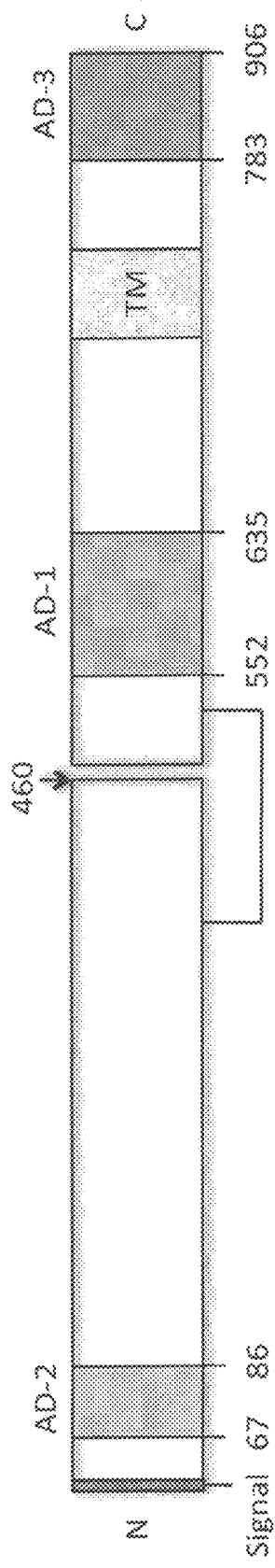
FIG. 1. This figure shows a schematic overview of the gB protein (strain AD169; SEQ ID No: 239), indicating the location of known antigenic domains AD-1, AD-2 and AD-3 (Ohlin et al., 1993; Wagner et al., 1992). There is a cleavage site at amino acid 460 and a disulphide bond linking the two moieties together, as indicated by the brackets. Signal: signal sequence (amino acids 1-22), TM: transmembrane domain (amino acids 751-771).

For this assay one representative AD-4-(Dom II) specific antibody (Ab-28) and two representative AD-5-(Dom I) specific antibodies (Ab-49 and Ab-50) were used. The x-axis shows IgG concentration (µg/ml) and the y-axis shows %-neutralisation. Legend: ● AD-5 antibody (Ab-49 or Ab-50) alone; ▲ AD-4 antibody alone; ■ AD-5 and AD-4 antibodies mixed. The starting concentration of the mixture was 3 µg/ml, as 1.5 µg/ml of each antibody was applied in the first well.

DETAILED DESCRIPTION OF THE INVENTION

It is convenient to point out here that 'and/or' where used herein is to be taken as specific disclosure of each of the two specified features or components with or without the other. For example 'A and/or B' is to be taken as specific disclosure of each of (i) A, (ii) B and (iii) A and B, just as if each is set out individually herein.

The full-length amino acid sequence of human cytomegalovirus (hCMV) has GenBank Acc. No. X17403 (Human cytomegalovirus strain AD169 complete genome) and may comprise a 229354 base pair sequence (Chee et al., 1990; Bankier et al., 1991).

gB complex is a surface glycoprotein complex of the virion envelope of CMV. There are a number of different strains of gB protein:

gB strain AD169—SwissProt Acc. No. P06473 (SEQ ID No: 239)

gB strain Towne—SwissProt Acc. No. P13201 (SEQ ID No: 240)

Known neutralising domains of gB include antigenic domain-1 (AD-1; amino acids 552-635 of SEQ ID No: 239 [AD169]) and antigenic domain-2 (AD-2; amino acids 67-86 of SEQ ID No: 239 [AD169]). A further antigenic domain, AD-3 also exists (amino acids 783-906 of SEQ ID No: 239 [AD169]). This domain is located intravirally and is not the target of neutralising antibodies.

Binding member describes one member of a pair of molecules that bind one another. The members of a binding pair may be naturally derived or wholly or partially synthetically produced. One member of a binding pair may be a polypeptide, nucleic acid, carbohydrate, lipid, small molecular weight compound, an oligonucleotide, an oligopeptide, RNA interference (RNAi; see Milhavet et al., 2003), antisense (see Opalinska & Gewirtz, 2003), a recombinant protein, an antibody, or fragments thereof or conjugates or fusion proteins thereof.

Antisense or RNAi inhibitors for use in the present invention may comprise nucleic acid molecules capable of modulating gene expression, for example capable of down regulating expression of a sequence encoding a hCMV gB protein. Such nucleic acid molecules may include, but are not limited to antisense molecules, short interfering nucleic acid (siNA), double-stranded RNA (dsRNA), micro RNA, short hairpin RNA (shRNA), nucleic acid sensor molecules, allozymes, enzymatic nucleic acid molecules and triplex oligonucleotides and any other nucleic acid molecule which can be used in mediating RNA interference 'RNAi' or gene silencing in a sequence-specific manner.

One member of the pair of molecules may have an area on its surface, or a cavity, which binds to and is therefore complementary to a particular spatial and polar organization of the other member of the pair of molecules. Examples of types of binding pairs are antigen-antibody, receptor-ligand and enzyme-substrate.

A binding member normally may comprise a molecule having a binding site. For example, a binding member may be an antibody molecule or a non-antibody protein that may comprise a binding site. A binding site may be provided by means of arrangement of CDRs on antibody framework regions and/or on non-antibody protein scaffolds, such as fibronectin or cytochrome B etc. (Haan & Maggos 2004; Koide et al., 1998; Nygren et al., 1997), or by randomising or mutating amino acid residues of a loop within a protein scaffold to confer binding specificity for a desired target. Scaffolds for engineering novel binding sites in proteins have been reviewed in detail by Nygren et al., ibid. Protein scaffolds for antibody mimics are disclosed in WO 00/034784 A1 (Lipovsek), in which proteins (antibody mimics) are described that include a fibronectin type III domain having at least one randomised loop. A suitable scaffold into which to graft one or more CDRs, e.g. a set of HCDRs, may be provided by any domain member of the immunoglobulin gene superfamily. The scaffold may be a human or non-human protein. An advantage of a non-antibody protein scaffold is that it may provide an antigen-binding site in a scaffold molecule that is smaller and/or easier to manufacture than at least some antibody molecules. Small size of a binding member may confer useful physiological properties, such as an ability to enter cells, penetrate deep into tissues or reach targets within other structures, or to bind within protein cavities of the target antigen. Use of antigen binding sites in non-antibody protein scaffolds is reviewed in Wess, 2004. Typical are proteins having a stable backbone and one or more variable loops, in which the amino acid sequence(s) of the loop or loops is/are specifically or randomly mutated to create an antigen-binding site that binds the target. Such proteins include the IgG-binding domains of protein A from *S. aureus*, transferrin, tetranectin, fibronectin, lipocalins as well as gamma-crystalline and other Affilin™ scaffolds (Scil Proteins).

Examples of other approaches include synthetic 'Microbodies' based on cyclotides—small proteins having intramolecular disulphide bonds, Microproteins (Versabodies™, Amunix) and ankyrin repeat proteins (DARPins, Molecular Partners).

In addition to antibody sequences and/or an antigen-binding site, a binding member according to the present invention may comprise other amino acids, e.g. forming a peptide or polypeptide, such as a folded domain, or to impart to the molecule another functional characteristic in addition to ability to bind antigen. Binding members of the invention may carry a detectable label, or may be conjugated to a toxin or a targeting moiety or enzyme (e.g. via a peptidyl bond or linker). For example, a binding member may comprise a catalytic site (e.g. in an enzyme domain) as well as an antigen binding site, wherein the antigen binding site binds to the antigen and thus targets the catalytic site to the antigen. The catalytic site may inhibit biological function of the antigen, e.g. by cleavage.

Although, as noted, CDRs can be carried by non-antibody scaffolds, the structure for carrying a CDR or a set of CDRs of the invention will generally be an antibody heavy or light chain sequence or substantial portion thereof in which the CDR or set of CDRs is located at a location corresponding to the CDR or set of CDRs of naturally occurring V.sub.H and V.sub.L antibody variable domains encoded by rearranged immunoglobulin genes. The structures and locations of immunoglobulin variable domains may be determined by reference to Kabat & Wu, (1991) and updates thereof. A number of academic and commercial on-line resources are available to query this database. For example, see Martin, 1996.

By CDR region or CDR, it is intended to indicate the hypervariable regions of the heavy and light chains of the immunoglobulin as defined by Kabat et al., ibid. An antibody typically contains 3 heavy chain CDRs, termed HCDR1, HCDR2, and HCDR3, and 3 light chain CDRs, termed LCDR1, LCDR2 and LCDR3. The term CDR or CDRs is used here in order to indicate one of these regions or several, or even the whole, of these regions which contain the majority of the amino acid residues responsible for the binding by affinity of the antibody for the antigen or the epitope which it recognises.

Among the six CDR sequences, the third CDR of the heavy chain (HCDR3) has a greatest size variability i.e. greater diversity, essentially due to the mechanism known in the art as V(D)J rearrangement of the V, D and J gene segments of the germline immunoglobulin heavy chain gene locus. The HCDR3 may be as short as two amino acids or as long as 26 amino acids, or may have any length in between these two extremes. CDR length may also vary according to the length that can be accommodated by the particular underlying framework. Functionally, HCDR3 can play an important role in the determination of the specificity of the antibody (Segal et al., 1974; Amit et al., 1986; Chothia et al., 1987, 1989; Caton et al., 1990; Sharon 1990a, Sharon 1990b, Kabat et al., 1991).

In binding members Ab-01 to Ab-46 of the present invention, as indicated in Tables 20a and b, HCDR1 may be 5 amino acids long, consisting of Kabat residues 31-35. HCDR2 may be 17 amino acids long, consisting of Kabat residues 50-65. HCDR3 may be 22 amino acids long, consisting of Kabat residues 95-102. LCDR1 may be 13 amino acids long, consisting of Kabat residues 24-34. LCDR2 may be 7 amino acids long, consisting of Kabat residues 50-56. LCDR3 may be 10 amino acids long, consisting of Kabat residues 89-97.

In binding members Ab-47 to Ab-50 of the present invention, HCDR1 may be 7 or 5 amino acids long, consisting of Kabat residues 31-37 or 31-35, respectively. HCDR2 may be 16 amino acids long and HCDR3 may be 10, 15, 17 or 22 amino acids long. LCDR1 may be 11 amino acids long, consisting of Kabat residues 24-34; or 13 amino acids long, consisting of Kabat residues 23-35; or 16 amino acids long, consisting of Kabat residues 24-39. LCDR2 may be 7 amino acids long and LCDR3 may be 9 amino acids long.

This describes an immunoglobulin whether naturally, or partly, or wholly synthetically produced. The term also covers any polypeptide or protein which may comprise an antibody antigen-binding site. It must be understood here that the invention does not relate to the antibodies in natural form, that is to say they are not in their natural environment but that they have been able to be isolated or obtained by purification from natural sources, or else obtained by genetic recombination, or by chemical synthesis, and that they can then contain unnatural amino acids. Antibody fragments that comprise an antibody antigen-binding site include, but are not limited to, molecules such as Fab, Fab', F(ab')$_2$, Fab'—SH, scFv, Fv, dAb and Fd. Various other antibody molecules including one or more antibody antigen-binding sites have been engineered, including for example Fab2, Fab3, diabodies, triabodies, tetrabodies and minibodies and also bispecific and trispecific antibodies. Antibody molecules and methods for their construction and use are described in Hollinger & Hudson (2005).

It is possible to take monoclonal and other antibodies and use techniques of recombinant DNA technology to produce other antibodies or chimeric molecules that bind the target antigen. Such techniques may involve introducing DNA encoding the immunoglobulin variable region, or the CDRs, of an antibody to the constant regions, or constant regions plus framework regions, of a different immunoglobulin. See for instance, EP0184187A (Kudo et al) or EP0239400A (Winter). A hybridoma or other cell producing an antibody may be subject to genetic mutation or other changes, which may or may not alter the binding specificity of antibodies produced.

As antibodies can be modified in a number of ways, the term 'antibody molecule' should be construed as covering any binding member or substance having an antibody antigen-binding site with the required specificity and/or binding to antigen. Thus, this term covers bispecifc or trispecific antibodies as well as antibody fragments and derivatives, including any polypeptide which may comprise an antibody antigen-binding site, whether natural or wholly or partially synthetic. Chimeric molecules which may comprise an antibody antigen-binding site, or equivalent, fused to another polypeptide (e.g. derived from another species or belonging to another antibody class or subclass) are therefore included. Cloning and expression of chimeric antibodies are described for example in EP0120694A (Boss et al) and EP0125023A (Cabilly et al).

Further techniques available in the art of antibody engineering have made it possible to isolate human and humanised antibodies. For example, human hybridomas can be made as described by Kontermann & Dubel (2001). Phage display, another established technique for generating binding members has been described in detail in many publications, such as Kontermann & Dubel, ibid and WO 92/01047 A1 (McCafferty et al).

Transgenic mice in which the mouse antibody genes are inactivated and functionally replaced with human antibody genes while leaving intact other components of the mouse immune system, can be used for isolating human antibodies (Mendez et al., 1997). Alternatively, the method described by Grawunder & Melchers (WO 03/068819 A1) can be used to generate genetically modified vertebrate precursor lymphocytes for the production of heterologous antibodies or binding proteins. Humanised antibodies can be produced using techniques known in the art such as those disclosed in for example WO 91/09967 A1 (Adair et al). Further, WO 04/006955 A1 (Foote) relates to methods for humanising antibodies, based on selecting variable region framework sequences from human antibody genes by comparing canonical CDR structure types for CDR sequences of the variable region of a non-human antibody to canonical CDR structure types for corresponding CDRs from a library of human antibody sequences, e.g. germline antibody gene segments. Human antibody variable regions having similar canonical CDR structure types to the non-human CDRs form a subset of member human antibody sequences from which to select human framework sequences. The subset members may be further ranked by amino acid similarity between the human and the non-human CDR sequences. In the method of WO 04/006955 A1 ibid, top ranking human sequences are selected to provide the framework sequences for constructing a chimeric antibody that functionally replaces human CDR sequences with the non-human CDR counterparts using the selected subset member human frameworks, thereby providing a humanized antibody of high affinity and low immunogenicity without need for comparing framework sequences between the non-human and human antibodies. Chimeric antibodies made according to the method are also disclosed.

It has been shown that fragments of a whole antibody can perform the function of binding antigens. Examples of binding fragments are (i) the Fab fragment consisting of $V_L$, $V_H$, $C_L$ and $C_H1$ domains; (ii) the Fd fragment consisting of the $V_H$ and $C_H1$ domains; (iii) the Fv fragment consisting of the $V_L$ and $V_H$ domains of a single antibody; (iv) the dAb fragment (Ward et al., 1989; McCafferty et al., 1990; Holt et al., 2003), which consists of a $V_H$ or a $V_L$ domain; (v) isolated CDR regions; (vi) F(ab')$_2$ fragments, a bivalent fragment which may comprise two linked Fab fragments (vii) single chain Fv molecules (scFv), wherein a $V_H$ domain and a $V_L$ domain are linked by a peptide linker which allows the two domains to associate to form an antigen binding site (Bird et al., 1998; Huston et al 1988); (viii) bispecific single chain Fv dimers (WO 93/011161 A1 (Whitlow et al)) and (ix) 'diabodies', multivalent or multispecific fragments constructed by gene fusion (Holliger et al., 1993 & WO 94/13804 A1). Fv, scFv or diabody molecules may be stabilized by the incorporation of disulphide bridges linking the $V_H$ and $V_L$ domains (Reiter et al., 1996). Minibodies which may comprise an scFv joined to a $C_H3$ domain may also be made (Hu et al; 1996). Other examples of binding fragments are Fab', which differs from Fab fragments by the addition of a few residues at the carboxyl terminus of the heavy chain $C_H1$ domain, including one or more cysteines from the antibody hinge region, and Fab'-SH, which is a Fab' fragment in which the cysteine residue(s) of the constant domains bear a free thiol group. Antibody molecules have also been described that containing just two CDRs linked by a framework region (Qui et al., 2007). CDR3 from the $V_H$ or $V_L$ domain was linked to the CDR1 or CDR2 loop of the other domain with linkage through the C terminus of the selected CDR1 or CDR2 to the N terminus of the CDR3, via a framework region.

A domain antibody (dAb) is a small monomeric antigen-binding fragment of an antibody, namely the variable region of an antibody heavy or light chain (Holt et al., 2003). $V_H$ dAbs occur naturally in camelids (e.g. camel, llama) and may be produced by immunising a camelid with a target antigen, isolating antigen-specific B cells and directly cloning dAb genes from individual B cells; however dAbs can also be produced in cell culture. A binding member of the present invention may be a dAb which may comprise a $V_H$ or $V_L$ domain substantially as set out herein, or a $V_H$ or $V_L$ domain which may comprise a set of CDRs substantially as set out herein.

Antibody fragments of the invention can be obtained starting from any of antibodies Ab-01 to Ab-50, by methods such as digestion by enzymes e.g. pepsin or papain and/or by cleavage of the disulfide bridges by chemical reduction. In another manner, the antibody fragments comprised in the present invention can be obtained by techniques of genetic recombination well known to the person skilled in the art or else by peptide synthesis or by nucleic acid synthesis and expression.

Functional antibody fragments according to the present invention include any functional fragment whose half-life is increased by a chemical modification, especially by PEGylation, or by incorporation in a liposome for example.

Bispecific or bifunctional antibodies form a second generation of monoclonal antibodies in which two different variable regions are combined in the same molecule (Holliger & Bohlen, 1999). Therefore, a bispecific antibody may have two different binding specificities encoded by the variable regions and therefore bind to two different epitopes on single or multiple target antigens. Their use has been demonstrated both in the diagnostic field and in the therapy field from their capacity to recruit new effector functions or to target several molecules on the surface of tumour cells. For example, antibodies can be armed with additional cytotoxic mechanisms such as radioisotopes, bacterial toxins, inflammatory cytokines, chemotherapuetics or prodrugs. Where bispecific antibodies are to be used, these may be conventional bispecific antibodies, which can be manufactured in a variety of ways (Holliger & Winter, 1993). Examples of bispecific antibodies include those of the BITE® (Bi-specific T-cell engager) technology (Micromet, Inc.) in which the binding domains of two antibodies with different specificity can be used and directly linked via short flexible peptides. This combines two antibodies on a short single polypeptide chain. Diabodies and scFv can be constructed without an Fc region, using only variable domains, potentially reducing the effects of anti-idiotypic reaction.

Bispecific antibodies can be constructed as entire IgG, as quadroma (dual-specific antigen binding fragment (Fab) plus Fcγ), as bispecific F(ab')$_2$, as Fab'PEG, as heterodimeric Fab, as diabodies or as bispecific or heterodimeric scFv (reviewed in Kufer et al., 2004). Further, two bispecific antibodies can be linked using routine methods known in the art to form tetravalent antibodies. Bispecific diabodies, as opposed to bispecific whole antibodies, may also be particularly useful because they can be readily constructed and expressed in *E. coli*.

Recent work on multi-specific antibodies has led to the development of mixtures antibodies wherein three to five recombinant human monoclonal antibodies are produced by a single, clonal cell. The component antibodies share the same immunoglobulin light chain variable region to ensure that all binding sites associated with the antibody species in the mixture are functional (Oligoclonics™; Merus Biopharmaceuticals BV; WO 04/106375 A1). The component antibodies may comprise different formats such as whole IgG or Fab fragments or mixtures of both full-length immunoglobulin and fragments of antibodies. The component antibodies are selected for superior biological activities such as increased potency in neutralisation of virus, improved neutralisation and removal of cytokines and chemokines, enhanced tumour cell killing and prevention of escape and improved breath of viral protection.

Various methods are available in the art for obtaining antibodies against hCMV. The antibodies may be monoclonal antibodies, especially of human origin, which can be obtained according to the standard methods well known to the person skilled in the art. In general, for the preparation of monoclonal antibodies or their functional fragments, especially of murine origin, it is possible to refer to techniques which are described in particular in the manual 'Antibodies'(Harlow & Lane, 1988) or to the technique of preparation from hybridomas described by Kohler and Milstein, 1975.

Monoclonal antibodies can be obtained, for example, from the B cells of an animal or human immunized against hCMV, or one of its fragments, for example gB, containing the epitope recognised by said monoclonal antibodies. Suitable fragments and peptides or polypeptides which may comprise them are described herein, and may be used to immunise animals to generate antibodies against hCMV. hCMV or one of its fragments can be produced according to the usual working methods, by genetic recombination starting with a nucleic acid sequence contained in the cDNA sequence coding for hCMV or fragment thereof and/or by peptide synthesis starting from a sequence of amino acids comprised in the peptide sequence of the hCMV and/or fragment thereof.

The monoclonal antibodies can, for example, be purified on an affinity column on which hCMV protein or one of its component proteins containing the epitope recognised by said monoclonal antibodies has previously been immobilized. More particularly, the monoclonal antibodies can be purified by chromatography on protein A and/or G, followed or not followed by ion-exchange chromatography aimed at eliminating the residual protein contaminants as well as the DNA and the LPS, in itself, followed or not followed by exclusion chromatography on Sepharose gel in order to eliminate the potential aggregates due to the presence of dimers or of other multimers. Any of these techniques can be used simultaneously or successively.

This describes the part of a molecule that binds to and is complementary to all or part of the target antigen. In an antibody molecule it is referred to as the antibody antigen-binding site, and may comprise the part of the antibody that binds to and is complementary to all or part of the target antigen. Where an antigen is large, an antibody may only bind to a particular part of the antigen, which part is termed an epitope. An antibody antigen-binding site may be provided by one or more antibody variable domains. An antibody antigen-binding site may comprise an antibody light chain variable region ($V_L$) and an antibody heavy chain variable region ($V_H$).

An antigen binding site may be engineered in a region of an antibody molecule separate from the natural location of the CDRs, e.g. in a framework region of a $V_H$ or $V_L$ domain, or in an antibody constant domain e.g. but not limited to $C_H1$ and/or $C_H3$. An antigen binding site engineered in a structural region may be additional to, or instead of, an antigen binding site formed by sets of CDRs of a $V_H$ and $V_L$ domain. Where multiple antigen binding sites are present in an antibody molecule, they may bind the same antigenic domain on hCMV, for example, thereby increasing valency of the binding member and thereby increasing its avidity. Alternatively, multiple antigen binding sites may bind different antigens on hCMV and/or one or more other antigens, and this may be used to add effector functions, prolong half-life or improve in vivo delivery of the antibody molecule.

This refers to the state in which binding members of the invention, or nucleic acid encoding such binding members, will generally be in accordance with the present invention. Thus, binding members, $V_H$ and/or $V_L$ domains, and encoding nucleic acid molecules and vectors according to the present invention may be provided isolated and/or purified, e.g. from their natural environment, in substantially pure or homogeneous form, or, in the case of nucleic acid, free or substantially free of nucleic acid or genes of origin other than the sequence encoding a polypeptide with the required function. Isolated members and isolated nucleic acid will be free or substantially free of material with which they are naturally associated, such as other polypeptides or nucleic acids with which they are found in their natural environment, or the environment in which they are prepared (e.g. cell culture) when such preparation is by recombinant DNA technology practised in vitro or in vivo. Members and nucleic acid may be formulated with diluents or adjuvants and still for practical purposes be isolated—for example the members will normally be mixed with gelatin or other carriers if used to coat microtitre plates for use in immunoassays, or will be mixed with pharmaceutically acceptable carriers or diluents when used in diagnosis or therapy. Binding members may be glycosylated, either naturally or by systems of heterologous eukaryotic cells (e.g. CHO or NS0 cells), or they may be non-glycosylated, if, for example, they are produced by expression in a prokaryotic cell.

Heterogeneous preparations which may comprise anti-hCMV antibody molecules also form part of the invention. For example, such preparations may be mixtures of antibodies with full-length heavy chains and heavy chains lacking the C-terminal lysine, with various degrees of glycosylation and/or with derivatized amino acids, such as cyclisation of an N-terminal glutamic acid to form a pyroglutamic acid residue.

As used herein, the phrase 'substantially as set out' refers to the characteristic(s) of the relevant CDRs of the $V_H$ or $V_L$ domain of binding members described herein will be either identical or highly similar to the specified regions of which the sequence is set out herein. As described herein, the phrase 'highly similar' with respect to specified region(s) of one or more variable domains, it is contemplated that from 1 to about 5, e.g. from 1 to 4, including 1 to 3, or 1, 2, 3 or 4, amino acid substitutions may be made in the CDR and/or $V_H$ or $V_L$ domain.

As noted above, a binding member in accordance with the present invention modulates and may neutralise a biological activity of hCMV. A high potency binding member may be obtained directly from an initial screen e.g. a biological hCMV neutralisation assay. Assays and potencies are described in more detail elsewhere herein.

Epstein-Barr Virus (EBV) transformation is a reliable method to immortalize mammalian cells and numerous EBV transformation protocols have been developed (Rosen et al., 1977; Steinitz et al., 1977; Steinitz et al., 1980; Kozbor & Roder, 1981; Lundgren et al., 1983; Rosen et al., 1983; Steinitz et al., 1984; Lanzavecchia, 1985; Bernasconi et al., 2002; Jung et al., 2002; Traggiai et al., 2004). The technique is most often used to obtain cell lines from human lymphocytes that serve as a permanent source for DNA and protein isolation and has found widespread use in clinical trials as the principal method of generating a permanent source of patient DNA for genotyping. EBV is a Herpes virus and its genome consists of a 172 kb linear double stranded DNA which has been completely sequenced. EBV molecular biology and pathogenesis are extensively studied and the roles of many crucial EBV and host cell genes in pathogenesis are known. EBV infects only certain mammalian epithelial cells and B lymphocytes. In vitro EBV immortalizes B cells by activating a number of cell cycle regulating genes as well as B cell specific genes including immunoglobulin genes. Growing clones secreting specific antibodies can then be selected for analysis. The antibodies of interest can then be cloned and their sequence determined by conventional methods.

An antibody $V_H$ variable domain with the amino acid sequence of a said selected binding member may be provided in isolated form, as may a binding member which may comprise such a $V_H$ domain.

The ability to bind hCMV may be further tested, also the ability to compete with e.g. any antibody molecule of Ab-01 to Ab-50 of the present invention (e.g. in scFv format and/or IgG format, e.g. $IgG_1$) for binding to hCMV. Ability to neutralise hCMV may be tested, as discussed further elsewhere herein.

Binding affinity and neutralisation potency of different binding members can be compared under appropriate conditions.

Variants of the $V_H$ and $V_L$ domains and CDRs of the present invention, including those for which amino acid sequences are set out herein, and which can be employed in binding members of the invention can be obtained by means of methods of sequence alteration or mutation and screening for antigen binding members with desired characteristics. Examples of desired characteristics include but are not limited to:

Increased binding affinity for antigen relative to known antibodies which are specific for the antigen Increased neutralisation of an antigen activity relative to known antibodies which are specific for the antigen if the activity is known Specified competitive ability with a known antibody or ligand to the antigen at a specific molar ratio Ability to immunoprecipitate complex Ability to bind to a specified epitope such as a linear epitope, e.g. using peptides screened in linear and/or constrained conformation or conformational epitope, formed by non-continuous residues Ability to modulate a new biological activity of hCMV, or a downstream molecule. Such methods are also provided herein.

An antibody antigen-binding site composed of a $V_H$ domain and a $V_L$ domain is typically formed by six loops of polypeptide: three from the light chain variable domain ($V_L$) and three from the heavy chain variable domain ($V_H$). Analysis of antibodies of known atomic structure has elucidated relationships between the sequence and three-dimensional structure of antibody combining sites. These relationships imply that, except for the third region (loop) in $V_H$ domains, binding site loops have one of a small number of main-chain conformations or canonical structures. The canonical structure formed in a particular loop has been shown to be determined by its size and the presence of certain residues at key sites in both the loop and in framework regions (Chothia et al., 1992; Al-Lazikani et al., 1997).

This study of sequence-structure relationship can be used for prediction of those residues in an antibody of known sequence, but of an unknown three-dimensional structure, which are important in maintaining the three-dimensional structure of its CDR loops and hence maintain binding specificity. In a structural approach, a model can be created of the antibody molecule (Chothia et al., 1986) using any freely available or commercial package, such as WAM (Whitelegg & Rees, 2000). A protein visualisation and analysis software package, such as Insight II (Accelrys, Inc.) or Deep View (Guex & Peitsch, 1997) may then be used to evaluate possible substitutions at each position in the CDR. This information may then be used to make substitutions likely to have a minimal or beneficial effect on activity.

The techniques required to make substitutions within amino acid sequences of CDRs, antibody $V_H$ or $V_L$ domains and binding members generally are available in the art. Variant sequences may be made, with substitutions that may or may not be predicted to have a minimal or beneficial effect on activity, and tested for ability to bind and/or neutralise hCMV and/or for any other desired property.

Variable domain amino acid sequence variants of any of the $V_H$ and $V_L$ domains whose sequences are specifically disclosed herein may be employed in accordance with the present invention, as discussed.

A further aspect of the invention is an antibody molecule which may comprise a $V_H$ domain that has at least 60, 70, 80, 85, 90, 95, 98 or 99% amino acid sequence identity with a $V_H$ domain of any of antibodies Ab-01 to Ab-50 shown in the appended sequence listing, and/or which may comprise a $V_L$ domain that has at least 60, 70, 80, 85, 90, 95, 98 or 99% amino acid sequence identity with a $V_L$ domain of any of antibodies Ab-01 to Ab-50 shown in the appended sequence listing. Algorithms that can be used to calculate % identity of two amino acid sequences include e.g. BLAST (Altschul et al., 1990), FASTA (Pearson & Lipman, 1988), or the Smith-Waterman algorithm (Smith & Waterman, 1981), e.g. employing default parameters. Particular variants may include one or more amino acid sequence alterations (addition, deletion, substitution and/or insertion of an amino acid residue).

Alterations may be made in one or more framework regions and/or one or more CDRs. The alterations normally do not result in loss of function, so a binding member which may comprise a thus-altered amino acid sequence may retain an ability to bind and/or neutralise hCMV. It may retain the same quantitative binding and/or neutralising ability as a binding member in which the alteration is not made, e.g. as measured in an assay described herein. The binding member which may comprise a thus-altered amino acid sequence may have an improved ability to bind and/or neutralise hCMV infectivity.

Alteration may comprise replacing one or more amino acid residue with a non-naturally occurring or non-standard amino acid, modifying one or more amino acid residue into a non-naturally occurring or non-standard form, or inserting one or more non-naturally occurring or non-standard amino acid into the sequence. Examples of numbers and locations of alterations in sequences of the invention are described elsewhere herein. Naturally occurring amino acids include the 20 'standard' L-amino acids identified as G, A, V, L, I, M, P, F, W, S, T, N, Q, Y, C, K, R, H, D, E by their standard single-letter codes. Non-standard amino acids include any other residue that may be incorporated into a polypeptide backbone or result from modification of an existing amino acid residue. Non-standard amino acids may be naturally occurring or non-naturally occurring. Several naturally occurring non-standard amino acids are known in the art, such as 4-hydroxyproline, 5-hydroxylysine, 3-methylhistidine, N-acetylserine (Voet & Voet, 2004). Those amino acid residues that are derivatised at their N-alpha position will only be located at the N-terminus of an amino-acid sequence. Normally in the present invention an amino acid is an L-amino acid, but it may be a D-amino acid. Alteration may therefore comprise modifying an L-amino acid into, or replacing it with, a D-amino acid. Methylated, acetylated and/or phosphorylated forms of amino acids are also known, and amino acids in the present invention may be subject to such modification.

Amino acid sequences in antibody domains and binding members of the invention may comprise non-natural or non-standard amino acids described above. Non-standard amino acids (e.g. D-amino acids) may be incorporated into an amino acid sequence during synthesis, or by modification or replacement of the 'original' standard amino acids after synthesis of the amino acid sequence.

Use of non-standard and/or non-naturally occurring amino acids increases structural and functional diversity, and can thus increase the potential for achieving desired hCMV-binding and neutralising properties in a binding member of the invention. Additionally, D-amino acids and analogues have been shown to have different pharmacokinetic profiles compared with standard L-amino acids, owing to in vivo degradation of polypeptides having L-amino acids after administration to an animal e.g. a human, meaning that D-amino acids are advantageous for some in vivo applications.

Novel $V_H$ or $V_L$ regions carrying CDR-derived sequences of the invention may be generated using random mutagenesis of one or more selected $V_H$ and/or $V_L$ genes to generate mutations within the entire variable domain. Such a technique is described by Gram et al., (1992), who used error-prone PCR. In some embodiments one or two amino acid substitutions are made within an entire variable domain or set of CDRs. Another method that may be used is to direct mutagenesis to CDR regions of $V_H$ or $V_L$ genes (Barbas et al., 1994; Schier et al., 1996).

All the above-described techniques are known as such in the art and the skilled person will be able to use such techniques to provide binding members of the invention using routine methodology in the art.

A further aspect of the invention provides a method for obtaining an antibody antigen-binding site for hCMV, the method which may comprise providing by way of addition, deletion, substitution or insertion of one or more amino acids in the amino acid sequence of a $V_H$ domain set out herein a $V_H$ domain which is an amino acid sequence variant of the $V_H$ domain, optionally combining the $V_H$ domain thus provided with one or more $V_L$ domains, and testing the $V_H$ domain or $V_H/V_L$ combination or combinations to identify a binding member or an antibody antigen-binding site for hCMV and optionally with one or more desired properties, e.g. ability to neutralise hCMV activity. Said $V_L$ domain may have an amino acid sequence which is substantially as set out herein. An analogous method may be employed in which one or more sequence variants of a $V_L$ domain disclosed herein are combined with one or more $V_H$ domains. As noted above, a CDR amino acid sequence substantially as set out herein may be carried as a CDR in a human antibody variable domain or a substantial portion thereof. The HCDR3 sequences substantially as set out herein represent embodiments of the present invention and each of these may be carried as a HCDR3 in a human heavy chain variable domain or a substantial portion thereof.

Variable domains employed in the invention may be obtained or derived from any germline or rearranged human variable domain, or may be a synthetic variable domain based on consensus or actual sequences of known human variable domains. A variable domain can be derived from a non-human antibody. A CDR sequence of the invention (e.g. CDR3) may be introduced into a repertoire of variable domains lacking a CDR (e.g. CDR3), using recombinant DNA technology. For example, Marks et al., (1992) describe methods of producing repertoires of antibody variable domains in which consensus primers directed at or adjacent to the 5' end of the variable domain area are used in conjunction with consensus primers to the third framework region of human VH genes to provide a repertoire of $V_H$ variable domains lacking a CDR3. Marks et al. further describe how this repertoire may be combined with a CDR3 of a particular antibody. Using analogous techniques, the CDR3-derived sequences of the present invention may be shuffled with repertoires of $V_H$ or $V_L$ domains lacking a CDR3, and the shuffled complete $V_H$ or $V_L$ domains combined with a cognate $V_L$ or $V_H$ domain to provide binding members of the invention. The repertoire may then be displayed in a suitable host system, such as a phage display, yeast display, bacterial display, T7 display, viral display, cell display, ribosome display or covalent display system.

Similarly, one or more, or all three CDRs may be grafted into a repertoire of $V_H$ or $V_L$ domains that are then screened for a binding member or binding members for hCMV.

For example, one or more of antibody Ab-01 to Ab-50 HCDR1, HCDR2 and HCDR3 or set of HCDRs may be employed, and/or one or more of antibody Ab-01 to Ab-50 LCDR1, LCDR2 and LCDR3 or set of LCDRs may be employed. Similarly, other $V_H$ and $V_L$ domains, sets of CDRs and sets of HCDRs and/or sets of LCDRs disclosed herein may be employed.

A substantial portion of an immunoglobulin variable domain may comprise at least the three CDR regions, together with their intervening framework regions. The portion may also include at least about 50% of either or both of the first and fourth framework regions, the 50% being the C-terminal 50% of the first framework region and the N-terminal 50% of the fourth framework region. Additional residues at the N-terminal or C-terminal end of the substantial part of the variable domain may be those not normally associated with naturally occurring variable domain regions. For example, construction of binding members of the present invention made by recombinant DNA techniques may result in the introduction of N- or C-terminal residues encoded by linkers introduced to facilitate cloning or other manipulation steps.

Other manipulation steps include the introduction of linkers to join variable domains of the invention to further protein sequences including antibody constant regions, other variable domains or detectable/functional labels as discussed in more detail elsewhere herein.

Although in some aspects of the invention, binding members comprise a pair of $V_H$ and $V_L$ domains, single binding domains based on either $V_H$ or $V_L$ domain sequences form further aspects of the invention. It is known that single immunoglobulin domains, especially $V_H$ domains, are capable of binding target antigens in a specific manner. In the case of either of the single binding domains, these domains may be used to screen for complementary domains capable of forming a two-domain binding member able to bind hCMV. This may be achieved by phage display screening methods using the so-called hierarchical dual combinatorial approach as disclosed in WO92/01047 (McCafferty et al) and in Marks et al., ibid.

Binding members of the present invention may further comprise antibody constant regions or parts thereof, e.g. human antibody constant regions or parts thereof. For example, a $V_L$ domain may be attached at its C-terminal end to antibody light chain constant domains including human Cκ or Cλ chains. Similarly, a binding member based on a $V_H$ domain may be attached at its C-terminal end to all or part (e.g. a $C_H1$ domain) of an immunoglobulin heavy chain derived from any antibody isotype, e.g. IgG, IgA, IgE and IgM and any of the isotype sub-classes, particularly $IgG_1$ and $IgG_4$. $IgG_1$ is advantageous, due to its effector function and ease of manufacture. Any synthetic or other constant region variant that has these properties and stabilizes variable regions may also be useful in the present invention.

Binding members of the invention may also comprise more than a pair of $V_H$ and $V_L$ domains, such as a bispecific or multispecific antibody, which forms a further aspect of the invention. In the case of a bispecific antibody, having two pairs of $V_H$ and $V_L$ domains, one of the pairs of $V_H$ and $V_L$ domains may be from any of antibodies Ab-01 to Ab-50 as described in the present invention. The second pair of $V_H$ and $V_L$ domains may be the same as the first pair or may be different. For example, the $V_H$ and $V_L$ domain pair may be selected from any of antibodies Ab-01 to Ab-50 or from a different antibody. In a preferred embodiment, a first $V_H$ and $V_L$ domain pair is selected from any of antibodies Ab-01 to Ab-50 and the second $V_H$ and $V_L$ domain pair is also selected from antibodies Ab-01 to Ab-50, but is different to the first domain pair, such that the bispecific antibody binds to hMCV. Furthermore, a first $V_H$ and $V_L$ domain pair is selected from any of antibodies Ab-01 to Ab-50 and the second $V_H$ and $V_L$ domain pair is selected from a different antibody. The bispecific antibody may therefore bind to hCMV and to a different antigen or to a different epitope on hCMV. Preferably, the bispecific antibody may comprise a first $V_H$ and $V_L$ domain pair that binds to AD-4 or AD-5 of hCMV (i.e. a first $V_H$ and V_L domain pair from any of antibodies Ab-01 to Ab-50) and a second V_H and V_L domain pair selected from the hCMV binding antibodies described in the following: U.S. Pat. No. 5,043,281 (Mashuho et al), U.S. Pat. No. 5,750,106 (Ostberg), WO93/021952 A1 (Borrebaeck et al), WO08/084,410 A2, WO10/007,463 A1 and WO10/007,533 A2 (Lanzavecchia & Macagno), WO08/071,806 A1, WO09/003,975 A1 and WO09/024,445 A1 (Funaro et al), WO09/114,560 A2 (Olsen), WO10/114,105 A1 and WO10/114,106 A1 (Takada et al).

Mixtures of antibodies such as mixtures of recombinant human monoclonal antibodies known in the art as Oligoclonics™ (Merus Biopharmaceutical BV; WO 04/106375) may be generated for use in neutralisation of hMCV. These mixtures may comprise binding members derived from any of antibodies Ab-01 to Ab-50. The mixture of antibodies may also comprise binding members from any of antibodies Ab-01 to Ab-50 in combination with a binding member for hCMV that recognises a different antigenic domain on gB protein such as AD-1 or AD-2, or recognises gH or recognises the hCMV proteins gpUL130, gpUL131A, gp128 etc. For example, the antibody mixture may comprise a $V_L$ domain from any of antibodies Ab-01 to Ab-50 and a $V_H$ domain selected from any of antibodies Ab-01 to Ab-50 and/or a $V_H$ domain selected from any of the hCMV binding antibodies described in the following: U.S. Pat. No. 5,043,281 (Mashuho et al), U.S. Pat. No. 5,750,106 (Ostberg), WO93/021952 A1 (Borrebaeck et al), WO08/084,410 A2, WO10/007,463 A1 and WO10/007,533 A2 (Lanzavecchia & Macagno), WO08/071,806 A1, WO09/003,975 A1 and WO09/024,445 A1 (Funaro et al), WO09/114,560 A2 (Olsen), WO10/114,105 A1 and WO10/114,106 A1 (Takada et al). In the alternative, the antibody mixture may comprise a $V_L$ domain selected from any of the hCMV binding antibodies described in the following: U.S. Pat. No. 5,043,281 (Mashuho et al), U.S. Pat. No. 5,750,106 (Ostberg), WO93/021952 A1 (Borrebaeck et al), WO08/084,410 A2, WO10/007,463 A1 and WO10/007,533 A2 (Lanzavecchia & Macagno), WO08/071,806 A1, WO09/003,975 A1 and WO09/024,445 A1 (Funaro et al), WO09/114,560 A2 (Olsen), WO10/114,105 A1 and WO10/114,106 A1 (Takada et al), together with a $V_H$ domain selected from any of the hCMV binding antibodies described in the afore mentioned list and/or a $V_H$ domain selected from any of antibodies Ab-01 to Ab-50.

Binding members of the present invention may also include antibodies or fragments which may comprise a modified Fc region, wherein the modified Fc region may comprise at least one amino acid modification relative to a wild-type Fc region. The variant Fc region may be designed, relative to a comparable molecule which may comprise the wild-type Fc region, so as to bind Fc receptors with a greater or lesser affinity. Fc region refers to naturally occurring or synthetic polypeptides homologous to the IgG C-terminal domain that is produced upon papain digestion of IgG. IgG Fc has a molecular weight of approximately 50 kD. For antibodies and/or fragments of the present invention, an entire Fc region can be used, or only a half-life enhancing portion.

The Fc region can be mutated, if desired, to inhibit its ability to fix complement and bind the Fc receptor with high affinity. In the present invention, antibodies or fragments may be provided with a modified Fc region where a naturally occurring Fc region is modified to increase the half-life of the antibody or fragment in a biological environment, for example, the serum half-life or a half-life measured by an in vitro assay. Methods for altering the original form of a Fc region of an IgG also are described in U.S. Pat. No. 6,998,253 (Presta & Snedecor). Effector functions that can be altered (e.g., enhanced) by making modifications to the Fc region, either by modifying glycosylation patterns or by modifying the amino acid sequence of the Fc region, include but are not limited to: increased Fc-mediated cellular cytotoxicity including increased antibody-dependent cellular cytotoxicity and increased complement-mediated lysis (e.g., of hCMV-infected cells), increased binding of antibody to Fc receptors, natural killer (NK) cells, macrophages, monocytes, and/or polymorphonuclear cells; increased dendritic cell maturation, and increased priming of T cells. Potential modifications include insertion, deletion or substitution of one or more amino acid residues, including substitution with alanine, a conservative substitution, a non-conservative substitution, or replacement with a corresponding amino acid residue at the same position from a different IgG subclass (e.g. replacing an $IgG_1$ residue with a corresponding $IgG_2$ residue at that position).

In other embodiments, an Fc polypeptide variant of the present invention may comprise one or more engineered glycoforms i.e. a carbohydrate composition that is covalently attached to a molecule which may comprise an Fc region. The Fc region of IgG-type antibodies contains a conserved N-linked glycosylation site at residue Asn297 of the CH2 domain. It has been shown that modification of the glycosylation pattern of oligosaccharides linked to this residue can increase effector functions mediated by the Fc region in interactions with Fc receptors. Engineered glycoforms may be useful for a variety of purposes, including but not limited to enhancing or reducing effector function. Engineered glycoforms may be generated by any method known to one skilled in the art, for example by using engineered or variant expression strains, by co-expression with one or more enzymes, for example $\beta(1,4)$-N-acetylglucosaminyl transferase III, by expressing a molecule which may comprise an Fc region in various organisms or cell lines from various organisms, or by modifying carbohydrate(s) after the molecule which may comprise Fc region has been expressed.

Methods for generating engineered glycoforms are known in the art, and include but are not limited to, those described in U.S. Pat. No. 6,602,684 (Umaña et al); US20030157108 (Presta et al); Umaña et al., (1999); Davies et al., (2001); Shields et al., (2002); Shinkawa et al., (2003); and patents and applications relating to Potelligent™ technology (Biowa, Inc., Princeton, N.J., U.S.) and GlycoMAb™ glycosylation engineering technology (GLYCART Biotechnology AG, Schlieren, CH).

Thus, in a further aspect, the present invention encompasses an hCMV binding member as described elsewhere herein, wherein said binding member may comprise an Fc region or an equivalent region that may comprise at least an IgG CH2 region, that has been modified to increase one or more effector functions. In one embodiment, the binding member is modified to alter the glycosylation pattern of the N-linked oligosaccharides at Asn 297 such that the activity of one or more effector functions is increased. In another embodiment, the binding member is modified to alter the amino acid sequence of the Fc region such that the activity of one or more effector functions is increased. Methods of measuring effector function activity and determining whether or not they are increased are well known in the art.

Binding members of the invention may be labelled with a detectable or functional label. Thus, a binding member or antibody molecule can be present in the form of an immunoconjugate so as to obtain a detectable and/or quantifiable signal. An immunoconjugate may comprise an antibody molecule of the invention, for example any of antibodies Ab-01 to Ab-50, conjugated with detectable or functional label. A label can be any molecule that produces or can be induced to produce a signal, including but not limited to fluorochromes, radiolabels, enzymes, chemiluminescers or photosensitizers. Thus, binding may be detected and/or measured by detecting fluorescence or luminescence, radioactivity, enzyme activity or light absorbance.

Suitable labels include, by way of illustration and not limitation, enzymes, such as alkaline phosphatase, glucose-6-phosphate dehydrogenase ('G6PDH'), alpha-D-galactosidase, glucose oxydase, glucose amylase, carbonic anhydrase, acetylcholinesterase, lysozyme, malate dehydrogenase and peroxidises, e.g. horseradish peroxidase; dyes; fluorescent labels or fluorochromes, such as fluorescein and its derivatives, rhodamine compounds and derivatives, green/yellow fluorescent protein (G/YFP), red fluorescent protein (RFP), blue fluorescent protein (BFP), dansyl, umbelliferone, phycoerythrin, phycocyanin, allophycocyanin, o-phthaldehyde, and fluorescamine; fluorophores such as lanthanide cryptates and chelates e.g. Europium etc (Perkin Elmer and Cis Biointernational), chemoluminescent labels or chemiluminescers, such as isoluminol, luminol and the dioxetanes; bio-luminescent labels, such as luciferase and luciferin; sensitizers; coenzymes; enzyme substrates; radiolabels including but not limited to bromine-77, carbon14, cobalt57, fluorine8, gallium67, gallium 68, hydrogen3 (tritium), indium111, indium113m, iodine123m, iodine125, iodine126, iodine131, iodine133, mercury107, mercury203, phosphorous32, rhenium99m, rhenium101, rhenium105, ruthenium95, ruthenium97, ruthenium103, ruthenium105, scandium47, selenium75, sulphur35, technetium99, technetium99m, tellurium121m, tellurium122m, tellurium125m, thulium165, thulium167, thulium168, yttrium199 and other radiolabels mentioned herein; particles, such as latex or carbon particles; metal sol; crystallite; liposomes; cells, etc., which may be further labelled with a dye, catalyst or other detectable group; molecules such as biotin, digoxygenin or 5-bromodeoxyuridine; toxin moieties, such as for example a toxin moiety selected from a group of *Pseudomonas* exotoxin (PE or a cytotoxic fragment or mutant thereof), Diptheria toxin or a cytotoxic fragment or mutant thereof, a botulinum toxin A, B, C, D, E or F, ricin or a cytotoxic fragment thereof e.g. ricin A, abrin or a cytotoxic fragment thereof, saporin or a cytotoxic fragment thereof, pokeweed antiviral toxin or a cytotoxic fragment thereof and bryodin 1 or a cytotoxic fragment thereof.

Suitable enzymes and coenzymes are disclosed in U.S. Pat. No. 4,275,149 (Litman et al) and U.S. Pat. No. 4,318,980 (Boguslaski et al) and suitable fluorescers and chemiluminescers are disclosed in U.S. Pat. No. 4,275,149, which are incorporated herein by reference in their entirety. Labels further include chemical moieties, such as biotin that may be detected via binding to a specific cognate detectable moiety, e.g. labelled avidin or streptavidin, or genetically engineered streptavidin, like streptactin (IBA GmbH, Göttingen, DE). Detectable labels may be attached to antibodies of the invention using conventional chemistry known in the art.

Immunoconjugates or their functional fragments can be prepared by methods known to the person skilled in the art. They can be coupled to enzymes or to fluorescent labels directly or by the intermediary of a spacer group or of a linking group, such as a polyaldehyde, like glutaraldehyde, ethylenediaminetetraacetic acid (EDTA), diethylene-triaminepentaacetic acid (DPTA), or in the presence of coupling agents, such as those mentioned above for the therapeutic conjugates. Conjugates containing labels of fluorescein type can be prepared by reaction with an isothiocyanate.

The methods known to the person skilled in the art existing for coupling the therapeutic radioisotopes to the antibodies either directly or via a chelating agent, such as EDTA, DTPA, mentioned above, can be used for the radio-elements which can be used in diagnosis. It is likewise possible to perform labelling with sodium125 by the chloramine T method (Hunter & Greenwood, 1962) or else with technetium-99m (Tc-99m) by the technique described in U.S. Pat. No. 4,424,200 (Crockford & Rhodes) or attached via DTPA as described in U.S. Pat. No. 4,479,930 (Hnatowich), both of which are herein incorporated by reference in their entirety.

There are numerous methods by which the label can produce a signal detectable by external means, for example, by visual examination, electromagnetic radiation, heat and chemical reagents. The label can also be bound to another binding member that binds the binding member of the invention, or to a support.

The label can directly produce a signal, and therefore, additional components are not required to produce a signal. Numerous organic molecules, for example fluorescers, are able to absorb ultraviolet and visible light, where the light absorption transfers energy to these molecules and elevates them to an excited energy state. This absorbed energy is then dissipated by emission of light at a second wavelength. This second wavelength emission may also transfer energy to a labelled acceptor molecule, and the resultant energy dissipated from the acceptor molecule by emission of light for example fluorescence resonance energy transfer (FRET). Other labels that directly produce a signal include radioactive isotopes and dyes.

Alternately, the label may need other components to produce a signal, and the signal producing system would then include all the components required to produce a measurable signal, which may include substrates, coenzymes, enhancers, additional enzymes, substances that react with enzymatic products, catalysts, activators, co-factors, inhibitors, scavengers, metal ions, and a specific binding substance required for binding of signal generating substances. A detailed discussion of suitable signal producing systems can be found in U.S. Pat. No. 5,185,243 (Ullman et al). The present invention provides a method which may comprise causing or allowing binding of a binding member as provided herein specific for hCMV. As noted, such binding may take place in vivo, e.g. following administration of a binding member, or nucleic acid encoding a binding member, or it may take place in vitro, for example in ELISA, Western blotting, affinity chromatography, immunocytochemistry, immunoprecipitation, neutralisation and biochemical or cell-based assays.

The present invention also provides methods for measuring levels of antigen directly, by employing a binding member according to the invention, e.g. in a biosensor system. For instance, the present invention may comprise a method of detecting and/or measuring binding to hCMV, which may comprise, (i) exposing said binding member to hCMV and (ii) detecting binding of said binding member to hCMV, wherein binding is detected using any method or detectable label described herein. This, and any other binding detection method described herein, may be interpreted directly by the person performing the method, for instance, by visually observing a detectable label. Alternatively, this method, or any other binding detection method described herein, may produce a report in the form of an autoradiograph, a photograph, a computer printout, a flow cytometry report, a graph, a chart, a test tube or container or well containing the result, or any other visual or physical representation of a result of the method.

The amount of binding of a binding member to hCMV may be determined. Quantitation may be related to the amount of the antigen in a test sample, which may be of diagnostic interest. Screening for hCMV binding and/or the quantitation thereof may be useful, for instance, in screening patients for diseases or disorders referred to herein and/or any other disease or disorder involving aberrant hCMV expression and/or activity.

A diagnostic method of the invention may comprise (i) obtaining a tissue or fluid sample from a subject, (ii) exposing said tissue or fluid sample to one or more binding members of the present invention; and (iii) detecting bound hCMV as compared with a control sample, wherein an increase in the amount of hCMV binding as compared with the control may indicate hCMV expression and/or activity. Tissue or fluid samples to be tested include blood, serum, saliva, urine, sputum, a biopsy material or any tissue suspected of containing hCMV. Subjects testing positive for hCMV may also benefit from the treatment methods disclosed later herein. Those skilled in the art are able to choose a suitable mode of determining binding of the binding member to an antigen according to their preference and general knowledge, in light of the methods disclosed herein.

The reactivities of binding members in a sample may be determined by any appropriate means. A competitive binding assay may be used with radioactive antigen, for example an isotope label such as $^{99}$Tc, $^{14}$C, $^{131}$I, $^{125}$I, $^{3}$H, $^{32}$P or $^{35}$S, or nonradioactive antigen using antigen or an analogue linked to a reporter molecule. The reporter molecule may be a fluorochrome, phosphor or laser dye with spectrally isolated absorption or emission characteristics. Suitable fluorochromes include fluorescein, rhodamine, phycoerythrin and Texas Red, and lanthanide chelates or cryptates. Suitable chromogenic dyes include diaminobenzidine.

Other reporters include macromolecular colloidal particles or particulate material, such as latex beads that are coloured, magnetic or paramagnetic, and biologically or chemically active agents that can directly or indirectly cause detectable signals to be visually observed, electronically detected or otherwise recorded. These molecules may be enzymes, which catalyze reactions that develop, or change colours or cause changes in electrical properties, for example. They may be molecularly excitable, such that electronic transitions between energy states result in characteristic spectral absorptions or emissions. They may include chemical entities used in conjunction with biosensors. Biotin/avidin or biotin/streptavidin and alkaline phosphatase or horseradish peroxidase detection systems may be employed.

The signals generated by individual binding member-reporter conjugates may be used to derive quantifiable absolute or relative data of the relevant binding member binding in samples (normal and test).

A kit which may comprise a binding member according to any aspect or embodiment of the present invention is also provided. In the kit, the binding member may be labelled to allow its reactivity in a sample to be determined, e.g. as described further below. Further the binding member may or may not be attached to a solid support. Components of a kit are generally sterile and in sealed vials or other containers. Kits may be employed in diagnostic analyses or other methods for which binding members are useful. A kit may contain instructions for use of the components in a method, e.g. a method in accordance with the present invention. Ancillary materials to assist in or to enable performing such a method may be included within a kit of the invention. The ancillary materials include a second, different binding member, which binds to the first binding member and is conjugated to a detectable label (e.g., a fluorescent label, radioactive isotope or enzyme). Antibody-based kits may also comprise beads for conducting immunoprecipitation. Each component of the kits is generally in its own suitable container. Thus, these kits generally comprise distinct containers suitable for each binding member. Further, the kits may comprise instructions for performing the assay and methods for interpreting and analysing the data resulting from the performance of the assay.

The present invention also provides the use of a binding member as above for measuring antigen levels in a competition assay, that is to say a method of measuring the level of antigen in a sample by employing a binding member as provided by the present invention in a competition assay. This may be where the physical separation of bound from unbound antigen is not required. Linking a reporter molecule to the binding member so that a physical or optical change occurs on binding is one possibility. The reporter molecule may directly or indirectly generate detectable signals, which may be quantifiable. The linkage of reporter molecules may be directly or indirectly, covalently, e.g. via a peptide bond or non-covalently. Linkage via a peptide bond may be as a result of recombinant expression of a gene fusion encoding antibody and reporter molecule.

In various aspects and embodiments, the present invention extends to a binding member that competes for binding to hCMV with any binding member defined herein, e.g. any of antibodies Ab-01 to Ab-50, e.g. in IgG format. Competition between binding members may be assayed in vitro, for example by tagging a specific reporter molecule to one binding member which can be detected in the presence of other untagged binding member(s), to enable identification of binding members which bind the same epitope or an overlapping epitope. Competition may be determined for example using ELISA or by surface plasmon resonance, in which hCMV is immobilised to a solid phase and a first tagged or labelled binding member along with one or more other untagged or unlabelled binding members is added to the solid phase. Presence of an untagged binding member that competes with the tagged binding member is observed by a decrease in the signal emitted by the tagged binding member.

For example, the present invention includes a method of identifying a hCMV binding compound, which may comprise (i) immobilising gB protein to a support, (ii) contacting said immobilized gB simultaneously or in a step-wise manner with at least one tagged or labelled binding member according to the invention and one or more untagged or unlabelled test binding compounds, and (iii) identifying a new hCMV binding compound by observing a decrease in the amount of bound tag from the tagged binding member. Such methods can be performed in a high-throughput manner using a multiwell or array format. Such assays may be also be performed in solution. See, for instance, U.S. Pat. No. 5,814,468 (Sliman et al), which is herein incorporated by reference in its entirety. As described above, detection of binding may be interpreted directly by the person performing the method, for instance, by visually observing a detectable label, or a decrease in the presence thereof. Alternatively, the binding methods of the invention may produce a report in the form of an autoradiograph, a photograph, a computer printout, a flow cytometry report or any other visual or physical representation of a result of the method.

Competition assays can also be used in epitope characterisation. In one instance epitope characterisation may be used to identify the epitope bound by a hCMV binding member which optionally may have optimized neutralising and/or modulating characteristics. Such an epitope can be linear or conformational. A conformational epitope can comprise at least two different domains of hCMV, wherein said domains are positioned in proximity to each other when hCMV proteins are folded in its tertiary or quaternary structure to form a conformational epitope which is recognised by an inhibitor of hCMV, such as an hCMV-binding member provided in this specification. In testing for competition a peptide fragment of the antigen may be employed, especially a peptide including or consisting of an epitope of interest. A peptide having the epitope sequence plus one or more amino acids at either end may be used. Binding members according to the present invention may be such that their binding for antigen is inhibited by a peptide with or including the sequence given.

The present invention further provides an isolated nucleic acid encoding a binding member of the present invention. Nucleic acid may include DNA and/or RNA. In one, the present invention provides a nucleic acid that codes for a CDR or set of CDRs or $V_H$ domain or $V_L$ domain or antibody antigen-binding site or antibody molecule, e.g. scFv or $IgG_1$, of the invention as defined above.

The present invention also provides constructs in the form of plasmids, vectors, transcription or expression cassettes which comprise at least one polynucleotide as above.

The present invention also provides a recombinant host cell that may comprise one or more constructs as above. A nucleic acid encoding any CDR or set of CDRs or $V_H$ domain or $V_L$ domain or antibody antigen-binding site or antibody molecule, e.g. scFv or $IgG_1$ as provided, itself forms an aspect of the present invention, as does a method of production of the encoded product, which method may comprise expression from encoding nucleic acid. Expression may conveniently be achieved by culturing said recombinant host cell containing the nucleic acid under appropriate conditions. Following production by expression a binding member which may comprise $V_H$ or $V_L$ domain as disclosed herein, the binding member may be isolated and/or purified using any suitable technique known in the art and deemed as appropriate.

Nucleic acid according to the present invention may comprise DNA or RNA and may be wholly or partially synthetic. Reference to a nucleotide sequence as set out herein encompasses a DNA molecule with the specified sequence, and encompasses a RNA molecule with the specified sequence in which U is substituted for T, unless context requires otherwise.

A yet further aspect provides a method of production of a binding member which may comprise $V_H$ and/or $V_L$ variable domain of the present invention, the method including causing expression from encoding nucleic acid. Such a method may comprise culturing recombinant host cells under conditions for production of said antibody $V_H$ and/or $V_L$ variable domain.

A method of production may comprise a step of isolation and/or purification of the product. A method of production may comprise formulating the product into a composition including at least one additional component, such as a pharmaceutically active excipient.

Systems for cloning and expression of a polypeptide in a variety of different host cells are well known. Suitable host cells include bacteria, mammalian cells, plant cells, filamentous fungi, yeast and insect cells and transgenic plants and animals. The expression of antibodies and antibody fragments in prokaryotic cells is well established in the art. For a review, see for example Pluckthun (1991). A common bacterial host is *E. coli*.

Expression in eukaryotic cells in culture is also available to those skilled in the art as an option for production of a binding member (Chadd & Chamow, 2001; Andersen & Krummen, 2002; Larrick & Thomas, 2001). Mammalian cell lines available in the art for expression of a heterologous polypeptide include Chinese hamster ovary (CHO) cells, HeLa cells, baby hamster kidney (BHK) cells, NS0 mouse melanoma cells, YB2/0 rat myeloma cells, human embryonic kidney (HEK) cells, human embryonic retina cells and many others.

Suitable vectors can be chosen or constructed, containing appropriate regulatory sequences, including promoter sequences, terminator sequences, polyadenylation sequences, enhancer sequences, marker genes and other sequences as appropriate. Vectors may be plasmids, phagemids, or viral vectors, e.g. retroviral vectors, as appropriate (Sambrook & Russell, 2001). Many known techniques and protocols for manipulation of nucleic acid, for example in preparation of nucleic acid constructs, mutagenesis, sequencing, introduction of DNA into cells and gene expression, as well as analysis of proteins, are described in detail in Ausubel et al., (1999).

A further aspect of the present invention provides a host cell containing nucleic acid as disclosed herein. Such a host cell may be maintained in vitro and may be propagated in tissue culture. Such a host cell may also be maintained in vivo, e.g. in order to produce binding members in ascites. In vivo presence of the host cell may allow intra-cellular expression of the binding members of the present invention as 'intrabodies' or intra-cellular antibodies. Intrabodies may be used for gene therapy.

A still further aspect provides a method which may comprise introducing nucleic acid of the invention into a host cell. The introduction may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus, or any combination thereof. Introducing nucleic acid in the host cell, in particular a eukaryotic cell may use a viral or a plasmid based system. The plasmid system may be maintained episomally or may be incorporated into the host cell genome or into an artificial chromosome. Incorporation may be either by random or targeted integration of one or more copies at single or multiple loci. For bacterial cells, suitable techniques may include calcium chloride transformation, electroporation and transfection using bacteriophage.

The introduction may be followed by causing or allowing expression from the nucleic acid, e.g. by culturing host cells under conditions for expression of the binding member. The purification of the expressed product may be achieved by methods known to one of skill in the art.

Nucleic acid of the invention may be integrated into the genome (e.g. chromosome) of the host cell. Integration may be promoted by inclusion of sequences that promote recombination with the genome, in accordance with standard techniques.

The present invention also provides a method that may comprise using a construct as stated above in an expression system in order to express a binding member or polypeptide as above.

There is evidence for involvement of hCMV infection in a variety of disorders, as discussed elsewhere herein. The binding members of the present invention may therefore be used in a method of diagnosis or treatment of a disorder associated with hCMV infection. Such a disorder may affect immunocompromised patients such as allograft recipients and HIV infected individuals, and may include for example: fever, hepatitis, retinitis, pneumonitis, myelosuppression, encephalopathy, polyradiculopathy, immunosuppression, rejection/graft-versus-host disease or atherosclerosis. A binding member of the present invention may also be used to treat intra-uterine infection in neonates. Frequently, neonates are born without signs or symptoms of the disorders listed above, but without treatment may develop progressive symptoms of CNS dysfunction and impairment, e.g. but not limited to hearing loss, loss of vision, and/or mental retardation.

Accordingly, the invention provides a method of treating an hCMV infection related disorder, which may comprise administering to a patient in need thereof an effective amount of one or more binding members of the present invention alone or in a combined therapeutic regimen with another appropriate medicament known in the art or described herein.

Evidence for involvement of hCMV infection in certain disorders is summarised elsewhere herein. In addition, the data presented herein further indicates that binding members of the invention can be used to treat such disorders, including preventative treatment and reduction of severity of the disorders. Accordingly, the invention provides a method of treating or reducing the severity of at least one symptom of any of the disorders mentioned herein, which may comprise administering to a patient in need thereof an effective amount of one or more binding members of the present invention alone or in a combined therapeutic regimen with another appropriate medicament known in the art or described herein such that the severity of at least one symptom of any of the above disorders is reduced.

Thus, the binding members of the present invention are useful as therapeutic agents in the treatment of diseases or disorders involving hCMV infection and/or activity, especially resulting from high viral load in a patient. A method of treatment may comprise administering an effective amount of a binding member of the invention to a patient in need thereof, wherein aberrant infection and/or activity of hCMV is decreased. A method of treatment may comprise (i) identifying a patient demonstrating hCMV infection levels or activity, for instance using the diagnostic methods described above, and (ii) administering an effective amount of a binding member of the invention to the patient, wherein expression and/or activity of hCMV is decreased. An effective amount according to the invention is an amount that decreases the expression and/or activity of hCMV so as to decrease or lessen the severity of at least one symptom of the hCMV infection or particular disease or disorder being treated, but not necessarily cure the disease or disorder.

The invention also provides a method of antagonising at least one effect of hCMV infection, which may comprise contacting with or administering an effective amount of one or more binding members of the present invention such that said at least one effect of hCMV infection is antagonised. Accordingly, further aspects of the invention provide methods of treatment which may comprise administration of a binding member as provided, pharmaceutical compositions which may comprise such a binding member, and use of such a binding member in the manufacture of a medicament for administration, for example in a method of making a medicament or pharmaceutical composition which may comprise formulating the binding member with a pharmaceutically active excipient. A pharmaceutically active excipient may be a compound or a combination of compounds entering into a pharmaceutical composition not provoking secondary reactions and which allows, for example, facilitation of the administration of the active compound(s), an increase in its lifespan and/or in its efficacy in the body, an increase in its solubility in solution or else an improvement in its conservation. These pharmaceutically acceptable vehicles are well known and will be adapted by the person skilled in the art as a function of the nature and of the mode of administration of the active compound(s) chosen.

Binding members of the present invention will usually be administered in the form of a pharmaceutical composition, which may comprise at least one component in addition to the binding member. Thus, pharmaceutical compositions according to the present invention, and for use in accordance with the present invention, may comprise, in addition to active ingredient, a pharmaceutically active excipient, carrier, buffer, stabilizer or other materials well known to those skilled in the art. Such materials should be non-toxic and should not interfere with the efficacy of the active ingredient. The precise nature of the carrier or other material will depend on the route of administration, which may be oral, inhaled, intra-tracheal, topical, intra-vesicular or by injection, as discussed below.

Pharmaceutical compositions for oral administration may be in tablet, capsule, powder, liquid or semisolid form. A tablet may comprise a solid carrier, such as gelatin or an adjuvant. Liquid pharmaceutical compositions generally comprise a liquid carrier, such as water, petroleum, animal or vegetable oils, mineral oil or synthetic oil. Physiological saline solution, dextrose or other saccharide solution or glycols, such as ethylene glycol, propylene glycol or polyethylene glycol may be included.

For intra-venous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles, such as Sodium Chloride Injection, Ringer's Injection, Lactated Ringer's Injection.

Preservatives, stabilizers, buffers, antioxidants and/or other additives may be employed as required including buffers such as phosphate, citrate and other organic acids; antioxidants, such as ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens, such as methyl or propyl paraben; catechol; resorcinol; cyclohexanol; 3'-pentanol; and m-cresol); low molecular weight polypeptides; proteins, such as serum albumin, gelatin or immunoglobulins; hydrophilic polymers, such as polyvinylpyrrolidone; amino acids, such as glycine, glutamine, asparagines, histidine, arginine, or lysine; monosaccharides, disaccharides and other carbohydrates including glucose, mannose or dextrins; chelating agents, such as EDTA; sugars, such as sucrose, mannitol, trehalose or sorbitol; salt-forming counter-ions, such as sodium; metal complexes (e.g. Zn-protein complexes); and/or non-ionic surfactants, such as TWEEN™, PLURONICS™ or polyethylene glycol (PEG).

Binding members of the present invention may be formulated in liquid, semi-solid or solid forms depending on the physicochemical properties of the molecule and the route of delivery. Formulations may include excipients or combinations of excipients, for example: sugars, amino acids and surfactants. Liquid formulations may include a wide range of antibody concentrations and pH. Solid formulations may be produced by lyophilisation, spray drying, or drying by supercritical fluid technology, for example. Formulations of binding members will depend upon the intended route of delivery. A binding member may be prepared with a carrier that will protect the binding member against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are known to those skilled in the art (Robinson, 1978).

Treatment may be given orally, or by injection (i.e. subcutaneously, intra-articular, intra-venously, intra-peritoneal, intra-arterial or intra-muscularly), by inhalation, intra-tracheal, by the intra-vesicular route (instillation into the urinary bladder), or topically (for example intra-ocular, intra-nasal, rectal, into wounds, on skin). The treatment may be administered by pulse infusion, particularly with declining doses of the binding member. The route of administration can be determined by the physicochemical characteristics of the treatment, by special considerations for the disease or by the requirement to optimize efficacy or to minimize side-effects. One particular route of administration is intra-venous. Another route of administering pharmaceutical compositions of the present invention is subcutaneously. It is envisaged that treatment will not be restricted to use in the clinic. Therefore, subcutaneous injection using a needle-free device is also advantageous.

A composition may be administered alone or in combination with other treatments, either simultaneously or sequentially dependent upon the condition to be treated.

A binding member of the invention may be used as part of a combination therapy in conjunction with an additional medicinal component. Combination treatments may be used to provide significant synergistic effects, particularly the combination of a binding member of the invention with one or more other antibodies such as antibodies Ab-01 to Ab-50 as disclosed herein or any of the hCMV antibodies described in the following publications: U.S. Pat. No. 5,043,281 (Mashuho et al), U.S. Pat. No. 5,750,106 (Ostberg), WO93/021952 A1 (Borrebaeck et al), WO08/084,410 A2, WO10/007,463 A1 and WO10/007,533 A2 (Lanzavecchia & Macagno), WO08/071,806 A1, WO09/003,975 A1 and WO09/024,445 A1 (Funaro et al), WO09/114,560 A2 (Olsen), WO10/114,105 A1 and WO10/114,106 A1 (Takada et al) or any other drug. A binding member of the invention may be administered concurrently or sequentially or as a combined preparation with another therapeutic agent or agents, for the treatment of one or more of the conditions listed herein.

A binding member of the invention may be used as a chemosensitiser, whereby it can increase therapeutic efficacy of anti-viral agents, and may thus be provided for administration in combination with one or more anti-viral agents, either simultaneously or sequentially.

A binding member according to the present invention may be provided in combination or addition with one or more of the following antiviral agents, e.g. acyclovir, famciclovir, valganciclovir, ganciclovir, cidofovir, amantadine, rimantadine, ribavirin, zanamavir and/or oseltamavir.

A binding member of the invention and one or more of the above additional medicinal components may be used in the manufacture of a medicament. The medicament may be for separate or combined administration to an individual, and accordingly may comprise the binding member and the additional component as a combined preparation or as separate preparations. Separate preparations may be used to facilitate separate and sequential or simultaneous administration, and allow administration of the components by different routes e.g. oral and parenteral administration.

In accordance with the present invention, compositions provided may be administered to mammals. Administration is normally in a 'therapeutically effective amount', this being sufficient to show benefit to a patient. Such benefit may be at least amelioration of at least one symptom. The actual amount administered, and rate and time-course of administration, will depend on the nature and severity of what is being treated, the particular mammal being treated, the clinical condition of the individual patient, the cause of the disorder, the site of delivery of the composition, the type of binding member, the method of administration, the scheduling of administration and other factors known to medical practitioners. Prescription of treatment, e.g. decisions on dosage etc, is within the responsibility of general practitioners and other medical doctors and may depend on the severity of the symptoms and/or progression of a disease being treated. Appropriate doses of antibody are well known in the art (Ledermann et al., 1991; Bagshawe et al., 1991). Specific dosages indicated herein or in the Physician's Desk Reference (2009) as appropriate for the type of medicament being administered may be used. A therapeutically effective amount or suitable dose of a binding member of the invention can be determined by comparing its in vitro activity and in vivo activity in an animal model. Methods for extrapolation of effective dosages in mice and other test animals to humans are known. The precise dose will depend upon a number of factors, including whether the antibody is for diagnosis, prevention or for treatment, the size and location of the area to be treated, the precise nature of the antibody (e.g. whole antibody or fragment) and the nature of any detectable label or other molecule attached to the antibody. A typical antibody dose will be in the range 100 μg to 1 g for systemic applications, and 1 μg to 1 mg for topical applications. An initial higher loading dose, followed by one or more lower doses, may be administered. Typically, the antibody will be a whole antibody, e.g. the $IgG_1$ isotype. This is a dose for a single treatment of an adult patient, which may be proportionally adjusted for children, infants and neonates, and also adjusted for other antibody formats in proportion to molecular weight. Treatments may be repeated at daily, twice-weekly, weekly or monthly intervals, at the discretion of the physician. Treatments may be every two to four weeks for subcutaneous administration and every four to eight weeks for intra-venous administration. Treatment may be periodic, and the period between administrations is about two weeks or more, e.g. about three weeks or more, about four weeks or more, or about once a month. Treatment may be given before, and/or after transplantation surgery, and/or may be administered or applied directly at the anatomical site of surgical treatment.

hCMV binding members of the invention may offer advantages in terms of dosage and administration requirements, compared with antibodies to hCMV disclosed previously in the art, as discussed above. For example, if the dose of an anti-hCMV therapeutic is lower there may be significant advantages in that the low dose facilitates sub-cutaneous injections as well as intra-venous injections. It is well known to those skilled in the art that sub-cutaneous dosing may be limited by the amount of binding member, e.g. antibody molecule, required per dose. This is due to the sub-cutaneous injections being limited by the volume that can be injected at one site in the skin. Sub-cutaneous injection volumes of 1.2 ml or less are typically utilised. As it may be increasingly difficult to formulate a binding member for sub-cutaneous injection at concentrations greater than 50 mg/ml, doses above 100 mg via this route usually require multiple injections and more discomfort for the patient. Thus, a lower dose of e.g., a more potent hCMV binding member, is advantageous because it expands the routes of administration.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1

Figure 2:
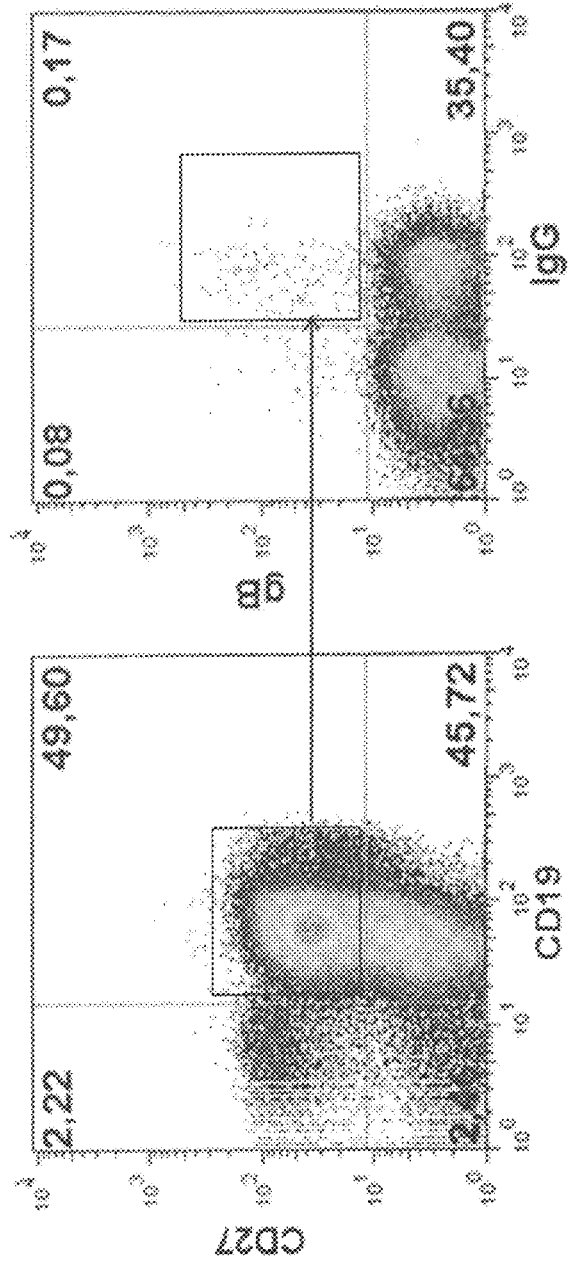
FIG. 2. This figure shows gB-specific memory B cell enrichment by preparative fluorescent activated cell sorting (FACS). In order to isolate gB-specific, IgG-positive memory B cells, anti-CD20 MACS-enriched (MACS=magnetic activated cell sorting) B cells were stained with the following antibodies: a. Anti-human CD19 (B cell marker); b. Anti-human CD27 (memory B cell marker); c. Anti-human IgG. Additionally, B cells were incubated with a recombinant glycoprotein B labelled with a fluorescent dye. CD19+/CD27+/IgG+/gB+ reactive B cells were sorted onto irradiated feeder cells and antibody-producing cell lines were established as described in Example 1.

FACS Sorting of hCMV Specific Memory B Cells and EBV Transformation of IgG-positive Memory B Cells After informed donor consent was obtained, peripheral blood (300 ml) was collected from healthy hCMV-seropositive blood donors, whose serum had been pre-screened for high gB-binding titers and efficient hCMV neutralising activity. Peripheral blood mononuclear cells (PBMCs) were purified by Ficoll-density gradient centrifugation (Lymphoflot, Biotest, Dreieich, Germany). After B cell enrichment using anti-human CD22-microbeads (Mitenyi Biotec, Bergisch Gladbach, Germany), B cells were labelled with the following reagents: a. Anti-human CD19-FITC (Miltenyi Biotec, Germany); b. Anti-human CD27-PE (BD Bioscience Pharmigen, Basel, Switzerland); c. anti-human IgG-bio (Jackson Immuno-Research, West Grove, Pa., USA); d. streptavidin, ALEXA FLUOR® 350 conjugate (streptavidin covalently attached to a fluorescent label, Molecular Probes Inc, Eugene, Oreg., USA) and e. Cy5-labeled glycoprotein B (100 ng per $1 \times 10^6$ B cells). gB-specific, IgG-positive memory B cells were isolated by sorting cells that fulfilled the following four criteria: FITC+/PE+/ALEXA FLUOR® (streptavidin covalently attached to a fluorescent label) 350+ and Cy5+ (see FIG. 2). Alternatively, B cells were labeled with the following reagents: a. Anti-human CD19-PerCP (Dianova, Hamburg, Germany); b. Anti-human CD27-PE (BD Bioscience Pharmigen, Basel, Switzerland); c. anti-human IgG-FITC (Dianova, Hamburg, Germany); d. Cy5-labeled glycoprotein B (100 ng per $1 \times 10^6$ B cells). These gB-specific, IgG-positive memory B cells were either analyzed using FACSCALIBUR® (flow cytometer, Becton Dickinson, Heidelberg, Germany) or isolated by sorting cells that fulfilled the criteria PerCP+/PE+/FITC+ and Cy5+.

Cells were sorted at a concentration of 5 or 10 cells/well, in 96-well flat-bottom microplates containing a confluent layer of irradiated feeder cells (human foreskin fibroblasts, HFFs), using a MoFlo™ cell sorter (Cytomation, Freiburg, Germany). Sorted cells were grown in complete RPMI-1640 medium supplemented with 2 mM glutamine, 100 IU/ml penicillin, 100 μg/ml streptomycin, 50 μM 2-mercaptoethanol and 10% fetal calf serum (heat-inactivated) (PAN-Biotech, Aidenbach, Germany) in the presence of EBV containing cell culture supernatant (30% supernatant of EBV producing cell line B95-8) and CpG ODN 2006 (2.5 μg/ml) as previously described (Rosen et al., 1977; Steinitz et al., 1977; Bernasconi et al., 2002; Jung et al., 2002; Traggiai et al., 2004). After three weeks, culture supernatants from the generated cell lines were screened for gB-specificity using enzyme-linked immunosorbent assay (ELISA). In brief, ELISA plates (Nunc) were coated with 0.5 μg/ml glycoprotein B in carbonate buffer, pH 9.6, for 16 h at 4° C. The gB-coated plates were washed six times with phosphate buffered saline (PBS) supplemented with 0.05% Tween (ELISA washing buffer) and blocked for 2 h with PBS supplemented with 0.05% Tween and 2% fetal calf serum (ELISA buffer). 50 μl of culture supernatant per well was incubated for 1 h at room temperature and, after another washing step, the antibody bound was revealed using Fcγ fragment-specific secondary antibodies coupled with peroxidase (Jackson ImmunoResearch, USA). After a 1 h incubation period unbound secondary antibody was removed by washing and the enzymatic activity was determined using 50 μl/well o-phenyl- diamine at a concentration of 0.04 mg/ml in 0.05M phosphate-citrate buffer (pH 5.0), 0.05% $H_2O_2$. After incubation for 10 min at room temperature, the reaction was stopped by addition of 50 μl/well 2M $H_2SO_4$ and the optical density (OD) was measured at 492 nm with a SPECTRAmax™ 190 ELISA photometer (Molecular Devices, Sunnyvale, Calif., USA). Software Softmax Pro 3.0 (Molecular Devices, USA) was used for analysis.

Example 2

In vitro hCMV Neutralisation Assay

The gB-specific culture supernatants were screened for neutralising activity using the hCMV recombinant strain AD169 (HB15-UL84prluc) containing a luciferase reporter gene expression cassette in the hCMV genome, and which results in the expression of luciferase enzyme upon infection of target cells (kindly provided by Prof. Dr. Thomas Stamminger, Institute of Clinical and Molecular Virology, University Hospital Erlangen, Germany). The infectious titer in viral supernatants was determined by TCID50 assays in primary fibroblast cells (either HFF or MRC-5 cells) on 96-well plates as described in Mahy & Kangro (1996). For the luciferase-based neutralisation assay, an equal volume of gB-specific culture supernatant and titered AD169ΔLuc supernatant (300 pfu) were incubated at 37° C. for 1 h in 96 U-bottom microplates. The antibody-virus mixtures were transferred onto previously seeded HFF monolayers. After an additional incubation at 37° C. for 4 h, the antibody-virus mixtures were replaced by complete medium. Following another 42 h incubation at 37° C., the cells were lysed with 100 μl Glo Lysis Buffer (Promega, Madison, Wis.) per well. 30 μl of each lysed well was placed into white 96-well LIA plates (Greiner Bioone, Frickenhausen, Germany). Per well, 50 μL assay buffer (15 mM $KH_2PO_4$, 25 mM glycylglycine, 1M $MgSO_4$, 0.5M EGTA, 5 mM ATP, 1 mM DTT) was added. Injection of 50 μL D-luciferin (P. J. K., Kleinbittersdorf, Germany) solution per well (in 25 mM glycylglycine, 1M $MgSO_4$, 0.5M EGTA, 2 mM DTT, and 0.05 mM D-Luciferin) and detection of chemiluminescence were performed by a Centro LB 960 Luminometer (Berthold Technologies, Bad Wildbad, Germany). MicroWin2000 Software (Mikrotek Laborsysteme, Overath, Germany) was used for analysis. The relative light units (RLU) measured by the luminometer were expressed in percent neutralisation using the following calculation:

$$\%\text{-neutralisation}=100\times(V_0-V_n)/V_0,$$

where $V_n$ represents the RLU in the wells containing virus and antibody, and $V_0$ represents the RLU in the wells that contained virus alone. The first screening revealed nine gB-specific culture supernatants that neutralised hCMV infectivity and a second screening revealed three further gB-specific culture supernatants that neutralised hCMV infectivity. The nine EBV-immortalised memory B cell lines and the neutralising antibodies produced by them were named SM1, SM3, SM4, SM5, SM6, SM7, SM9, SM10 and SM11 (see Table 1 below). The three additional EBV-immortalised memory B cell lines and the neutralising antibodies produced by them were named SM12, 2C2 and 1G2 (see Table 1 below).

A 50%-neutralising titre ($IC_{50}$) is indicated as the concentration of antibody that results in a 50% reduction of hCMV infection. Similarly, a 90%-neutralising titre ($IC_{90}$) is indicated as the concentration of antibody that results in a 90% reduction of hCMV infection. To calculate the neutralising activities of the antibodies, the IgG-concentrations of the culture supernatants were determined by ELISA. For this purpose, ELISA plates were coated with anti-human IgG, Fcγ fragment-specific catching antibody (Jackson ImmunoResearch, USA). Two-fold serial dilutions of SM-antibody culture supernatants in ELISA buffer were compared to polyclonal IgG standard of known concentration (11.1 mg/ml stock concentration; Cat No: 009-000-003, Jackson ImmunoResearch, USA). The IgG-concentrations of samples were calculated using the ELISA software Softmax Pro 3.0 (Molecular Devices, Sunnyvale, Calif., USA). The neutralisation activities relative to IgG concentration of the EBV line cell culture supernatant are shown in Table 1 below:

TABLE 1

Properties of EBV-immortalised memory B cell lines

| EBV line | IgG conc. of supernatant (µg/ml) | No of cells in pellet | 50% neutralisation activity (µg/ml) | 90% neutralisation activity (µg/ml) |
|---|---|---|---|---|
| SM1 | 10.8 | $3.6 \times 10^5$ | 0.8 | 2.0 |
| SM3 | 14.7 | $3.5 \times 10^5$ | 0.5 | 1.0 |
| SM4 | 19.5 | $6.0 \times 10^5$ | 0.3 | 0.6 |
| SM5 | 18.5 | $3.3 \times 10^5$ | 0.4 | 0.9 |
| SM6 | 8.7 | $2.2 \times 10^5$ | 0.3 | 1.0 |
| SM7 | 13.4 | $3.8 \times 10^5$ | 0.4 | 1.0 |
| SM9 | 21.5 | $1.0 \times 10^6$ | 1.0 | 9.0 |
| SM10 | 6.9 | $5.0 \times 10^5$ | 0.3 | 1.0 |
| SM10 | 28.5 | n.d. | 0.3 | 1.0 |
| SM11 | 18.2 | $7.0 \times 10^5$ | 1.0 | 6.0 |
| SM12 | 22.5 | n.d. | 1.6 | 8.0 |
| 2C2 | 11.9 | n.d. | 0.3 | 1.3 |
| 1G2 | 25.5 | n.d. | 0.1 | 0.4 |

Having determined the IgG-concentrations of the EBV line supernatants, a further neutralisation assay for six of the cell line supernatants was performed; these supernatants showed $IC_{50}$ values between 0.5 and 2.3 µg/ml (Table 2; see below). The neutralisation assay was performed as described in the paragraph above with the modification that two-fold serial dilutions of antibody supernatants in complete medium were prepared, in triplicate, prior to the addition of virus.

TABLE 2 hCMV neutralising activities of gB-specific antibodies produced by EBV-immortalised memory B cell lines

| EBV line | 50% Neutralisation activity (µg/ml) |
|---|---|
| SM1 | 1.3 |
| SM3 | 0.8 |
| SM4 | 0.6 |
| SM5 | 0.6 |
| SM6 | 0.5 |
| SM11 | 2.3 |
| ITC88* | 1.5 |

Results reflect mean values of three independent assays. Variations between assays were in the range 10-20%.
*ITC88 was used as a positive control (Ohlin et al., 1993).

The EBV-immortalised memory B cell lines producing neutralising antibodies were pelleted and frozen at −80° C., until required for further processing.

Example 3

Cloning of Antibody Variable Regions from Anti-hCMV EBV Cell Lines

In the Examples 3.1 to 3.4 the variable regions of anti-hCMV neutralising antibodies from nine EBV transformed human B cell lines (SM1, 3-7, 9-11) were amplified by semi-nested PCR and cloned in pCDNA3 vectors (Invitrogen) containing the appropriate immunoglobulin constant region. These constructs were subsequently used to transfect CHO cells and the expressed antibodies were tested using suspension array technology and surface plasmon resonance (BIACORE®, (surface plasmon resonance, GE Healthcare) (Example 5) and neutralisation assays (Example 4), for first screenings. In Examples 3.5-3.7, the variable regions of anti-hCMV neutralising antibodies from four EBV transformed human B cell lines (SM10, SM12, 2C2 and 1G2) were amplified by nested PCR and cloned in expression vectors containing the appropriate immunoglobulin constant region according to the method described in Tiller et al., 2008. These constructs were subsequently used to transfect HEK 293T cells and the expressed antibodies were tested in neutralisation assays (Example 4) as part of the initial screenings.

The term 'variable region' means VDJ rearranged genes for heavy chains and VJ rearranged genes for light chains.

3.1 RNA Purification and First-strand cDNA Synthesis

Frozen cell pellets of EBV transformed memory B cell lines SM1, 3-7 and 9-11 were subjected to total RNA purification with TRIZOL® reagent (guanidinium thiocyanate and phenol, Invitrogen). The cell pellets were taken out of the −80° C. freezer and immediately lysed with TRIZOL® (guanidinium thiocyanate and phenol). After 5 min incubation at room temperature, 0.2 ml of chloroform (Roth, Germany) per 1 ml of TRIZOL® (guanidinium thiocyanate and phenol) was added and the tubes were mixed gently for 1 min. Lysates were incubated for 3 min on ice and centrifuged at 14000 rpm for 15 min at 4° C. The aqueous upper phase was transferred to a fresh tube and 0.5 ml of isopropanol (Roth, Germany) per 1 ml of TRIZOL® (guanidinium thiocyanate and phenol) was added. After incubation for 10 min at room temperature, the tubes were centrifuged at 14000 rpm for 10 min at 4° C. Supernatants were discarded and the RNA pellets were washed with 1 ml of 70% ethanol (Roth, Germany). Pellets were air-dried for 10 to 15 min at room temperature and were dissolved by adding 30 to 50 µl of RNAse-free double-distilled water (Fermentas Life Sciences) and by incubation for 10 min at 55° C. RNA concentration was measured by UV spectrophotometry and the RNA samples were stored at −80° C. First-strand cDNA synthesis was performed using a RevertAid™ first-strand cDNA synthesis kit (Fermentas Life Sciences) following the manufacture's manual.

3.2 Semi-nested PCR

Variable coding regions of human antibodies were amplified by semi-nested PCR. The semi-nested PCR was performed by running two successive PCRs (PCR parameters are shown in Table 3 below), both with the same program (TDN-PCR1; Table 4a below), with different 5' forward primers and the same 3' reverse primer mix (Table 5 below; all J-segment primers together). As a template for the 1st PCR 1 µl cDNA was used. For the 2nd PCR 1 µl of the PCR product from the 1st PCR was used (undiluted or diluted 1:10-1:100, depending on the DNA yield after the 1st PCR). The cDNA of all EBV-lines were amplified using all $V_H$, Vκ and Vλ primer combinations. Five different forward primers were used in combination with five reverse primers to amplify the kappa light chain variable regions (Table 5a). Three different forward primers were used in combination with 4 different reverse primers to amplify the lambda light chain variable regions (Table 5b). Six different forward primers were used in combination with four different reverse primers to amplify the heavy chain variable regions (Table 5c).

In all EBV lines more than one heavy and one light chain variable region were amplified. Amplified variable regions were digested with HindIII/Eco47III (heavy chains and kappa light chains) or with HindIII/AvrII (lambda light chains) and cloned into pcDNA3 (Invitrogen) already containing the matching constant coding regions for human γ1, κ or λ, as described in Example 3.4.

The resulting PCR products of predicted length were blunt end-ligated into PCR4Blunt-TOPO (Invitrogen) and after sequence analysis, variable regions were further sub-cloned into pcDNA3 (Invitrogen) as described in Example 3.4. However, to further increase the yield of amplified λ light chain variable regions, the PCR conditions were further optimized (PCR Programme FWUWPCR, see Table 4b below).

TABLE 3

PCR parameters

| Volume per reaction: 30 µl | Final concentration |
|---|---|
| Polymerase: | 0.75 u/30 µl (0.15 µl) |
| High fidelity PCR Enzyme Mix 5 u/µl, | |
| Fermentas Cat No K0192 | |
| dNTP Mix 10 mM each | 300 µM (0.9 µl) |
| MgCl$_2$ 25 mM | 2 mM (2.4 µl) |
| 5' forward primer 10 pmol/µl | 0.5 µM (1.5 µl) |
| 3' reverse primer mix (all J-segment primers together) | J$_H$1-6: 2 µM, or Jκ1-5: 1 µM, or Jλ1-7: 0.5 µM |

TABLE 4

PCR Programs a) TDNPCR1

| | | | | |
|---|---|---|---|---|
| 1. | Initial denaturation | 95° C. | 2 min | 10 cycles |
| 2. | Denaturation | 95° C. | 20 s | |
| 3. | Annealing | 60° C. | 30 s | |
| 4. | Elongation | 72° C. | 1 min | |

10 cycles with decreasing annealing temp. (−0.5° C. each cycle)

| | | | | |
|---|---|---|---|---|
| 5. | Denaturation | 95° C. | 20 s | 10 cycles |
| 6. | Annealing | 55° C. | 30 s | |
| 7. | Elongation | 72° C. | 1 min | |

10 cycles with 55° C. annealing temp.

| | | | | |
|---|---|---|---|---|
| 8. | Denaturation | 95° C. | 20 s | 15 cycles |
| 9. | Annealing | 53° C. | 30 s | |
| 10. | Elongation | 72° C. | 1 min | |

15 cycles with 53° C. annealing temp.

| | | | | |
|---|---|---|---|---|
| 11. | Final elongation | 72° C. | 10 min | |
| 12. | Cooling | 10° C. | hold | | b) FWUWPCR

| | | | | |
|---|---|---|---|---|
| 1. | Initial denaturation | 94° C. | 5 min | |
| 2. | Annealing | 55° C. | 40 s | |
| 3. | Elongation | 72° C. | 1 min | |
| 4. | Denaturation | 94° C. | 40 s | 30 cycles |
| 5. | Annealing | 55° C. | 40 s | |
| 6. | Elongation | 72° C. | 1 min | |
| 7. | Final elongation | 72° C. | 3 min | |
| 8. | Cooling | 10° C. | hold | |

TABLE 5a

Primers to amplify the κ light chain variable region

| Name | Number | Sequence | SEQ ID |
|---|---|---|---|

1. PCR forward Primers (5')

| Name | Number | Sequence | SEQ ID |
|---|---|---|---|
| nes Vκ1 | 074-Je | 5' GTC AGW CCC AGT CAG GAC ACA GC 3' | No: 198 |
| nes Vκ2 | 075-Je | 5' ACT CCT CAG TTC ACC TTC TCA CM 3' | No: 199 |
| nes Vκ3 | 076-Je | 5' TCA GTT AGG ACC CAG ASG GAA 3' | No: 200 |
| nes Vκ4 | 150-Je | 5' CAA CAG GCA GGC AGG GGC AGC AAG 3' | No: 201 |
| nes Vκ5 | 151-Je | 5' CAC CTG CAG GTC AGG GCC AAG GTT 3' | No: 202 |

2. PCR forward Primers (5')

| Name | Number | Sequence | SEQ ID |
|---|---|---|---|
| Vκ1 5'-forward neu | 077-Je | 5' CTG AAG CTT CCA TGG ACA TGA GGG TCC CCG CTC AGC TCC 3' | No: 203 |
| Vκ2 5'-forward | 078-Je | 5' CTG AGG CTT CCA TGA GGC TCC CTG CTC AGC TCC TGG GGC TG 3' | No: 204 |
| Vκ3 5' forward | 007-Je | 5' CTG AAG CTT CCA TGG AAG CCC CAG CGC AGC TTC TCT TCC TC 3' | No: 205 |
| Vκ4 5' forward | 152-Je | 5' CTG AAG CTT CCA TGG TGT TGC AGA CCC AGG TCT TCA TTT CTC 3' | No: 206 |
| Vκ5 5' forward | 153-Je | 5' CTG AAG CTT CCA TGG GGT CCC AGG TTC ACC TCC TCA GCT TCC 3' | No: 207 |

TABLE 5a-continued

Primers to amplify the κ light chain variable region

| Name | Number | Sequence | SEQ ID |
|---|---|---|---|

1. + 2. PCR reverse primers (3')
Mix "Jκ1-5": 66-Je + 67-Je + 68-Je + 69-Je + 70-Je

| Name | Number | Sequence | SEQ ID |
|---|---|---|---|
| Jκ1 HindIII/ Eco47III | 066-Je | 5' TAG AGC GCT TGA TTT CCA CCT TGG TCC CTT GG 3' | No: 208 |
| Jκ2 HindIII/ Eco47III | 067-Je | 5' TAG AGC GCT TGA TCT CCA GCT TGG TCC CCT GG 3' | No: 209 |
| Jκ3 HindIII/ Eco47III | 068-Je | 5' TAG AGC GCT TGA TAT CCA CTT TGG TCC CAG GG 3' | No: 210 |
| Jκ4 HindIII/ Eco47III | 069-Je | 5' TAG AGC GCT TGA TCT CCA CCT TGG TCC CTC CG 3' | No: 211 |
| Jκ5 HindIII/ Eco47III | 070-Je | 5' TAG AGC GCT TAA TCT CCA GTC GTG TCC CTT GG 3' | No: 212 |

TABLE 5b

Primers to amplify the lambda λ chain variable region

| Name | Number | Sequence | SEQ ID |
|---|---|---|---|
| | | PCR forward Primers (5') | |
| Vλ1-upstream | 258-Je | 5' CAG GAC TCA GGA CAA TCT CCA GC 3' | No: 213 |
| Vλ2-upstream | 259-Je | 5' YYY CSG GAC GTC YYC ACC 3' | No: 214 |
| Vλ3-upstream | 260-Je | 5' ATC TGG GGG KCT YYC RCC 3' | No: 215 |
| Vλ1-leader | 261-Je | 5' GAT AAG CTT CCA TGG CCT GST CCC CTC TCC TCC TCA C 3' | No: 216 |
| Vλ2-leader | 262-Je | 5' GAT AAG CTT CCA TGG CCT GGG CTC TGC TCC TCC TC 3' | No: 217 |
| Vλ3-leader | 263-Je | 5' GAT AAG CTT CCA TGG CCT GGA CCC CTC TCC TSC TC 3' | No: 218 |
| | | 1. + 2. PCR reverse Primers (3'), Mix "Jλ1-7": 264-Je + 265-Je + 266-Je + 267-Je | |
| Jλ1, 2, 3, 6 | 264-Je | 5' GAG CCT AGG ACG GTG ACC TTG GTC CC 3' | No: 219 |
| Jλ4 | 265-Je | 5' GAG CCT AGG ATG ATC AGC TGG GTT CCT CC 3' | No: 220 |
| Jλ5 | 266-Je | 5' GAG CCT AGG ACG GTC AGC TCG CTC CCC TC 3' | No: 221 |
| Jλ7 | 267-Je | 5' GAG CCT AGG GCG GTC AGC TGG GTG CCT CC 3' | No: 222 |

TABLE 5c

Primers to amplify the heavy chain variable region

| name | number | sequence | SEQ No |
|---|---|---|---|
| *1. PCR forward Primers (5')* | | | |
| nes $V_H1$ | 84-B | 5' CCC TGA GAG CAC AGY TCC TCA CC 3' | No: 223 |
| nes $V_H2$ | 155-Je | 5' AGT GAC TCC TGT GCM CCA CC 3' | No: 224 |
| nes $V_H3$ | 85-B | 5' GCA CTG AAC ACA GAG GCA TCA CC 3' | No: 225 |
| nes $V_H4$ v1 | 161-Je | 5' CMT GGA YCT CMT GYR CRA GAA C 3' | No: 226 |
| nes $V_H5$ | 162-Je | 5' AGG GCT TCA TTT TCT GTC CTC CAC CAT C 3' | No: 227 |
| nes $V_H6$ | 154-Je | 5' GGG CAG TCA CCA GAG CTC CAG ACA 3' | No: 228 |
| *2. PCR forward Primers (5')* | | | |
| $V_H1$ 5' forward | 001-Je | 5' CTG AAG CTT CCA TGG ACT GGA CCT GGA GGA TCC TCT TCT TG 3' | No: 229 |
| $V_H2$ 5' forward neu | 158-Je | 5' CTG AAG CTT CCA TGG ACA CAC TTT GCT CCA CGC TCC TG 3' | No: 230 |
| $V_H3$ 5' forward | 003-Je | 5' CTG AAG CTT CCA TGG AGT TTG GGC TGA GCT GGG TTT CC TTG 3' | No: 231 |
| $V_H4$ 5' forward neu | 159-Je | 5' CTG AAG CTT CCA TGA AAC ACC TGT GGT TCT TCC TCC TSC TGG 3' | No: 232 |
| $V_H5$ 5' forward | 156-Je | 5' CTG AAG CTT CCA TGG GGT CAA CCG CCA TCC TCG CCC TCC TCC 3' | No: 233 |
| $V_H6$ 5' forward | 157-Je | 5' CTG AAG CTT CCA TGT CTG TCT CCT TCC TCA TCT TCC TGC CCG 3' | No: 234 |
| *1. + 2. PCR reverse Primers (3'), Mix "$J_H1$-6": 62-Je + 63-Je + 65-Je + 64-Je* | | | |
| $J_H$ 1, 4, 5 HindIII/ Eco47III | 062-Je | 5' TAG AGC GCT GGA GAC GGT GAC CAG GGT TCC CTG G 3' | No: 235 |
| $J_H2$ HindIII/ Eco47III | 063-Je | 5' TAG AGC GCT GGA GAC AGT GAC CAG GGT GCC ACG 3' | No: 236 |
| $J_H3$ HindIII/ Eco47III | 065-Je | 5' TAG AGC GCT AGA GAC GGT GAC CAT TGT CCC TTGG 3' | No: 237 |
| $J_H6$ HindIII/ Eco47III | 064-Je | 5' TAG AGC GCT GGA GAC GGT GAC CGT GGT GCC TTT TT 3' | No: 238 |

3.3 Vector Backbone Preparation

Amplified variable regions were cloned into a pcDNA3 vector (Invitrogen) containing the appropriate immunoglobulin heavy and light chain constant regions. For the cloning of heavy chain variable regions, construct pd1612-Je (pcDNA3-EGFP-Cγ) was digested with HindIII/Eco47III (generates two bands of 6505 bp and 727 bp), dephosphorylated with CIP and the 6505 bp fragment was gel-purified. For the cloning of lambda light chain variable regions, construct pd1864-Je (pcDNA3-2-4 Vλ2-AvrII(−) was digested with HindIII/AvrII (generates two bands of 5858 bp and 394 bp), dephosphorylated with CIP and the 5858 bp fragment was gel-purified. For cloning the kappa light chain variable regions, construct pd703-Je (pcDNA3-ITC88 Vκ) was digested with HindIII/Eco47III (generates two bands of 6050 bp and 392 bp), dephosphorylated with CIP and the 6050 bp band was gel-purified.

3.4 Insert Preparation

The PCR products of the amplified antibody variable regions were gel purified, digested with either HindIII/Eco47III (heavy chain and kappa light chain variable regions) or with HindIII/AvrII (lambda light chain variable regions) and were then ligated in-frame into a pcDNA3 vector containing the appropriate immunoglobulin constant region using T4 DNA ligase as recommended by the enzyme manufacturer. DNA-ligation was performed overnight at 16° C. As an exception to this method, the PCR products of the antibody variable regions SM1 Vλ1, SM4 Vλ1 and SM9 Vλ2 were first blunt end-ligated into PCR4Blunt-TOPO (Invitrogen) following the user manual of the blunt-end ligation kit (Invitrogen). After analysing the sequences of various minipreps, unique clones containing bona fide Vλ sequences were digested with HindIII/AvrII and the variable regions were gel-purified and sub-cloned into the appropriate pcDNA3 vector (pd 1864-Je; see below). 1 µl of each ligation was electroporated into DH10B cells (1900V/5 ms). Then 200 µl of the electroporated bacteria were plated onto LB-agar+100 µg/ml ampicillin plates. From each construct about 10 colonies were picked, grown overnight and minipreps were performed (each colony was also streaked onto LB-agar+100 µg/ml ampicillin plate). A control digestion to identify positive clones was performed with HindIII/Eco47III (H/E) for constructs with a heavy chain or a kappa light chain and with HindIII/AvrII (H/A) for constructs with a lambda light chain. Positive clones were analysed by DNA-sequencing with primer 179-Je (Sequence: 5' AGA GAA CCC ACT GCT TAC TG 3'; SEQ ID No: 196).

As mentioned above, a minority of variable regions were cloned first into a pCR4Blunt-TOPO (Invitrogen) vector backbone. After sequence analysis, positive clones were sub-cloned into pcDNA3 vectors as described above. For the insert preparation, Pd1887-Je (pCR4Blunt-TOPO-SM9 Vλ1_J$_L$7 #2) and pd1888-Je (pCR4Blunt-TOPO-SM1 VI1_J17 #4) were digested with HindIII/AvrII. The variable regions (394 bp) were gel-purified and ligated into pcDNA3. 1 µl of each ligation was electroporated into DH10B cells (1900V/5 ms). 250 µl of the electroporated bacteria were plated onto LB-agar+100 µg/ml ampicillin plates. Five colonies from each ligation were picked, minipreps were performed and DNA was digested with HindIII/AvrII to identify positive clones.

A summary of the number of antibody heavy chain (HC) variable regions and light chain (LC) variable regions cloned from EBV transformed human B cells is presented in Table 6 below. The 46 neutralising antibodies (final column) are the result of different combinations of 18 unique heavy chains and 18 unique lambda light chains. None of the combinations of heavy chains with kappa light chains resulted in hCMV neutralising antibodies. All heavy chains (V$_H$1-family; 151 amino acids, including leader sequence) are derived from one V-germline gene: IGHV1-1. All lambda light chains (Vλ1 family; 128 amino acids, including leader sequence) are derived from one V-germline gene: IGVλ1-51. These variable regions of the hCMV neutralising antibodies are marked in bold in Table 6. Heavy and light chains derived from other V-germline genes were also recovered but did not result in the generation of neutralising antibodies. An overview of all heavy and lambda light chain combinations resulting in neutralising antibodies is given in Table 7 below. Table 19 on pages 149-150 summarises the SEQ ID numbers of the accompanying Sequence Listing, for the heavy and light chain CDRs of the neutralising antibodies shown in Table 7 below.

TABLE 7

Heavy and Light chain antibody combinations

| | $V_L$ | | | | | |
|---|---|---|---|---|---|---|
| $V_H$ | SM5-1 | SM4-10 | SM6-5 | SM1-6 | SM3-1 | SM5-6 |
| SM5-1 | Ab-28 | | | | | Ab-03 |
| SM4-10 | | Ab-02 | | | | |
| SM6-5 | | | Ab-04 | | | |
| SM1-6 | | | | Ab-11 | | |
| SM3-1 | | | | | Ab-14 | |
| SM11-17 | | | | Ab-42 | | |
| SM11-21 | | | | Ab-46 | | |
| SM6-11 | | | Ab-01 | | | |
| SM4-3 | | Ab-20 | | Ab-27 | | |
| SM5-9 | Ab-10 | | | | | Ab-31 |
| SM1-7 | | | | Ab-12 | | |
| SM1-8 | | | | Ab-13 | | |

TABLE 6

Summary of anti-CMV antibodies cloned from nine EBV lines

| EBV line | HC (amino acids) | No. of HCs | LC kappa (amino acids) | LC lambda (amino acids) | No. of LCs | Theoretical combinations of H and L | Expressed antibodies | Neutralizing antibodies |
|---|---|---|---|---|---|---|---|---|
| SM 1 | Vh1 (151) | 2 | Vk1 (130) | | 1 | 5 | 2 | |
| | | | | Vl1 (130) | 1 | 5 | | |
| | Vh3 (142) | 3 | | Vl1 (128)* | 2 | 10 | 9 | 3 |
| SM 3 | Vh1 (151) | 3 | | Vl1 (128) | 8 | 24 | 6 | 4 |
| SM 4 | Vh1 (151) | 2 | | **Vl1 (128*, 129**, 133) | 10 | 20 | 16 | 13 |
| | | | Vk1 (131) | | 2 | 4 | 1 | |
| | | | Vk3 (129) | | 1 | 2 | 1 | |
| SM 5 | Vh1 (151) | 3 | | Vl1 (128) | 4 | 12 | 9 | 9 |
| SM 6 | Vh1 (151) | 3 | | Vl1 (128, 129, 130, 131), Vl2 (130, 131) | 15 | 75 | 25 | 12 |
| | Vh5 (148) | 2 | | | | 28 | 9 | |
| SM 7 | Vh1 (151) | 4 | Vk1 (130) | | 2 | 8 | 2 | 0 |
| SM 9 | Vh1 (142) | 2 | | Vl1 (128), Vl2 (130) | 5 | 10 | 4 | 0 |
| SM 10 | Vh1 (138) | 3 | Vk2 (133) | | 2 | 6 | 2 | 0 |
| SM 11 | Vh1 (151) | 10 | Vk1 (130) | | 2 | 20 | 9 | |
| | | | | Vl1 (128)* | 6 | 60 | 5 | 5 |
| | | | | Vl1 (130) | 1 | 10 | | |
| | | 37 | | | 62 | 295 | 100 | 46 |

*Indicates chain cloned from 3 different SM lines.

TABLE 7-continued

Heavy and Light chain antibody combinations

| | | | $V_L$ | | | |
|---|---|---|---|---|---|---|
| SM3-4 | | | | | | |
| SM6-23 | | Ab-35 | | | | |
| SM11-18 | | | Ab-43 | | | |
| SM11-19 | | | Ab-44 | | | |
| SM5-3 | Ab-29 | | | | | |
| SM11-20 | | | Ab-45 | | | |

| $V_H$ | SM6-48 | SM4-3 | SM5-9 | SM4-12 | SM5-5 | SM3-2 |
|---|---|---|---|---|---|---|
| SM5-1 | | | Ab-32 | | Ab-30 | |
| SM4-10 | | Ab-26 | | Ab-08 | | |
| SM6-5 | Ab-37 | | | | | |
| SM3-1 | | | | | | Ab-15 |
| SM6-11 | Ab-05 | | | | | |
| SM4-3 | | Ab-06 | | Ab-22 | | |
| SM5-9 | | | Ab-07 | | Ab-09 | |
| SM3-4 | | | | | | Ab-17 |
| SM6-23 | Ab-38 | | | | | |

| $V_H$ | SM3-4 | SM4-1 | SM4-5 | SM4-7 | SM6-6 | SM6-51 |
|---|---|---|---|---|---|---|
| SM4-10 | | Ab-25 | Ab-23 | Ab-24 | | |
| SM6-5 | | | | | Ab-33 | Ab-39 |
| SM6-11 | | | | | Ab-34 | Ab-40 |
| SM4-3 | | Ab-18 | Ab-19 | Ab-21 | | |
| SM3-4 | Ab-16 | | | | | |
| SM6-23 | | | | | Ab-36 | Ab-41 |

3.5 RNA Purification and First-strand cDNA Synthesis

RNA purification of frozen cell pellets from EBV transformed memory B cell lines SM10, SM12, 2C2, 1G2 was performed using the RNEASY® Mini Kit (RNA purification kit, Qiagen) according to the manufacturer's manual. cDNA synthesis was performed using the Transcriptor High Fidelity cDNA Synthesis Kit (Roche) according to the manufacturer's instructions.

3.6 Nested PCR

From the cDNA synthesised in Example 3.5 above, variable coding regions of human antibodies were amplified by nested PCR by running two successive PCRs (PCR parameters are shown in Table 8 below) starting from 1-2 µl of cDNA as template. Both PCR reactions were performed with the same program (Table 9) with different 5' forward primers and 3' reverse primers (Table 10). As a template, for the first PCR round 50 ng of template cDNA was used and for the second PCR round 1-2 µl of the PCR product (purified using QIAGEN PCR Purification Kit) from the first PCR round was used. The cDNA of all EBV-lines was amplified using $V_H$, Vκ and Vλ primer combinations for the first PCR round as shown in Table 10a and the $V_H$, Vκ and Vλ primer combinations for the second PCR round as shown in Table 10b. For the second round of PCR, a 'best fit' primer was selected (Table 2, Tiller et al., ibid.) for the sequence obtained from the first round of PCR.

TABLE 8

PCR parameters

Expand ™ High Fidelity PCR System dNTPack

1x Expand ™ High Fidelity buffer (with 15 mM $MgCl_2$)
10 mM/dNTP Expand ™ High Fidelity dNTPs
20 pmol of each primer
50 ng template DNA or 1-2 µl cDNA
2.6 U Expand ™ High Fidelity Enzyme Mix

TABLE 9

PCR Program

| | | | |
|---|---|---|---|
| 1. Initial denaturation | 94° C. | 5 min | 1 cycle |
| 2. Denaturation | 94° C. | 10 s | 40 cycles |
| 3. Annealing | 50° C. | 20 s | |
| 4. Elongation | 72° C. | 55 s | |
| 5. Final elongation | 72° C. | 7 min | |
| 6. End | 18° C. | ∞ | 1 cycle |

TABLE 10a

Primers for the first round of PCR amplification

| EBV line | Primer Name | | Sequence | SEQ ID No: |
|---|---|---|---|---|
| 1st round PCR forward Primers (5') | | | | |
| SM10 VH | 5' Ig L VH chain 4/6 | 5' | CCC AGA TGG GTC CTG TCC CAG GTG CAG 3' | 296 |
| SM10 Vκ | 5' Ig L Vκ chain 1/2 | 5' | ATG AGG STC CCY GCT CAG CTG CTG G 3' | 297 |
| SM12 VH | as SM10 VH | | as SM10 VH | 296 |
| SM12 Vκ | as SM10 Vκ | | as SM10 Vκ | 297 |
| SM12 Vλ | 5' Ig L Vλ chain 3 | 5' | GCT CTG TGA CCT CCT ATG AGC TG 3' | 298 |
| 2C2 VH | as SM10 VH | | as SM10 VH | 296 |
| 2C2 Vκ | as SM10 Vκ | | as SM10 Vκ | 297 |
| 1G2 VH | as SM10 VH | | as SM10 VH | 296 |
| 1G2 Vλ | 5' Ig L Vλ chain 1 | 5' | GGT CCT GGG CCC AGT CTG TGC TG 3' | 299 |

TABLE 10a-continued

Primers for the first round of PCR amplification

| EBV line | Primer Name | Sequence | SEQ ID No: |
|---|---|---|---|
| *1st round PCR reverse Primers (3')* | | | |
| SM10 VH | 3' Ig Cγ CH chain 1 | 5' GGA AGG TGT GCA CGC CGC TGG TC 3' | 300 |
| SM10 Vκ | 3' Ig Cκ chain 543 | 5' GTT TCT CGT AGT CTG CTT TGC TCA 3' | 301 |
| SM12 VH | as SM10 VH | as SM10 VH | 300 |
| SM12 Vκ | as SM10 Vκ | as SM10 Vκ | 301 |
| SM12 Vλ | as 1G2 Vλ | as 1G2 Vλ | 302 |
| 2C2 VH | as SM10 VH | as SM10 VH | 300 |
| 2C2 Vκ | as SM10 Vκ | as SM10 Vκ | 301 |
| 1G2 VH | as SM10 VH | as SM10 VH | 300 |
| 1G2 Vλ | 3' Ig Cλ chain | 5' CAC CAG TGT GGC CTT GTT GGC TTG 3' | 302 |

TABLE 10b

Primers for the second round of PCR amplification

| EBV line | Primer Name | Sequence | SEQ ID No: |
|---|---|---|---|
| *2nd round PCR forward Primers (5')* | | | |
| SM10 VH | 5' Ig AgeI VH 4 | 5' CTG CAA CCG GTG TAC ATT CCC AGG TGC AGC TGC AGG AG 3' | 303 |
| SM10 Vκ | 5' Ig AgeI Vκ 2-24 | 5' CTG CAA CCG GTG TAC ATG GGG ATA TTG TGA TGA CCC AGA C 3' | 304 |
| SM12 VH | as SM10 VH | as SM10 Vκ | 304 |
| SM12 Vκ | 5' Ig AgeI Vκ 2-28 | 5' CTG CAA CCG GTG TAC ATG GGG ATA TTG TGA TGA CTC AGT C 3' | 305 |
| SM12 Vλ | 5' Ig AgeI Vλ 3 | 5' CTG CTA CCG GTT CTG TGA CCT CCT ATG AGC TGA CWC AG 3' | 306 |
| 2C2 VH | as SM10 VH | same as SM10 VH | 303 |
| 2C2 Vκ | 5' Ig AgeI Vκ 1-5 | 5' CTG CAA CCG GTG TAC ATT CTG ACA TCC AGA TGA CCC AGT C 3' | 307 |
| 1G2 VH | 5' Ig AgeI VH 4-39 | 5' CTG CAA CCG GTG TAC ATT CCC AGC TGC AGC TGC AGG AG 3' | 308 |
| 1G2 Vλ | 5' Ig AgeI Vλ 1 | 5' CTG CTA CCG GTT CCT GGG CCC AGT CTG TGC TGA CKC AG 3' | 309 |
| *2nd round PCR reverse Primers (3')* | | | |
| SM10 VH | 3' Ig SalI JH 1/2/4/5 | 5' TGC GAA GTC GAC GCT GAG GAG ACG GTG ACC AG 3' | 310 |
| SM10 Vκ | 3' Ig BsiWI Jκ 2 | 5' GCC ACC GTA CGT TTG ATC TCC AGC TTG GTC 3' | 311 |
| SM12 VH | 3' Ig SalI JH 6 | 5' TGC GAA GTC GAC GCT GAG GAG ACG GTG ACC GTG 3' | 312 |

TABLE 10b-continued

Primers for the second round of PCR amplification

| EBV line | Primer Name | Sequence | SEQ ID No: |
|---|---|---|---|
| SM12 Vκ | as SM10 Vκ | as SM10 Vκ | 311 |
| SM12 Vλ | as 1G2 Vλ | as 1G2 Vλ | 314 |
| 2C2 VH | as SM12 VH | as SM12 VH | 312 |
| 2C2 Vκ | 3' Ig BsiWI Jκ 1/4 | 5' GCC ACC GTA CGT TTG ATY TCC ACC TTG GTC 3' | 313 |
| 1G2 VH | as SM10 VH | as SM10 VH | 310 |
| 1G2 Vλ | 3' Ig XhoI Cλ | 5' CTC CTC ACT CGA GGG YGG AAC CAG AGT G 3' | 314 |

Restriction enzyme cutting sites are underlined 3.7 Expression Vector Cloning

Before cloning, aliquots of the V.sub.H, V.kappa. and V.lamda. chain second PCR products were purified with QIAGEN PCR Purification Kit according to the manufacturer's instructions and sequenced with the respective forward or reverse primer (Table 10). Sequences were analysed by IgBLAST to identify germline V(D)J gene segments with highest identity.

Amplified variable regions from the EBV lines were digested with AgeI/SalI (γ1 heavy chain), AgeI/BsiWI (κ light chain) or AgeI/XhoI (λ light chain) and cloned into human Igγ1, Igκ and Igλ, expression vectors containing a murine Ig gene signal peptide sequence (GenBank Accession No: DQ407610) and a multiple cloning site upstream of the human Igγ1, Igκ or Igλ constant regions. Also present in the expression vector is a human CMV promoter to drive transcription and an ampicillin resistance gene for selection. Ligation was performed in a total volume of 20 μl with 1U T4 DNA-Ligase (Invitrogen), 7.5 μl of digested and purified PCR product and 25 ng linearised vector. Competent *E. coli* DH10B bacteria (Invitrogen) were transformed at 42° C. with 2 μl of the ligation product in 96-well plates by either electroporation or by heat-shock transformation. Colonies were screened by PCR using the 5'Absense forward primer (5'-GCT TCG TTA GAA CGC GGC TAC-3'; SEQ ID No: 315) and the 3'IgG internal reverse primer (5'-GTT CGG GGA AGT AGT CCT TGA C-3'; SEQ ID No: 316), the 3'Cκ494 reverse primer (5' GTG CTG TCC TTG CTG TCC TGC T 3'; SEQ ID No: 317) or the 3'Cλ reverse primer (5' CAC CAG TGT GGC CTT GTT GGC TTG 3'; SEQ ID No: 318), respectively. PCR products of the expected size were sequenced to confirm identity with the original PCR products.

A summary of the number of antibody heavy chain (HC) variable regions and light chain (LC) variable regions cloned from EBV transformed human B cells is presented in Table 11 below. The four neutralising antibodies (final column) are the result of combination of 4 unique heavy chains and unique lambda or kappa light chains. The heavy chains are derived from two V-germline genes: IGHV4-39 and IGHV4-59. The kappa light chains are derived from two V-germline genes: IGKV2D-28 and IGKV1D-33 and the lambda light chain is derived from the V-germline gene: IGLV1-47. The lambda light chain derived from the V-germline gene IGLV3-10 did not result in antigen recognition when paired with a heavy chain. The combinations of the neutralising antibody heavy and light chains are described in Table 12 below.

TABLE 11

Summary of anti-hCMV antibodies cloned from four EBV lines

| EBV line | HC (amino acids) | No of HCs | LC kappa (amino acids) | LC lambda (amino acids) | No of LCs | Theoretical combinations of H and L | Expressed antibodies | Neutralizing antibodies |
|---|---|---|---|---|---|---|---|---|
| SM 10 | Vh4-39 (125) | 1 | Vk2-24 (112) | | 1 | 1 | 1 | 1 |
| SM 12 | Vh4-59 (125) | 1 | Vk2-28 (112) | Vl3-10 (109) | 2 | 2 | 1 | 1 |
| 2C2 | Vh4-59 (130) | 1 | Vk1D-33 (107) | | 1 | 1 | 1 | 1 |
| 1G2 | Vh4-39 (120) | 1 | | Vl1-47 (108) | 1 | 1 | 1 | 1 |
| | | 4 | | | 5 | 5 | 4 | 4 |

TABLE 12

Heavy and Light chain antibody combinations

| Antibody | Heavy chain | Light chain |
|---|---|---|
| Ab-47 | SM10 Vh | SM10 Vκ |
| Ab-48 | SM12 Vh | SM12 Vκ |
| Ab-49 | 2C2 Vh | 2C2 Vκ |
| Ab-50 | 1G2 Vh | 1G2 Vλ |

Table 19 on page 149 summarises the SEQ ID numbers of the accompanying Sequence Listing, for the heavy and light chain CDRs of the neutralising antibodies shown in Table 12 above.

Example 4

Expression and Purification of Recombinant Antibodies

Further characterisation of the cloned anti-hCMV antibodies required their expression and subsequent purification. Forty-six recombinant antibodies (Ab-01 to Ab-46) were expressed by transient transfection of CHO cells (DSMZ, Braunschweig, DE). Briefly, cells were seeded into cell culture dishes (diameter 10 cm; Greiner Bio-One, GmbH) at a density of $2.2 \times 10^6$ cells per dish in SF-IMDM medium (Invitrogen) containing 2% FCS (Sigma). After 24 h, the transfection mixture was prepared by mixing 1 ml MEM (PAA Laboratories) with 6.45 µg of expression plasmid for heavy chain, 6.45 µg of expression vector for light chain, and 12.9 µl of MATra transfection reagent (IBA GmbH, Göttingen, DE) per dish. This transfection mixture was incubated for 20 min at room temperature. The medium of the seeded cells was exchanged for 10 ml of MEM and the transfection mixture was added to cells dropwise. Subsequently, the culture dish was incubated on a magnetic plate (IBA GmbH) for 15 min. The medium was then aspirated and 10 ml of SF-IMDM medium with 2% FCS containing ultra low levels of bovine IgG (Lonza) was added to the cells. 24 h later, the medium was renewed. After two additional days, the medium was renewed and the supernatant containing recombinant antibody was harvested by centrifugation at 244 g for 5 min. Three days later, conditioned cell culture supernatant was harvested again by centrifugation and the cleared, antibody-containing supernatants were pooled.

A Vivacell 70 ultrafiltration device (MWCO 10 kDa; Sartorius Stedim Biotech) was used to concentrate the conditioned cell culture supernatant 100-fold by centrifugation at 1,000 g and 20° C. for 1 h. For purification of recombinant antibody, a Protein A HP Spin Trap column (GE Healthcare) was equilibrated with binding buffer (50 mM Tris-HCl, 150 mM NaCl, pH7.5) and 300 µl of concentrate were loaded. The column was sealed with a lid and was incubated on an end-over-end mixer at room temperature. After 1 h the spin column was centrifuged for 1 min at 150 g. After washing the column with 400 µl of binding buffer and centrifugation at 150 g for 1 min, the loading process was repeated for an additional three times until the whole concentrate had been loaded. After the final loading step, the column was washed four times by application of 400 µl binding buffer and subsequent centrifugation at 150 g for 1 min. Bound recombinant antibody was eluted from the spin column twice by adding 200 µl elution buffer (100 mM glycine/HCl, pH 2.5) and centrifugation at 150 g for 1 min. Eluates were immediately neutralised with 30 µl of neutralisation buffer (1M Tris-HCl, pH9.0). The buffer was exchanged by loading the combined eluates onto a Zeba Desalt Spin column (Pierce) pre-equilibrated with PBS and subsequent centrifugation at 150 g for 2 min. Purified recombinant antibody was stored in protein LoBind tubes (Eppendorf) at 4° C. until further processing for characterisation studies. The produced antibody culture supernatants were analysed for gB recognition either by ELISA or by Biacore, as described in Examples 1 and 5. After IgG-concentrations were determined, as explained in Examples 2 and 5, gB-specific culture supernatants were analysed for neutralising activity, using the luciferase assay as described in Example 2 (luciferase assay) using primary fibroblast cells HFF. Seven anti-hCMV antibodies displaying efficient 50%-neutralising activities were chosen for further experiments (see Table 13 below).

TABLE 13

| 50% neutralising activities of monoclonal SM-antibodies produced by CHO cells | |
|---|---|
| Monoclonal antibody | 50% Neutralising activity (µg/ml) |
| Ab-02 | 0.3 |
| Ab-04 | 0.5 |
| Ab-11 | 1.3 |
| Ab-14 | 0.4 |
| Ab-19 | 0.6 |
| Ab-28 | 0.3 |
| Ab-42 | 1.0 |
| ITC88* | 1.5 |
| Cytotect | 200 |
| Cytotect♦ | |

Results reflect mean values of three independent assays. Variations between assays were in the range 10-20%.
*Ohlin et al., (1993);

Cytotect♦ Cytotect (Biotest) is a pool of HCMV hyperimmune IgG.

For the expression of the four recombinant antibodies Ab-47 to Ab-50, the method according to Tiller et al., ibid was followed. Briefly, HEK 293T cells (DSMZ, Braunschweig, DE) were cultured in 75 cm² flasks (Greiner Bio-One, GmbH) under standard conditions in DMEM medium (GibcoBRL) supplemented with 10% heat-inactivated FCS (PAN Biotech GmbH), 350 µg/ml L-glutamine (Merck) and 100 µg/ml gentamycine (SERVA Electrophoresis GmbH). Transient transfections of exponentially growing 293T cells were performed by $CaPO_4$ precipitation at 80% cell confluency. Equal amounts (12.5-20 µg each) of heavy and corresponding light chain expression vector DNA were mixed in 1 ml sterile water and 2.5M $CaCl_2$ was added drop-wise to a concentration of 250 mM. An equal volume of 2×HEPES-buffered saline was mixed with the calcium-DNA solution under slow vortexing and incubated at room temperature for 1 min (1 min RT+1 min 37° C.) to allow formation of precipitates. The precipitation mixture was distributed evenly to the culture dish. The cells were washed with 10 ml PBS after 6-8 h and cultured for 6-7 days in 15 ml DMEM before supernatants were harvested.

The culture supernatants were analysed for gB recognition by ELISA as described in Example 1. After IgG-concentrations were determined, as explained in Example 2, gB-specific culture supernatants were analysed for neutralising activity, using the luciferase assay (as described in Example 2) using primary fibroblast cells HFF. The 50% neutralising activities of the monoclonal antibodies produced by HEK-293T cells are shown in Table 14 below:

TABLE 14

| 50% neutralising activities of monoclonal antibodies produced by HEK-293T cells | |
|---|---|
| Monoclonal antibody | 50% Neutralising activity (µg/ml) |
| Ab-47 | 0.14 |
| Ab-48 | 0.33 |
| Ab-49 | 0.53 |

TABLE 14-continued

50% neutralising activities of monoclonal
antibodies produced by HEK-293T cells

| Monoclonal antibody | 50% Neutralising activity (µg/ml) |
|---|---|
| Ab-50 | 0.23 |
| C23* | 0.23 |

Results reflect mean values of two independent assays.
*C23 is a gB specific antibody used as a control (T123; a kind gift from Teijin Pharma Limited, Japan)

Example 5

Characterisation of Anti-hCMV Antibodies 5.1: Quantification of hCMV Antibodies Using Suspension Array Technology (LUMINEX®)

Cell culture supernatants containing human IgG were diluted in assay buffer (Roche, Cat# 1112589) and dilutions were assessed in duplicate in a 96-half well plate (Corning, Cat#3 884). Briefly, 25 µl samples were incubated in the dark (20° C., 650 rpm) for 1 h with 5 µl containing 1200 Luminex-COOH-beads loaded by amine coupling with anti-human IgG-Fc-specific (Caltag, Cat#H10500). Standard Curves were generated using duplicates of 25 µl of a 1:3 dilution series (0.08-60 ng/ml) of ChromPure human IgG whole molecule (Jackson Immuno-Research, USA Cat# 009-000-003). Detection was done by the addition of 30 µl anti-human IgG-Fc-specific labelled with R-PE (5 µg/ml; JIR Cat# 109-116-098) and further incubation for 1 h. Plates were then read and analysed using a LUMINEX® 200 instrument (flow cytometry, Millipore) using the following settings: 100 beads, 50 µl sample size.

5.2: Quantification of gB Protein (hCMV) Using Suspension Array Technology

Cell culture supernatants containing gB (hCMV) were diluted in assay buffer (Roche Cat# 1112589) and dilutions were assessed in triplicate in a 96-well filter plate (Millipore Cat# MABVN 1250). Briefly, 25 µl samples were incubated in the dark (20° C., 650 rpm) for 1.5 h with 5 µl containing 1500 Luminex-COOH-beads loaded by amine coupling with the human-anti-hCMV-IgG antibody $V_H3/65$-Vκ1/19, a non-neutralising, but very high affinity hCMV specific antibody previously identified in-house. Standard curves were generated using triplicates of 25 µl of a 1:3 dilution series (6-1458 ng/ml) of gB. Plates were washed twice (100 µl PBS per well) using a vacuum manifold and for detection 50 µl biotinylated anti-hCMV-IgG antibody ITC52 (5 µg/ml; generated in-house; Ohlin et al., 1993) was added for further 1.5 h. After two wash steps (with 100 µl PBS each) 50 µl 1.2 µg/ml Neutravidin labelled with R-PE (Invitrogen, Cat# A2660) was added for 30 min before plates were read and analysed using the LUMINEX® 200 instrument (flow cytometry) (settings: 100 beads, 40 µl sample size).

5.3: Biacore

Protein-protein interactions were analysed by surface plasmon resonance technique using a BIACORE® T100 instrument (Biacore, GE Healthcare, Munich) with BIACORE® T100 control software v2.0.1. All interactions were analysed at 25° C. in 1×DPBS with P20 (0.05%). Each binding interaction was assayed at least twice. The hCMV gB protein was coupled to the flowcells of a CM5 sensor chip (carboxymethylated dextran matrix, GE Healthcare) via standard amine-coupling procedure. The carboxymethylated dextran matrix was activated with 0.4 M 1-ethyl-3-(3-dimethylaminopropyl)-carbodiimide (EDC) and 0.1 M N-hydroxysuccinimide (NHS) according to the instructions of the manufacturer (GE Healthcare). Two flowcells were activated and gB protein was diluted with 10 mM sodium acetate, pH 5.0, to 50 µg/ml and injected at a flow rate of 5 µl/min until an appropriate level of coupling for the binding experiments (5,000 resonance units) or for the kinetics experiments (2,000 resonance units) was reached. Unreactive groups were inactivated by injection of 1M ethanolamine-HCl, pH 8.5. A control flowcell was prepared accordingly with ovalbumine (Imject, Pierce, Thermo Fisher Scientific, Schwerte, lot. JF124260) at pH 4.0. Before the binding experiments, the flowcells were washed thoroughly with running buffer.

For binding analyses cell culture supernatants containing anti-gB-specific antibodies were adjusted to 2.5 µg/ml IgG by diluting in SF-IMDM 2% ultra low IgG and injected for 90 sec in PBS with 0.02% BSA and 0.05% Tween 20 at 10 µl/min. After a dissociation time of 90 sec the binding stability was plotted using BIACORE® (surface plasmon resonance) T100 Evaluation Software version 2.0.1.

For kinetic analysis, Fab fragments of Antibodies Ab-02, Ab-04, Ab-11, Ab-14, Ab-28, Ab-42 and ITC88, as positive control, were prepared from protein A-purified human IgG using immobilised papain according to standard protocol of the manufacturer (Pierce, Thermo Fisher Scientific). The cleavage products were confirmed by SDS-PAGE with silver staining and by LUMINEX® bead array Fab/Fc detection. For kinetic analyses, the flow rate was raised to 70 µl/min and three blank curves (zero concentrations) were introduced into each run. The surface was regenerated with 10 mM glycine/HCl at pH 2.0. The binding curves were evaluated using BIACORE® (surface plasmon resonance) T100 Evaluation Software version 2.0.1 applying a Langmuir 1:1 model with global fit of $R_{max}$.

TABLE 15

Summary of on- and off-rates and calculated $K_D$

| anti-gB Fab | $k_a$(1/Ms) | $k_d$(1/s) | $K_D$(M) |
|---|---|---|---|
| Ab-02 | 3.8(±0.3) × 10$^5$ | 1.3(±0.1) × 10$^{-4}$ | 3.5(±0.1) × 10$^{-10}$ |
| Ab-04 | 7.7(±0.3) × 10$^4$ | 1.2(±0.1) × 10$^{-4}$ | 1.5(±0.1) × 10$^{-9}$ |
| Ab-11 | 7.6(±0.4) × 10$^4$ | 5.1(±0.1) × 10$^{-4}$ | 6.8(±0.4) × 10$^{-9}$ |
| Ab-14 | 5.6(±0.3) × 10$^4$ | 8.4(±0.1) × 10$^{-4}$ | 1.5(±0.1) × 10$^{-8}$ |
| Ab-28* | 4.0(±0.6) × 10$^5$ | 2.4(±0.8) × 10$^{-5}$ | 5.7(±1.2) × 10$^{-11}$ |
| Ab-42 | 5.7(±0.1) × 10$^4$ | 3.2(±0.01) × 10$^{-4}$ | 5.6(±0.1) × 10$^{-9}$ |
| ITC88**§ | 4.5(±0.04) × 10$^4$ | 4.7(±0.1) × 10$^{-5}$ | 1.0(±0.01) × 10$^{-9}$ | based on three measurements on two Biacore chip surfaces
*reaches limitation of the method
**based on two measurements on two Biacore chip surfaces
§published affinity ($K_D$) for ITC88 on pHM90-5 antigen is 2 nM (Ohlin et al., 1993)

Example 6

Neutralisation of Different hCMV gB-genotypes

HCMV lab strains and clinical isolates were classified in several gB genotypes (Chou and Dennison, 1991). 50%-neutralising activities of anti-HCMV antibodies were determined using additional different hCMV gB-genotypes using indirect immunofluorescence as a read-out. The virus strains Towne, AD169 and the clinical isolate Altu are classified as gB-genotype 1, gB-genotype 2 and gB-genotype 3, respectively. All virus strains were propagated on human foreskin fibroblasts (HFFs) by standard procedures and titres of infectivity in viral supernatants were determined by the method as described in Mahy & Kangro (1996). An indirect immunofluorescence assay was carried out as described in Andreoni et al. (1989). In brief, two-fold serial dilutions of six monoclonal antibodies (Antibodies Ab-04, Ab-11, Ab-14, Ab-19, Ab-28 and Ab-42) were incubated with a titered amount of the respective HCMV gB-genotype (300 pfu) for 1 h at 37° C. After incubation, virus-antibody mixtures were added to HFF cultures grown to confluence in 96-well microplates. All samples were tested in triplicate. The viral supernatants were removed from the HFFs, after an incubation of 4 h at 37° C. and replaced by complete medium. After another 16 h to 20 h incubation period, the cells were washed and fixed with ethanol. Infected cells were stained using the monoclonal antibody p63-27, which is specific for the major immediate-early (I E) protein, UL123, of hCMV and Cy3-conjugated anti-mouse IgG secondary antibodies (Jackson ImmunoResearch, USA). Following extensive washing, the IE-positive nuclei were counted under a fluorescence microscope and percent neutralisation was calculated as follows:

%-neutralisation=$100 \times (V_0 - V_n)/V_0$, where $V_n$ is the number of IE-positive nuclei in the wells containing virus and antibody, and $V_0$ is the number of IE-positive nuclei in the wells that were incubated with virus alone. In general, the infectious dose was adjusted to produce 1000 infected cells per well. Table 16 below summarizes the 50%-neutralising activities of various recombinant antibodies on hCMV representing different gB-genotypes. The monoclonal antibodies tested were found to neutralise hCMV gB-genotypes 1, 2 and 3 with comparable efficiency.

TABLE 16

50%-neutralising activities of monoclonal recombinant antibodies against 3 different hCMV gB-genotypes

| | 50% neutralising activity (μg/ml) | | |
|---|---|---|---|
| Monoclonal antibody | gB-genotype 1 (Towne strain) | gB-genotype 2 (AD169 strain) | gB-genotype 3 (Altu isolate) |
| Ab-04 | 0.5 | 0.7 | 0.3 |
| Ab-11 | 1.0 | 1.9 | 0.7 |
| Ab-14 | 1.3 | 1.5 | 0.6 |
| Ab-19 | 0.6 | 1.4 | 0.4 |
| Ab-28 | 0.4 | 0.5 | 0.1 |
| Ab-42 | 2.0 | 2.9 | 0.5 |
| ITC88* | 1.0 | 1.9 | 0.4 |

*(Ohlin et al., 1993)

Example 7

Neutralisation of hCMV Entry into Endothelial, Epithelial and Dendritic Cells of Recombinant Antibodies The neutralisation assays described in the previous examples were all carried out using fibroblasts as target cells. To investigate whether the previously identified neutralising recombinant antibodies are capable of also neutralising the infection of endothelial, epithelial and dendritic cells, an endothelio- and epitheliotropic HCMV isolate TB40E (a generous gift from Dr. Christian Sinzger, Institute of Medical Virology and Epidemiology of Viral Diseases, University of Tübingen, Germany) was utilised. TB40E was propagated in HFFs and titers of infectivity in viral supernatants were determined as described by Mahy & Kangro (1996). Human umbilical vein endothelial cells (HUVEC) were cultured in endothelial cell basal medium EBM-2 supplemented with EGM-2MV-kit (Lonza, Verviers, Belgium) and were used for experiments at passage 4-7. Human ARPE-19 retinal pigment epithelial cells (ATCC CRL-2302) were propagated in Dulbecco's modified Eagle medium: Nutrient Mixture F12, 1:1 mixture, supplemented with 2.5 mM glutamine, 15 mM Hepes buffer, pyridoxine HCl, 55 mg/l sodium pyruvate, 10% fetal calf serum (heat-inactivated), 100 IU/ml penicillin, 100 μg/ml streptomycin (PAN-Biotech, Aidenbach, Germany). Primary dendritic cells (DC) were isolated as follows: Purified peripheral blood mononuclear cells (PBMCs) of HCMV-seronegative blood donors were incubated in RPMI-1640 medium supplemented with 2 mM glutamine, 10 mM Hepes buffer, 100 IU/ml penicillin, 100 μg/ml streptomycin in the presence of autologous serum (2% v/v, heat-inactivated) for 2 h at 37° C. Following the incubation period, non-adhering cells were removed by washing with cell culture medium and adhering monocytes differentiated into DCs after the addition of IL-4 (25 U/ml) and GM-CSF (800 U/ml) (CellGenix Technologie Transfer GmbH, Freiburg, Germany) day two and four after isolation. On day six, neutralisation assays were performed by incubating antibody and virus for 1 h at 37° C. as described above. The infection of DCs required a 500-fold higher amount of virus particles. The antibody-virus mixtures were added to the DCs followed by another incubation period of 12 h. After fixation and permeabilization with ice-cold Methanol infected cells were stained using the monoclonal antibody E13 (Morphosys AbD GmbH, Duesseldorf, Germany) which is specific for the major immediate-early (1E) protein, UL123, of HCMV and FITC-conjugated anti-mouse IgG secondary antibodies (Jackson ImmunoResearch, West Grove, Pa.). Fluorescence activated cell sorting (FACS) was used as read-out. Both FlowJo 5.7.2. (Tree Star Inc., Ashland, Oreg.) and Graph Pad Prism 4 (GraphPad Software, Inc., La Jolla, Calif.) were used for analysis. Results are summarized in Tables 17a and 17b.

Neutralisation assays with endothelial and epithelial cells were carried out as described in Example 6 using indirect immunofluorescence assay as a read-out; however the following modifications to that method were made: HUVECs were incubated in EBM-2 supplemented with EGM-2MV-kit without hFGF-B for 1 h at 37° C. prior to infection. This was necessary to remove FGF-associated heparin, which showed an inhibitory effect on infection. Furthermore, a 10-fold higher amount of viral particles (3000 pfu) was applied both for the infection of HUVECs and ARPE.

All antibodies tested were observed to neutralise the infection of endothelial, epithelial and dendritic cells with comparable efficiency to the neutralisation of HFFs (see Tables 17a and 17b below).

TABLE 17a

Comparison of 50% neutralising activities of the tested monoclonal antibodies in different cell types

| | 50% neutralising activity (μg/ml) | | | |
|---|---|---|---|---|
| mAb | Fibroblast cells (HFFs) | Endothelial cells (HUVECs) | Epithelial cells (ARPE-19) | Dendritic cells (donor dependent°) |
| Ab-02 | 0.3 | 0.3 | 0.3 | 0.2/0.4 |
| Ab-04 | 0.5 | 0.4 | 0.3 | 0.3/0.5 |
| Ab-11 | 1.3 | 1.3 | 0.3 | 0.2/1.0 |
| Ab-14 | 0.4 | 1.0 | 0.4 | 0.2/1.0 |
| Ab-19 | 0.6 | 0.6 | 0.9 | n.d. |
| Ab-28 | 0.3 | 0.2 | 0.2 | 0.3/0.5 |

TABLE 17a-continued

Comparison of 50% neutralising activities of the tested monoclonal antibodies in different cell types

| | 50% neutralising activity (μg/ml) | | | |
|---|---|---|---|---|
| mAb | Fibroblast cells (HFFs) | Endothelial cells (HUVECs) | Epithelial cells (ARPE-19) | Dendritic cells (donor dependent°) |
| Ab-42 | 1.0 | 1.0 | 0.3 | 0.6/1.0 |
| ITC88* | 1.2 | 0.6 | 0.4 | 0.3/0.9 |

*(Ohlin et al., 1993)
°Dendritic cells of six different HCMV seronegative donors were analysed. The lowest and highest IgG-concentrations for 50%-neutralisation are shown.
n.d.: not determined

TABLE 17b

Comparison of 50% neutralising activities of the tested monoclonal antibodies in different cell types

| | 50% neutralising activity (μg/ml) | | | |
|---|---|---|---|---|
| mAb | Fibroblast cells (HFFs) | Endothelial cells (HUVECs) | Epithelial cells (ARPE-19) | Dendritic cells (donor dependent) |
| Ab-47 | 0.1 | 0.4 | 1.0 | n.d. |
| Ab-48 | 0.3 | 0.7 | n.d. | n.d. |
| Ab-49 | 0.5 | 1.8 | n.d. | n.d. |
| Ab-50 | 0.2 | 0.5 | 1.5 | n.d. |
| C23* | 0.2 | 0.6 | 0.8 | n.d. |

*C23 control antibody;
n.d.: not determined

Example 8

Epitope Characterisation of hCMV Neutralising Antibodies 8.1 Epitope-binding Competition Assay by Biacore of Novel Anti-hCMV Antibodies For epitope competition analysis, antibodies Ab-02 (18,900 RU), Ab-04 (16,800 RU) and Ab-28 (18,300 RU) were coupled to the flowcells of a CM5 sensor chip via standard amine-coupling. A control flowcell was prepared accordingly using an irrelevant human IgG$_1$ antibody (12,500 RU). Prior to the binding experiments, the flowcells were washed thoroughly with running buffer. The hCMV gB protein was captured onto the immobilized anti-gB antibodies for 180 s at a flow rate of 5 μl/min from the supernatant of a stable gB-producing CHO cell line 6-H5 (lot 080527 KS), which contained approximately 13 μg/ml gB. Secondary reference antibodies ITC48 (recognising gB epitope AD-1), ITC52 (recognising gB epitope AD-1) and ITC88 (recognising epitope gB AD-2) were applied at a concentration of 1000 nM. Binding was analysed in PBS with 0.02% BSA and 0.05% Tween 20 at a flow rate of 30 μl/min. The surface was regenerated with 10 mM glycine at pH 1.8. Binding curves were evaluated using BIACORE® (surface plasmon resonance) T100 Evaluation Software version 2.0.1. The results are summarised in Table 18 below where '+' indicates that the secondary binding antibody could bind to gB protein at the same time as the immobilised capture antibody.

The tested antibodies (immobilised capture antibody Ab-02, Ab-04 and Ab-28) all appear to bind gB epitopes that are outside of the gB epitopes AD-1 and AD-2 recognised by the ITC48, ITC52, ITC88 reference antibodies, since the reference antibodies were able to efficiently bind gB protein at the same time as the tested antibodies.

TABLE 18

Summary of antibody epitope mapping by Biacore

| Immobilised capture Ab | Secondary binding Ab | | |
|---|---|---|---|
| | ITC88 | ITC52 | ITC48 |
| Ab-02 | + | + | + |
| Ab-04 | + | + | + |
| Ab-28 | + | + | + |

8.2 Analysis of the Epitope Recognised by the Novel Anti-hCMV Antibodies

To further investigate whether or not the antibodies of the present invention recognise the known antigenic domains on gB, antigenic domain-1 (AD-1) and antigenic domain-2 (AD-2), an ELISA was performed. For this purpose, AD-1 (a procaryotically expressed fusion protein) and AD-2 (a synthetic peptide, pep90, amino acid sequence: NETIYNTLKYGDVVGV (SEQ ID No: 197), Meyer et al., 1992) were both coated at 1 μg/ml on ELISA plates. 50 μl of undiluted supernatant per well was incubated for 1 h at room temperature. The ELISA was performed as described in Example 1 above. ELISA analysis revealed that the antibodies of the present invention are neither AD-1- nor AD-2-specific, thereby confirming the Biacore competition assay of Example 8.1.

In order to positively identify the epitopes recognised by the antibodies of the present invention, a mammalian expression vector encoding amino acids 100-447 of gB was constructed. This region may comprise all amino acids in between the AD-1 and AD-2 gB epitopes. Transient transfection of Cos-7 cells with this expression construct was carried out with LIPOFECTAMINE® 2000 (transfection reagent, Invitrogen, Karlsruhe, Germany) according to the manufacturer's instructions. At 48 h post transfection, the cells were washed twice with PBS, fixed and permeabilised with cold methanol. After washing with PBS, the cells were incubated with primary antibody (tested antibodies or control antibodies) for 45 min at 37° C. in a humid atmosphere. Following another washing step, slides were incubated with FITC-conjugated anti-human IgG or FITC-conjugated anti-mouse IgG (Jackson ImmunoResearch, USA) for 45 min at 37° C. in a humid atmosphere. After washing the slides with PBS, coverslips were applied using the DAPI containing mounting medium VECTASHIELD® (LINARIS GmbH, Wertheim-Bettingen, Germany).

Antibody binding was documented by fluorescence microscopy (Axioplan 2, Carl Zeiss MicroImaging GmbH, Jena). Recombinant, neutralising monoclonal antibodies Ab-02, Ab-04, Ab-28 were shown to specifically react with the truncated gB protein covering amino acids 100-447 (AD169; SEQ ID NO: 239). Therefore, the antibody-binding domain of the recombinant, neutralising monoclonal antibodies Ab-02, Ab-04, Ab-28 has positively been identified to be located within a region encoded by amino acids 100-447 of gB (numbering of gB strain AD169; SEQ ID NO: 239). This unequivocally demonstrates that the monoclonal antibodies Ab-01 to Ab-46 of the present invention react with a novel antigenic epitope of gB protein and not with known AD-1 and AD-2 epitopes of gB protein that are recognised by previously identified human monoclonal antibodies in the prior art.

8.3: Competition ELISA with Anti-hCMV Antibodies

Figure 4A:
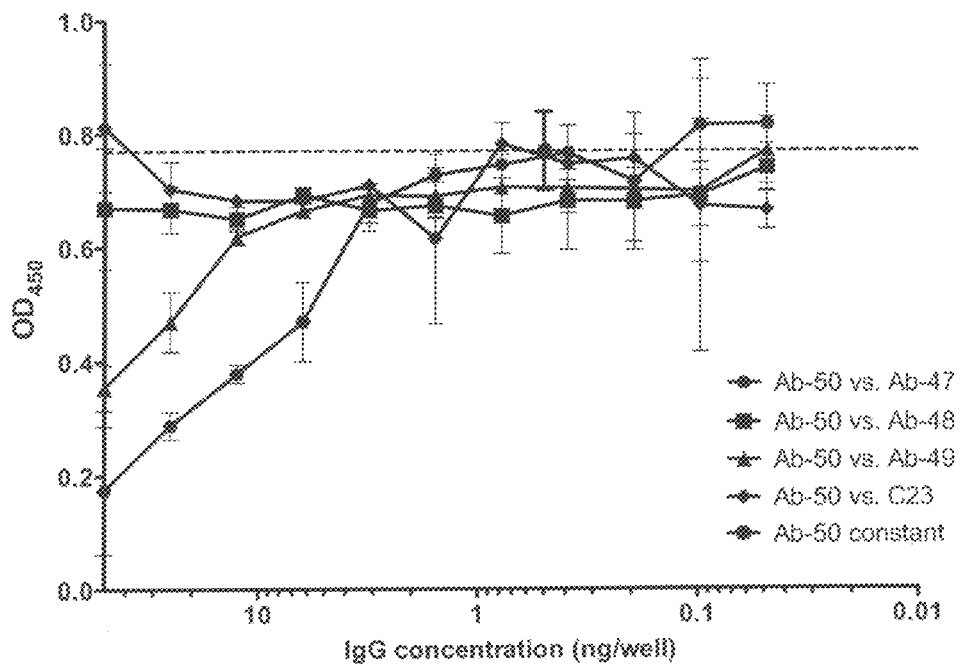
FIG. 4a shows Ab-50 in competition with antibodies Ab-47, Ab-48, Ab-49 and C23 (gB specific control antibody). Competition for binding to gB protein is observed for Ab-50 vs Ab-47 and Ab-49, but not for Ab-48 (or C23 control antibody).
Figure 4B:
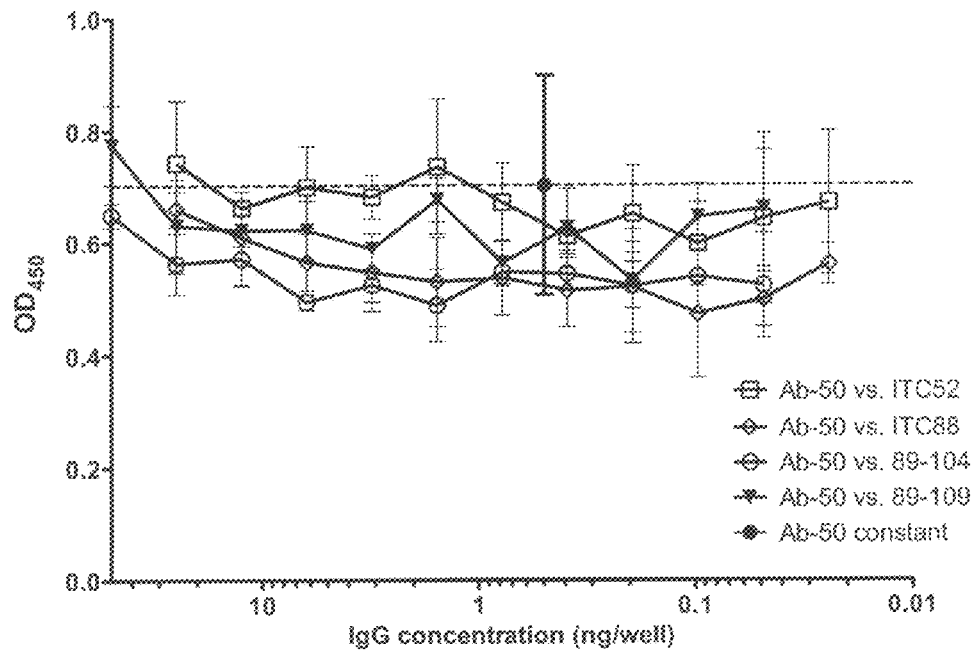
FIG. 4b shows Ab-50 in competition with antibody ITC52, ITC88, 89-104 and 89-109. No competition for binding is observed between Ab-50 and any of these tested antibodies. The dashed line across the top part of graphs 4a and 4b indicates Ab-50 at a concentration of 0.5 ng/well.

To determine potential competition between a number of anti-hCMV antibodies versus the anti-hCMV antibody Ab-50 for binding to gB protein, an ELISA was performed using a method similar to that described in Example 1. In brief, a sequential dilution of antibodies Ab-47, Ab-48, Ab-49, C23 (control), ITC52 (AD-1 specific), ITC88 (AD-2 specific), 89-104 (gH specific) or 89-109 (gH specific) was pre-incubated in PBS/2% FCS, with a constant concentration of Ab-50 (0.5 ng per well; termed 'Antibody Mixture') in a 96-well plate to prevent premature binding of gB by any of the investigated antibodies. In addition, five wells of Ab-50 alone at a concentration of 5 ng per well were prepared to determine the $OD_{450}$ of Ab-50 without a potential competing antibody. 96-well ELISA-plates (Nunc) were coated with 25 ng per well gB protein in carbonate buffer, p119.6 for 16 h at 4° C. The gB-coated plates were washed three times with PBS supplemented with 0.1% Tween (ELISA washing buffer) and blocked for 2 h with PBS/2% FCS (ELISA buffer) and washed again three times with ELISA washing buffer. Plates were then incubated with 50 µl Antibody Mixture diluted in PBS/2% FCS for 1 h at 37° C. Following a further washing step, the binding of Ab-50 was revealed using anti-λ-specific secondary antibodies coupled with peroxidase (antibodies-online.com). After a 1 h incubation period, unbound secondary antibody was removed by washing and the enzymatic activity was determined using tetramethylbenzidine (TMB) reagent at a concentration of 100 µl per well (1:1 mix of TMB peroxidase substrate and peroxidase solution B, (KPL, Inc., USA). After incubation for 5 min at room temperature, the reaction was stopped with 100 µl 1M phosphoric acid per well. Absorption (optical density (OD)) was detected at 450 nm using an Emax microplate reader and the software Softmax Pro 3.0 (Molecular Devices, USA) was used for analysis.

Where competition existed between the tested antibodies and Ab-50, a reduction of the $OD_{450}$ signal in each Antibody Mixture when compared to Ab-50 alone was observed. Additionally, a gB ELISA was performed with identical IgG-concentrations in order to visualise binding of all antibodies tested to gB. Here detection was performed using Fcγ fragment-specific secondary antibodies coupled with peroxidase (Jackson ImmunoResearch, USA). The results are shown in FIG. 4 and demonstrate that Ab-50 competes for binding to gB protein with antibodies Ab-47 and Ab-49. No competition was observed between Ab-48 and Ab-50 (FIG. 4a). In addition, no competition for binding to gB protein was observed between Ab-50 and antibodies ITC52 (AD-1 specific), ITC88 (AD-2 specific), 89-104 (gH specific), 89-109 (gH specific) (FIG. 4b), indicating that Ab-50 recognises a different epitope on hCMV than these antibodies and therefore does not bind to AD-1 or AD-2 on gB protein.

Example 9

Structural Model of hCMV gB

As there is currently no structural information available for the hCMV gB protein, a three dimensional model of the trimeric conformation of the ectodomain of HCMV gB strain AD169 (SEQ ID NO: 239) based on the crystal structure of HSV-1 gB was generated, which most likely represents the postfusion conformation (Heldwein et al., 2006). This model of the hCMV gB postfusion structure was generated by standard homology modelling procedures using the program MODELLER (Eswar et al., 2006), based on a sequence alignment with the template structure of HSV-1 gB (Heldwein et al., ibid).

Figure 3:
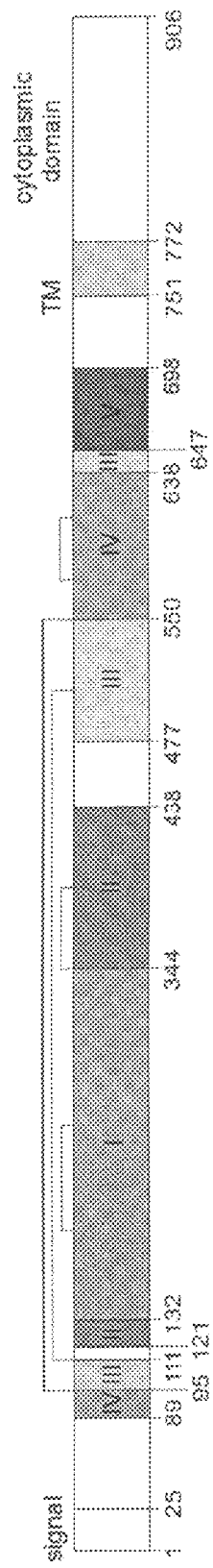
FIG. 3. Domain architecture of HCMV gB. The regions representing individual domains are displayed in different shades and the numbers of the starting residues are given. Brackets indicate disulfide bonds. Signal: signal sequence, TM: transmembrane domain.

Glycoprotein B (gB) is the most conserved of all herpes virus envelope glycoproteins, and protein sequences of HSV-1 and HCMV gB share 28% identity and 40% similarity. The hCMV gB monomer consists of 906 amino acids (gB strain AD169; SEQ ID NO: 239), of which almost the entire ectodomain (residues $Tyr_{89}$ to $Val_{700}$) is included in the model (FIG. 3). The individual domains I to V, which were previously defined based on the HSV-1 gB structure, can be clearly identified from the homology model of HCMV gB. Domain I (Dom I) ($Ile_{133}$ to $Thr_{343}$) constitutes part of the trimer interface and is located proximal to the membrane. The discontinuous Dom II is composed of residues $Leu_{121}$ to $Asn_{132}$ and $Cys_{344}$ to $Ser_{438}$ (FIG. 3). The flexible loops which may comprise residues $Val_{306}$ to $Glu_{317}$ and $Leu_{439}$ to $His_{468}$ are not included in the model, since they are not resolved in the template structure of HSV-1 gB. Dom III which may comprise three discontinuous segments, $Ser_{95}$ to $Cys_{111}$, $Asn_{477}$ to $Ser_{549}$, and $Leu_{638}$ to $Ser_{646}$ (FIG. 3). Like in HSV-1 gB, its long α helix forms, together with the respective segments from the other monomers, form the interface of the trimer. Dom IV ($Tyr_{89}$ to $Cys_{94}$ and $Cys_{550}$ to $Asp_{637}$) is located at the top of the molecule and contains the AD-1 epitope, while Dom V ($Met_{647}$ to $Asp_{698}$) represents the bridging element between the extracellular part and the transmembrane helix. The overall structure of the HCMV gB monomer and also the arrangement of the subunits in the trimer are thus suggested to be highly similar to that of HSV-1 gB, as would be expected from the degree of sequence similarity.

The HSV-1 gB crystal structure was chosen as template for the modelling studies, as two crystal structures of the gB-proteins from HSV-1 (Heldwein et al., ibid) and EBV (Backovic et al., 2009) already exist. Both these proteins display a sequence identity of 30% and show a highly similar tertiary structure. The sequence identity of hCMV gB to these two proteins of known structure is 28 to 33%, strongly suggesting that hCMV gB also shares the same three-dimensional fold. HSV-1 gB was chosen as a modelling template because the resolution of the crystal structure is significantly better than that of EBV gB. The resulting model of HCMV gB was found to exhibit a good local geometry and no steric clashes were detected. In addition, pairs of cysteines are located in disulfide-bonding distance indicating that not only the global structural features, but also local structural details were reflected correctly by the model. This model also provided the basis for the design of a construct that allowed the expression of Dom II as a single continuous peptide chain. For this domain, which is discontinuous in the primary amino acid sequence, a five-residue linker was designed to connect the two parts of the domain as described in Example 10 below.

Example 10 hCMV gB Protein Recognition by Human Sera

To investigate Dom I and Dom II for antibody binding, expression plasmids were constructed which allowed for the synthesis of either domain in eukaryotic cells. In both cases the cloning strategy involved the attachment of a HA-epitope tag at the amino terminus of the respective peptide in order to facilitate detection.

Example 10.1: Expression of hCMV gB Protein Dom II and Recognition by Human Sera Based on the structural model of hCMV gB, it was analysed, whether recombinantly expressed gB Dom II would be immunogenic during natural infection. To this end a eukaryotic expression vector was constructed which allowed the expression of Dom II in mammalian cells. Dom II is a discontinuous epitope that is generated by amino acids 121-132 and amino acids 344-438 of gB strain AD169 (SEQ ID NO: 239). To express Dom II, the nucleotide sequences coding for the gB-specific residues 121-132 and 344-438 were joined by a nucleotide stretch encoding a flexible five amino acid linker (Ile-Ala-Gly-Ser-Gly; SEQ ID NO: 319). This nucleotide sequence was inserted into the expression vector pcUL132sigHA, a pcDNA3.1-based vector containing the authentic signal sequence of the envelope glycoprotein gpUL132 of hCMV (amino acids 1-27; SEQ ID No: 320; Spaderna et al., 2005), followed by an influenza hemagglutinin (HA)-epitope tag (YPYDVPDYA; SEQ ID NO: 321). The Dom II encoding nucleotide sequence was inserted downstream of the HA-tag sequence using the restriction sites EcoRI and XbaI. Correct protein expression from the plasmid gives rise to a HA-tagged Dom II fusion protein, which is transported through the endoplasmic reticulum and trans-golgi network, and thus properly modified by glycosylation. The coding region for the linker-coupled discontinuous Dom II was chemically synthesized (GeneArt, Regensburg, Germany).

To analyse the Dom II peptide for antibody recognition, Dom II was transiently expressed in Cos7 cells and analysed for reactivity in indirect immunofluorescence using 13 sera from randomly selected hCMV-seropositive donors. Cos7 cells grown on glass coverslips in 24-well plates were transfected with 0.8 µg of the expression plasmid DNA encoding Dom II using Lipofectamine (Invitrogen, Karlsruhe, Germany). 48 h after transfection the cells were fixed and permeabilised with ice-cold methanol. Patient sera were then added as primary antibody. Unbound serum antibodies were removed by three washing steps using PBS. Binding of the primary antibody from human sera was detected with the appropriate secondary antibody conjugated with FITC (fluorescein isothiocyanate) (Dako, Hamburg, Germany). Counterstaining of cell nuclei was done with DAPI (4',6-diamidino-2-phenylindole). Images were collected using a Zeiss Axioplan 2 fluorescence microscope fitted with a Visitron Systems charge-coupled device camera (Puchheim, Germany). Images were processed using MetaView software and Adobe Photoshop. Antibodies: Controls: gB-specific human monoclonal antibody C23 (TI-23; Meyer et al., 1990), gN-specific murine monoclonal antibody 14-16A (Mach et al., 2000), and gH-specific murine monoclonal antibody SA4 (Urban et al., 1992), murine anti-HA (Sigma Aldrich, Steinheim, Germany), and murine anti-GST (BIOZOL, Eching, Germany). A plasmid expressing total gB (amino acids 1-906) served as additional control. While all of the sera showed a positive reaction with whole gB, only four out of 13 sera stained positive for Dom II. This demonstrates that Dom II is responsible for inducing antibodies during natural hCMV infection.

To test the frequency of patient sera containing antibodies directed against gB Dom II on a larger panel of human sera and to compare it to the frequency of sera containing antibodies against the known antigenic domains of gB, AD-1 and AD-2, the Dom II coding sequence was bacterially expressed as a GST-fusion protein, purified and used in ELISA. Plasmids for the expression of Dom II-GST (Glutathione-S-transferase) fusion proteins in E. coli were generated using the expression vector pGEX-6P-1 (Pharmacia Biotech, Freiburg, Germany). Plasmid DNA was used to transform E. coli DH10B for expression of GST fusion proteins. The respective fusion proteins were induced and the soluble form of the protein was purified from E. coli lysates according to the manufacturer's instructions. To prepare an affinity matrix, 2.6 mg of purified Dom II-GST fusion protein was dialysed against coupling buffer and conjugated to AminoLink Plus Coupling Resin (Thermo Fisher Scientific, Rockford, USA), according to the manufacturer's instructions. 4 ml of an hCMV hyperimmune globulin preparation, diluted 1:3 (v/v) with PBS, was passed over 2 ml antigen-coupled beads, followed by extensive washing with PBS. Bound IgG was eluted with 0.2M Glycine-HCl, pH 3.0, in 1 ml fractions and fractions were dialysed against PBS. Total IgG concentration was determined by an ELISA. In brief, polystyrene 96-well plates were coated with 100 ng AffiniPure goat anti-human IgG, Fcy-specific (Jackson Immuno Research, West Grove, USA) in 0.5M carbonate buffer, pH 9.6, overnight at 4° C. Serial $\log_2$ dilutions of the eluted fractions in a volume of 50 µl were added and bound IgG was detected by using a polyclonal peroxidase-conjugated goat F(ab)$_2$-fragment anti-human IgG, Fcy-specific (Jackson Immuno Research, West Grove, USA). A human IgG preparation (Jackson Immuno Research, West Grove, USA) with known concentration was used as standard.

Figure 5:
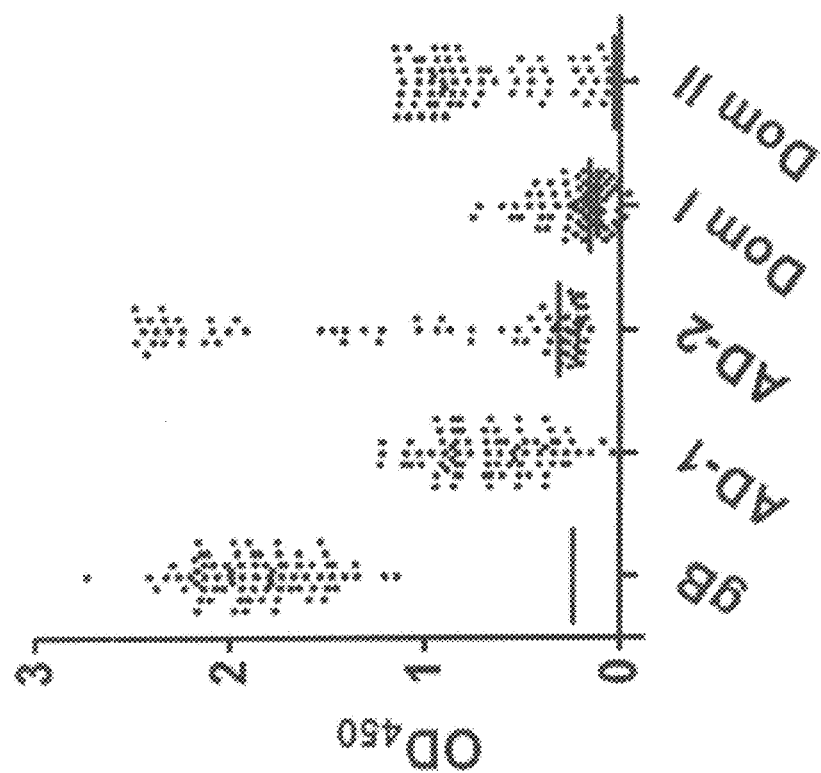
FIG. 5. Antibody titers in human sera against gB and gB fragments. Eighty randomly selected sera from HCMV seropositive individuals were analysed in an ELISA for reactivity against recombinant gB and the antigenic domains 1 (AD-1), 2 (AD-2), 4 (AD-4/Dom II) and 5 (AD-5/Dom I). The horizontal line represents the cut off for the individual antigens.

The purity of the Dom II-GST fusion protein was >90% as estimated from Coomassie staining of the protein following PAGE. A total of 80 randomly selected sera from hCMV seropositive individuals, as determined by a commercially available test, were analysed. Ten sera from hCMV negative donors served as negative controls. Within the serum panel from hCMV-seropositive individuals reactivity for gB was 100%, highlighting the high immunogenicity of this protein (FIG. 5). In accordance with Applicants' previous observations, positive reaction with AD-1 of gB was also 100%. 57% of the sera contained antibodies against AD-2 (Schoppel et al., 1996). The Dom II fusion protein was recognised by 94% of the sera. Thus, Dom II represents another highly immunogenic domain of gB. Since a procaryotically expressed fusion protein could be used as antigen, this would suggest that protein glycosylation is not essential for antibody binding. The differences in recognition frequency between the immunofluorescence analysis that was initially used for analysis of Dom II binding antibodies and the ELISA may be due to the different sensitivities of the assays.

For the sake of consistency in nomenclature of gB antigenic domains, Dom II was designated AD-4.

Example 10.2: Expression of hCMV gB Protein Dom I with a HA Tag and Recognition by Human Sera To express Dom I, the nucleotide sequence coding for amino acids 132-343 of gB strain AD169 (SEQ ID NO: 239) was inserted into expression vector pcUL132sigHA (described above) to generate the vector pcAD-5. To analyse the Dom I peptide for antibody recognition, Dom I was transiently expressed in Cos7 cells and analysed for reactivity by indirect immunofluorescence using the same method as that described in Example 10.1 above.

Dom I specific antibodies in human sera were measured in a capture ELISA. For recombinant antibody production, 293T cells in 75 cm$^2$ flasks were transfected with 20 µg of plasmid pcAD-5 DNA by calcium phosphate precipitation. The flasks were incubated for 6 days and then the cells and their supernatant were harvested. For the capture-ELISA, ELISA plates were coated with 125 ng/well of mouse anti-HA monoclonal antibody (Sigma), washed, blocked and washed again, as described in Example 8.3 above, and then incubated with supernatant of transfected 293T cells (containing HA-tagged Dom I) for 2 h at 37° C. Plates were then rinsed and incubated with human sera in a 1:50 dilution for 2 h at 37° C. Unbound antibody was removed by washing and peroxidase-conjugated anti-human or anti-mouse IgG (Dako, Hamburg, Germany) was added at an appropriate dilution for 1 h. The plate was then washed and 100 µl TMB peroxidase substrate diluted 1:1 in peroxidase substrate solution B (KPL, Inc., USA) was added for 5 min. The reaction was stopped by the addition of 100 µl 1M $H_3PO_4$ and the $OD_{450}$ was determined using an Emax microplate reader (Eurofins MWG Operon, Ebersberg, Germany). The plates were washed and developed as described in Example 10.1 above. All antibodies were diluted in PBS with 2% FCS. Antibody binding analysed by indirect immunofluorescence confirmed that the four antibodies tested (Ab-47. Ab-48, Ab-49 and Ab-50) were reactive with the Dom I-specific peptide (results not shown).

Having identified Dom I as a new target to neutralising antibodies, clonal antibody supernatants from four individuals were re-tested to obtain information about the overall frequency of Dom I specific antibodies in hCMV-infected individuals. The frequency of Dom I specific memory B cells was variable among different donors; however 100% of Dom I antibodies (6/6) that were tested, showed neutralising activity (results not shown).

To obtain information on the frequency of recognition of Dom I antibodies, antibody reactivity was determined against Dom I in a larger serum panel of hCMV-infected individuals and compared to known antigenic domains. As described in Example 10.1 above, a total of 80 randomly selected sera from hCMV seropositive individuals were analysed (FIG. 5). Dom I was recognised by 57% of the sera therefore indicating that this domain represents an antigenic domain on gB protein which induces antibodies with high frequency during infection.

For the sake of consistency in nomenclature of gB antigenic domains, Dom I was designated AD-5.

Example 11

Correlation between AD-4 (Dom II) Antibody Titer and Neutralising Capacity in Human Sera Data in the literature support the assumption that gB is one of the dominant antigens with respect to induction of neutralising antibodies during natural infection and a correlation between anti-gB titer and neutralisation capacity has been reported (Marshall et al., 1992). It is unclear whether this correlation resides on a variety of different antibody specificities directed against a number of different epitopes or whether a limited number of domains are responsible. To investigate whether Ad-4 (Dom II) specific antibodies contribute significantly to the overall neutralisation capacity of a given serum, Applicants determined the neutralisation titer in the serum panel and correlated it to the ELISA titer against recombinant gB, AD-1, AD-2 and AD-4, respectively. Proteins were diluted between 25 ng and 200 ng (depending on antigen) in 0.5M sodium carbonate buffer, pH 9.6, or in 6M urea (AD-1) and 50 µl was used to coat microtiter plates overnight at 4° C. All subsequent steps were carried out at room temperature. Reaction wells were rinsed with PBS supplemented with 0.1% Tween 20 and blocked for 2 h with PBS containing 2% FCS. Plates were again rinsed with PBS supplemented with 0.1% Tween 20 and incubated with monoclonal antibodies, human serum, polyclonal eluted antibody fractions or mouse serum (50 µl/well) for 2 h. Unbound antibody was removed by washing and peroxidase-conjugated anti-human or anti-mouse IgG (Dako, Hamburg, Germany) was added at an appropriate dilution for 1 h. The plate was washed and 100 µl tetramethylbenzidine (TMB) peroxidase substrate, diluted 1:1 in peroxidase substrate solution B (KPL, Inc., USA), was added for 5 min. The reaction was stopped by the addition of 100 µl 1M $H_3PO_4$ and the $OD_{450}$ was determined using Emax microplate reader (Eurofins MWG Operon, Ebersberg, Germany). Dilution of all antibodies was done in PBS with 2% FCS. In all assays involving gB fusion proteins, the respective prokaryotic fusion partner was assayed in parallel and the optical density subtracted from values obtained with the gB-fusion protein.

Figure 6:
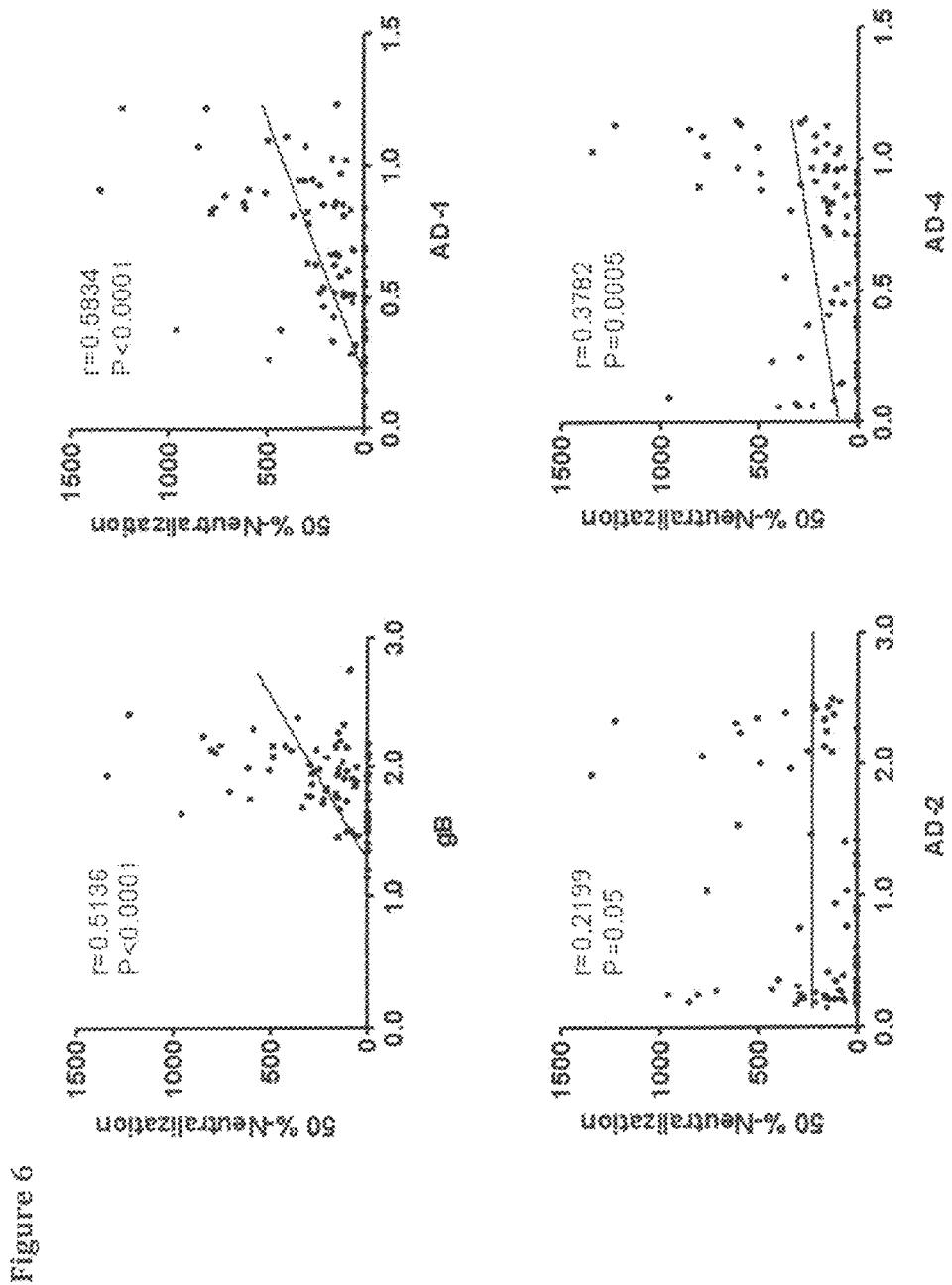
FIG. 6. This figure shows the correlation between antibody titer against the different antigenic regions (as measured by ELISA) and 50% neutralisation titer. r: Spearman rank correlation coefficient.

As reported previously, there was a correlation between recognition of gB in ELISA and neutralisation capacity (Marshall et al., ibid). The analysis also showed statistically significant correlation between neutralisation capacity and antibody binding titer against AD-1 and AD-4 (Dom II) but not AD-2 (FIG. 6).

Example 12

AD-4 (Dom II) Induces Virus Neutralising Antibodies During Natural Infection

To investigate in more detail the question of whether AD-4 induces virus neutralising antibodies during natural infection Applicants used two approaches: First, Applicants isolated polyclonal anti-AD-4 antibodies from a pooled human IgG preparation using the purified AD-4-GST (Dom II-GST) fusion protein as affinity matrix. As expected, the pooled human IgG preparation contained antibodies reactive with a number of different hCMV-specific envelope glycoproteins in indirect immunofluorescence analysis following transient expression of the respective glycoprotein complexes in Cos-7 cells.

Second, Applicants tested the gB-specific human monoclonal antibodies disclosed in this invention for binding to AD-4. All of the recombinant antibodies were found to bind to AD-4 in indirect immunofluorescence using the transiently expressed AD-4 protein in Cos7 cells. Therefore, AD-4 represents a conformational epitope that is recognised by the human monoclonal antibodies disclosed in this invention.

Figure 7A:
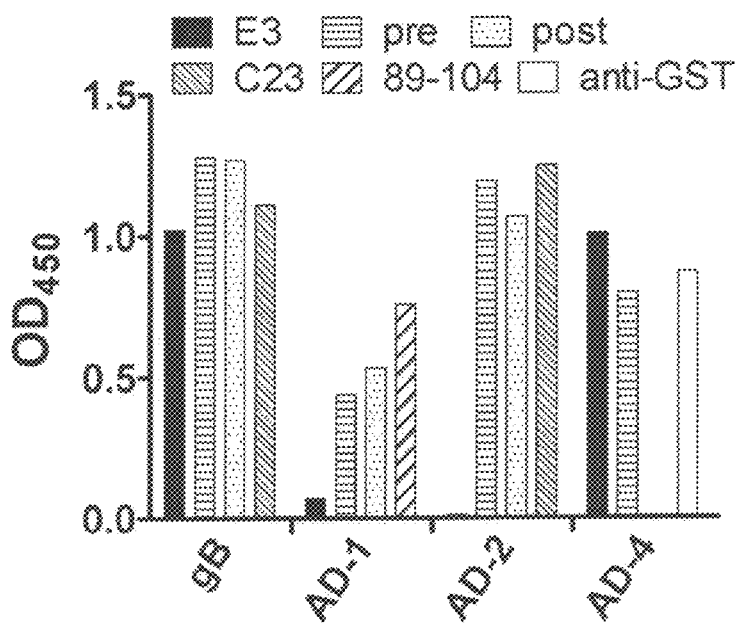
FIG. 7. Specificity and neutralisation capacity of affinity purified anti-AD-4 polyclonal antibodies. a) ELISA plates were coated with gB, AD-1, AD-2 and AD-4 respectively, and tested with various antibodies. E3: affinity purified IgG fraction; Pre: serum pool before affinity purification; Post: serum pool after affinity purification; C23: human AD-2-specific monoclonal antibody; 89-104: human anti-AD-1 specific monoclonal antibody; anti-GST: murine monoclonal antibody specific for GST. b) Neutralising assay using the serum pool, the human monoclonal antibody C23 and the affinity purified AD-4 specific IgG fraction (E3).
Figure 7B:
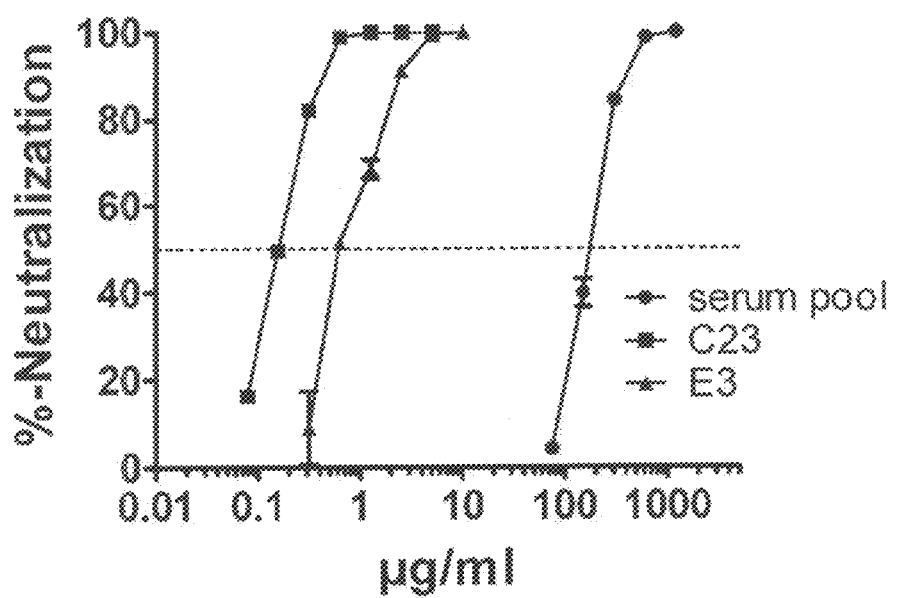

To prepare a matrix for the isolation of AD-4-specific antibodies, 2.6 mg of the purified AD-4-GST fusion protein was covalently coupled to Sepharose and used to affinity purify AD-4-specific IgG from 4 ml of the human IgG preparation. A total of 127 µg IgG was obtained. ELISA tests verified that the affinity purified IgG fraction (E3) showed specific binding to AD-4 and gB but not to AD-1 and AD-2 (FIG. 7*a*). To further exclude contamination of the affinity purified AD-4 antibodies with antibodies directed against additional neutralisation-relevant antigens on hCMV Applicants performed indirect immunofluorescence analysis with Cos7 cells transiently expressing gH or the gM/gN complex; viral envelope proteins which are known to induce neutralising antibodies during natural infection (Shimamura et al., 2006; Urban et al., 1996). The purified polyclonal anti-AD-4 IgG fraction did not contain detectable antibodies specific against non-gB envelope complexes. Moreover, the IgG fraction was free of IgM (not shown). The affinity purified IgG preparation (E3) was then tested in neutralisation assays. 50% neutralisation of virus infectivity was achieved at IgG concentrations of approximately 0.2 µg/ml, which is within the range of the potent gB-specific human monoclonal antibodies disclosed in this invention (FIG. 7*b*). In comparison, the original serum pool from which the affinity purified IgG fraction was derived showed 50% neutralisation of input virus at approximately 200 µg/ml IgG (FIG. 7*b*). In summary, these data provide further evidence that AD-4 not only represents a highly immunogenic domain of gB, but it is also the target of virus neutralising antibodies.

Example 13

Specificity of Human Recombinant Antibody Binding 13.1: Fine Specificity of Human Recombinant Antibodies Binding to AD-4

Figure 8:
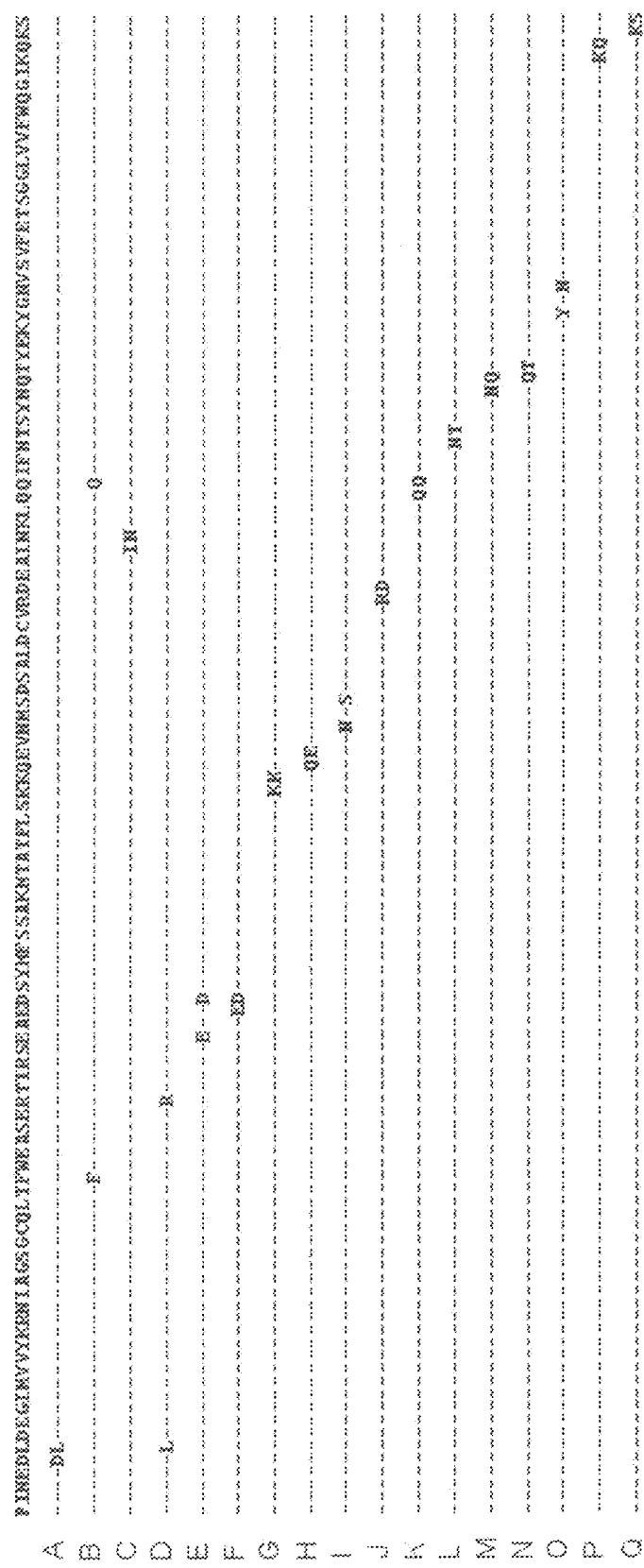
FIG. 8. This figure shows the amino acid sequence of AD-4 and mutant proteins. The amino acid sequence of AD-4 as used for the mammalian cell expression is shown in the top lane. Residues that were exchanged to alanine are indicated in lanes A-Q. Dashes indicate identity with the wild type sequence.
Figure 9A:
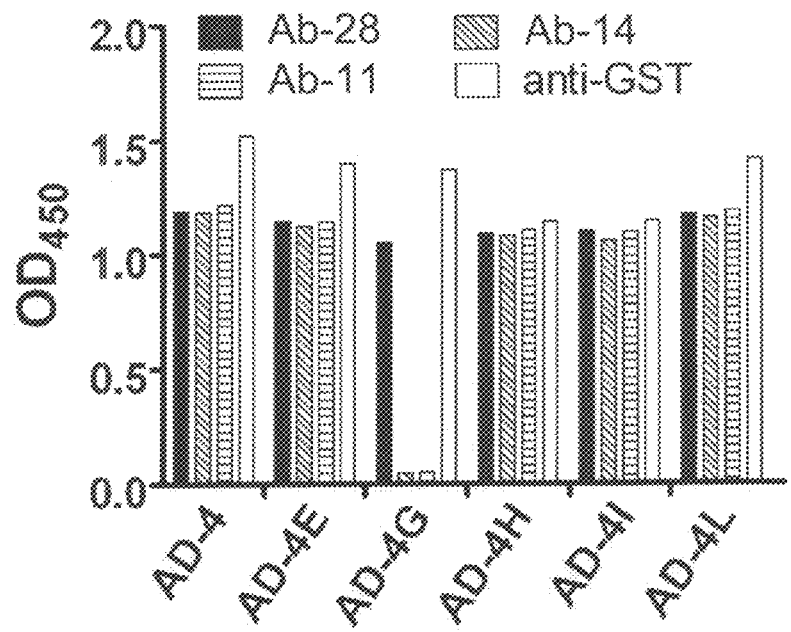
FIG. 9a) or the affinity purified IgG fraction (E3.
Figure 9B:
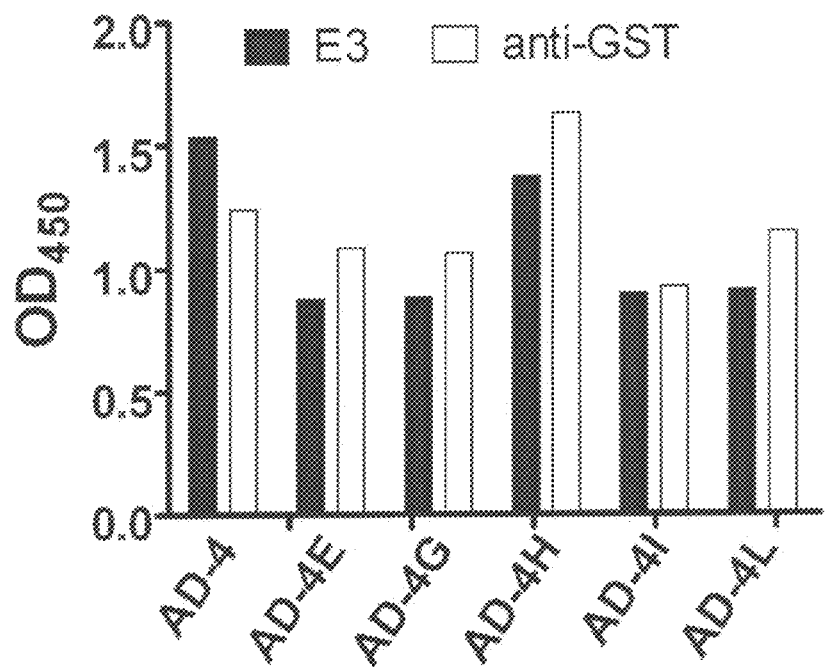
FIG. 9b). An anti-GST antibody was used to control for coating efficiency of the antigens.
Figure 10:
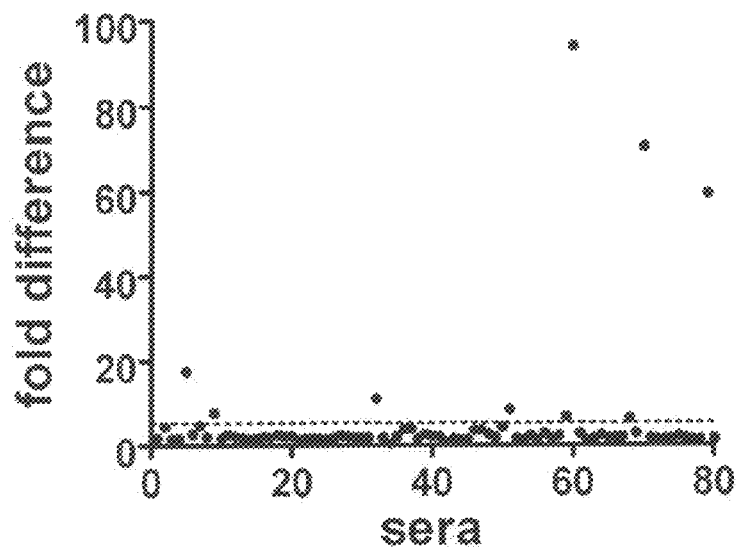
FIG. 10. Recognition of AD-4 mutants by human sera. The serum panel (80 specimens) was tested in an ELISA against GST fusion proteins containing AD-4 or the mutant peptides AD-4G (K378K379), AD-4H (Q380E381), AD-4E (E359D362), AD-4I (N3835385) and AD-4L (N405T406), respectively. For each serum a ratio was calculated between the highest and lowest OD value and plotted as fold difference. The dotted line represents the mean difference of all serum samples.
Figure 11:
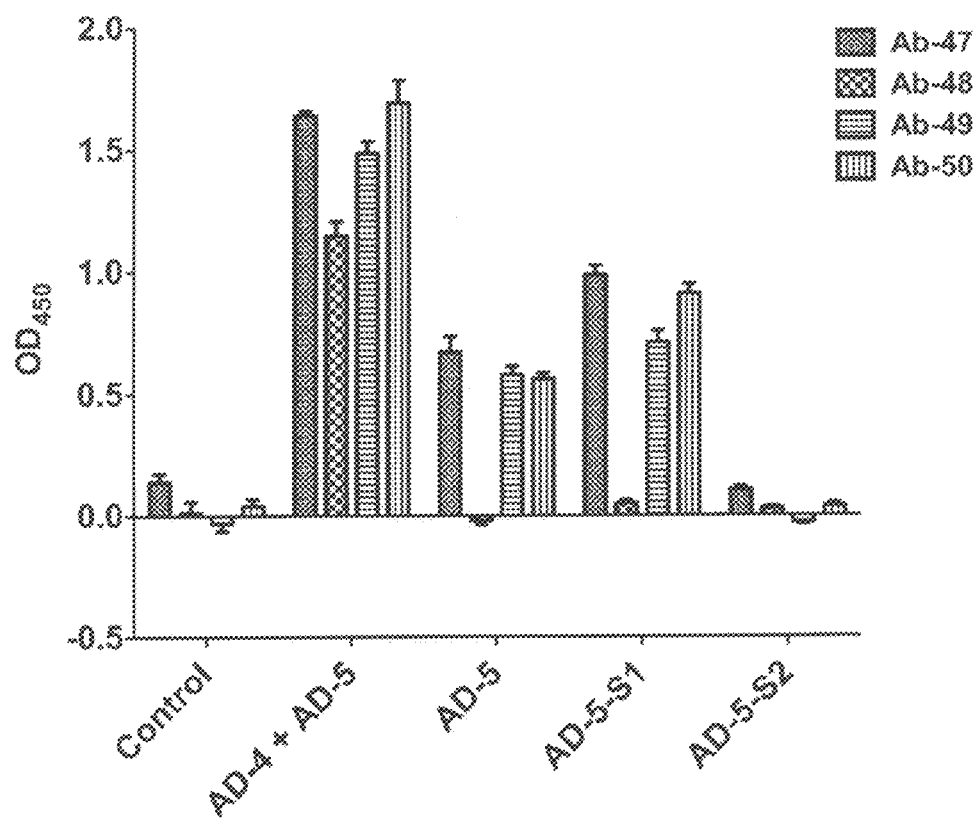
FIG. 11. This figure shows the results of a capture-ELISA determining antibody recognition of gB protein antigenic domains and subdomains. 293T cells were transfected with Control (pcUL132SigHA), AD-4+AD-5, Subdomain 1 of AD-5 (AD-5-S1) or Subdomain 2 of AD-5 (AD-5-S2). Antibodies Ab-47 to Ab-50 were used for detection. Results were detected by indirect immunofluorescence.

The size of AD-4 (>100 amino acids) is large enough to harbour several antibody binding epitopes. Close proximity of epitopes that can be bound by neutralising and non-neutralising antibodies have been found for AD-1 and AD-2 of gB and have been implicated as a mechanism to evade effective virus neutralisation. Thus, it was of interest to obtain more information on potential epitopes within AD-4. Initial attempts to shorten AD-4 by omission of amino acids 121-132 at the amino terminal end or the last five amino acids at the carboxy terminal end resulted in complete loss of antibody binding indicating that only the entire domain is capable of forming the antibody binding structure. To identify potentially critical antibody contact residues within AD-4, a number (n=17) of eukaryotic expression plasmids was constructed which expressed AD-4 mutant peptides, in each of which two adjacent surface exposed residues were changed to alanine (FIG. 8). Surface exposure of residues was identified from the hCMV gB model as described in Example 9.

When the human monoclonal antibodies Ab-11, Ab-14, and Ab-28 were tested in indirect immunofluorescence, following transient expression of the respective mutant AD-4 proteins, two patterns of recognition were found. Antibody Ab-28 bound to all AD-4 mutant proteins, whereas the remaining antibodies did not recognise the mutants in which the lysine residues 378 and 379 were exchanged for alanine. This proves that AD-4 is recognised by the recombinant human monoclonal antibodies disclosed in this specification.

In addition, these data indicate that the di-lysine sequence (K378K379) within AD-4 represents a critical antibody binding site. However, the signals obtained in indirect immunofluorescence are difficult to quantify and there was a possibility that the lack of reaction with the AD-4G mutant peptide was just reflecting reduced binding of antibodies below the detection limit of the assay. Thus, to obtain more quantitative data and to confirm the results obtained by indirect immunofluorescence, five of the AD-4 mutant proteins were expressed as GST-fusion proteins, purified and used in an ELISA. Purity of the GST-fusion proteins was comparable for all peptides to the wild type AD-4 shown above in FIG. 5. Besides the AD-4G (K378K379) mutant, the fusion proteins included AD-4H (Q380E381), AD-4E (E359D362) and AD-4I (N383S385), which affect sterically adjacent residues, as well as the more distantly located mutant AD-4L (N405T406). The results obtained by the ELISA were in accordance with the immunofluorescence data. With the exception of AD-4G, the mutant proteins were recognised by the monoclonal antibodies with comparable efficiency. AD-4G however, was only recognised by Antibody Ab-28 (FIG. 9*a*). Interestingly, the affinity purified IgG fraction showed similar reactivity with all AD-4 fusion proteins indicating that the majority of antibodies bound independently of the AD-4G mutation (FIG. 9*b*). The affinity purified IgG preparation was derived from a serum pool of an unknown number of donors and thus individual differences in the recognition of the AD-4 epitopes would expect to be averaged.

To obtain more information of potential AD-4 epitope specificity, Applicants tested whether the two lysines at positions 378 and 379 are also important residues for reactivity with antibodies present in individual human sera. To this end, the five AD-4 mutant peptides were tested with the same serum panel as above and a quotient was calculated between the lowest and highest absorbance value for each serum. As can be seen in FIG. 10, most sera recognised the five AD-4 peptides with similar efficiency resulting in a low maximal difference of 1 to 5 fold. However, five sera showed maximal differences in the range of 10 to 100 fold. Interestingly, the difference was due to a reduced recognition of the mutant protein AD-4G with one exception. The serum with the highest maximal difference showed reduced binding to the mutant protein AD-4H (Q380E381), which in the 3D model of AD-4 is situated in close proximity to the di-lysine motif in AD-4G (K378K379). Thus, although binding of a few sera showed almost complete dependence on the original gB peptide sequence between 378 and 381, recognition of AD-4 by individual human sera was to a large extent independent of this sequence. In line with this result was the finding that IgG fractions that were affinity purified using the AD-4G mutant protein as antigen had a similar recognition pattern in ELISA of AD-4 mutant proteins and comparable neutralisation titer as IgG purified on AD-4 wild type.

13.2: Fine Specificity of Human Recombinant Antibodies Binding to AD-5 (Dom I)

Similar experiments to those described in Example 13.1 above could not be performed with AD-5 (Dom I) because, in contrast to AD-4, AD-5 does not fold correctly after prokaryotic expression and therefore antigen for affinity purification could not be generated. However, it was possible to subdivide AD-5 into two domains, which were then tested for antibody recognition. Based on structural information, AD-5 was divided into Subdomain 1 (AD-5-S1), which comprised amino acids 133-144 and 251-343 of gB protein AD169 (SEQ ID No: 239) and Subdomain 2 (AD-5-S2), which comprised amino acids 140-255 of gB protein AD169 (SEQ ID No: 239).

In order to determine whether the AD-5 antibodies described in the present invention recognised these subdomains, a capture ELISA was performed as described in Example 10.2 wherein 293T cells were transfected with subdomains AD-5-S1 and AD-5-S2, as well as AD-4+AD-5. Recombinant AD-5 antibodies Ab-47 to Ab-50 were used for detection rather than patient sera. Results of indirect immunofluorescence performed showed that antibodies Ab-47 and Ab-50 recognised AD-5-S1 (results not shown). Results from the capture ELISA are shown in FIG. 11, and these show that all of antibodies Ab-47 to Ab-50 recognise gB AD-4+AD-5 and that antibodies Ab-47, Ab-49 and Ab-50 recognise gB AD-5 and in particular AD-5-S1. None of antibodies Ab-47 to Ab-50 recognised gB AD-5-S2. From these results it can be deduced therefore that antibodies Ab-47, Ab-49 and Ab-50 recognise an epitope on gB protein that is located in AD-5-S1, i.e. within amino acids 133-144 and 251-343 of gB protein (strain AD169; SEQ ID No: 239).

Example 14

Model of a Prefusion Conformation of hCMV gB

Within the structure of hCMV gB that was modelled according to HSV-1 gB, AD-4 is situated at a hump in the middle of the molecule. The di-lysine motif is easily accessible at the surface. In the absence of data on the orientation of AD-4 binding antibodies in the 3D space it can be predicted that antibody binding in this protein conformation may influence the interaction of gB with neighbouring proteins. For a number of herpes viruses, including hCMV, it is known that gB needs to interact with additional envelope glycoproteins in order to properly function during the fusion process (Avitabile et al., 2009; Patrone et al., 2007). Most probably, however, the HSV-1 gB represents the postfusion conformation. This assumption is based on the structural homology of HSV-1 gB to VSV-G for which both post- and prefusion structures are available (Roche et al., 2006 & 2007). It is thought that the prefusion form is prevalent on the virion whereas the postfusion form resides mainly in some, as yet unidentified, cellular compartment. AD-4-specific antibodies can apparently recognise both gB conformations since they bind to cellular as well as viral forms of gB. Since for VSV-G the pre- and postfusion forms show extensive structural rearrangements of individual protein domains Applicants modelled the prefusion form of HCMV gB in order to gain more insight into the potential localisation of AD-4 within the prefusion trimer and the position of the residues which are important for antibody binding.

Single hCMV gB domains I, II, III and IV were taken from the postfusion model and superimposed on the prefusion structure of VSV-G (Roche et al., 2007) using the MultiProt algorithm (Shatsky et al., 2004). HCMV gB domain V and residues Leu469 to Arg496 of domain III were excluded, since they are not globular and there are no equivalent structures present in the VSV-G template. Connection loops between the individually fitted domains were modelled with ModLoop (Fiser et al., 2003). The trimeric prefusion model was obtained by applying the VSV-G prefusion geometry.

While the postfusion conformation of hCMV gB can readily be modelled based on the homologous crystal structure of HSV-gB, there is no experimental structural information yet available for the prefusion conformation of this family of molecules. From the two conformations of VSV-G it is known that the individual protein domains keep their folds but the relative arrangement of the domains drastically changes upon transition between pre-fusion and post-fusion state. In order to gain further insights into the potential localization of AD-4 within the pre fusion trimer and the position of the residues, which are important for antibody binding, a hypothetical model of the hCMV gB prefusion conformation was created. To this end, the individual domain folds were obtained from the postfusion model and employed information about the domain arrangement from the prefusion structure of glycoprotein G from VSV-G (Roche et al., ibid). The resulting model exhibits no steric clashes and the linking sequences are sufficiently long to connect the domains in this alternative geometry suggesting that this domain arrangement is structurally feasible in hCMV gB. The domain arrangement of the hCMV gB prefusion structure is highly similar to that of a previous model of the EBV gB pre-fusion conformation that was generated based on the respective post-fusion crystal structure (Backovic et al., 2009).

A key difference between the pre-fusion and post-fusion conformation of hCMV gB is found in the composition of the apical part of the protein. In the post-fusion conformation this region is formed by domain IV, in which AD-1 is located. In contrast, in the pre-fusion model Dom II/AD-4 is situated on top of the molecule, with the di-lysine motif (Lys378, Lys379) being located in a central position on the apical surface of Dom II/AD-4. Thus, the spatial organisation of bound IgG molecules to the pre-fusion form of gB is likely to be different from the post-fusion form and may interfere with binding of gB to components of the target cell. Apart from blocking interactions with non-gB molecules, IgG molecules bound to Dom II/AD-4 may also be capable of constraining the conformational changes within the protein that may be necessary for proper function.

Example 15

Neutralisation Assays in the Presence of Human Sera

In a clinical setting, the antibodies of the present invention may be administered prophylactically or therapeutically by means of intravenous infusion. Therefore the possibility that antibody function is impaired by the presence of antibodies in human serum, needs to be excluded. Three different types of sera were examined: serum negative for hCMV-specific antibodies, serum positive for hCMV-specific antibodies and INTRATECT® (human normal immunoglobulin, Biotest AG), a hCMV serum preparation enriched with CMV-specific antibodies. First the IgG concentration and the 50% neutralising activity of each analysed serum was determined by titration. Briefly, ELISA plates were coated with anti human IgG, Fcγ fragment-specific catching antibody (Jackson ImmunoResearch, USA). Two-fold serial dilutions of sera in ELISA buffer were compared to an IgG standard of known concentration (Jackson ImmunoResearch, USA). The IgG-concentration was calculated using the ELISA software Softmax Pro 3.0 (Molecular Devices, Sunnyvale, Calif., USA). The 50% neutralization activities of the sera were determined by performing a luciferase-based neutralization assay as described above in Example 2.

Figure 12:
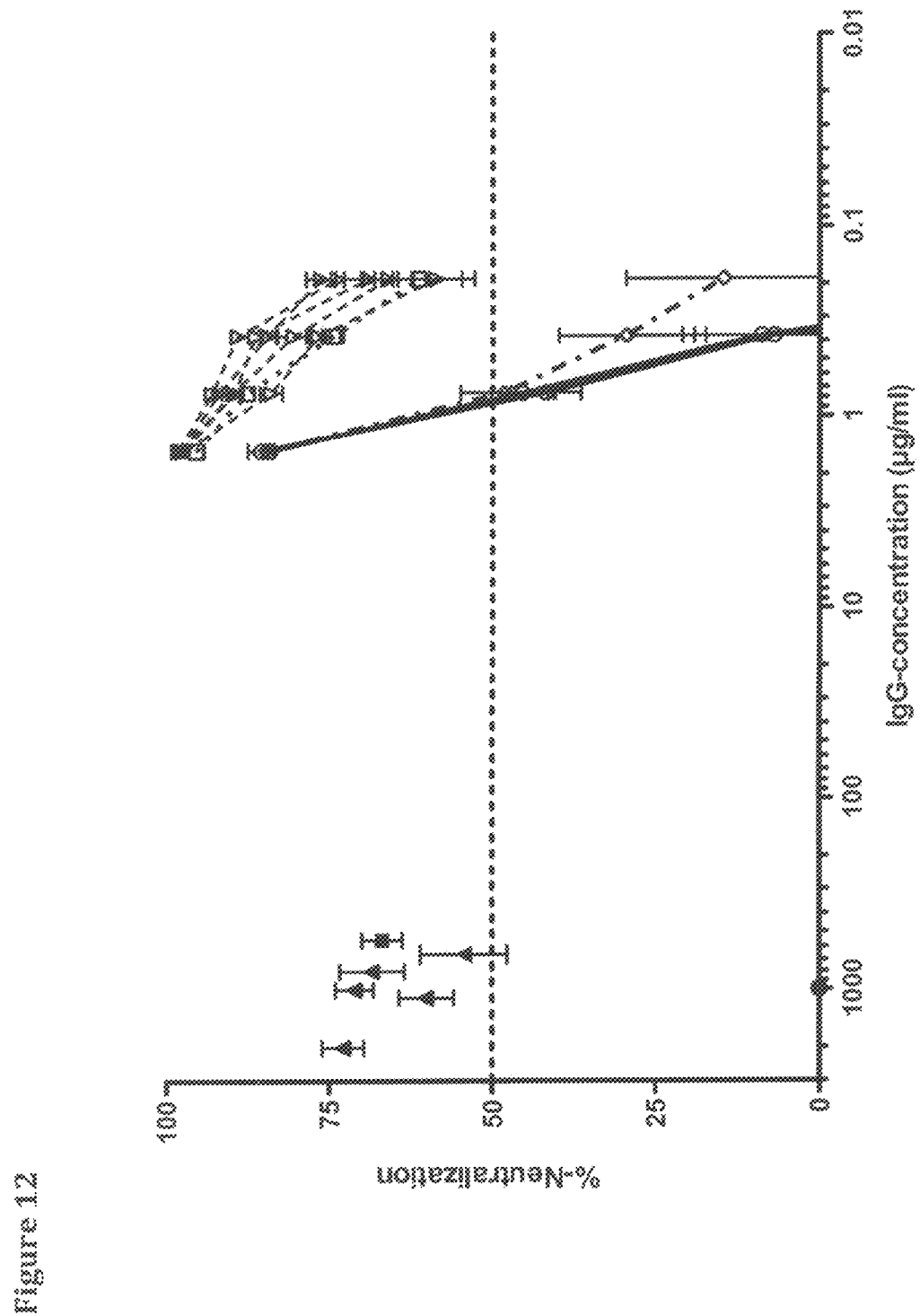
FIG. 12. Competitive neutralisation assay with the neutralising antibody Ab-28 and different human sera. The data on the left side of the graph represent triplicates of different hCMV-positive sera and hCMV-negative sera (on the x-axis) applied at a constant concentration around their 50% neutralising activity. The curves on the right side of the graph represent a combination of titrated Ab-28 with hCMV-positive or hMCV-negative sera added at a constant concentration identical with that concentration represented by the data on the left side of the diagram. All curves reflect the IgG-concentration of Ab-28 alone without adding the constant IgG-concentration of the sera. All samples were analysed in triplicate. Legend: ● constant concentration of hCMV-negative serum; ▲ constant concentration of hCMV-positive serum; ■ constant concentration of INTRATECT® (human normal immunoglobulin); ○ titrated Ab-28 with a constant concentration of hCMV-negative serum; ▼ titrated Ab-28 with a constant concentration of hCMV-positive serum; □ titrated Ab-28 with a constant concentration of INTRATECT® (human normal immunoglobulin); ◊ titrated Ab-28 alone.

Next, in a competitive neutralisation assay as previously described in Example 2, antibody Ab-28 was titrated so that it would cross the 50% neutralisation mark, prior to the addition of serum at a constant concentration. Sera that were either negative or positive for hCMV-specific antibodies and INTRATECT® (human normal immunoglobulin) were added to the titrated Ab-28 at a constant concentration around their respective 50%-neutralising activities. As is shown in FIG. 12, there appeared to be no inhibition of Ab-28 neutralising potency by serum antibodies. After adding hCMV-negative serum to titrated Ab-28, the curve looked identical to the curve of Ab-28 alone. This result indicates that there is no unspecific reagent in human serum that might impair the neutralising capacity of Ab-28. When adding hCMV-positive serum or INTRATECT® (human normal immunoglobulin) to Ab-28, an enhancement of both Ab-28 and serum neutralising activity was observed. Serum neutralising activity was increased by about 20-40% in the presence of Ab-28 and the neutralising capacity of Ab-28 was increased by about 15% after the addition of hCMV positive sera or INTRATECT® (human normal immunoglobulin).

Example 16

Post-adsorption Neutralisation Assay

Figure 13:
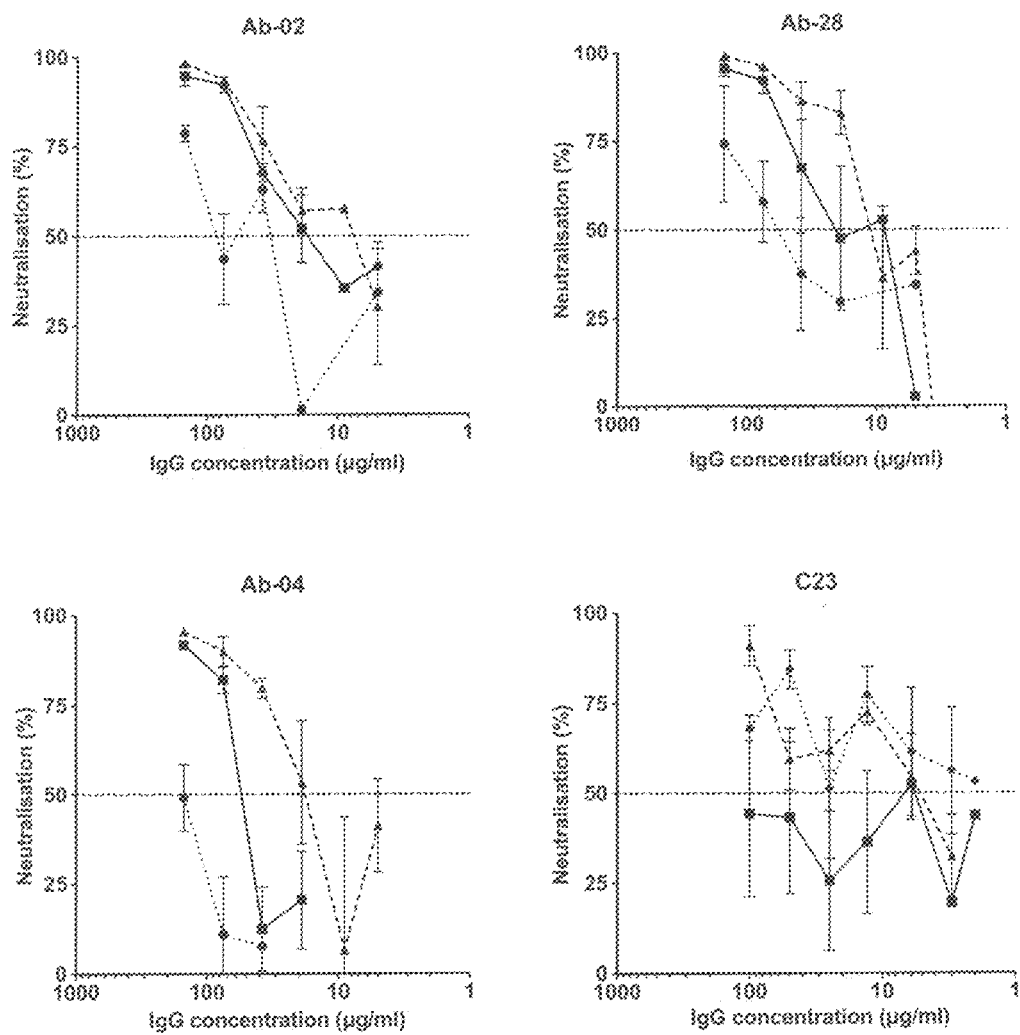
FIG. 13. Post-adsorption assay with Ab-02, Ab-04 and Ab-28. hCMV virus was allowed to adsorb but not to penetrate into human foreskin fibroblasts for 1 h at 4° C. and then antibodies Ab-02, Ab-04 or Ab-28 were added and allowed to incubate for a period of either 30, 80 or 120 mins at 4° C. 1:2 serial dilutions from 150 to 5 μg/ml were performed for each antibody in triplicate. C23 (AD-2 specific antibody) was used as a control antibody for inhibition of virus penetration into cells. The x-axis shows IgG concentration (μg/ml) and the y-axis shows %-neutralisation. Legend: ● 30 min incubation period; ■ 80 min incubation period; ▲ 120 min incubation period.

To determine whether the antibodies of the present invention might block an early stage of virus penetration into cells, Applicants performed a post-adsorption neutralisation assay. The method of the neutralisation assay was similar to that described in Example 2; however initially HFFs and the luciferase expressing hCMV were incubated for 1 h at 4° C. to allow only virus adsorption but not fusion of virus- and cell membrane. After this adsorption period, non-adsorbed virus was washed away with 1×PBS. The antibodies were titrated from very high IgG-concentrations of 150 µg/ml to 5 µg/ml in a separate plate and then added to the pre-adsorbed virus-cell mixtures. Antibodies Ab-02, Ab-28, Ab-04 and a control antibody C23 (T123; a kind gift from Teijin Pharma Limited, Japan) were used for this experiment and each antibody was incubated for 30, 80 or 120 min at 4° C. with the pre-adsorbed virus-cell mixtures. The AD-2-specific antibody C23 has been shown to inhibit virus penetration into cells (Ohizumi et al., 1992). After the 30, 80 or 120 min incubation periods, plates were washed once more and then incubated for 48 h at 37° C. From this point on, the assay was continued as per Example 2. The results are shown in FIG. 13 and are summarised as follows. After an incubation period of 30 min, at least 100 µg/ml of each antibody was required to achieve 50% reduction of virus infectivity. C23, on the other hand, appeared to inhibit virus penetration even at very low concentrations of 5 µg/ml after an incubation of 30 min. After 80 min only 20 µg/ml of Ab-02 and Ab-28 was needed for 50% neutralization. For Ab-04 however, 55 µg/ml was required to neutralize virus infectivity by 50%. The 80 min curve of the control antibody C23 did not show the expected result. It would be expected that this antibody would be at least as good, if not better after a longer incubation time. Also, the standard errors of the mean were very disperse for C23 at the 80 min incubation period and therefore this time point was excluded from the results. When incubating the pre-adsorbed virus with the antibodies for 120 min only around 5-15 µg/ml of each antibody or C23 is required for a 50% reduction of viral infectivity. In conclusion, the antibodies Ab-02, Ab-28 and Ab-04 are able to prevent penetration of already adsorbed virus into cells.

Example 17

Competitive Neutralisation Assays with other gB-specific Antibodies

Figure 14:
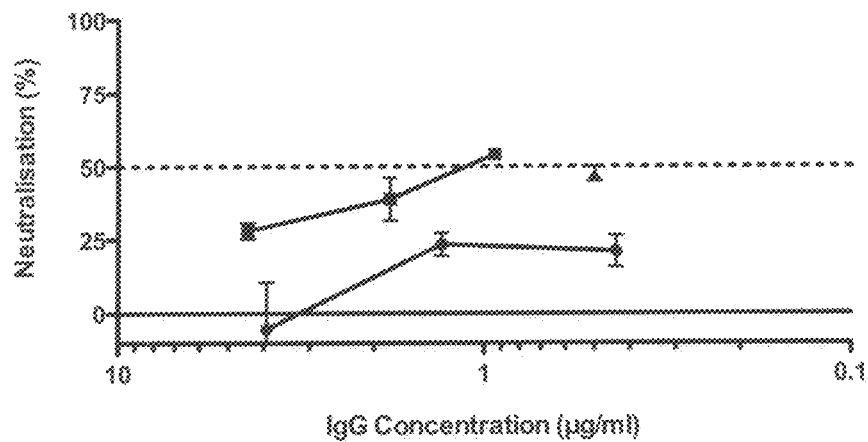
FIG. 14. Representative competitive neutralisation assay between AD-1 and AD-2-specific antibodies and Ab-28. As shown, ITC52 (an AD-1 specific antibody) or ITC88 (an AD-2 specific antibody) were titrated in the absence (●) or presence (■) of Ab-28, respectively. Ab-28 was added to the titrated antibody at a constant concentration of 0.5 µg/ml (▲).
Figure 14:
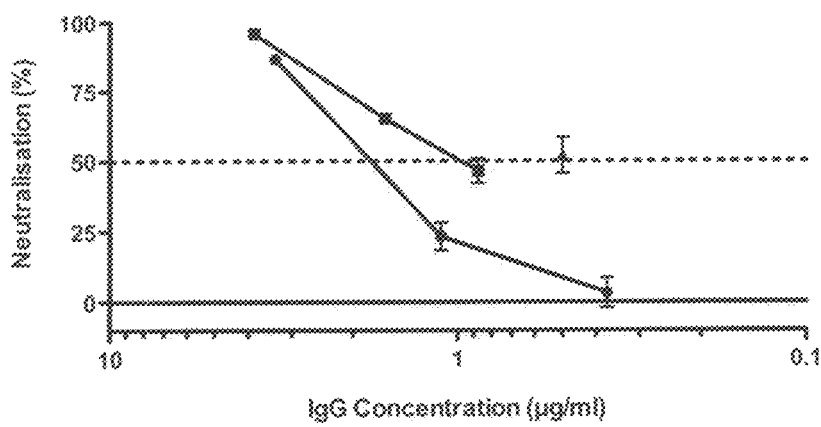
Figure 14:
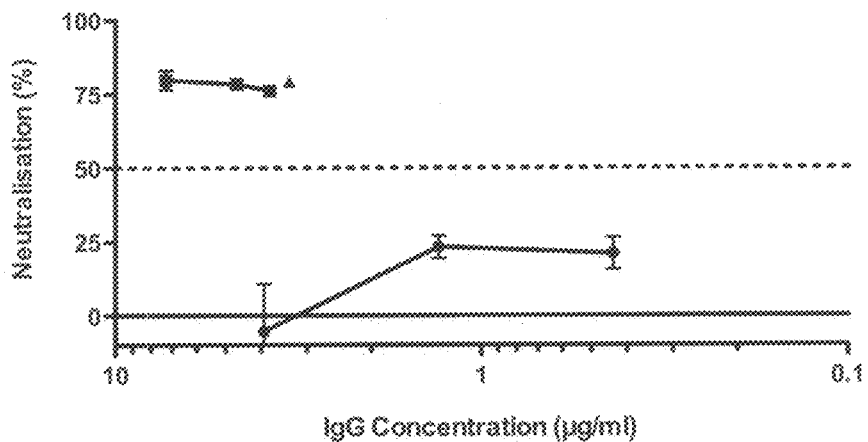

Competition for gB-epitope binding between neutralizing and non-neutralizing antibodies has been reported for AD-1-specific antibodies (Ohlin et al., 1993). To investigate possible competitive or even synergistic effects between antibodies of the present invention and other gB-specific antibodies, competitive neutralization assays were performed to determine the effect of AD-1 (ITC52) and AD-2-specific (ITC88) antibodies on the neutralizing activity of the antibodies of the present invention. To do this, one antibody was titrated and the other antibody added at a constant concentration around its 50%-neutralizing activity. These competitive neutralisation assays were conducted with each of the antibodies: Ab-11, Ab-14, Ab-19, Ab-28, Ab-04, Ab-42. Two different approaches were compared whereby the test antibody was titrated and ITC52 or ITC88 were added at a constant concentration or the ITC-antibodies were titrated and the test antibody was added at a constant concentration. Since ITC52 is a non-neutralizing antibody, it was added at a concentration of 3 µg/ml, the same concentration at which the neutralizing antibody ITC88 was added. Only the data for Ab-28 are shown, since the other antibodies tested behaved similarly. Also, only one approach is shown, namely leaving Ab-28 at a constant concentration and titrating the ITC-antibody, because the alternative approach showed comparable results (FIG. 14).

The results indicate that there appears to be a slight impairment of Ab-28's neutralizing activity in the presence of a high concentration of the AD-1-specific antibody ITC52. This effect was observed for each antibody tested and has been reproduced in a further independent experiment (data not shown). However, a high concentration of ITC52 appears not to decrease the neutralization activity of ITC88. Ab-28 and ITC88 together resulted in an improved neutralization activity. This is particularly visible at the second data point of ITC88 alone as opposed when mixed. A 40% increase of ITC88's neutralizing activity in the presence of Ab-28 is observed at this point with Ab-28 also showing an increase in neutralisation of around 15% with ITC88 than by itself.

Figure 15:
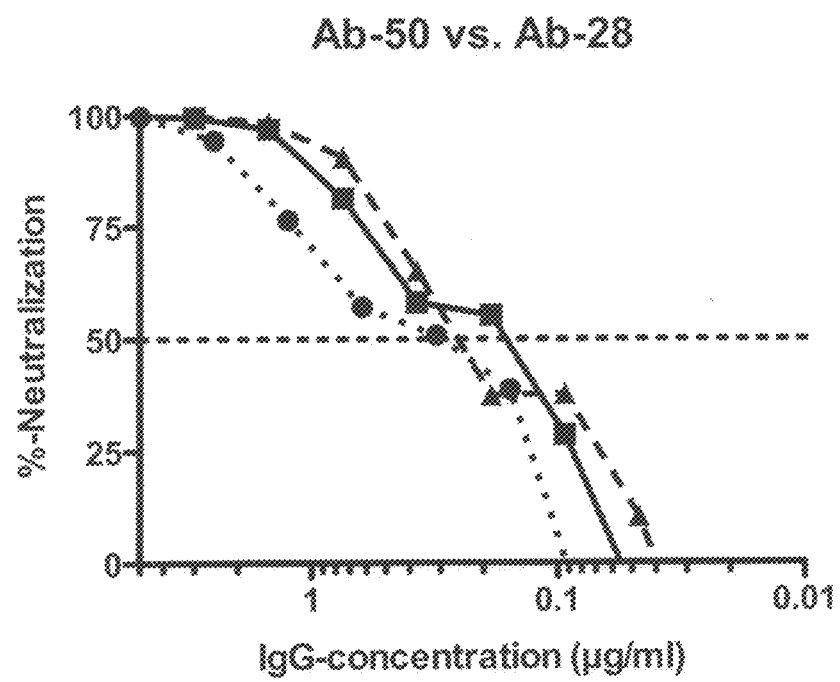
FIG. 15. Competitive neutralisation assay between AD-4-specific and AD-5-specific antibodies.
Figure 15:
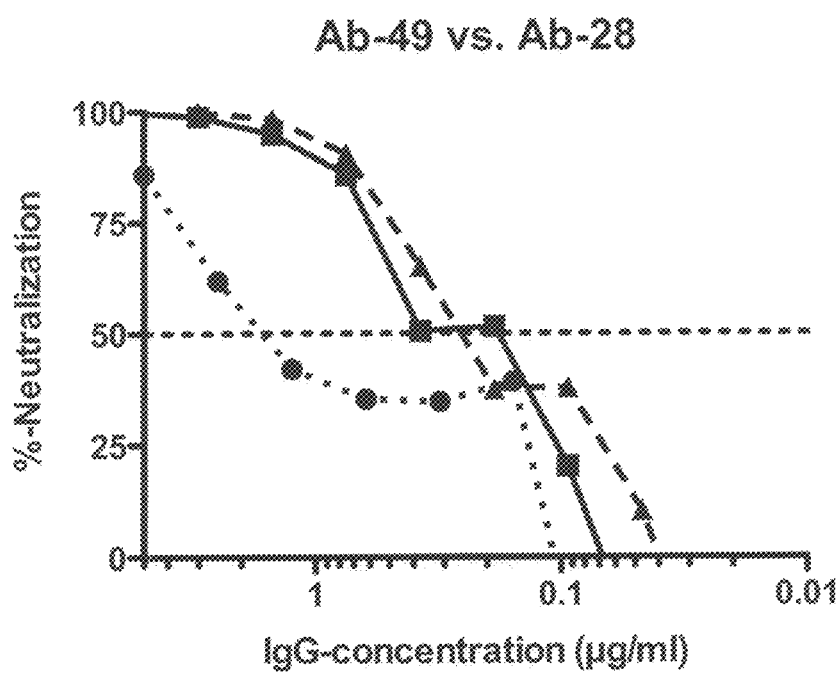

In addition to the above experiment analyzing potential inhibitory, additive or synergistic effects between different AD-4-specific antibodies and AD-1 or AD-2-specific antibodies, Applicants also investigated whether similar effects could be observed between AD-4 (Dom II) and AD-5 (Dom I)-specific antibodies. Ab-28 (AD-4-specific) was mixed with either Ab-50 or Ab-49 (AD-5-specific) in a ratio of 50:50 in the first well and continued with 1:2 serial dilutions before adding luciferase-expressing hCMV. The neutralising activities of these antibody mixtures were compared to the single titrations of the respective antibodies (FIG. 15). Only a slight additive effect between AD-4- and AD-5-specific antibodies was observed with no inhibitory or synergistic effects observed. This experiment was repeated on two further occasions with comparable results (data not shown).

TABLE 19

Summary of the SEQ ID numbers in the accompanying Sequence Listing, for the heavy and light chain CDRs of the neutralising antibodies shown in Tables 7 and 13 above.

| Antibody | SEQ ID NO: | | | | | |
|---|---|---|---|---|---|---|
| | CDRH1 | CDRH2 | CDRH3 | CDRl1 | CDRl2 | CDRl3 |
| Ab-01 | 38 | 39 | 40 | 103 | 104 | 105 |
| Ab-02 | 8 | 9 | 10 | 98 | 99 | 100 |
| Ab-03 | 3 | 4 | 5 | 118 | 119 | 120 |
| Ab-04 | 13 | 14 | 15 | 103 | 104 | 105 |
| Ab-05 | 38 | 39 | 40 | 123 | 124 | 125 |
| Ab-06 | 43 | 44 | 45 | 128 | 129 | 130 |
| Ab-07 | 53 | 54 | 55 | 133 | 134 | 135 |
| Ab-08 | 8 | 9 | 10 | 138 | 139 | 140 |
| Ab-09 | 53 | 54 | 55 | 143 | 144 | 145 |
| Ab-10 | 53 | 54 | 55 | 93 | 94 | 95 |
| Ab-11 | 18 | 19 | 20 | 108 | 109 | 110 |
| Ab-12 | 58 | 59 | 60 | 108 | 109 | 110 |
| Ab-13 | 63 | 64 | 65 | 108 | 109 | 110 |
| Ab-14 | 23 | 24 | 25 | 113 | 114 | 115 |
| Ab-15 | 23 | 24 | 25 | 148 | 149 | 150 |
| Ab-16 | 68 | 69 | 70 | 153 | 154 | 155 |
| Ab-17 | 68 | 69 | 70 | 148 | 149 | 150 |
| Ab-18 | 43 | 44 | 45 | 158 | 159 | 160 |
| Ab-19 | 43 | 44 | 45 | 163 | 164 | 165 |
| Ab-20 | 43 | 44 | 45 | 98 | 99 | 100 |
| Ab-21 | 43 | 44 | 45 | 168 | 169 | 170 |
| Ab-22 | 43 | 44 | 45 | 138 | 139 | 140 |
| Ab-23 | 8 | 9 | 10 | 163 | 164 | 165 |
| Ab-24 | 8 | 9 | 10 | 168 | 169 | 170 |
| Ab-25 | 8 | 9 | 10 | 158 | 159 | 160 |
| Ab-26 | 8 | 9 | 10 | 128 | 129 | 130 |
| Ab-27 | 43 | 44 | 45 | 108 | 109 | 110 |
| Ab-28 | 3 | 4 | 5 | 93 | 94 | 95 |
| Ab-29 | 48 | 49 | 50 | 93 | 94 | 95 |
| Ab-30 | 3 | 4 | 5 | 143 | 144 | 145 |
| Ab-31 | 53 | 54 | 55 | 118 | 119 | 120 |
| Ab-32 | 3 | 4 | 5 | 133 | 134 | 135 |
| Ab-33 | 13 | 14 | 15 | 173 | 174 | 175 |
| Ab-34 | 38 | 39 | 40 | 173 | 174 | 175 |
| Ab-35 | 73 | 74 | 75 | 103 | 104 | 105 |
| Ab-36 | 73 | 74 | 75 | 173 | 174 | 175 |
| Ab-37 | 13 | 14 | 15 | 123 | 124 | 125 |
| Ab-38 | 73 | 74 | 75 | 123 | 124 | 125 |
| Ab-39 | 13 | 14 | 15 | 178 | 179 | 180 |
| Ab-40 | 38 | 39 | 40 | 178 | 179 | 180 |
| Ab-41 | 73 | 74 | 75 | 178 | 179 | 180 |
| Ab-42 | 28 | 29 | 30 | 108 | 109 | 110 |
| Ab-43 | 78 | 79 | 80 | 108 | 109 | 110 |
| Ab-44 | 83 | 84 | 85 | 108 | 109 | 110 |
| Ab-45 | 88 | 89 | 90 | 108 | 109 | 110 |
| Ab-46 | 33 | 34 | 35 | 108 | 109 | 110 |
| Ab-47 | 243 | 244 | 245 | 263 | 264 | 265 |
| Ab-48 | 248 | 249 | 250 | 268 | 269 | 270 |
| Ab-49 | 253 | 254 | 255 | 273 | 274 | 275 |
| Ab-50 | 258 | 259 | 260 | 278 | 278 | 280 |

TABLE 20a

Table 14a

| Kabatt No. | HCDR1 | | | | | HCDR2 | | | | | | | | | | | | | | | | |
|---|---|---|---|---|---|---|---|---|---|---|---|---|---|---|---|---|---|---|---|---|---|---|
| | 31 | 32 | 33 | 34 | 35 | 50 | 51 | 52 | 52A | 53 | 54 | 55 | 56 | 57 | 58 | 59 | 60 | 61 | 62 | 63 | 64 | 65 |
| Ab28 | D | H | Y | M | V | W | I | N | P | Q | S | G | G | T | G | Y | G | Q | K | F | Q | G |
| Ab02 | | | | L | | | | | | | | | | | | | | | | | | |
| Ab04 | | Y | | L | N | S | | | | N | T | | | | K | | A | | | | | |
| Ab11 | G | Y | | | N | C | | | | N | | | | | N | | A | | | | | |
| Ab14 | | Y | | | N | C | | | | H | | | | | N | | A | | | | | |
| Ab42 | | F | | I | N | S | | | | H | | | | | H | | A | | | | | |
| Ab46 | | F | | I | N | S | | | | H | | | | | H | | A | | | | | |
| Ab03 | | | | | | | | | | | | | | | | | | | | | | |
| Ab01 | | Y | | L | N | S | | | | N | T | | | | K | | A | | | | R | |
| Ab20 | | | | L | | | | | | | | | | | | | A | | | | | |
| Ab27 | | | | L | | | | | | | | | | | | | A | | | | | |
| Ab10 | | | | | | | | | | | | | | | | | | | | | | |
| Ab31 | | | | | | | | | | | | | | | | | | | | | | |
| Ab12 | G | Y | | | | C | | | | N | | | | | N | | A | | | | | |
| Ab13 | G | Y | | | N | C | | | | N | | | | | N | | A | | | | | |
| Ab35 | | Y | | L | N | S | | | | N | T | | | | K | | A | | | | | |
| Ab43 | G | Y | | | N | C | | | | N | | | | | N | | A | | | | | |
| Ab44 | G | Y | | | N | C | | | | N | | | | | N | | A | | | | | |
| Ab29 | | | | | | | | | | | | | | | | | | | | | | |
| Ab45 | | F | | I | N | S | | | | H | | | | | H | | A | | | | | |
| Ab32 | | | | | | | | | | | | | | | | | | | | | | |
| Ab30 | | | | | | | | | | | | | | | | | | | | | | |
| Ab26 | | | | L | | | | | | | | | | | | | A | | | | | |
| Ab08 | | | | L | | | | | | | | | | | | | A | | | | | |
| Ab37 | | Y | | L | N | S | | | | N | T | | | | K | | A | | | | | |
| Ab15 | | Y | | | N | C | | | | H | | | | | N | | A | | | | | |
| Ab05 | | Y | | L | N | S | | | | N | T | | | | K | | A | | | | R | |
| Ab06 | | | | L | | | | | | | | | | | | | A | | | | | |
| Ab22 | | | | L | | | | | | | | | | | | | A | | | | | |
| Ab07 | | | | | | | | | | | | | | | | | | | | | | |
| Ab09 | | | | | | | | | | | | | | | | | | | | | | |
| Ab17 | | Y | | | N | C | | | | H | | | | | N | | A | | | | | |
| Ab38 | | Y | | L | N | S | | | | N | T | | | | K | | A | | | | | |
| Ab25 | | | | L | | | | | | | | | | | | | A | | | | | |
| Ab23 | | | | L | | | | | | | | | | | | | A | | | | | |
| Ab24 | | | | L | | | | | | | | | | | | | A | | | | | |
| Ab33 | | Y | | L | N | S | | | | N | T | | | | K | | A | | | | | |
| Ab39 | | Y | | L | N | S | | | | N | T | | | | K | | A | | | | | |
| Ab34 | | Y | | L | N | S | | | | N | T | | | | K | | A | | | | | |
| Ab40 | | Y | | L | N | S | | | | N | T | | | | K | | A | | | | | |
| Ab18 | | | | L | | | | | | | | | | | | | A | | | | | |
| Ab19 | | | | L | | | | | | | | | | | | | A | | | | | |
| Ab21 | | | | L | | | | | | | | | | | | | A | | | | | |
| Ab16 | | Y | | | N | C | | | | H | | | | | N | | A | | | | | |
| Ab36 | | Y | | L | N | S | | | | N | T | | | | K | | A | | | | | |
| Ab41 | | Y | | L | N | S | | | | N | T | | | | K | | A | | | | | |

| Kabatt No. | HDCR3 | | | | | | | | | | | | | | | | | | | | | |
|---|---|---|---|---|---|---|---|---|---|---|---|---|---|---|---|---|---|---|---|---|---|---|
| | 95 | 96 | 97 | 98 | 99 | 100 | 100A | 100B | 100C | 100D | 100E | 100F | 100G | 100H | 100I | 100J | 100K | 100L | 100M | 100N | 101 | 102 |
| Ab28 | D | G | A | K | T | V | S | N | S | G | L | S | L | L | Y | Y | H | N | R | L | D | A |
| Ab02 | | | | | | | | | | G | | | | | | | | S | | | | |
| Ab04 | | | | | | M | T | T | | | | | | | | | Y | D | V | | M | V |
| Ab11 | | | | | | | T | T | | | M | | | | | | Y | D | V | | M | I |
| Ab14 | | | | | | | T | T | F | | A | | | | | | Y | D | I | | M | V |
| Ab42 | | | | | | | T | T | | | M | | | | | | Y | D | V | | M | I |
| Ab46 | | | | | | | T | T | F | | A | | | | | | Y | D | I | | M | V |
| Ab03 | | | | | | | | | | | | | | | | | | | | | | |
| Ab01 | | | | | | M | T | T | | | | | | | | | Y | D | V | | M | V |
| Ab20 | | | | | | | | | | | G | | | | | | | S | | | | |
| Ab27 | | | | | | | | | | | G | | | | | | | S | | | | |
| Ab10 | | | | | A | | | | | | | | | | | | | | | | | |
| Ab31 | | | | | A | | | | | | | | | | | | | | | | | |
| Ab12 | | | | | | | T | T | | | M | | | | | | Y | D | V | | M | I |
| Ab13 | | | | | | | T | T | | | M | | | | | | Y | D | V | | M | I |
| Ab35 | | | | | | M | T | T | | | | | | | | | | D | V | | M | V |
| Ab43 | | | | | | | T | T | F | | M | | | | | | Y | D | V | | M | I |
| Ab44 | | | | | | | T | T | | | M | | | | | | Y | D | V | | M | G | I |
| Ab29 | | | | | | | | | | | | | | | | | | | | | | |
| Ab45 | | | | | | | T | T | | | M | | | | | | Y | D | V | | M | I |
| Ab32 | | | | | | | | | | | | | | | | | | | | | | |
| Ab30 | | | | | | | | | | | | | | | | | | | | | | |
| Ab26 | | | | | | | | | | | | | | G | | | | | | S | | |

TABLE 20a-continued

Table 14a

| Ab | 1 | 2 | 3 | 4 | 5 | 6 | 7 | 8 | 9 | 10 | 11 | 12 |
|---|---|---|---|---|---|---|---|---|---|---|---|---|
| Ab08 |   |   |   |   |   |   | G |   | S |   |   |   |
| Ab37 |   | M | T | T |   |   |   | Y | D | V | M | V |
| Ab15 |   |   | T | T | F | A |   | Y | D | I | M | V |
| Ab05 |   | M | T | T |   |   |   | Y | D | V | M | V |
| Ab06 |   |   |   |   |   |   | G |   | S |   |   |   |
| Ab22 |   |   |   |   |   |   | G |   | S |   |   |   |
| Ab07 | A |   |   |   |   |   |   |   |   |   |   |   |
| Ab09 | A |   |   |   |   |   |   |   |   |   |   |   |
| Ab17 |   |   | T | T | F | A |   | Y | D | I | M | V |
| Ab38 |   | M | T | T |   |   |   |   | D | V | M | V |
| Ab25 |   |   |   |   |   |   | G |   | S |   |   |   |
| Ab23 |   |   |   |   |   |   | G |   | S |   |   |   |
| Ab24 |   |   |   |   |   |   | G |   | S |   |   |   |
| Ab33 |   | M | T | T |   |   |   | Y | D | V | M | V |
| Ab39 |   | M | T | T |   |   |   | Y | D | V | M | V |
| Ab34 |   | M | T | T |   |   |   | Y | D | V | M | V |
| Ab40 |   | M | T | T |   |   |   | Y | D | V | M | V |
| Ab18 |   |   |   |   |   |   | G |   | S |   |   |   |
| Ab19 |   |   |   |   |   |   | G |   | S |   |   |   |
| Ab21 |   |   |   |   |   |   | G |   | S |   |   |   |
| Ab16 |   |   | T | T | F | A |   | Y | D | I | M | V |
| Ab36 |   | M | T | T |   |   |   |   | D | V | M | V |
| Ab41 |   | M | T | T |   |   |   |   | D | V | M | V |

TABLE 20b

| Kabat No. | 24 | 25 | 26 | 27 | 27A | 27B | 28 | 29 | 30 | 31 | 32 | 33 | 34 | 50 | 51 | 52 | 53 | 54 | 55 | 56 |
|---|---|---|---|---|---|---|---|---|---|---|---|---|---|---|---|---|---|---|---|---|
|   | LCDR1 |   |   |   |   |   |   |   |   |   |   |   |   | LCDR2 |   |   |   |   |   |   |
| Ab28 | S | G | S | S | S | N | I | G | K | N | Y | V | S | D | N | K | R |   | P | S |
| Ab02 |   |   |   | R |   |   |   |   |   |   |   |   |   |   |   |   |   |   |   |   |
| Ab04 |   |   |   |   |   |   |   |   |   |   |   |   |   |   |   |   |   |   |   |   |
| Ab11 |   |   |   |   |   |   |   |   |   |   |   |   |   |   |   |   |   |   |   |   |
| Ab14 |   |   |   |   |   |   |   |   |   |   |   |   |   |   |   |   |   |   |   |   |
| Ab42 |   |   |   |   |   |   |   |   |   |   |   |   |   |   |   |   |   |   |   |   |
| Ab46 |   |   |   |   |   |   |   |   |   |   |   |   |   |   |   |   |   |   |   |   |
| Ab03 |   |   |   |   |   |   |   |   |   |   |   |   |   |   |   |   |   |   |   |   |
| Ab01 |   |   |   |   |   |   |   |   |   |   |   |   |   |   |   |   |   |   |   |   |
| Ab20 |   |   |   | R |   |   |   |   |   |   |   |   |   |   |   |   |   |   |   |   |
| Ab27 |   |   |   |   |   |   |   |   |   |   |   |   |   |   |   |   |   |   |   |   |
| Ab10 |   |   |   |   |   |   |   |   |   |   |   |   |   |   |   |   |   |   |   |   |
| Ab31 |   |   |   |   |   |   |   |   |   |   |   |   |   |   |   |   |   |   |   |   |
| Ab12 |   |   |   |   |   |   |   |   |   |   |   |   |   |   |   |   |   |   |   |   |
| Ab13 |   |   |   |   |   |   |   |   |   |   |   |   |   |   |   |   |   |   |   |   |
| Ab35 |   |   |   |   |   |   |   |   |   |   |   |   |   |   |   |   |   |   |   |   |
| Ab43 |   |   |   |   |   |   |   |   |   |   |   |   |   |   |   |   |   |   |   |   |
| Ab44 |   |   |   |   |   |   |   |   |   |   |   |   |   |   |   |   |   |   |   |   |
| Ab29 |   |   |   |   |   |   |   |   |   |   |   |   |   |   |   |   |   |   |   |   |
| Ab45 |   |   |   |   |   |   |   |   |   |   |   |   |   |   |   |   |   |   |   |   |
| Ab32 |   |   |   |   |   |   |   |   |   |   |   |   |   |   |   |   |   |   |   |   |
| Ab30 |   |   |   |   |   |   |   |   |   |   |   |   |   |   |   |   |   |   |   |   |
| Ab26 |   |   | R |   |   |   |   |   |   |   |   |   |   |   |   |   |   |   |   |   |
| Ab08 |   |   | R |   |   |   |   |   |   |   |   |   |   |   |   |   |   |   |   |   |
| Ab37 |   |   |   |   |   |   |   |   |   |   |   |   |   |   |   |   |   |   |   |   |
| Ab15 |   |   |   |   |   |   |   |   |   |   |   |   |   |   |   |   |   |   | P |   |
| Ab05 |   |   |   |   |   |   |   |   |   |   |   |   |   |   |   |   |   |   |   |   |
| Ab06 |   |   | R |   |   |   |   |   |   |   |   |   |   |   |   |   |   |   |   |   |
| Ab22 |   |   | R |   |   |   |   |   |   |   |   |   |   |   |   |   |   |   |   |   |
| Ab07 |   |   |   |   |   |   |   |   |   |   |   |   |   |   |   |   |   |   |   |   |
| Ab09 |   |   |   |   |   |   |   |   |   |   |   |   |   |   |   |   |   |   |   |   |
| Ab17 |   |   |   |   |   |   |   |   |   |   |   |   |   |   |   |   |   |   | P |   |
| Ab38 |   |   |   |   |   |   |   |   |   |   |   |   |   |   |   |   |   |   |   |   |
| Ab25 |   |   | R |   |   |   |   |   |   |   |   |   |   |   |   |   |   |   |   |   |
| Ab23 |   |   | R |   |   |   |   |   |   |   |   |   |   |   |   |   |   |   |   |   |
| Ab24 |   |   | R |   |   |   |   |   |   |   |   |   |   |   |   |   |   |   |   |   |
| Ab33 |   | N |   |   |   |   |   |   |   |   |   |   |   |   |   |   |   |   |   |   |
| Ab39 |   |   |   |   |   |   |   |   |   |   |   |   |   |   |   |   |   |   |   |   |
| Ab34 |   | N |   |   |   |   |   |   |   |   |   |   |   |   |   |   |   |   |   |   |
| Ab40 |   |   |   |   |   |   |   |   |   |   |   |   |   |   |   |   |   |   |   |   |
| Ab18 |   |   | R |   |   |   |   |   |   |   |   |   |   |   |   |   |   |   |   |   |
| Ab19 |   |   | R |   |   |   |   |   |   |   |   |   |   |   |   |   |   |   |   |   |
| Ab21 |   |   | R |   |   |   |   |   |   |   |   |   |   |   |   |   |   |   |   |   |
| Ab16 |   |   |   |   |   |   |   |   |   |   |   |   |   |   |   |   |   |   |   |   |
| Ab36 |   | N |   |   |   |   |   |   |   |   |   |   |   |   |   |   |   |   |   |   |

TABLE 20b-continued

Ab41

| | Kabat | | | | | LCDR3 | | | | | | |
|---|---|---|---|---|---|---|---|---|---|---|---|---|
| | No. | 89 | 90 | 91 | 92 | 93 | 94 | 95 | 95A | 95B | 96 | 97 |
| | Ab28 | G | T | P | D | R | S | L | S | — | V | I |
| | Ab02 | | | W | | S | | | | | | V |
| | Ab04 | A | | W | | S | | | G | | | V |
| | Ab11 | | | W | | S | | | | | | V |
| | Ab14 | A | | W | | | | | | | | V |
| | Ab42 | | | W | | S | | | | | | V |
| | Ab46 | | | W | | S | | | | | | V |
| | Ab03 | | | | | | | | | | | V |
| | Ab01 | A | | W | | S | | | G | | | V |
| | Ab20 | | | W | | S | | | | | | V |
| | Ab27 | | | W | | S | | | | | | V |
| | Ab10 | | | | | | | | | | | |
| | Ab31 | | | | | | | | | | | V |
| | Ab12 | | | W | | S | | | | | | V |
| | Ab13 | | | W | | S | | | | | | V |
| | Ab35 | A | | W | | S | | | G | | | V |
| | Ab43 | | | W | | S | | | | | | V |
| | Ab44 | | | W | | S | | | | | | V |
| | Ab29 | | | | | | | | | | | |
| | Ab45 | | | W | | S | | | | | | V |
| | Ab32 | | | | | | | | | | | V |
| | Ab30 | | | | | | | | | | | V |
| | Ab26 | | | W | | S | | | | | | V |
| | Ab08 | | | W | | S | | | | | | V |
| | Ab37 | A | | W | | S | | | G | | | V |
| | Ab15 | A | | W | | | | | | | | V |
| | Ab05 | A | | W | | S | | | G | | | V |
| | Ab06 | | | W | | S | | | | | | V |
| | Ab22 | | | W | | S | | | | | | V |
| | Ab07 | | | | | | | | | | | V |
| | Ab09 | | | | | | | | | | | V |
| | Ab17 | A | | W | | | | | | | | V |
| | Ab38 | A | | W | | S | | | G | | | V |
| | Ab25 | | | W | | S | | | | | | V |
| | Ab23 | | | W | | S | D | | | A | Y | V |
| | Ab24 | | | W | | S | | | | | | V |
| | Ab33 | A | | W | | S | | | G | | | V |
| | Ab39 | A | | W | | S | | | G | | | V |
| | Ab34 | A | | W | | S | | | G | | | V |
| | Ab40 | A | | W | | S | | | G | | | V |
| | Ab18 | | | W | | S | | | | | | V |
| | Ab19 | | | W | | S | D | | | A | Y | V |
| | Ab21 | | | W | | S | | | | | | V |
| | Ab16 | A | | W | | | | | | | | V |
| | Ab36 | A | | W | | S | | | G | | | V |
| | Ab41 | A | | W | | S | | | G | | | V |

SEQUENCES $V_H$ domain, $V_L$ domain and CDR sequences of binding members are shown in the appended sequence listing, in which SEQ ID NOS correspond as follows:

| 1 | SM5-1 $V_H$ nucleotide |
|---|---|
| 2 | SM5-1 $V_H$ amino acid |
| 3 | SM5-1 $V_H$ CDR 1 aa |
| 4 | SM5-1 $V_H$ CDR 2 aa |
| 5 | SM5-1 $V_H$ CDR 3 aa |
| 6 | SM4-10 $V_H$ nucleotide |
| 7 | SM4-10 $V_H$ amino acid |
| 8 | SM4-10 $V_H$ CDR 1 aa |
| 9 | SM4-10 $V_H$ CDR 2 aa |
| 10 | SM4-10 $V_H$ CDR 3 aa |
| 11 | SM6-5 $V_H$ nucleotide |
| 12 | SM6-5 $V_H$ amino acid |
| 13 | SM6-5 $V_H$ CDR 1 aa |
| 14 | SM6-5 $V_H$ CDR 2 aa |
| 15 | SM6-5 $V_H$ CDR 3 aa |
| 16 | SM1-6 VH nucleotide |

-continued

| 17 | SM1-6 VH amino acid |
|---|---|
| 18 | SM1-6 VH CDR 1 aa |
| 19 | SM1-6 VH CDR 2 aa |
| 20 | SM1-6 VH CDR 3 aa |
| 21 | SM3-1 VH nucleotide |
| 22 | SM3-1 VH amino acid |
| 23 | SM3-1 VH CDR 1 aa |
| 24 | SM3-1 VH CDR 2 aa |
| 25 | SM3-1 VH CDR 3 aa |
| 26 | SM11-17 VH nucleotide |
| 27 | SM11-17 VH amino acid |
| 28 | SM11-17 VH CDR 1 aa |
| 29 | SM11-17 VH CDR 2 aa |
| 30 | SM11-17 VH CDR 3 aa |
| 31 | SM11-21 VH nucleotide |
| 32 | SM11-21 VH amino acid |
| 33 | SM11-21 VH CDR 1 aa |
| 34 | SM11-21 VH CDR 2 aa |
| 35 | SM11-21 VH CDR 3 aa |
| 36 | SM6-11 VH nucleotide |
| 37 | SM6-11 VH amino acid |
| 38 | SM6-11 VH CDR 1 aa |

| | |
|---|---|
| 39 | SM6-11 VH CDR 2 aa |
| 40 | SM6-11 VH CDR 3 aa |
| 41 | SM4-3 VH nucleotide |
| 42 | SM4-3 VH amino acid |
| 43 | SM4-3 VH CDR 1 aa |
| 44 | SM4-3 VH CDR 2 aa |
| 45 | SM4-3 VH CDR 3 aa |
| 46 | SM5-3 VH nucleotide |
| 47 | SM5-3 VH amino acid |
| 48 | SM5-3 VH CDR 1 aa |
| 49 | SM5-3 VH CDR 2 aa |
| 50 | SM5-3 VH CDR 3 aa |
| 51 | SM5-9 VH nucleotide |
| 52 | SM5-9 VH amino acid |
| 53 | SM5-9 VH CDR 1 aa |
| 54 | SM5-9 VH CDR 2 aa |
| 55 | SM5-9 VH CDR 3 aa |
| 56 | SM1-7 VH nucleotide |
| 57 | SM1-7 VH amino acid |
| 58 | SM1-7 VH CDR 1 aa |
| 59 | SM1-7 VH CDR 2 aa |
| 60 | SM1-7 VH CDR 3 aa |
| 61 | SM1-8 VH nucleotide |
| 62 | SM1-8 VH amino acid |
| 63 | SM1-8 VH CDR 1 aa |
| 64 | SM1-8 VH CDR 2 aa |
| 65 | SM1-8 VH CDR 3 aa |
| 66 | SM3-4 VH nucleotide |
| 67 | SM3-4 VH amino acid |
| 68 | SM3-4 VH CDR 1 aa |
| 69 | SM3-4 VH CDR 2 aa |
| 70 | SM3-4 VH CDR 3 aa |
| 71 | SM6-23 VH nucleotide |
| 72 | SM6-23 VH amino acid |
| 73 | SM6-23 VH CDR 1 aa |
| 74 | SM6-23 VH CDR 2 aa |
| 75 | SM6-23 VH CDR 3 aa |
| 76 | SM11-18 VH nucleotide |
| 77 | SM11-18 VH amino acid |
| 78 | SM11-18 VH CDR 1 aa |
| 79 | SM11-18 VH CDR 2 aa |
| 80 | SM11-18 VH CDR 3 aa |
| 81 | SM11-19 VH nucleotide |
| 82 | SM11-19 VH amino acid |
| 83 | SM11-19 VH CDR 1 aa |
| 84 | SM11-19 VH CDR 2 aa |
| 85 | SM11-19 VH CDR 3 aa |
| 86 | SM11-20 VH nucleotide |
| 87 | SM11-20 VH amino acid |
| 88 | SM11-20 VH CDR 1 aa |
| 89 | SM11-20 VH CDR 2 aa |
| 90 | SM11-20 VH CDR 3 aa |
| 91 | SM5-1 VL nucleotide |
| 92 | SM5-1 VL amino acid |
| 93 | SM5-1 VL CDR 1 aa |
| 94 | SM5-1 VL CDR 2 aa |
| 95 | SM5-1 VL CDR 3 aa |
| 96 | SM4-10 VL nucleotide |
| 97 | SM4-10 VL amino acid |
| 98 | SM4-10 VL CDR 1 aa |
| 99 | SM4-10 VL CDR 2 aa |
| 100 | SM4-10 VL CDR 3 aa |
| 101 | SM6-5 VL nucleotide |
| 102 | SM6-5 VL amino acid |
| 103 | SM6-5 VL CDR 1 aa |
| 104 | SM6-5 VL CDR 2 aa |
| 105 | SM6-5 VL CDR 3 aa |
| 106 | SM1-6 VL nucleotide |
| 107 | SM1-6 VL amino acid |
| 108 | SM1-6 VL CDR 1 aa |
| 109 | SM1-6 VL CDR 2 aa |
| 110 | SM1-6 VL CDR 3 aa |
| 111 | SM3-1 VL nucleotide |
| 112 | SM3-1 VL amino acid |
| 113 | SM3-1 VL CDR 1 aa |
| 114 | SM3-1 VL CDR 2 aa |
| 115 | SM3-1 VL CDR 3 aa |
| 116 | SM5-6 VL nucleotide |
| 117 | SM5-6 VL amino acid |
| 118 | SM5-6 VL CDR 1 aa |
| 119 | SM5-6 VL CDR 2 aa |
| 120 | SM5-6 VL CDR 3 aa |
| 121 | SM6-48 VH nucleotide |
| 122 | SM6-48 VH amino acid |
| 123 | SM6-48 VH CDR 1 aa |
| 124 | SM6-48 VH CDR 2 aa |
| 125 | SM6-48 VH CDR 3 aa |
| 126 | SM4-3 VL nucleotide |
| 127 | SM4-3 VL amino acid |
| 128 | SM4-3 VL CDR 1 aa |
| 129 | SM4-3 VL CDR 2 aa |
| 130 | SM4-3 VL CDR 3 aa |
| 131 | SM5-9 VL nucleotide |
| 132 | SM5-9 VL amino acid |
| 133 | SM5-9 VL CDR 1 aa |
| 134 | SM5-9 VL CDR 2 aa |
| 135 | SM5-9 VL CDR 3 aa |
| 136 | SM4-12 VL nucleotide |
| 137 | SM4-12 VL amino acid |
| 138 | SM4-12 VL CDR 1 aa |
| 139 | SM4-12 VL CDR 2 aa |
| 140 | SM4-12 VL CDR 3 aa |
| 141 | SM5-5 VL nucleotide |
| 142 | SM5-5 VL amino acid |
| 143 | SM5-5 VL CDR 1 aa |
| 144 | SM5-5 VL CDR 2 aa |
| 145 | SM5-5 VL CDR 3 aa |
| 146 | SM3-2 VL nucleotide |
| 147 | SM3-2 VL amino acid |
| 148 | SM3-2 VL CDR 1 aa |
| 149 | SM3-2 VL CDR 2 aa |
| 150 | SM3-2 VL CDR 3 aa |
| 151 | SM3-4 VL nucleotide |
| 152 | SM3-4 VL amino acid |
| 153 | SM3-4 VL CDR 1 aa |
| 154 | SM3-4 VL CDR 2 aa |
| 155 | SM3-4 VL CDR 3 aa |
| 156 | SM4-1 VL nucleotide |
| 157 | SM4-1 VL amino acid |
| 158 | SM4-1 VL CDR 1 aa |
| 159 | SM4-1 VL CDR 2 aa |
| 160 | SM4-1 VL CDR 3 aa |
| 161 | SM4-5 VL nucleotide |
| 162 | SM4-5 VL amino acid |
| 163 | SM4-5 VL CDR 1 aa |
| 164 | SM4-5 VL CDR 2 aa |
| 165 | SM4-5 VL CDR 3 aa |
| 166 | SM4-7 VL nucleotide |
| 167 | SM4-7 VL amino acid |
| 168 | SM4-7 VL CDR 1 aa |
| 169 | SM4-7 VL CDR 2 aa |
| 170 | SM4-7 VL CDR 3 aa |
| 171 | SM6-6 VL nucleotide |
| 172 | SM6-6 VL amino acid |
| 173 | SM6-6 VL CDR 1 aa |
| 174 | SM6-6 VL CDR 2 aa |
| 175 | SM6-6 VL CDR 3 aa |
| 176 | SM6-51 VL nucleotide |
| 177 | SM6-51 VL amino acid |
| 178 | SM6-51 VL CDR 1 aa |
| 179 | SM6-51 VL CDR 2 aa |
| 180 | SM6-51 VL CDR 3 aa |
| 181 | VH FWR1 |
| 182 | VH FWR3 |
| 183 | VH FWR3 (*02, *03, *04) |
| 184 | VH FWR4 (*01) |
| 185 | VL FWR1 |
| 186 | VL FWR2 |
| 187 | VL FWR3 |
| 188 | IGHJ6*02 aa |
| 189 | IGHJ3*02 aa |
| 190 | IGHJ5*01 aa |
| 191 | IGHJ5*02 aa |
| 192 | IGLJ1*01 aa |
| 193 | IGLJ2*01 aa |
| 194 | IGLJ3*01 aa |
| 195 | IGLG3*02 aa |
| 196 | Primer 179-Je |

| | |
|---|---|
| 197 | Synthetic peptide |
| 198 | Primer 074-Je |
| 199 | Primer 075-Je |
| 200 | Primer 076-Je |
| 201 | Primer 150-Je |
| 202 | Primer 151-Je |
| 203 | Primer 077-Je |
| 204 | Primer 078-Je |
| 205 | Primer 007-Je |
| 206 | Primer 152-Je |
| 207 | Primer 153-Je |
| 208 | Primer 066-Je |
| 209 | Primer 067-Je |
| 210 | Primer 068-Je |
| 211 | Primer 069-Je |
| 212 | Primer 070-Je |
| 213 | Primer 258-Je |
| 214 | Primer 259-Je |
| 215 | Primer 260-Je |
| 216 | Primer 261-Je |
| 217 | Primer 262-Je |
| 218 | Primer 263-Je |
| 219 | Primer 264-Je |
| 220 | Primer 265-Je |
| 221 | Primer 266-Je |
| 222 | Primer 267-Je |
| 223 | Primer 84-B |
| 224 | Primer 155-Je |
| 225 | Primer 85-B |
| 226 | Primer 161-Je |
| 227 | Primer 162-Je |
| 228 | Primer 154-Je |
| 229 | Primer 001-Je |
| 230 | Primer 158-Je |
| 231 | Primer 003-Je |
| 232 | Primer 159-Je |
| 233 | Primer 156-Je |
| 234 | Primer 157-Je |
| 235 | Primer 062-Je |
| 236 | Primer 063-Je |
| 237 | Primer 065-Je |
| 238 | Primer 064-Je |
| 239 | gB strain AD169 |
| 240 | gB strain Towne |
| 241 | SM10 $V_H$ nucleotide |
| 242 | SM10 $V_H$ amino acid |
| 243 | SM10 $V_H$ CDR 1 aa |
| 244 | SM10 $V_H$ CDR 2 aa |
| 245 | SM10 $V_H$ CDR 3 aa |
| 246 | SM12 $V_H$ nucleotide |
| 247 | SM12 $V_H$ amino acid |
| 248 | SM12 $V_H$ CDR 1 aa |
| 249 | SM12 $V_H$ CDR 2 aa |
| 250 | SM12 $V_H$ CDR 3 aa |
| 251 | 2C2 $V_H$ nucleotide |
| 252 | 2C2 $V_H$ amino acid |
| 253 | 2C2 $V_H$ CDR 1 aa |
| 254 | 2C2 $V_H$ CDR 2 aa |
| 255 | 2C2 $V_H$ CDR 3 aa |
| 256 | 1G2 $V_H$ nucleotide |
| 257 | 1G2 $V_H$ amino acid |
| 258 | 1G2 $V_H$ CDR 1 aa |
| 259 | 1G2 $V_H$ CDR 2 aa |
| 260 | 1G2 $V_H$ CDR 3 aa |
| 261 | SM10 $V_L$ nucleotide |
| 262 | SM10 $V_L$ amino acid |
| 263 | SM10 $V_L$ CDR 1 aa |
| 264 | SM10 $V_L$ CDR 2 aa |
| 265 | SM10 $V_L$ CDR 3 aa |
| 266 | SM12 $V_L$ nucleotide |
| 267 | SM12 $V_L$ amino acid |
| 268 | SM12 $V_L$ CDR 1 aa |
| 269 | SM12 $V_L$ CDR 2 aa |
| 270 | SM12 $V_L$ CDR 3 aa |
| 271 | 2C2 $V_L$ nucleotide |
| 272 | 2C2 $V_L$ amino acid |
| 273 | 2C2 $V_L$ CDR 1 aa |
| 274 | 2C2 $V_L$ CDR 2 aa |
| 275 | 2C2 $V_L$ CDR 3 aa |
| 276 | 1G2 $V_L$ nucleotide |
| 211 | 1G2 $V_L$ amino acid |
| 278 | 1G2 $V_L$ CDR 1 aa |
| 279 | 1G2 $V_L$ CDR 2 aa |
| 280 | 1G2 $V_L$ CDR 3 aa |
| 281 | IGHV4-39 FWR1 |
| 282 | IGHV4-39 FWR2 |
| 283 | IGHV4-39 FWR3 |
| 284 | IGHV4-59 FWR1 |
| 285 | IGHV4-59 FWR2 |
| 286 | IGHV4-59 FWR3 |
| 287 | IGKV2D-28 FWR1 |
| 288 | IGKV2D-28 FWR2 |
| 289 | IGKV2D-28 FWR3 |
| 290 | IGKV1D-33 FWR1 |
| 291 | IGKV1D-33 FWR2 |
| 292 | IGKV1D-33 FWR3 |
| 293 | IGLV1-47 FW1 |
| 294 | IGLV1-47 FW2 |
| 295 | IGLV1-47 FW3 |
| 296 | Primer 5'Ig L VH ⁴⁄₆ |
| 297 | Primer 5'Ig L Vκ ½ |
| 298 | Primer 5'Ig L Vλ 3 |
| 299 | Primer 5'Ig L Vλ 1 |
| 300 | Primer 3'Ig Cγ CH 1 |
| 301 | Primer 3'Ig Cκ 543 |
| 302 | Primer 3'Ig Cλ chain |
| 303 | Primer 5'Ig AgeI VH4 |
| 304 | Primer 5'Ig AgeI Vκ 2-24 |
| 305 | Primer 5'Ig AgeI Vκ 2-28 |
| 306 | Primer 5'Ig AgeI Vλ 3 |
| 307 | Primer 5'Ig AgeI Vκ 1-5 |
| 308 | Primer 5'Ig AgeI VH 4-39 |
| 309 | Primer 5'Ig AgeI Vλ 1 |
| 310 | Primer 3'Ig SalI JH |
| 311 | Primer 3'Ig BsiWI Jκ 2 |
| 312 | Primer 3'Ig SalI JH 6 |
| 313 | Primer 3'Ig Bsi WIJκ ¼ |
| 314 | Primer 3'Ig XhoI Cλ |
| 315 | Primer 5' Absense |
| 316 | Primer 3'IgG internal |
| 317 | Primer 3'Cκ494 |
| 318 | Primer 3'Cλ |
| 319 | synthetic linker |
| 320 | gpUL132 signal sequence |
| 321 | HA epitope tag |

REFERENCES

All references cited anywhere in this specification, including those cited anywhere above, are incorporated herein by reference in their entirety and for all purposes.

Al-Lazikani B, Lesk A M, Chothia C. (1997) J. Mol. Biol. 273(4): 927-948.

Altschul S F, Gish W, Miller W, Myers E W, Lipman D J. (1990) J. Mol. Biol. 215(3): 403-10.

Amit A G, Mariuzza R A, Phillips S E, Poljak R J. (1986) Science 233(4765): 747-53.

Andersen D C & Krummen L. (2002) Curr. Op. Biotech. 13: 117.

Andreoni M, Faircloth M, Vugler L, Britt W J. (1989) J. Virol. Methods 23(2): 157-67.

Ausubel et al. eds. Short Protocols in Molecular Biology: A Compendium of Methods from Current Protocols in Molecular Biology, John Wiley & Sons, 4th edition 1999.

Avitabile E, Forghieri C, Campadelli-Fiume G. (2009) J. Virol. 83: 10752-10760.

Backovic M, Longnecker R, Jardetzky T S. (2009) PNAS USA 106: 2880-5.

Bagshaw S M, Crabtree T, Green F, Stewart D A. (1991) Antibody, Immunoconjugates and Radiopharmaceuticals 4: 915-922.

Bankier A T, Beck S, Bohni R, Brown C M, Cerny R, et al. (1991) DNA Seq. 2(1): 1-12.
Barbas C F 3rd, Hu D, Dunlop N, Sawyer L, Cababa D. (1994) PNAS USA 91: 3809-3813.
Bernasconi N L, Traggiai E, Lanzavecchia A. (2002) Science 298: 2199-2202.
Bird R E, Hardman K D, Jacobson J W, Johnson S, Kaufman B M, et al. (1998) Science 242(4877): 423-6.
Boeckh M, Bowden R A, Storer B, Chao N J, Spielberger R, Tierney D K, Gallez-Hawkins G, Cunningham T, Blume K G, Levitt D, Zaia J A. (2001) Biol. Blood Marrow Transplant. 7: 343-351.
Britt W J, Vugler L, Butfiloski E J, Stephens E B. (1990) J. Virol. 64(3): 1079-85.
Borucki M J, Spritzler J, Asmuth D M, Gnann J, Hirsch M S, Nokta M, Aweeka F, Nadler P I, Sattler F, Alston B, Nevin T T, Owens S, Waterman K, Hubbard L, Caliendo A, Pollard R B; AACTG 266 Team. (2004) Antiviral Res. 64(2): 103-111.
Casali P. (1986) Science 234: 476-9.
Caton A J, Herlyn D, Ross A H, Koprowski H. (1990) J. Immunol. 144(5): 1965-8.
Chadd H E & Chamow S M. (2001) Curr. Op. Biotech. 12: 188-194.
Chee M S, Bankier A T, Beck S, Bohni R, Brown C M, et al. (1990) Curr. Top Microbiol. Immunol. 154:125-69.
Chothia C, Lesk A M, Levitt M, Amit A G, Mariuzza R A, et al. (1986) Science 223: 755-758.
Chothia C, Lesk A M. (1987) J. Mol. Biol. 196(4): 901-17.
Chothia C, Lesk A M, Tramontano A, Levitt M, Smith-Gill S J, et al. (1989) Nature 342(6252): 877-83.
Chothia C, Lesk A M, Gherardi E, Tomlinson I M, Walter G, et al. (1992) J. Molecular Biology 227, 799-817.
Chou S W, Dennison K M. (1991) J. Infect. Dis. 163(6): 1229-34.
Davies J, Jiang L, Pan L Z, LaBarre M J, Anderson D, Reff M. (2001) Biotechnol. Bioeng. 74(4): 288-94.
Eswar N, Webb B, Marti-Renom M A, Madhusudhan M S, Eramian D, Shen M Y, Pieper U, Sali A. (2006) Curr. Protoc. Bioinformatics, Chapter 5: Unit.
Fiser A & Sali A. (2003) Bioinformatics 19(18): 2500-1.
Gram H, Marconi L A, Barbas C F 3rd, Collet T A, Lerner R A, Kang A S. (1992) PNAS USA 89(8): 3576-80.
Guex N. & Peitsch M C. (1997) Electrophoresis 18: 2714-2723.
Haan & Maggos (2004) BioCentury, 12(5): A1-A6.
Hamilton A A, Manuel D M, Grundy J E, Turner A J, King S I, Adair J R, White P, Carr F J, Harris W J. (1997) J. Infect. Dis. 176: 59-68.
Harlow and Lane, Antibodies: A Laboratory Manual, Cold Spring Harbor Laboratory, Cold Spring Harbor N.Y., pp. 726, 1988.
Heldwein E E, Lou H, Bender F C, Cohen G H, Eisenberg R J, Harrison S C. (2006) Science 313: 217-220.
Hieter P A, Maizel J V Jr, Leder P. (1982) J. Biol. Chem. 257(3): 1516-22.
Holliger P, Prospero T, Winter G. (1993) PNAS USA. 90(14): 6444-8.
Holliger P & Winter G. (1993) Curr. Op. Biotech. 4: 446-449.
Holliger P & Bohlen H. (1999) Cancer & Metastasis Rev. 18: 411-419.
Holliger P & Hudson P J. (2005) Nature Biot. 23(9): 1126-1136.
Holt L J, Herring C, Jespers L S, Woolven B P, Tomlinson I M. (2003) Trends in Biotechnology 21: 484-490.
Hu S, Shively L, Raubitschek A, Sherman M, Williams L E, et al. (1996) Cancer Res. 56: 3055-3061.
Hunter W M & Greenwood F C. (1962) Nature 194: 495-6.
Huston J S, Levinson D, Mudgett-Hunter M, Tai M S, Novotny J, et al. (1988) PNAS USA, 85: 5879-5883.
Jung J, Yi A K, Zhang X, Jongseon C, Li L Choi Y S. (2002) J. Immunol. 169: 2368-73.
Kabat, E A, Wu T T, Perry H M, Gottesman K S, Foeller C. (1991) Sequences of Proteins of Immunological Interest, 5th Edition. US Department of Health and Human Services, Public Service, NIH, Washington.
Kahan E A & Wu T T. (1991) J. Immunol. 147: 1709-1719.
Kari B, Gehrz R. (1991) J. Gen. Virol. 72: 1975-83.
Kenneson A, Cannon M J. (2007) Rev. Med. Virol. 17: 253-276.
Kniess N, Mach M, Fay J, Britt W J. (1991) J. Virol. 65: 138-46.
Köhler G & Milstein C. (1975) Nature 256(5517): 495-7.
Koide A, Bailey C W, Huang X, Koide S. (1998) J. Mol. Biol. 284: 1141-1151.
Kontermann R & Dubel S. (2001) Antibody Engineering, Springer-Verlag New York, LLC; ISBN: 3540413545.
Kozbor D, Roder J C. (1981) J. Immunol. 127(4): 1275-80.
Kufer P, Lutterbiise R, Baeuerle P A. (2004) TRENDS in Biotechnology 22(5): 238-244.
Lanzavecchia A. (1985) Nature 314(6011): 537-9.
Larrick J W & Thomas D W (2001) Curr. Op. Biotech. 12: 411-418.
Ledermann J A, Begent R H, Massof C, Kelly A M, Adam T, Bagshawe K D. (1991) Int. J. Cancer 47: 659-664.
Lundgren K, Wahlgren M, Troye-Blomberg M, Berzins K, Perlmann H, et al. (1983) J. Immunol. 131(4): 2000-3.
Mach M, Kropff B, Dal-Monte P, Britt W J. (2000) J. Virol. 74: 11881-11892.
Mahy B W J, Kangro H O. (1996) Virology Methods Manual, pages 35-37. San Diego: Academic Press.
Marks J D, Griffiths A D, Malmqvist M, Clackson T P, Bye J M, Winter G. (1992) Biotechnology 10(7): 779-83.
Marshall G S, Rabalais G P, Stout G G, Waldeyer S L. (1992) J. Infect. Dis. 165: 381-384.
Martin, AC R. (1996) PROTEINS: Structure, Function and Genetics, 25, 130-133.
McCafferty J, Griffiths A D, Winter G, Chiswell D J. (1990) Nature 348(6301): 552-4.
Mendez M J, Green L L, Corvalan J R, Jia X C, Maynard-Currie C E (1997) Nature Genet. 15(2): 146-156.
Meyer H, Masuho Y, Mach M. (1990) J. Gen. Virol. 71: 2443-50.
Meyer H, Sundqvist V A, Pereira L, Mach M. (1992) J. Gen. Virol. 73(9): 2375-83.
Milhavet O, Gary D S, Mattson M P (2003) Pharmacol. Rev. 55(4): 629-48.
Moss P, Rickinson A. (2005) Nat. Rev. Immunol. 5: 9-20.
Nigro G, Adler S P, La T R, Best A M. (2005) N. Engl. J. Med. 353: 1350-1362.
Nygren P A, Uhlen M. (1997) Curr. Op. Struct. Biol. 7: 463-469.
Ohizumi Y, Suzuki H, Matsumoto Y, Masuho Y, Numazaki Y. (1992) J. Gen. Virol. 73(10): 2705-7.
Ohlin M, Sundqvist V A, Mach M, Wahren B, Borrebaeck C A. (1993) J. Virol. 67(2): 703-10.
Opalinska J B & Gewirtz A M (2003) Sci. STKE 206: pe47
Patrone M, Secchi M, Bonaparte E, Milanesi G, Gallina A. (2007) J. Virol. 81: 11479-11488.
Pearson W R, Lipman D J. (1988) PNAS USA 85(8): 2444-8.
Plückthun A. (1991) BioTechnology 9: 545-551.
Posner M R, Hideshima T, Cannon T, Mukherjee M, Mayer K H, Byrn R A. (1991) J. Immunol. 146(12): 4325-32.

Qiu X Q, Wang H, Cai B, Wang L L, Yue S T. (2007) Nat. Biotechnol. 25: 921-929.

Raanani P, Gafter-Gvili A, Paul M, Ben-Bassat I, Leibovici L, Shpilberg O. (2009) J. Clin. Oncol. 27: 770-781.

Raff H V, Siscoe P J, Wolff E A, Maloney G, Shuford W. (1988) J. Exp. Med. 168(3): 905-17.

Ravetch J V, Siebenlist U, Korsmeyer S, Waldmann T, Leder P. (1981) Cell 3(2): 583-91.

Razonable R R, Paya C V. (2003) Herpes 10: 60-65.

Reiter Y, Brinkmann U, Lee B, Pastan I. (1996) Nature Biotech, 14: 1239-1245.

Robinson J R. ed., (1978) Sustained and Controlled Release Drug Delivery Systems, Marcel Dekker, Inc., New York.

Roche S, Bressanelli S, Rey F A, Gaudin Y. (2006) Science 313: 187-191.

Roche S, Rey F A, Gaudin Y, Bressanelli S. (2007) Science 315: 843-8.

Rosén A, Gergely P, Jondal M, Klein G, Britton S. (1977) Nature 267(5606): 52-4.

Rosén A, Persson K, Klein G. (1983) J. Immunol. 130(6): 2899-902.

Sambrook and Russell, Molecular Cloning: a Laboratory Manual: 3rd edition, 2001, Cold Spring Harbor Laboratory Press.

Schier R, McCall A, Adams G P, Marshall K W, Merritt H, et al. (1996) J. Mol. Biol. 263: 551-567.

Schoppel K, Kropff B, Schmidt C, Vornhagen R, Mach M. (1997) J. Infect. Dis. 175: 533-544.

Schreiber A, Harter G, Schubert A, Bunjes D, Mertens T, Michel D. (2009) Expert. Opin. Pharmacother. 10: 191-209.

Segal D M, Padlan E A, Cohen G H, Rudikoff S, Potter M, Davies D R. (1974) Proc Natl Acad Sci USA. 71(11): 4298-302.

Sharon J. (1990a) PNAS USA. 87(12): 4814-7.

Sharon J. (1990b) J. Immunol. 144: 4863-4869.

Shatsky M, Nussinov R, Wolfson H J. (2004) Proteins 56(1): 143-156.

Shields R L, Lai J, Keck R, O'Connell L Y, Hong K, et al (2002) J. Biol. Chem. 277(30): 26733-40.

Shimamura M, Mach M, Britt W J. (2006) J. Virol. 80: 4591-4600.

Shinkawa T, Nakamura K, Yamane N, Shoji-Hosaka E, Kanda Y, et al (2003) J. Biol. Chem. 278(5): 3466-73.

Smith T F, & Waterman M S. (1981) J. Mol. Biol. 147(1): 195-7.

Sokos D R, Berger M, Lazarus H M. (2002) Biol. Blood Marrow Transplant. 8: 117-130.

Spadema S, Kropff B, Kodel Y, Shen S, Coley S, Lu S, Britt W, Mach M. (2005) J Virol 79: 11837-11847.

Steenbakkers P G, Van Wezenbeek P M, van Zanten J, The TH. (1993) Hum. Antibodies Hybridomas 4(4): 166-73.

Steenbakkers P G, Hubers H A, Rijnders A W. (1994) Mol. Biol. Rep. 19(2):125-34.

Steinitz M, Klein G, Koskimies S, Makel O. (1977) Nature 269(5627): 420-2.

Steinitz M, Izak G, Cohen S, Ehrenfeld M, Flechner I. (1980) 287(5781): 443-5.

Steinitz M, Tamir S, Goldfarb A. (1984) J. Immunol. 132(2): 877-82.

Streblow D N, Orloff S L, Nelson J A. (2007) Curr. Opin. Immunol. 19: 577-582.

Tiller T, Meffre E, Yurasov S, Tsuiji M, Nussenzweig M C, Wardemann H. (2008) J. Immunol. Methods 329: 112-24 and Corrigendum (2008) J. Immunol. Methods 334: 142.

Traggiai E, Becker S, Subbarao K, Kolesnikova L, Uematsu Y, Gismondo M R, Murphy B R, Rappuoli R, Lanzavecchia A. (2004) Nat. Med. 10(8): 871-5.

Udey J A, Blomberg B. (1987) Immunogenetics 25(1): 63-70.

Umaña P, Jean-Mairet J, Moudry R, Amstutz H, Bailey J E. (1999) Nat. Biotechnol. 17(2): 176-80.

Urban M, Britt W, Mach M. (1992) J. Virol. 66: 1303-1311.

Urban M, Klein M, Britt W J, Hassfurther E, Mach M. (1996) J. Gen. Virol. 77(7): 1537-1547.

Vasicek T J, Leder P. J. Exp. Med. 172(2): 609-20.

Voet & Voet, Biochemistry, 3rd Edition, (Wiley) 2004.

Wagner B, Kropff B, Kalbacher H, Britt W, Sundqvist V A, Ostberg L, Mach M. (1992) J. Virol. 66: 5290-5297.

Ward E S, Güssow D, Griffiths A D, Jones P T, Winter G. (1989) Nature 341(6242): 544-6.

Wess L. (2004) In: BioCentury, The Bernstein Report on BioBusiness, 12(42), A1-A7.

Whitelegg N R U & Rees A R. (2000) Prot. Eng. 12: 815-824.

Yamaguchi H, Furukawa K, Fortunato S R, Livingston P O, Lloyd K O, Oettgen H F, Old L J. (1987) Proc. Natl. Acad. Sci USA 84: 2416-20.

EP0120694A: Boss M A et al.
EP0125023A: Cabilly S et al.
EP0184187A: Kudo A et al.
EP0239400A: Winter G P.
EP0664834B: Harris W J et al.
U.S. Pat. No. 4,275,149: Litman D J et al.
U.S. Pat. No. 4,318,980: Boguslaski R C et al.
U.S. Pat. No. 4,424,200: Crockford D R, Rhodes B A
U.S. Pat. No. 4,479,930: Hnatowich D J.
U.S. Pat. No. 5,043,281: Masuho Y et al.
U.S. Pat. No. 5,750,106: Ostberg L.
U.S. Pat. No. 5,814,468: Sliman O et al.
U.S. Pat. No. 6,602,684: Umaña P et al.
U.S. Pat. No. 6,998,253: Presta L G, Snedecor B R
US20030157108: Presta L G et al.
US2009004198: Nakajima K et al.
WO 91/009967 A1: Adair J R et al.
WO 92/001047 A1: McCafferty J et al.
WO 93/011161 A1: Whitlow M D et al.
WO 93/021952 A1: Borrebaeck C et al.
WO 00/034784 A1: Lipovsek D.
WO 03/068819 A1: Grawunder U & Melchers G F.
WO 04/006955 A1: Foote J.
WO 04/076677 A2: Lanzavecchia A.
WO 04/106375 A1: Hoogenboom H R J M et al.
WO 07/068,758 A1: Funaro A et al.
WO 08/084,410 A2: Lanzavecchia A, Macagano A.
WO 08/071,806 A1: Funaro A et al.
WO 09/003,975 A1: Funaro A et al.
WO 09/024,445 A1: Funaro A et al.
WO 09/114,560 A2: Olsen O.
WO 10/007,463 A1: Lanzavecchia A, Macagano A.
WO 10/007,533 A2: Lanzavecchia A, Macagano A.
WO 10/114,105 A1: Takada K, Kurino R, Watanabe M.
WO 10/114,106 A1: Takada K, Kurino R, Torashima T.

The invention is further described by the following numbered paragraphs:

1. An isolated binding member for human cytomegalovirus (hcmv) gb protein, which binds hcmv gb protein at a region within residues 121 to 132 and 344 to 438, the residue numbering being defined according to the full length gb strain ad169 amino acid sequence seq id no: 239, Said isolated binding member comprising a set of cdrs: hcdr1, hcdr2, hcdr3, lcdr1, lcdr2 and lcdr3, wherein the set of cdrs has 22 or fewer amino acid alterations from a set of cdrs in which:

Hcdr1 has amino acid sequence seq id no: 3;
Hcdr2 has amino acid sequence seq id no: 4;
Hcdr3 has amino acid sequence seq id no: 5;
Lcdr1 has amino acid sequence seq id no: 93;
Lcdr2 has amino acid sequence seq id no: 94; and
Lcdr3 has amino acid sequence seq id no: 95,
And wherein the binding member has a kd of not more than 50 nm as defined by surface plasmon resonance.

2. The isolated binding member for hcmv gb protein of paragraph 1, which binds hcmv gb protein with a kd of not more than 1 nm as defined by surface plasmon resonance.

3. The isolated binding member according to paragraph 2, wherein the kd is not more than 0.5 nm.

4. The isolated binding member according to paragraph 2 or paragraph 3, wherein the kd is not more than 0.1 nm.

5. The isolated binding member according to any of the preceding paragraphs, wherein the binding member does not bind to antigenic domain 1 (ad-1) or antigenic domain 2 (ad-2) of hcmv gb protein.

6. The isolated binding member according to any of the preceding paragraphs, wherein the concentration of binding member required for 50% neutralisation of a clinical isolate of hcmv is 10 µg/ml or less in a neutralisation assay for neutralisation of hcmv infection of human foreskin fibroblasts.
7. The isolated binding member according to paragraph 6, comprising an hcdr1 wherein:
Kabat residue 31 is asp or gly;
Kabat residue 32 is his, phe or tyr;
Kabat residue 33 is tyr;
Kabat residue 34 is met, ile or leu; and
Kabat residue 35 is val or asn.
8. The isolated binding member according to paragraph 7, wherein hcdr1 is seq id no: 3.
9. The isolated binding member according to any of paragraphs 6 to 8, comprising an hcdr2 wherein:
Kabat residue 50 is trp, ser or cys;
Kabat residue 53 is gln, asn or his;
Kabat residue 54 is ser or thr;
Kabat residue 58 is gly, lys, asn or his;
Kabat residue 60 is gly or ala; and
Kabat residue 64 is gln or arg.
10. The isolated binding member according to paragraph 9, wherein hcdr2 has amino acid sequence seq id no: 4.
11. The isolated binding member according to any of the preceding paragraphs, comprising an hcdr3 wherein:
Kabat residue 99 is thr or ala;
Kabat residue 100 is val or met;
Kabat residue 100a is ser or thr
Kabat residue 100b is asn or thr;
Kabat residue 100c is ser or phe;
Kabat residue 100e is leu, met or ala;
Kabat residue 100f is ser or gly;
Kabat residue 100k is his or tyr;
Kabat residue 100l is asn, ser or asp;
Kabat residue 100m is arg, val or ile;
Kabat residue 100n is leu or met;
Kabat residue 101 is asp or gly; and
Kabat residue 102 is ala, val or ile.
12. The isolated binding member according to paragraph 11, wherein hcdr3 has amino acid sequence seq id no: 5.
13. The isolated binding member according to any of paragraphs 7 to 12, wherein kabat residue 26 in lcdr1 is ser or asn or where kabat residue 27 in lcdr1 is ser or arg.
14. The isolated binding member according to paragraph 13, wherein lcdr1 is seq id no: 93.
15. The isolated binding member according to any of paragraphs 7 to 14, wherein kabat residue 56 in lcdr2 is ser or pro.
16. The isolated binding member according to paragraph 15, wherein lcdr2 is seq id no: 94.
17. The isolated binding member according to any of the preceding paragraphs, comprising an lcdr3 wherein:
Kabat residue 89 is gly or ala;
Kabat residue 91 is pro or trp;
Kabat residue 93 is arg or ser;
Kabat residue 94 is ser or asp;
Kabat residue 95a is ser, gly or ala;
Kabat residue 96 is val or tyr; and
Kabat residue 97 is ile or val.
18. The isolated binding member according to paragraph 17, comprising an lcdr3 having amino acid sequence seq id no: 95.
19. The isolated binding member according to any of the preceding paragraphs, comprising a set of cdrs: hcdr1, hcdr2, hcdr3, lcdr1, lcdr2 and lcdr3, wherein:
Hcdr1 is seq id no: 3;
Hcdr2 is seq id no: 4;
Hcdr3 is seq id no: 5;
Lcdr1 is seq id no: 93;
Lcdr2 is seq id no: 94; and
Lcdr3 is seq id no: 95.
20. The isolated binding member according to any of the preceding paragraphs, wherein the binding member comprises an antibody molecule or functional fragment thereof comprising an antibody vh domain, and wherein the vh domain has the vh domain amino acid sequence shown in seq id no: 2.
21. The isolated binding member according to any of the preceding paragraphs, wherein the binding member comprises an antibody molecule or functional fragment thereof comprising an antibody vl domain wherein the vl domain has the vl domain amino acid sequence shown in seq id no: 92.
22. An isolated antibody molecule comprising a heavy chain comprising amino acid sequence seq id no: 2 and a light chain comprising amino acid sequence seq id no: 92.
23. An isolated antibody molecule that binds hcmv gb protein, wherein the antibody molecule comprises a vh domain amino acid sequence at least 90% identical to seq id no: 2 and a vl domain amino acid sequence at least 90% identical to seq id no: 92.
24. A binding member or antibody molecule that competes for binding to hcmv gb protein with a binding member or isolated antibody molecule of any of the preceeding paragraphs.
25. An antibody molecule according to paragraph 22 or 23, wherein the antibody molecule is an igg.
26. An isolated vh domain of an antibody molecule according to any of paragraphs 20 or 22 to 25.
27. An isolated vl domain of an antibody molecule according to any of paragraphs 21 to 25.
28. A composition comprising an isolated binding member according to any of paragraphs 1 to 21, or an antibody molecule according to any of paragraphs 22 to 25, and a pharmaceutically acceptable excipient.
29. A composition comprising an isolated binding member according to any of paragraphs 1 to 21, or an antibody molecule according to any of paragraphs 22 to 25, for use in a method of treatment of the human or animal body by therapy.
30. The composition according to paragraph 29 for use in treating a disorder associated with hcmv.

31. A composition comprising an isolated binding member according to any of paragraphs 1 to 21, or an antibody molecule according to any of paragraphs 22 to 25, for use in the treatment of a disorder associated with hcmv.
32. The composition according to paragraph 30 or the composition for use according to paragraph 31, wherein the disorder is a hcmv infection.
33. The composition according to any one of paragraphs 29 to 32, further comprising an isolated binding member or antibody molecule that binds hcmv gb, gh, gl, ul128, ul130 and/or ul131a protein.
34. A method of treating a disorder associated with hcmv in an individual, comprising administering a binding member according to any of paragraphs 1 to 21, or an antibody molecule according to any of paragraphs 22 to 25, to the individual, and preferably wherein the individual has a compromised immune system.
35. The method according to paragraph 34, wherein the individual is a pregnant woman, a newborn, a transplant recipient or an individual infected with hiv.
36. An isolated nucleic acid molecule comprising a nucleotide sequence encoding a binding member according to any of paragraphs 1 to 21, a vh domain according to paragraph 26, a vl domain according to paragraph 27, or an antibody molecule according to any of paragraphs 22 to 25.
37. A host cell in vitro transfected or transduced with a nucleic acid molecule according to paragraph 36.
38. A method of producing a binding member, an antibody molecule or an antibody vh or vl domain, comprising culturing a host cell according to paragraph 37 under conditions for production of the binding member, antibody molecule or antibody vh or vl domain.
39. The method according to paragraph 38, further comprising isolating and/or purifying the binding member, antibody molecule, vh domain or vl domain.
40. The method according to paragraph 38 or paragraph 39, further comprising formulating the binding member, antibody molecule, vh domain or vl domain into a composition comprising at least one additional component.
41. A method of neutralising hcmv in a subject or sample, comprising administering to said subject or sample a binding member according to any of paragraphs 1 to 21, or an antibody molecule according to any of paragraphs 22 to 25, in an amount sufficient to reduce hcmv infectivity by at least 50% at a concentration of from about 0.1 to about 5.0 µg/ml.

\* \* \*

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

---

What is claimed is:

1. An isolated antibody or antigen-binding fragment thereof for human cytomegalovirus (HCMV) gB protein, said isolated antibody or antigen binding fragment thereof comprising: SEQ ID NO: 3; SEQ ID NO: 4; SEQ ID NO: 5; SEQ ID NO: 93; SEQ ID NO: 94; and SEQ ID NO: 95.

2. The isolated antibody or antigen-binding fragment thereof according to claim 1, wherein the antibody or antigen-binding fragment thereof does not bind to antigenic domain 1 (AD-1) or antigenic domain 2 (AD-2) of HCMV gB protein.

3. The isolated antibody or antigen-binding fragment thereof according to claim 1, wherein the concentration of antibody or antigen-binding fragment thereof required for 50% neutralisation of a clinical isolate of HCMV is 10 μg/ml or less in a neutralisation assay for neutralisation of HCMV infection of human foreskin fibroblasts.

4. The isolated antibody or antigen-binding fragment thereof according to claim 1, wherein the isolated antibody or antigen-binding fragment thereof comprises an antibody heavy chain variable domain ($V_H$), and wherein the heavy chain variable domain ($V_H$) comprises SEQ ID NO:2.

5. The isolated antibody or antigen-binding fragment thereof according to claim 1, wherein the isolated antibody or antigen-binding fragment thereof comprises an antibody light chain variable domain ($V_L$), and wherein the light chain variable domain ($V_L$) comprises SEQ ID NO: 92.

6. An isolated antibody molecule comprising a heavy chain comprising amino acid sequence SEQ ID NO: 2 and a light chain comprising amino acid sequence SEQ ID NO: 92.

7. The isolated antibody molecule according to claim 6, wherein the isolated antibody molecule is an IgG.

8. A method of neutralising HCMV in a subject or sample, comprising administering to said subject or sample an isolated antibody or antigen-binding fragment thereof according to claim 1, or an isolated antibody molecule according to claim 6, in an amount sufficient to reduce HCMV infectivity by at least 50% at a concentration of from about 0.1 to about 5.0 μg/ml.

9. The method of claim 8, wherein said administering is to said subject.

10. The method of claim 9, comprising administering to said subject an isolated antibody molecule comprising a heavy chain comprising amino acid sequence SEQ ID NO: 2 and a light chain comprising amino acid sequence SEQ ID NO: 92.

11. The method of claim 8, wherein said administering is to said sample.

12. The method of claim 11, comprising administering to said sample an isolated antibody molecule comprising a heavy chain comprising amino acid sequence SEQ ID NO: 2 and a light chain comprising amino acid sequence SEQ ID NO: 92.

13. A method of reducing HCMV titer in an individual, comprising administering an isolated antibody or antigen-binding fragment thereof according to claim 1, or an isolated antibody molecule according to claim 6, to the individual in an effective amount.

14. The method of claim 13, wherein the individual has a compromised immune system.

15. The method of claim 13, wherein the individual is a pregnant woman, a newborn, a transplant recipient, or an individual infected with HIV.

16. The method of claim 13, comprising administering an isolated antibody molecule comprising a heavy chain comprising amino acid sequence SEQ ID NO: 2 and a light chain comprising amino acid sequence SEQ ID NO: 92 to the individual.

17. The method of claim 13, wherein the antibody or antigen-binding fragment thereof or the isolated antibody molecule is administered to the individual at a dosage of between 100 μg and 1 g.

18. A pharmaceutical composition comprising the isolated antibody or antigen-binding fragment thereof of claim 1 and a pharmaceutically acceptable carrier.

19. The pharmaceutical composition of claim 18, wherein the pharmaceutical composition comprises a stabilizer.

20. A pharmaceutical composition comprising the isolated antibody molecule of claim 6 and a pharmaceutically acceptable carrier.

21. The pharmaceutical composition of claim 20, wherein the pharmaceutical composition comprises a stabilizer.

22. The isolated antibody molecule according to claim 7, wherein the IgG is an $IgG_1$.

23. The isolated antibody molecule according to claim 7, wherein the IgG is an IgG$_4$.

24. The isolated antibody or antigen-binding fragment thereof according to claim 1, wherein the antibody or antigen-binding fragment thereof binds HCMV gB protein at a region within residues 121 to 132 and 344 to 438, the residue numbering corresponding to positions 121 to 132 and 344 to 438 of SEQ ID NO: 239.

25. An isolated antibody or antigen-binding fragment thereof that binds to HCMV gB protein, wherein said isolated antibody or antigen-binding fragment thereof comprises a V$_H$ domain comprising SEQ ID NO: 2 and a V$_L$ domain comprising SEQ ID NO: 92.

* * * * *

SEQUENCE LISTING

```
<160> NUMBER OF SEQ ID NOS: 321

<210> SEQ ID NO 1
<211> LENGTH: 393
<212> TYPE: DNA
<213> ORGANISM: Homo sapiens

<400> SEQUENCE: 1
caggtgcagc tggtgcagtc tggggctgag gtgaggaagc ctggggcctc agtgaaggtc      60
tcctgcaagg cttctggata cagcctcaaa gaccactata tggtctgggt gcgacaggcc     120
cctggccaag ggcttgagtg gatgggatgg atcaaccctc agagtggtgg cacaggctac     180
ggacagaagt tcagggcag ggtcaccatg acccgggaca cgtccaccaa cacagcctac     240
atgatactga gcagcctgag atctgacgac acggccgtgt atttctgtgc gagagatggg     300
gctaagacgg tgtccaattc cggactgtct ttgttgtact atcacaaccg tctggacgcc     360
tggggccaag ggacaatggt caccgtctct agc                                  393

<210> SEQ ID NO 2
<211> LENGTH: 131
<212> TYPE: PRT
<213> ORGANISM: Homo sapiens

<400> SEQUENCE: 2

Gln Val Gln Leu Val Gln Ser Gly Ala Glu Val Arg Lys Pro Gly Ala
 1               5                  10                  15

Ser Val Lys Val Ser Cys Lys Ala Ser Gly Tyr Ser Leu Lys Asp His
             20                  25                  30

Tyr Met Val Trp Val Arg Gln Ala Pro Gly Gln Gly Leu Glu Trp Met
         35                  40                  45

Gly Trp Ile Asn Pro Gln Ser Gly Gly Thr Gly Tyr Gly Gln Lys Phe
     50                  55                  60
```

Gln Gly Arg Val Thr Met Thr Arg Asp Thr Ser Thr Asn Thr Ala Tyr
65                  70                  75                  80

Met Ile Leu Ser Ser Leu Arg Ser Asp Asp Thr Ala Val Tyr Phe Cys
                85                  90                  95

Ala Arg Asp Gly Ala Lys Thr Val Ser Asn Ser Gly Leu Ser Leu Leu
            100                 105                 110

Tyr Tyr His Asn Arg Leu Asp Ala Trp Gly Gln Gly Thr Met Val Thr
        115                 120                 125

Val Ser Ser
    130

<210> SEQ ID NO 3
<211> LENGTH: 5
<212> TYPE: PRT
<213> ORGANISM: Homo sapiens

<400> SEQUENCE: 3

Asp His Tyr Met Val
1               5

<210> SEQ ID NO 4
<211> LENGTH: 17
<212> TYPE: PRT
<213> ORGANISM: Homo sapiens

<400> SEQUENCE: 4

Trp Ile Asn Pro Gln Ser Gly Gly Thr Gly Tyr Gly Gln Lys Phe Gln
1               5                   10                  15

Gly

<210> SEQ ID NO 5
<211> LENGTH: 22
<212> TYPE: PRT
<213> ORGANISM: Homo sapiens

<400> SEQUENCE: 5

Asp Gly Ala Lys Thr Val Ser Asn Ser Gly Leu Ser Leu Leu Tyr Tyr
1               5                   10                  15

His Asn Arg Leu Asp Ala
            20

<210> SEQ ID NO 6
<211> LENGTH: 393
<212> TYPE: DNA
<213> ORGANISM: Homo sapiens

<400> SEQUENCE: 6
caggtgcagc tggtgcagcc tggggctgag gtgaagaagc ctggggcctc agtgaaggtc      60
tcctgcaagg cttctggatt caccctcagc gaccactatc tggtctgggt gcgacaggcc    120
cctggccaag ggtttgagtg gatgggatgg atcaaccctc agagtggtgg cacaggctac    180
gcacagaagt tcagggcag ggtcaccatg accagggact cgtccagcaa cacagcgttc     240
atggacctga gcaagctgac atctgacgac acggccgtgt acttctgtgc gagagatggg    300
gctaagacgg tgtctaattc cggactgggt ctactgtatt atcacagccg actggacgcc    360
tggggccagg gaaccctggt caccgtctcc agc                                 393

<210> SEQ ID NO 7
<211> LENGTH: 131

```
<212> TYPE: PRT
<213> ORGANISM: Homo sapiens

<400> SEQUENCE: 7

Gln Val Gln Leu Val Gln Pro Gly Ala Glu Val Lys Lys Pro Gly Ala
1               5                   10                  15

Ser Val Lys Val Ser Cys Lys Ala Ser Gly Phe Thr Leu Ser Asp His
            20                  25                  30

Tyr Leu Val Trp Val Arg Gln Ala Pro Gly Gln Gly Phe Glu Trp Met
        35                  40                  45

Gly Trp Ile Asn Pro Gln Ser Gly Gly Thr Gly Tyr Ala Gln Lys Phe
    50                  55                  60

Gln Gly Arg Val Thr Met Thr Arg Asp Ser Ser Asn Thr Ala Phe
65                  70                  75                  80

Met Asp Leu Ser Lys Leu Thr Ser Asp Thr Ala Val Tyr Phe Cys
                85                  90                  95

Ala Arg Asp Gly Ala Lys Thr Val Ser Asn Ser Gly Leu Gly Leu Leu
            100                 105                 110

Tyr Tyr His Ser Arg Leu Asp Ala Trp Gly Gln Gly Thr Leu Val Thr
        115                 120                 125

Val Ser Ser
    130

<210> SEQ ID NO 8
<211> LENGTH: 5
<212> TYPE: PRT
<213> ORGANISM: Homo sapiens

<400> SEQUENCE: 8

Asp His Tyr Leu Val
1               5

<210> SEQ ID NO 9
<211> LENGTH: 17
<212> TYPE: PRT
<213> ORGANISM: Homo sapiens

<400> SEQUENCE: 9

Trp Ile Asn Pro Gln Ser Gly Gly Thr Gly Tyr Ala Gln Lys Phe Gln
1               5                   10                  15

Gly

<210> SEQ ID NO 10
<211> LENGTH: 22
<212> TYPE: PRT
<213> ORGANISM: Homo sapiens

<400> SEQUENCE: 10

Asp Gly Ala Lys Thr Val Ser Asn Ser Gly Leu Gly Leu Leu Tyr Tyr
1               5                   10                  15

His Ser Arg Leu Asp Ala
            20

<210> SEQ ID NO 11
<211> LENGTH: 393
<212> TYPE: DNA
<213> ORGANISM: Homo sapiens

<400> SEQUENCE: 11
caggtgcacc tggtgcaatc tggggctgag gtgaggaagc ctggggcctc agtgaaggtc    60
```

```
tcctgcaagg cttctggata caccttcacc gactactatc tgaactgggt gcgacaggcc    120
cctggacaag ggcttgagtg gatgggaagc atcaaccca acactggtgg cacaaagtat    180
gcacagaaat ttcagggcag ggtcactatg accagggaca cgtccatcag ggcagcctac    240
atggagctga gcagcctgag atctgacgac acggccgtct attactgtgc gagagatggg    300
gctaaaacga tgactacgtc tggactgtct tgttgtact actacgacgt tatggacgtc    360
tggggccagg gaaccctggt caccgtctcc agc                                393
```

<210> SEQ ID NO 12
<211> LENGTH: 131
<212> TYPE: PRT
<213> ORGANISM: Homo sapiens

<400> SEQUENCE: 12

Gln Val His Leu Val Gln Ser Gly Ala Glu Val Arg Lys Pro Gly Ala
1               5                   10                  15

Ser Val Lys Val Ser Cys Lys Ala Ser Gly Tyr Thr Phe Thr Asp Tyr
            20                  25                  30

Tyr Leu Asn Trp Val Arg Gln Ala Pro Gly Gln Gly Leu Glu Trp Met
        35                  40                  45

Gly Ser Ile Asn Pro Asn Thr Gly Gly Thr Lys Tyr Ala Gln Lys Phe
    50                  55                  60

Gln Gly Arg Val Thr Met Thr Arg Asp Thr Ser Ile Arg Ala Ala Tyr
65                  70                  75                  80

Met Glu Leu Ser Ser Leu Arg Ser Asp Asp Thr Ala Val Tyr Tyr Cys
                85                  90                  95

Ala Arg Asp Gly Ala Lys Thr Met Thr Thr Ser Gly Leu Ser Leu Leu
            100                 105                 110

Tyr Tyr Tyr Asp Val Met Asp Val Trp Gly Gln Gly Thr Leu Val Thr
        115                 120                 125

Val Ser Ser
    130

<210> SEQ ID NO 13
<211> LENGTH: 5
<212> TYPE: PRT
<213> ORGANISM: Homo sapiens

<400> SEQUENCE: 13

Asp Tyr Tyr Leu Asn
1               5

<210> SEQ ID NO 14
<211> LENGTH: 17
<212> TYPE: PRT
<213> ORGANISM: Homo sapiens

<400> SEQUENCE: 14

Ser Ile Asn Pro Asn Thr Gly Gly Thr Lys Tyr Ala Gln Lys Phe Gln
1               5                   10                  15

Gly

<210> SEQ ID NO 15
<211> LENGTH: 22
<212> TYPE: PRT
<213> ORGANISM: Homo sapiens

<400> SEQUENCE: 15

Asp Gly Ala Lys Thr Met Thr Thr Ser Gly Leu Ser Leu Leu Tyr Tyr
1               5                   10                  15

Tyr Asp Val Met Asp Val
            20

<210> SEQ ID NO 16
<211> LENGTH: 393
<212> TYPE: DNA
<213> ORGANISM: Homo sapiens

<400> SEQUENCE: 16
caggtgcagc tgatgcagtc tggggctgag gtgaagaagc ctggggcctc agtgaaggtc     60
tcctgcaagg cttctggata caccttcacc ggctactata tgaactgggt gcgacaggcc    120
cctggacaag gcttgagtg gatgggatgc atcaacccga acagtggtgg cacaaactat    180
gcacagaagt tcagggcag gtcaccatg accagggaca cgtccatcag cacagcctac    240
atggaactga ccaggctcag atctgacgac acggccgtat attactgtgc gagagatggg    300
gctaagacgg tgactacctc cggaatgtct ttgttgtact actacgacgt tatggacatc    360
tggggccaag ggacaatggt caccgtctct agc                                  393

<210> SEQ ID NO 17
<211> LENGTH: 131
<212> TYPE: PRT
<213> ORGANISM: Homo sapiens

<400> SEQUENCE: 17

Gln Val Gln Leu Met Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met Asn Trp Val Arg Gln Ala Pro Gly Gln Gly Leu Glu Trp Met
        35                  40                  45

Gly Cys Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Thr Arg Leu Arg Ser Asp Asp Thr Ala Val Tyr Tyr Cys
                85                  90                  95

Ala Arg Asp Gly Ala Lys Thr Val Thr Thr Ser Gly Met Ser Leu Leu
            100                 105                 110

Tyr Tyr Tyr Asp Val Met Asp Ile Trp Gly Gln Gly Thr Met Val Thr
        115                 120                 125

Val Ser Ser
    130

<210> SEQ ID NO 18
<211> LENGTH: 5
<212> TYPE: PRT
<213> ORGANISM: Homo sapiens

<400> SEQUENCE: 18

Gly Tyr Tyr Met Asn
1               5

<210> SEQ ID NO 19
<211> LENGTH: 17
<212> TYPE: PRT

```
<213> ORGANISM: Homo sapiens

<400> SEQUENCE: 19

Cys Ile Asn Pro Asn Ser Gly Gly Thr Asn Tyr Ala Gln Lys Phe Gln
1               5                   10                  15

Gly

<210> SEQ ID NO 20
<211> LENGTH: 22
<212> TYPE: PRT
<213> ORGANISM: Homo sapiens

<400> SEQUENCE: 20

Asp Gly Ala Lys Thr Val Thr Thr Ser Gly Met Ser Leu Leu Tyr Tyr
1               5                   10                  15

Tyr Asp Val Met Asp Ile
            20

<210> SEQ ID NO 21
<211> LENGTH: 393
<212> TYPE: DNA
<213> ORGANISM: Homo sapiens

<400> SEQUENCE: 21
caggtgcagc tggtgcagtc tgaggctgag gtggagaagc ctggggcctc agtgaaggtc      60
tcctgcaagg cttctggata caccttcacc gactactata tgaactgggt gcgacaggcc     120
cctggacaag gcttgagtg gatgggatgc atcaaccctc acagtggtgg cacaaactat      180
gcacagaagt ttcagggcag ggtcaccatg accagggaca cgtccatcag cacagcctac     240
atggagttga gcaggctaaa atctgacgac acggccgtct attactgtgc gagagatggg     300
gctaaaacgg tgactacctt cggagcgtct ttgttgtact actacgacat tatggacgtc     360
tggggccagg gaaccctggt caccgtctcc agc                                  393

<210> SEQ ID NO 22
<211> LENGTH: 131
<212> TYPE: PRT
<213> ORGANISM: Homo sapiens

<400> SEQUENCE: 22

Gln Val Gln Leu Val Gln Ser Glu Ala Glu Val Glu Lys Pro Gly Ala
1               5                   10                  15

Ser Val Lys Val Ser Cys Lys Ala Ser Gly Tyr Thr Phe Thr Asp Tyr
            20                  25                  30

Tyr Met Asn Trp Val Arg Gln Ala Pro Gly Gln Gly Leu Glu Trp Met
        35                  40                  45

Gly Cys Ile Asn Pro His Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Lys Ser Asp Asp Thr Ala Val Tyr Tyr Cys
                85                  90                  95

Ala Arg Asp Gly Ala Lys Thr Val Thr Thr Phe Gly Ala Ser Leu Leu
            100                 105                 110

Tyr Tyr Tyr Asp Ile Met Asp Val Trp Gly Gln Gly Thr Leu Val Thr
        115                 120                 125

Val Ser Ser
    130
```

<210> SEQ ID NO 23
<211> LENGTH: 5
<212> TYPE: PRT
<213> ORGANISM: Homo sapiens

<400> SEQUENCE: 23

Asp Tyr Tyr Met Asn
1               5

<210> SEQ ID NO 24
<211> LENGTH: 17
<212> TYPE: PRT
<213> ORGANISM: Homo sapiens

<400> SEQUENCE: 24

Cys Ile Asn Pro His Ser Gly Gly Thr Asn Tyr Ala Gln Lys Phe Gln
1               5                   10                  15

Gly

<210> SEQ ID NO 25
<211> LENGTH: 22
<212> TYPE: PRT
<213> ORGANISM: Homo sapiens

<400> SEQUENCE: 25

Asp Gly Ala Lys Thr Val Thr Thr Phe Gly Ala Ser Leu Leu Tyr Tyr
1               5                   10                  15

Tyr Asp Ile Met Asp Val
            20

<210> SEQ ID NO 26
<211> LENGTH: 393
<212> TYPE: DNA
<213> ORGANISM: Homo sapiens

<400> SEQUENCE: 26
caggtgcagc tggtgcagtc tgaggctgag gtggagaaac ctggggcctc agtgaaggtc      60
tcctgcaagg cttctggata caccttcacc gacttctata tcaactgggt gcgacaggcc     120
cctggacagg gcttgagtg gatgggatcc atcaaccctc acagtggtgg cacacactat     180
gcacagaagt ttcagggcag ggtcaccatg accagggaca cgtccatcag cacagcctac     240
atggaactga ccaggctcag atctgacgac acggccgtat attactgtgc gagagatggg     300
gctaaaacgg tgactaccct cggaatgtct tgttgtact actacgacgt tatggacatc     360
tggggccaag ggacaatggt caccgtctct agc                                  393

<210> SEQ ID NO 27
<211> LENGTH: 131
<212> TYPE: PRT
<213> ORGANISM: Homo sapiens

<400> SEQUENCE: 27

Gln Val Gln Leu Val Gln Ser Glu Ala Glu Val Glu Lys Pro Gly Ala
1               5                   10                  15

Ser Val Lys Val Ser Cys Lys Ala Ser Gly Tyr Thr Phe Thr Asp Phe
                20                  25                  30

Tyr Ile Asn Trp Val Arg Gln Ala Pro Gly Gln Gly Leu Glu Trp Met
            35                  40                  45

Gly Ser Ile Asn Pro His Ser Gly Gly Thr His Tyr Ala Gln Lys Phe

```
                    50                  55                  60

Gln Gly Arg Val Thr Met Thr Arg Asp Thr Ser Ile Ser Thr Ala Tyr
 65                  70                  75                  80

Met Glu Leu Thr Arg Leu Arg Ser Asp Asp Thr Ala Val Tyr Tyr Cys
                 85                  90                  95

Ala Arg Asp Gly Ala Lys Thr Val Thr Thr Ser Gly Met Ser Leu Leu
            100                 105                 110

Tyr Tyr Tyr Asp Val Met Asp Ile Trp Gly Gln Gly Thr Met Val Thr
        115                 120                 125

Val Ser Ser
    130

<210> SEQ ID NO 28
<211> LENGTH: 5
<212> TYPE: PRT
<213> ORGANISM: Homo sapiens

<400> SEQUENCE: 28

Asp Phe Tyr Ile Asn
 1               5

<210> SEQ ID NO 29
<211> LENGTH: 17
<212> TYPE: PRT
<213> ORGANISM: Homo sapiens

<400> SEQUENCE: 29

Ser Ile Asn Pro His Ser Gly Gly Thr His Tyr Ala Gln Lys Phe Gln
 1               5                  10                  15

Gly

<210> SEQ ID NO 30
<211> LENGTH: 22
<212> TYPE: PRT
<213> ORGANISM: Homo sapiens

<400> SEQUENCE: 30

Asp Gly Ala Lys Thr Val Thr Thr Ser Gly Met Ser Leu Leu Tyr Tyr
 1               5                  10                  15

Tyr Asp Val Met Asp Ile
            20

<210> SEQ ID NO 31
<211> LENGTH: 393
<212> TYPE: DNA
<213> ORGANISM: Homo sapiens

<400> SEQUENCE: 31
caggtgcagc tgatgcagtc tggggctgag gtgaagaagc ctggggcctc agtgaaggtc     60
tcctgcaagg cttctggata caccttcacc gacttctata tcaactgggt gcgacaggcc    120
cctggacagg ggcttgagtg gatgggatcc atcaaccctc acagtggtgg cacacactat    180
gcacagaagt ttcagggcag ggtcaccatg accagggaca cgtccatcag cacagcctac    240
atggagttga aagtctaaa ttctgacgac acggccgtct attactgtgc gagagatggg    300
gctaaaacgg tgactacctt cggagcgtct tgttgtact actacgacat catggacgtc    360
tggggccagg gaaccctggt caccgtctcc agc                                  393

<210> SEQ ID NO 32
```

```
<211> LENGTH: 131
<212> TYPE: PRT
<213> ORGANISM: Homo sapiens

<400> SEQUENCE: 32

Gln Val Gln Leu Met Gln Ser Gly Ala Glu Val Lys Lys Pro Gly Ala
1               5                   10                  15

Ser Val Lys Val Ser Cys Lys Ala Ser Gly Tyr Thr Phe Thr Asp Phe
            20                  25                  30

Tyr Ile Asn Trp Val Arg Gln Ala Pro Gly Gln Gly Leu Glu Trp Met
        35                  40                  45

Gly Ser Ile Asn Pro His Ser Gly Gly Thr His Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Arg Ser Leu Asn Ser Asp Asp Thr Ala Val Tyr Tyr Cys
                85                  90                  95

Ala Arg Asp Gly Ala Lys Thr Val Thr Thr Phe Gly Ala Ser Leu Leu
            100                 105                 110

Tyr Tyr Tyr Asp Ile Met Asp Val Trp Gly Gln Gly Thr Leu Val Thr
        115                 120                 125

Val Ser Ser
    130

<210> SEQ ID NO 33
<211> LENGTH: 5
<212> TYPE: PRT
<213> ORGANISM: Homo sapiens

<400> SEQUENCE: 33

Asp Phe Tyr Ile Asn
1               5

<210> SEQ ID NO 34
<211> LENGTH: 17
<212> TYPE: PRT
<213> ORGANISM: Homo sapiens

<400> SEQUENCE: 34

Ser Ile Asn Pro His Ser Gly Gly Thr His Tyr Ala Gln Lys Phe Gln
1               5                   10                  15

Gly

<210> SEQ ID NO 35
<211> LENGTH: 22
<212> TYPE: PRT
<213> ORGANISM: Homo sapiens

<400> SEQUENCE: 35

Asp Gly Ala Lys Thr Val Thr Thr Phe Gly Ala Ser Leu Leu Tyr Tyr
1               5                   10                  15

Tyr Asp Ile Met Asp Val
            20

<210> SEQ ID NO 36
<211> LENGTH: 393
<212> TYPE: DNA
<213> ORGANISM: Homo sapiens

<400> SEQUENCE: 36
```

```
caggtgcacc tggtgcaatc tgggctgag gtgaggaagc ctggggcctc agtgaaggtc      60
tcctgcaagg cttctggata caccttcacc gactactatc tgaactgggt gcgacaggcc     120
cctggacaag ggcttgagtg gatgggaagc atcaacccca acactggtgg cacaaagtat    180
gcacagaaat tcggggcag ggtcactatg accagggaca cgtccatcag gcagcctac      240 atggagctga gcagcctgag atctgacgac acggccgtct attactgtgc gagagatggg    300
gctaaaacga tgactacgtc tggactgtct tgttgtact actacgacgt tatggacgtc     360
tggggccagg gaaccctggt caccgtctcc agc                                 393
```

<210> SEQ ID NO 37
<211> LENGTH: 131
<212> TYPE: PRT
<213> ORGANISM: Homo sapiens

<400> SEQUENCE: 37

```
Gln Val His Leu Val Gln Ser Gly Ala Glu Val Arg Lys Pro Gly Ala
1               5                   10                  15

Ser Val Lys Val Ser Cys Lys Ala Ser Gly Tyr Thr Phe Thr Asp Tyr
            20                  25                  30

Tyr Leu Asn Trp Val Arg Gln Ala Pro Gly Gln Gly Leu Glu Trp Met
        35                  40                  45

Gly Ser Ile Asn Pro Asn Thr Gly Gly Thr Lys Tyr Ala Gln Lys Phe
    50                  55                  60

Arg Gly Arg Val Thr Met Thr Arg Asp Thr Ser Ile Arg Ala Ala Tyr
65                  70                  75                  80

Met Glu Leu Ser Ser Leu Arg Ser Asp Asp Thr Ala Val Tyr Tyr Cys
                85                  90                  95

Ala Arg Asp Gly Ala Lys Thr Met Thr Thr Ser Gly Leu Ser Leu Leu
            100                 105                 110

Tyr Tyr Tyr Asp Val Met Asp Val Trp Gly Gln Gly Thr Leu Val Thr
        115                 120                 125

Val Ser Ser
    130
```

<210> SEQ ID NO 38
<211> LENGTH: 5
<212> TYPE: PRT
<213> ORGANISM: Homo sapiens

<400> SEQUENCE: 38

```
Asp Tyr Tyr Leu Asn
1               5
```

<210> SEQ ID NO 39
<211> LENGTH: 17
<212> TYPE: PRT
<213> ORGANISM: Homo sapiens

<400> SEQUENCE: 39

```
Ser Ile Asn Pro Asn Thr Gly Gly Thr Lys Tyr Ala Gln Lys Phe Arg
1               5                   10                  15

Gly
```

<210> SEQ ID NO 40
<211> LENGTH: 22
<212> TYPE: PRT
<213> ORGANISM: Homo sapiens

```
<400> SEQUENCE: 40

Asp Gly Ala Lys Thr Met Thr Thr Ser Gly Leu Ser Leu Leu Tyr Tyr
1               5                   10                  15

Tyr Asp Val Met Asp Val
            20

<210> SEQ ID NO 41
<211> LENGTH: 393
<212> TYPE: DNA
<213> ORGANISM: Homo sapiens

<400> SEQUENCE: 41
caggtgcagc tggtgcagtc tggggctgag gtgaagaagc ctggggcctc agtgaaggtc      60
tcctgcaagg cttctggatt caccctcagc gaccactatc tggtctgggt gcgacaggcc     120
cctggccaag gcttgagtg gatgggatgg atcaaccctc agagtggtgg cacaggctac     180
gcacagaagt tcagggcag ggtcaccatg accgggact cgtccagcaa cacagcgttc      240
atggacctga gcaagctgac atctgacgac acggccgtgt acttctgtgc gagagatggg    300
gctaagacgg tgtctaattc cggactgggt ctactgtatt atcacagccg actggacgcc   360
tggggccaag ggacaatggt caccgtctct agc                                  393

<210> SEQ ID NO 42
<211> LENGTH: 131
<212> TYPE: PRT
<213> ORGANISM: Homo sapiens

<400> SEQUENCE: 42

Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Leu Ser Asp His
            20                  25                  30

Tyr Leu Val Trp Val Arg Gln Ala Pro Gly Gln Gly Leu Glu Trp Met
        35                  40                  45

Gly Trp Ile Asn Pro Gln Ser Gly Gly Thr Gly Tyr Ala Gln Lys Phe
    50                  55                  60

Gln Gly Arg Val Thr Met Thr Arg Asp Ser Ser Ser Asn Thr Ala Phe
65                  70                  75                  80

Met Asp Leu Ser Lys Leu Thr Ser Asp Asp Thr Ala Val Tyr Phe Cys
                85                  90                  95

Ala Arg Asp Gly Ala Lys Thr Val Ser Asn Ser Gly Leu Gly Leu Leu
            100                 105                 110

Tyr Tyr His Ser Arg Leu Asp Ala Trp Gly Gln Gly Thr Met Val Thr
        115                 120                 125

Val Ser Ser
    130

<210> SEQ ID NO 43
<211> LENGTH: 5
<212> TYPE: PRT
<213> ORGANISM: Homo sapiens

<400> SEQUENCE: 43

Asp His Tyr Leu Val
1               5

<210> SEQ ID NO 44
<211> LENGTH: 17
```

```
<212> TYPE: PRT
<213> ORGANISM: Homo sapiens

<400> SEQUENCE: 44

Trp Ile Asn Pro Gln Ser Gly Gly Thr Gly Tyr Ala Gln Lys Phe Gln
1               5                   10                  15

Gly

<210> SEQ ID NO 45
<211> LENGTH: 22
<212> TYPE: PRT
<213> ORGANISM: Homo sapiens

<400> SEQUENCE: 45

Asp Gly Ala Lys Thr Val Ser Asn Ser Gly Leu Gly Leu Leu Tyr Tyr
1               5                   10                  15

His Ser Arg Leu Asp Ala
            20

<210> SEQ ID NO 46
<211> LENGTH: 393
<212> TYPE: DNA
<213> ORGANISM: Homo sapiens

<400> SEQUENCE: 46
caggtgcagc tggtgcagtc tggggctgag gtgaggaagc ctggggcctc agtgaaggtc      60
tcctgcaagg cttctggata cagcctcaaa gaccactata tggtctgggt gcgacaggcc     120
cctggccaag gcttgagtg gatgggatgg atcaaccctc agagtggtgg cacaggctac      180
ggacagaagt tcagggcag ggtcaccatg acccgggaca cgtccaccaa cacagcctac      240
atgatactga gcagcctgag atctgacgac acggccgtgt atttctgtgc gagagatggg     300
gctaagacgg tgtccaattc cggactgtct ttgttgtact atcacaaccg tctggacgcc     360
tggggccagg gaaccctggt caccgtctcc agc                                  393

<210> SEQ ID NO 47
<211> LENGTH: 131
<212> TYPE: PRT
<213> ORGANISM: Homo sapiens

<400> SEQUENCE: 47

Gln Val Gln Leu Val Gln Ser Gly Ala Glu Val Arg Lys Pro Gly Ala
1               5                   10                  15

Ser Val Lys Val Ser Cys Lys Ala Ser Gly Tyr Ser Leu Lys Asp His
                20                  25                  30

Tyr Met Val Trp Val Arg Gln Ala Pro Gly Gln Gly Leu Glu Trp Met
            35                  40                  45

Gly Trp Ile Asn Pro Gln Ser Gly Gly Thr Gly Tyr Gly Gln Lys Phe
    50                  55                  60

Gln Gly Arg Val Thr Met Thr Arg Asp Thr Ser Thr Asn Ala Tyr
65                  70                  75                  80

Met Ile Leu Ser Ser Leu Arg Ser Asp Asp Thr Ala Val Tyr Phe Cys
                85                  90                  95

Ala Arg Asp Gly Ala Lys Thr Val Ser Asn Ser Gly Leu Ser Leu Leu
                100                 105                 110

Tyr Tyr His Asn Arg Leu Asp Ala Trp Gly Gln Gly Thr Leu Val Thr
            115                 120                 125

Val Ser Ser
```

<210> SEQ ID NO 48
<211> LENGTH: 5
<212> TYPE: PRT
<213> ORGANISM: Homo sapiens

<400> SEQUENCE: 48

Asp His Tyr Met Val
1               5

<210> SEQ ID NO 49
<211> LENGTH: 17
<212> TYPE: PRT
<213> ORGANISM: Homo sapiens

<400> SEQUENCE: 49

Trp Ile Asn Pro Gln Ser Gly Gly Thr Gly Tyr Gly Gln Lys Phe Gln
1               5                   10                  15

Gly

<210> SEQ ID NO 50
<211> LENGTH: 22
<212> TYPE: PRT
<213> ORGANISM: Homo sapiens

<400> SEQUENCE: 50

Asp Gly Ala Lys Thr Val Ser Asn Ser Gly Leu Ser Leu Leu Tyr Tyr
1               5                   10                  15

His Asn Arg Leu Asp Ala
            20

<210> SEQ ID NO 51
<211> LENGTH: 393
<212> TYPE: DNA
<213> ORGANISM: Homo sapiens

<400> SEQUENCE: 51
caggtgcagc tggtgcagtc tggggctgag gtgaggaagc ctggggcctc agtgaaggtc      60
tcctgcaagg cttctggata cagcctcaaa gaccactata tggtctgggt gcgacaggcc     120
cctggccaag ggcttgagtg gatgggatgg atcaaccctc agagtggtgg cacaggctac     180
ggacagaagt tcagggcag ggtcaccatg acccgggaca cgtccaccaa cacagcctac     240
atgatactga gcagcctgag atctgacgac acggccgtgt atttctgtgc gagagatggg     300
gctaaggcgg tgtccaattc cggactgtct tgttgtact atcacaaccg tctggacgcc     360
tggggccaag ggcaatggt caccgtctct agc                                   393

<210> SEQ ID NO 52
<211> LENGTH: 131
<212> TYPE: PRT
<213> ORGANISM: Homo sapiens

<400> SEQUENCE: 52

Gln Val Gln Leu Val Gln Ser Gly Ala Glu Val Arg Lys Pro Gly Ala
1               5                   10                  15

Ser Val Lys Val Ser Cys Lys Ala Ser Gly Tyr Ser Leu Lys Asp His
            20                  25                  30

Tyr Met Val Trp Val Arg Gln Ala Pro Gly Gln Gly Leu Glu Trp Met
        35                  40                  45

```
Gly Trp Ile Asn Pro Gln Ser Gly Gly Thr Gly Tyr Gly Gln Lys Phe
 50                  55                  60
Gln Gly Arg Val Thr Met Thr Arg Asp Thr Ser Thr Asn Thr Ala Tyr
 65                  70                  75                  80
Met Ile Leu Ser Ser Leu Arg Ser Asp Asp Thr Ala Val Tyr Phe Cys
                 85                  90                  95
Ala Arg Asp Gly Ala Lys Ala Val Ser Asn Ser Gly Leu Ser Leu Leu
             100                 105                 110
Tyr Tyr His Asn Arg Leu Asp Ala Trp Gly Gln Gly Thr Met Val Thr
         115                 120                 125
Val Ser Ser
130

<210> SEQ ID NO 53
<211> LENGTH: 5
<212> TYPE: PRT
<213> ORGANISM: Homo sapiens

<400> SEQUENCE: 53

Asp His Tyr Met Val
1               5

<210> SEQ ID NO 54
<211> LENGTH: 17
<212> TYPE: PRT
<213> ORGANISM: Homo sapiens

<400> SEQUENCE: 54

Trp Ile Asn Pro Gln Ser Gly Gly Thr Gly Tyr Gly Gln Lys Phe Gln
1               5                   10                  15
Gly

<210> SEQ ID NO 55
<211> LENGTH: 22
<212> TYPE: PRT
<213> ORGANISM: Homo sapiens

<400> SEQUENCE: 55

Asp Gly Ala Lys Ala Val Ser Asn Ser Gly Leu Ser Leu Leu Tyr Tyr
1               5                   10                  15
His Asn Arg Leu Asp Ala
            20

<210> SEQ ID NO 56
<211> LENGTH: 393
<212> TYPE: DNA
<213> ORGANISM: Homo sapiens

<400> SEQUENCE: 56
caggtgcagc tgatgcagtc tggggctgag gtgaagaagc ctggggcctc agtgaaggtc      60
tcctgcaagg cttctggata caccttcacc ggctactata tgaactgggt gcgacaggcc     120
cctggacaag gcttgagtg gatgggatgc atcaacccga acagtggtgg cacaaactat      180
gcacagaagt tcagggcag ggtcaccatg accagggaca cgtccatcag cacagcctac      240
atggaactga ccaggctcag atctgacgac acggccgtat attactgtgc gagagatggg     300
gctaagacgg tgactacctc cggaatgtct tgttgtact actacgacgt tatggacatc      360
tggggccagg gaaccctggt caccgtctcc agc                                  393
```

```
<210> SEQ ID NO 57
<211> LENGTH: 131
<212> TYPE: PRT
<213> ORGANISM: Homo sapiens

<400> SEQUENCE: 57

Gln Val Gln Leu Met Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met Asn Trp Val Arg Gln Ala Pro Gly Gln Gly Leu Glu Trp Met
        35                  40                  45

Gly Cys Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Thr Arg Leu Arg Ser Asp Asp Thr Ala Val Tyr Tyr Cys
                85                  90                  95

Ala Arg Asp Gly Ala Lys Thr Val Thr Thr Ser Gly Met Ser Leu Leu
            100                 105                 110

Tyr Tyr Tyr Asp Val Met Asp Ile Trp Gly Gln Gly Thr Leu Val Thr
        115                 120                 125

Val Ser Ser
    130

<210> SEQ ID NO 58
<211> LENGTH: 5
<212> TYPE: PRT
<213> ORGANISM: Homo sapiens

<400> SEQUENCE: 58

Gly Tyr Tyr Met Asn
1               5

<210> SEQ ID NO 59
<211> LENGTH: 17
<212> TYPE: PRT
<213> ORGANISM: Homo sapiens

<400> SEQUENCE: 59

Cys Ile Asn Pro Asn Ser Gly Gly Thr Asn Tyr Ala Gln Lys Phe Gln
1               5                   10                  15

Gly

<210> SEQ ID NO 60
<211> LENGTH: 22
<212> TYPE: PRT
<213> ORGANISM: Homo sapiens

<400> SEQUENCE: 60

Asp Gly Ala Lys Thr Val Thr Thr Ser Gly Met Ser Leu Leu Tyr Tyr
1               5                   10                  15

Tyr Asp Val Met Asp Ile
            20

<210> SEQ ID NO 61
<211> LENGTH: 393
<212> TYPE: DNA
<213> ORGANISM: Homo sapiens

<400> SEQUENCE: 61
```

```
caggtgcagc tgacgcagtc tggggctgag gtgaagaagc ctggggcctc agtgaaggtc      60
tcctgcaagg cttctggata caccttcacc ggctactata tgaactgggt gcgacaggcc     120
cctggacaag ggcttgagtg gatgggatgc atcaacccga acagtggtgg cacaaactat     180
gcacagaagt ttcagggcag ggtcaccatg accaggaca cgtccatcag cacagcctac      240
atggaactga ccaggctcag atctgacgac acggccgtat attactgtgc gagagatggg     300
gctaagacgg tgactacctc cggaatgtct ttgttgtact actacgacgt tatggacatc     360
tggggccaag ggacaatggt caccgtctct agc                                  393
```

<210> SEQ ID NO 62
<211> LENGTH: 131
<212> TYPE: PRT
<213> ORGANISM: Homo sapiens

<400> SEQUENCE: 62

Gln Val Gln Leu Thr Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met Asn Trp Val Arg Gln Ala Pro Gly Gln Gly Leu Glu Trp Met
        35                  40                  45

Gly Cys Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Thr Arg Leu Arg Ser Asp Asp Thr Ala Val Tyr Tyr Cys
                85                  90                  95

Ala Arg Asp Gly Ala Lys Thr Val Thr Thr Ser Gly Met Ser Leu Leu
            100                 105                 110

Tyr Tyr Tyr Asp Val Met Asp Ile Trp Gly Gln Gly Thr Met Val Thr
        115                 120                 125

Val Ser Ser
    130

<210> SEQ ID NO 63
<211> LENGTH: 5
<212> TYPE: PRT
<213> ORGANISM: Homo sapiens

<400> SEQUENCE: 63

Gly Tyr Tyr Met Asn
1               5

<210> SEQ ID NO 64
<211> LENGTH: 17
<212> TYPE: PRT
<213> ORGANISM: Homo sapiens

<400> SEQUENCE: 64

Cys Ile Asn Pro Asn Ser Gly Gly Thr Asn Tyr Ala Gln Lys Phe Gln
1               5                   10                  15

Gly

<210> SEQ ID NO 65
<211> LENGTH: 22
<212> TYPE: PRT
<213> ORGANISM: Homo sapiens

<400> SEQUENCE: 65

Asp Gly Ala Lys Thr Val Thr Thr Ser Gly Met Ser Leu Leu Tyr Tyr
1               5                   10                  15

Tyr Asp Val Met Asp Ile
            20

<210> SEQ ID NO 66
<211> LENGTH: 393
<212> TYPE: DNA
<213> ORGANISM: Homo sapiens

<400> SEQUENCE: 66

```
caggtgcagc tggtgcagtc tgaggctgag gtggagaagc ctggggcctc agtgaaggtc    60
tcctgcaagg cttctggata caccttcacc gactactata tgaactgggt gcgacaggcc   120
cctggacaag ggcttgagtg gatgggatgc atcaaccctc acagtggtgg cacaaactat   180
gcacagaagt tcagggcag ggtcaccatg accaggaca cgtccatcag cacagtctac     240
atggagttga gcaggctaaa atctgacgac acggccgtct attactgtgc gagagatggg   300
gctaaaacgg tgactacctt cggagcgtct ttgttgtact actacgacat tatggacgtc   360
tggggccagg gaaccctggt caccgtctcc agc                                393
```

<210> SEQ ID NO 67
<211> LENGTH: 131
<212> TYPE: PRT
<213> ORGANISM: Homo sapiens

<400> SEQUENCE: 67

Gln Val Gln Leu Val Gln Ser Glu Ala Glu Val Glu Lys Pro Gly Ala
1               5                   10                  15

Ser Val Lys Val Ser Cys Lys Ala Ser Gly Tyr Thr Phe Thr Asp Tyr
            20                  25                  30

Tyr Met Asn Trp Val Arg Gln Ala Pro Gly Gln Gly Leu Glu Trp Met
        35                  40                  45

Gly Cys Ile Asn Pro His Ser Gly Gly Thr Asn Tyr Ala Gln Lys Phe
    50                  55                  60

Gln Gly Arg Val Thr Met Thr Arg Asp Thr Ser Ile Ser Thr Val Tyr
65                  70                  75                  80

Met Glu Leu Ser Arg Leu Lys Ser Asp Asp Thr Ala Val Tyr Tyr Cys
                85                  90                  95

Ala Arg Asp Gly Ala Lys Thr Val Thr Thr Phe Gly Ala Ser Leu Leu
            100                 105                 110

Tyr Tyr Tyr Asp Ile Met Asp Val Trp Gly Gln Gly Thr Leu Val Thr
        115                 120                 125

Val Ser Ser
    130

<210> SEQ ID NO 68
<211> LENGTH: 5
<212> TYPE: PRT
<213> ORGANISM: Homo sapiens

<400> SEQUENCE: 68

Asp Tyr Tyr Met Asn
1               5

<210> SEQ ID NO 69

```
<211> LENGTH: 17
<212> TYPE: PRT
<213> ORGANISM: Homo sapiens

<400> SEQUENCE: 69

Cys Ile Asn Pro His Ser Gly Gly Thr Asn Tyr Ala Gln Lys Phe Gln
1               5                   10                  15

Gly

<210> SEQ ID NO 70
<211> LENGTH: 22
<212> TYPE: PRT
<213> ORGANISM: Homo sapiens

<400> SEQUENCE: 70

Asp Gly Ala Lys Thr Val Thr Thr Phe Gly Ser Leu Leu Tyr Tyr
1               5                   10                  15

Tyr Asp Ile Met Asp Val
            20

<210> SEQ ID NO 71
<211> LENGTH: 393
<212> TYPE: DNA
<213> ORGANISM: Homo sapiens

<400> SEQUENCE: 71
caggtgcacc tggtgcaatc tgggctgag gtgaggaagc ctggggcctc agtgaaggtc      60
tcctgcaagg cttctggata caccttcacc gactactatc tgaactgggt gcgacaggcc    120
cctggacaag ggcttgagtg gatgggaagc atcaacccca cactggtgg cacaaagtat    180 gcacagaaat ttcagggcag ggtcactatg accagggaca cgtccatcag gcagcctac    240 atggagctga gcagcctgag atctgacgac acggccgtct attactgtgc gagagatggg    300
gctaaaacga tgactacgtc tggactgtct tgttgcact actacgacgt tatggacgtc    360
tggggccagg gaaccctggt caccgtctcc agc                                 393

<210> SEQ ID NO 72
<211> LENGTH: 131
<212> TYPE: PRT
<213> ORGANISM: Homo sapiens

<400> SEQUENCE: 72

Gln Val His Leu Val Gln Ser Gly Ala Glu Val Arg Lys Pro Gly Ala
1               5                   10                  15

Ser Val Lys Val Ser Cys Lys Ala Ser Gly Tyr Thr Phe Thr Asp Tyr
                20                  25                  30

Tyr Leu Asn Trp Val Arg Gln Ala Pro Gly Gln Gly Leu Glu Trp Met
            35                  40                  45

Gly Ser Ile Asn Pro Asn Thr Gly Gly Thr Lys Tyr Ala Gln Lys Phe
        50                  55                  60

Gln Gly Arg Val Thr Met Thr Arg Asp Thr Ser Ile Arg Ala Ala Tyr
65                  70                  75                  80

Met Glu Leu Ser Ser Leu Arg Ser Asp Asp Thr Ala Val Tyr Tyr Cys
                85                  90                  95

Ala Arg Asp Gly Ala Lys Thr Met Thr Thr Ser Gly Leu Ser Leu Leu
                100                 105                 110

His Tyr Tyr Asp Val Met Asp Val Trp Gly Gln Gly Thr Leu Val Thr
            115                 120                 125
```

```
Val Ser Ser
    130

<210> SEQ ID NO 73
<211> LENGTH: 5
<212> TYPE: PRT
<213> ORGANISM: Homo sapiens

<400> SEQUENCE: 73

Asp Tyr Tyr Leu Asn
1               5

<210> SEQ ID NO 74
<211> LENGTH: 17
<212> TYPE: PRT
<213> ORGANISM: Homo sapiens

<400> SEQUENCE: 74

Ser Ile Asn Pro Asn Thr Gly Gly Thr Lys Tyr Ala Gln Lys Phe Gln
1               5                   10                  15

Gly

<210> SEQ ID NO 75
<211> LENGTH: 22
<212> TYPE: PRT
<213> ORGANISM: Homo sapiens

<400> SEQUENCE: 75

Asp Gly Ala Lys Thr Met Thr Thr Ser Gly Leu Ser Leu Leu His Tyr
1               5                   10                  15

Tyr Asp Val Met Asp Val
            20

<210> SEQ ID NO 76
<211> LENGTH: 393
<212> TYPE: DNA
<213> ORGANISM: Homo sapiens

<400> SEQUENCE: 76
caggtgcagc tgatgcagtc tggggctgag gtgaagaagc ctggggcctc agtgaaggtc      60
tcctgcaagg cttctggata caccttcacc ggctactata tgaactgggt gcgacaggcc     120
cctggacaag gcttgagtg gatgggatgc atcaacccga acagtggtgg cacaaactat      180
gcacagaagt ttcagggcag ggtcaccatg accagggaca cgtccatcag cacagcctac     240
atggaactga ccaggctcag atctgacgac acggccgtat attactgtgc gagagatggg     300
gctaaaacgg tgactacctt cggaatgtct ttgttgtact actacgacgt tatggacatc     360 tgggggccaag ggacaatggt caccgtctct agc                                 393

<210> SEQ ID NO 77
<211> LENGTH: 131
<212> TYPE: PRT
<213> ORGANISM: Homo sapiens

<400> SEQUENCE: 77

Gln Val Gln Leu Met Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met Asn Trp Val Arg Gln Ala Pro Gly Gln Gly Leu Glu Trp Met
            35                  40                  45
```

```
Gly Cys Ile Asn Pro Asn Ser Gly Gly Thr Asn Tyr Ala Gln Lys Phe
        50                  55                  60
Gln Gly Arg Val Thr Met Thr Arg Asp Thr Ser Ile Ser Thr Ala Tyr
65                  70                  75                  80
Met Glu Leu Thr Arg Leu Arg Ser Asp Asp Thr Ala Val Tyr Tyr Cys
                85                  90                  95
Ala Arg Asp Gly Ala Lys Thr Val Thr Thr Phe Gly Met Ser Leu Leu
            100                 105                 110
Tyr Tyr Tyr Asp Val Met Asp Ile Trp Gly Gln Gly Thr Met Val Thr
        115                 120                 125
Val Ser Ser
    130

<210> SEQ ID NO 78
<211> LENGTH: 5
<212> TYPE: PRT
<213> ORGANISM: Homo sapiens

<400> SEQUENCE: 78

Gly Tyr Tyr Met Asn
1               5

<210> SEQ ID NO 79
<211> LENGTH: 17
<212> TYPE: PRT
<213> ORGANISM: Homo sapiens

<400> SEQUENCE: 79

Cys Ile Asn Pro Asn Ser Gly Gly Thr Asn Tyr Ala Gln Lys Phe Gln
1               5                   10                  15

Gly

<210> SEQ ID NO 80
<211> LENGTH: 22
<212> TYPE: PRT
<213> ORGANISM: Homo sapiens

<400> SEQUENCE: 80

Asp Gly Ala Lys Thr Val Thr Thr Phe Gly Met Ser Leu Leu Tyr Tyr
1               5                   10                  15

Tyr Asp Val Met Asp Ile
            20

<210> SEQ ID NO 81
<211> LENGTH: 393
<212> TYPE: DNA
<213> ORGANISM: Homo sapiens

<400> SEQUENCE: 81
caggtgcagc tgatgcagtc tggggctgag gtgaagaagc ctggggcctc agtgaaggtc      60
tcctgcaagg cttctggata caccttcacc ggctactata tgaactgggt gcgacaggcc     120
cctggacaag gcttgagtg gatgggatgc atcaacccga acagtggtgg cacaaactat      180
gcacagaagt tcagggcag ggtcaccatg accagggaca cgtccatcag cacagcctac      240
atggagttga aagtctaaa ttctgacgac acggccgtct attactgtgc gagagatggg      300
gctaagacgg tgactacctc cggaatgtct ttgttgtact actacgacgt tatgggcatc     360
tggggccaag ggacaatggt caccgtctct agc                                  393
```

<210> SEQ ID NO 82
<211> LENGTH: 131
<212> TYPE: PRT
<213> ORGANISM: Homo sapiens

<400> SEQUENCE: 82

Gln Val Gln Leu Met Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met Asn Trp Val Arg Gln Ala Pro Gly Gln Gly Leu Glu Trp Met
        35                  40                  45

Gly Cys Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Arg Ser Leu Asn Ser Asp Asp Thr Ala Val Tyr Tyr Cys
                85                  90                  95

Ala Arg Asp Gly Ala Lys Thr Val Thr Thr Ser Gly Met Ser Leu Leu
            100                 105                 110

Tyr Tyr Tyr Asp Val Met Gly Ile Trp Gly Gln Gly Thr Met Val Thr
        115                 120                 125

Val Ser Ser
    130

<210> SEQ ID NO 83
<211> LENGTH: 5
<212> TYPE: PRT
<213> ORGANISM: Homo sapiens

<400> SEQUENCE: 83

Gly Tyr Tyr Met Asn
1               5

<210> SEQ ID NO 84
<211> LENGTH: 17
<212> TYPE: PRT
<213> ORGANISM: Homo sapiens

<400> SEQUENCE: 84

Cys Ile Asn Pro Asn Ser Gly Gly Thr Asn Tyr Ala Gln Lys Phe Gln
1               5                   10                  15

Gly

<210> SEQ ID NO 85
<211> LENGTH: 22
<212> TYPE: PRT
<213> ORGANISM: Homo sapiens

<400> SEQUENCE: 85

Asp Gly Ala Lys Thr Val Thr Thr Ser Gly Met Ser Leu Leu Tyr Tyr
1               5                   10                  15

Tyr Asp Val Met Gly Ile
            20

<210> SEQ ID NO 86
<211> LENGTH: 393
<212> TYPE: DNA
<213> ORGANISM: Homo sapiens

<400> SEQUENCE: 86

```
caggtgcagc tggtgcagtc tgaggctgag gtggagaaac ctggggcctc agtgaaggtc        60
tcctgcaagg cttctggata caccttcacc gacttctata tcaactgggt gcgacaggcc       120
cctggacagg gcttgagtg gatgggatcc atcaaccctc acagtggtgg cacacactat        180
gcacagaagt ttcagggcag ggtcaccatg accagggaca cgtccatcag cacagcctac       240
atggaactga ccaggctcag atctgacgac acggccgtat attactgtgc gagagatggg       300
gctaaaacgg tgactacctc cggaatgtct ttgttgtact actacgacgt tatggacatc       360
tggggccaag ggacaatggt caccgtctct agc                                    393
```

<210> SEQ ID NO 87
<211> LENGTH: 131
<212> TYPE: PRT
<213> ORGANISM: Homo sapiens

<400> SEQUENCE: 87

```
Gln Val Gln Leu Val Gln Ser Glu Ala Glu Val Glu Lys Pro Gly Ala
1               5                   10                  15

Ser Val Lys Val Ser Cys Lys Ala Ser Gly Tyr Thr Phe Thr Asp Phe
            20                  25                  30

Tyr Ile Asn Trp Val Arg Gln Ala Pro Gly Gln Gly Leu Glu Trp Met
        35                  40                  45

Gly Ser Ile Asn Pro His Ser Gly Gly Thr His Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Thr Arg Leu Arg Ser Asp Asp Thr Ala Val Tyr Tyr Cys
                85                  90                  95

Ala Arg Asp Gly Ala Lys Thr Val Thr Thr Ser Gly Met Ser Leu Leu
            100                 105                 110

Tyr Tyr Tyr Asp Val Met Asp Ile Trp Gly Gln Gly Thr Met Val Thr
        115                 120                 125

Val Ser Ser
    130
```

<210> SEQ ID NO 88
<211> LENGTH: 5
<212> TYPE: PRT
<213> ORGANISM: Homo sapiens

<400> SEQUENCE: 88

```
Asp Phe Tyr Ile Asn
1               5
```

<210> SEQ ID NO 89
<211> LENGTH: 17
<212> TYPE: PRT
<213> ORGANISM: Homo sapiens

<400> SEQUENCE: 89

```
Ser Ile Asn Pro His Ser Gly Gly Thr His Tyr Ala Gln Lys Phe Gln
1               5                   10                  15

Gly
```

<210> SEQ ID NO 90
<211> LENGTH: 22
<212> TYPE: PRT

<213> ORGANISM: Homo sapiens

<400> SEQUENCE: 90

Asp Gly Ala Lys Thr Val Thr Thr Ser Gly Met Ser Leu Leu Tyr Tyr
1               5                   10                  15

Tyr Asp Val Met Asp Ile
            20

<210> SEQ ID NO 91
<211> LENGTH: 328
<212> TYPE: DNA
<213> ORGANISM: Homo sapiens

<400> SEQUENCE: 91
cagtctgtgt tgacgcagcc gccctcagtg tctgcggccc caggacagat ggtcaccatc      60
tcctgctctg gaagcagctc caacattggg aagaattatg tgtcctggta ccagcaactc     120
ccaggtgcag cccccaaact cctcatcttt gacaataata agcgaccctc agggactcct     180
gaccgattct ctggctccaa gtctggcacg tcagccaccc tggtcatcac cggactccag     240
acaggggacg aggccgatta ttactgcgga acaccggata aagcctgag tgtgatattc      300 ggcggaggga ccaaggtcac cgtcctag                                        328

<210> SEQ ID NO 92
<211> LENGTH: 109
<212> TYPE: PRT
<213> ORGANISM: Homo sapiens

<400> SEQUENCE: 92

Gln Ser Val Leu Thr Gln Pro Pro Ser Val Ser Ala Ala Pro Gly Gln
1               5                   10                  15

Met Val Thr Ile Ser Cys Ser Gly Ser Ser Ser Asn Ile Gly Lys Asn
            20                  25                  30

Tyr Val Ser Trp Tyr Gln Gln Leu Pro Gly Ala Ala Pro Lys Leu Leu
        35                  40                  45

Ile Phe Asp Asn Asn Lys Arg Pro Ser Gly Thr Pro Asp Arg Phe Ser
    50                  55                  60

Gly Ser Lys Ser Gly Thr Ser Ala Thr Leu Val Ile Thr Gly Leu Gln
65                  70                  75                  80

Thr Gly Asp Glu Ala Asp Tyr Tyr Cys Gly Thr Pro Asp Arg Ser Leu
                85                  90                  95

Ser Val Ile Phe Gly Gly Gly Thr Lys Val Thr Val Leu
            100                 105

<210> SEQ ID NO 93
<211> LENGTH: 13
<212> TYPE: PRT
<213> ORGANISM: Homo sapiens

<400> SEQUENCE: 93

Ser Gly Ser Ser Ser Asn Ile Gly Lys Asn Tyr Val Ser
1               5                   10

<210> SEQ ID NO 94
<211> LENGTH: 7
<212> TYPE: PRT
<213> ORGANISM: Homo sapiens

<400> SEQUENCE: 94

Asp Asn Asn Lys Arg Pro Ser

<210> SEQ ID NO 95
<211> LENGTH: 10
<212> TYPE: PRT
<213> ORGANISM: Homo sapiens

<400> SEQUENCE: 95

Gly Thr Pro Asp Arg Ser Leu Ser Val Ile
1               5                   10

<210> SEQ ID NO 96
<211> LENGTH: 328
<212> TYPE: DNA
<213> ORGANISM: Homo sapiens

<400> SEQUENCE: 96
cagtctgtgt tgacgcagcc gccctcagtg tctgcggccc caggacagag ggtcaccatc    60
tcctgctctg gaagcagatc caacattggg aagaattatg tatcctggta ccagcaaccc   120
ccaggtacag cccccaaact cctcattttt gacaataata agcgaccctc agggattcct   180
gaccgattct ctggctccaa gtctggcacg tcagccaccc tggccatctc cggactccag   240
gctgcggacg aggccgatta ctactgcgga acatgggata gcagcctgag tgtggtattc   300
ggcgggggga ccaaggtcac cgtcctag                                      328

<210> SEQ ID NO 97
<211> LENGTH: 109
<212> TYPE: PRT
<213> ORGANISM: Homo sapiens

<400> SEQUENCE: 97

Gln Ser Val Leu Thr Gln Pro Pro Ser Val Ser Ala Ala Pro Gly Gln
1               5                   10                  15

Arg Val Thr Ile Ser Cys Ser Gly Ser Arg Ser Asn Ile Gly Lys Asn
            20                  25                  30

Tyr Val Ser Trp Tyr Gln Gln Pro Pro Gly Thr Ala Pro Lys Leu Leu
        35                  40                  45

Ile Phe Asp Asn Asn Lys Arg Pro Ser Gly Ile Pro Asp Arg Phe Ser
    50                  55                  60

Gly Ser Lys Ser Gly Thr Ser Ala Thr Leu Ala Ile Ser Gly Leu Gln
65                  70                  75                  80

Ala Ala Asp Glu Ala Asp Tyr Tyr Cys Gly Thr Trp Asp Ser Ser Leu
                85                  90                  95

Ser Val Val Phe Gly Gly Gly Thr Lys Val Thr Val Leu
            100                 105

<210> SEQ ID NO 98
<211> LENGTH: 13
<212> TYPE: PRT
<213> ORGANISM: Homo sapiens

<400> SEQUENCE: 98

Ser Gly Ser Arg Ser Asn Ile Gly Lys Asn Tyr Val Ser
1               5                   10

<210> SEQ ID NO 99
<211> LENGTH: 7
<212> TYPE: PRT
<213> ORGANISM: Homo sapiens

<400> SEQUENCE: 99

Asp Asn Asn Lys Arg Pro Ser
1               5

<210> SEQ ID NO 100
<211> LENGTH: 10
<212> TYPE: PRT
<213> ORGANISM: Homo sapiens

<400> SEQUENCE: 100

Gly Thr Trp Asp Ser Ser Leu Ser Val Val
1               5                   10

<210> SEQ ID NO 101
<211> LENGTH: 328
<212> TYPE: DNA
<213> ORGANISM: Homo sapiens

<400> SEQUENCE: 101
cagtctgtgt tgacgcagcc gccctcagtg tctgcggccc caggacagaa ggtcaccatc      60
tcctgctctg gaagcagctc caacattggg aagaattatg tatcctggta ccagcagctc     120
ccaggaacag cccccaaaact cctcattgat gacaataata gcgaccctc agggattcct      180 gaccgattct ctggctccaa gtctggcacg tcagccaccc tgggcatcac cggactccag     240
actggggacg aggccgatta ttactgcgca acatgggata gcagcctggg tgtggtcttc     300
ggcggaggga ccaaggtcac cgtcctag                                        328

<210> SEQ ID NO 102
<211> LENGTH: 109
<212> TYPE: PRT
<213> ORGANISM: Homo sapiens

<400> SEQUENCE: 102

Gln Ser Val Leu Thr Gln Pro Pro Ser Val Ala Ala Pro Gly Gln
1               5                   10                  15

Lys Val Thr Ile Ser Cys Ser Gly Ser Ser Asn Ile Gly Lys Asn
                20                  25                  30

Tyr Val Ser Trp Tyr Gln Gln Leu Pro Gly Thr Ala Pro Lys Leu Leu
            35                  40                  45

Ile Asp Asp Asn Asn Lys Arg Pro Ser Gly Ile Pro Asp Arg Phe Ser
        50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Ala Thr Trp Asp Ser Ser Leu
                85                  90                  95

Gly Val Val Phe Gly Gly Gly Thr Lys Val Thr Val Leu
            100                 105

<210> SEQ ID NO 103
<211> LENGTH: 13
<212> TYPE: PRT
<213> ORGANISM: Homo sapiens

<400> SEQUENCE: 103

Ser Gly Ser Ser Ser Asn Ile Gly Lys Asn Tyr Val Ser
1               5                   10

<210> SEQ ID NO 104
<211> LENGTH: 7

```
<212> TYPE: PRT
<213> ORGANISM: Homo sapiens

<400> SEQUENCE: 104

Asp Asn Asn Lys Arg Pro Ser
1               5

<210> SEQ ID NO 105
<211> LENGTH: 10
<212> TYPE: PRT
<213> ORGANISM: Homo sapiens

<400> SEQUENCE: 105

Ala Thr Trp Asp Ser Ser Leu Gly Val Val
1               5                   10

<210> SEQ ID NO 106
<211> LENGTH: 328
<212> TYPE: DNA
<213> ORGANISM: Homo sapiens

<400> SEQUENCE: 106
cagtctgtgt tgacgcagcc gccctcagtg tctgcggccc caggacagaa ggtcacgatc      60
tcctgctctg gaagcagctc caacattggg aaaaattatg tatcctggta ccagcagctc     120
ccaggaacag cccccaaact cctcatttat gacaataata agcgaccctc agggattcct     180
gaccgattct ctggctccaa gtctggcacg tcagccaccc tgggaatcac cggactccag     240
actggggacg aggccgatta tttctgcgga acatgggata gcagcctgag tgtggtattc     300
ggcggaggga ccaaggtcac cgtcctag                                        328

<210> SEQ ID NO 107
<211> LENGTH: 109
<212> TYPE: PRT
<213> ORGANISM: Homo sapiens

<400> SEQUENCE: 107

Gln Ser Val Leu Thr Gln Pro Pro Ser Val Ala Ala Pro Gly Gln
1               5                   10                  15

Lys Val Thr Ile Ser Cys Ser Gly Ser Ser Ser Asn Ile Gly Lys Asn
                20                  25                  30

Tyr Val Ser Trp Tyr Gln Gln Leu Pro Gly Thr Ala Pro Lys Leu Leu
            35                  40                  45

Ile Tyr Asp Asn Asn Lys Arg Pro Ser Gly Ile Pro Asp Arg Phe Ser
        50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Phe Cys Gly Thr Trp Asp Ser Ser Leu
                85                  90                  95

Ser Val Val Phe Gly Gly Gly Thr Lys Val Thr Val Leu
            100                 105

<210> SEQ ID NO 108
<211> LENGTH: 13
<212> TYPE: PRT
<213> ORGANISM: Homo sapiens

<400> SEQUENCE: 108

Ser Gly Ser Ser Ser Asn Ile Gly Lys Asn Tyr Val Ser
1               5                   10
```

<210> SEQ ID NO 109
<211> LENGTH: 7
<212> TYPE: PRT
<213> ORGANISM: Homo sapiens

<400> SEQUENCE: 109

Asp Asn Asn Lys Arg Pro Ser
1               5

<210> SEQ ID NO 110
<211> LENGTH: 10
<212> TYPE: PRT
<213> ORGANISM: Homo sapiens

<400> SEQUENCE: 110

Gly Thr Trp Asp Ser Ser Leu Ser Val Val
1               5                   10

<210> SEQ ID NO 111
<211> LENGTH: 328
<212> TYPE: DNA
<213> ORGANISM: Homo sapiens

<400> SEQUENCE: 111
cagtctgtgt tgacgcagcc gccctcagtg tctgcggccc caggacagaa ggtcaccatc      60
tcctgctctg gaagcagctc caacattggg aaaaattatg tatcctggta ccagcacttc     120
ccaggaacag cccccaaact cctcatttat gacaataata agcgaccctc agggattcct     180
gaccgattct ctggttccaa gtctggcacg tcagccaccc tgggcatcac cggactccag     240
actggggacg aggccgatta ttactgcgca acatgggata gaagcctgag tgtggtattc     300
ggcggaggga ccaaggtcac cgtcctag                                        328

<210> SEQ ID NO 112
<211> LENGTH: 109
<212> TYPE: PRT
<213> ORGANISM: Homo sapiens

<400> SEQUENCE: 112

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Lys Asn
            20                  25                  30

Tyr Val Ser Trp Tyr Gln His Phe Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Ala Thr Trp Asp Arg Ser Leu
                85                  90                  95

Ser Val Val Phe Gly Gly Gly Thr Lys Val Thr Val Leu
            100                 105

<210> SEQ ID NO 113
<211> LENGTH: 13
<212> TYPE: PRT
<213> ORGANISM: Homo sapiens

<400> SEQUENCE: 113

Ser Gly Ser Ser Ser Asn Ile Gly Lys Asn Tyr Val Ser
1               5                   10

<210> SEQ ID NO 114
<211> LENGTH: 7
<212> TYPE: PRT
<213> ORGANISM: Homo sapiens

<400> SEQUENCE: 114

Asp Asn Asn Lys Arg Pro Ser
1               5

<210> SEQ ID NO 115
<211> LENGTH: 10
<212> TYPE: PRT
<213> ORGANISM: Homo sapiens

<400> SEQUENCE: 115

Ala Thr Trp Asp Arg Ser Leu Ser Val Val
1               5                   10

<210> SEQ ID NO 116
<211> LENGTH: 328
<212> TYPE: DNA
<213> ORGANISM: Homo sapiens

<400> SEQUENCE: 116
cagtctgtgt tgacgcagcc gccctcagtg tctgcggccc caggacagat ggtcaccatc      60
tcctgctctg gaagcagctc caacattggg aagaattatg tgtcctggta ccagcaactc     120
ccaggtgcag cccccaaact cctcatcttt gacaataata gcgaccctc agggactcct      180 gaccgattct ctggctccaa gtctggcacg tcagccaccc tggtcatcac cggactccag     240
acaggggacg agaccgatta ttactgcgga acaccggata agagcctgag tgtggtattc     300
ggcggaggga ccaaggtcac cgtcctag                                        328

<210> SEQ ID NO 117
<211> LENGTH: 109
<212> TYPE: PRT
<213> ORGANISM: Homo sapiens

<400> SEQUENCE: 117

Gln Ser Val Leu Thr Gln Pro Pro Ser Val Ala Ala Pro Gly Gln
1               5                   10                  15

Met Val Thr Ile Ser Cys Ser Gly Ser Ser Ser Asn Ile Gly Lys Asn
            20                  25                  30

Tyr Val Ser Trp Tyr Gln Gln Leu Pro Gly Ala Ala Pro Lys Leu Leu
        35                  40                  45

Ile Phe Asp Asn Asn Lys Arg Pro Ser Gly Thr Pro Asp Arg Phe Ser
    50                  55                  60

Gly Ser Lys Ser Gly Thr Ser Ala Thr Leu Val Ile Thr Gly Leu Gln
65                  70                  75                  80

Thr Gly Asp Glu Thr Asp Tyr Tyr Cys Gly Thr Pro Asp Arg Ser Leu
                85                  90                  95

Ser Val Val Phe Gly Gly Gly Thr Lys Val Thr Val Leu
            100                 105

<210> SEQ ID NO 118
<211> LENGTH: 13
<212> TYPE: PRT
<213> ORGANISM: Homo sapiens

<400> SEQUENCE: 118

Ser Gly Ser Ser Ser Asn Ile Gly Lys Asn Tyr Val Ser
1               5                   10

<210> SEQ ID NO 119
<211> LENGTH: 7
<212> TYPE: PRT
<213> ORGANISM: Homo sapiens

<400> SEQUENCE: 119

Asp Asn Asn Lys Arg Pro Ser
1               5

<210> SEQ ID NO 120
<211> LENGTH: 10
<212> TYPE: PRT
<213> ORGANISM: Homo sapiens

<400> SEQUENCE: 120

Gly Thr Pro Asp Arg Ser Leu Ser Val Val
1               5                   10

<210> SEQ ID NO 121
<211> LENGTH: 328
<212> TYPE: DNA
<213> ORGANISM: Homo sapiens

<400> SEQUENCE: 121
cagtctgtgt tgacgcagcc gccctcagtg tctgcggccc caggacagaa ggtcaccatc      60
tcctgctctg gaagcagctc aacattggg aagaattatg tatcctggta ccagcagctc     120
ccaggaacag ccccccaaact cctcattgat gacaataata agcgaccctc agggattcct    180
gaccgattct ctggctccaa gtctggcacg tcagccaccc tgggcatcac cggactccag    240
actggggacg aggccgatta ttactgcgca catgggata gcagcctggg tgtggtcttc     300
ggcggaggaa cccagctgat catcctag                                        328

<210> SEQ ID NO 122
<211> LENGTH: 109
<212> TYPE: PRT
<213> ORGANISM: Homo sapiens

<400> SEQUENCE: 122

Gln Ser Val Leu Thr Gln Pro Pro Ser Val Ala Ala Pro Gly Gln
1               5                   10                  15

Lys Val Thr Ile Ser Cys Ser Gly Ser Ser Ser Asn Ile Gly Lys Asn
            20                  25                  30

Tyr Val Ser Trp Tyr Gln Gln Leu Pro Gly Thr Ala Pro Lys Leu Leu
        35                  40                  45

Ile Asp Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Ala Thr Trp Asp Ser Ser Leu
                85                  90                  95

Gly Val Val Phe Gly Gly Gly Thr Gln Leu Ile Ile Leu
            100                 105

<210> SEQ ID NO 123

```
<211> LENGTH: 13
<212> TYPE: PRT
<213> ORGANISM: Homo sapiens

<400> SEQUENCE: 123

Ser Gly Ser Ser Ser Asn Ile Gly Lys Asn Tyr Val Ser
1               5                   10

<210> SEQ ID NO 124
<211> LENGTH: 7
<212> TYPE: PRT
<213> ORGANISM: Homo sapiens

<400> SEQUENCE: 124

Asp Asn Asn Lys Arg Pro Ser
1               5

<210> SEQ ID NO 125
<211> LENGTH: 10
<212> TYPE: PRT
<213> ORGANISM: Homo sapiens

<400> SEQUENCE: 125

Ala Thr Trp Asp Ser Ser Leu Gly Val Val
1               5                   10

<210> SEQ ID NO 126
<211> LENGTH: 328
<212> TYPE: DNA
<213> ORGANISM: Homo sapiens

<400> SEQUENCE: 126
cagtctgtgt tgacgcagcc gccctcagtg tctgcggccc caggacagag ggtcaccatc      60
tcctgctctg gaagcagatc caacattggg aagaattatg tatcctggta ccagcaactc     120
ccaggtacag cccccaaact cctcattttt gacaataata agcgaccctc agggattcct     180
gaccgattct ctggctccaa gtctggcacg tcagccaccc tggccatctc cggactccag     240
gctgcggacg aggccgatca ctactgcgga acatgggata gcagcctgag tgtggtattc     300
ggcgggggga ccaaggtcac cgtcctag                                        328

<210> SEQ ID NO 127
<211> LENGTH: 109
<212> TYPE: PRT
<213> ORGANISM: Homo sapiens

<400> SEQUENCE: 127

Gln Ser Val Leu Thr Gln Pro Pro Ser Val Ser Ala Ala Pro Gly Gln
1               5                   10                  15

Arg Val Thr Ile Ser Cys Ser Gly Ser Arg Ser Asn Ile Gly Lys Asn
            20                  25                  30

Tyr Val Ser Trp Tyr Gln Gln Leu Pro Gly Thr Ala Pro Lys Leu Leu
        35                  40                  45

Ile Phe Asp Asn Asn Lys Arg Pro Ser Gly Ile Pro Asp Arg Phe Ser
    50                  55                  60

Gly Ser Lys Ser Gly Thr Ser Ala Thr Leu Ala Ile Ser Gly Leu Gln
65                  70                  75                  80

Ala Ala Asp Glu Ala Asp His Tyr Cys Gly Thr Trp Asp Ser Ser Leu
                85                  90                  95

Ser Val Val Phe Gly Gly Gly Thr Lys Val Thr Val Leu
            100                 105
```

<210> SEQ ID NO 128
<211> LENGTH: 13
<212> TYPE: PRT
<213> ORGANISM: Homo sapiens

<400> SEQUENCE: 128

Ser Gly Ser Arg Ser Asn Ile Gly Lys Asn Tyr Val Ser
1               5                   10

<210> SEQ ID NO 129
<211> LENGTH: 7
<212> TYPE: PRT
<213> ORGANISM: Homo sapiens

<400> SEQUENCE: 129

Asp Asn Asn Lys Arg Pro Ser
1               5

<210> SEQ ID NO 130
<211> LENGTH: 10
<212> TYPE: PRT
<213> ORGANISM: Homo sapiens

<400> SEQUENCE: 130

Gly Thr Trp Asp Ser Ser Leu Ser Val Val
1               5                   10

<210> SEQ ID NO 131
<211> LENGTH: 328
<212> TYPE: DNA
<213> ORGANISM: Homo sapiens

<400> SEQUENCE: 131
cagtctgtgt tgacgcagct gccctcagtg tctgcggccc caggacagat ggtcaccatc     60
tcctgctctg gaagcagctc aacattggg aagaattatg tgtcctggta ccagcaactc    120
ccaggtgcag cccccaaaact cctcatcttt gacaataata gcgaccctc agggactcct    180 gaccgattct ctggctccaa gtctggcacg tcagccaccc tggtcatcac cggactccag    240
acaggggacg aggccgatta ttactgcgga acaccggata aagcctgag tgtggtattc    300 ggcggaggga ccaaggtcac cgtcctag                                       328

<210> SEQ ID NO 132
<211> LENGTH: 109
<212> TYPE: PRT
<213> ORGANISM: Homo sapiens

<400> SEQUENCE: 132

Gln Ser Val Leu Thr Gln Leu Pro Ser Val Ser Ala Ala Pro Gly Gln
1               5                   10                  15

Met Val Thr Ile Ser Cys Ser Gly Ser Ser Ser Asn Ile Gly Lys Asn
                20                  25                  30

Tyr Val Ser Trp Tyr Gln Gln Leu Pro Gly Ala Ala Pro Lys Leu Leu
            35                  40                  45

Ile Phe Asp Asn Asn Lys Arg Pro Ser Gly Thr Pro Asp Arg Phe Ser
        50                  55                  60

Gly Ser Lys Ser Gly Thr Ser Ala Thr Leu Val Ile Thr Gly Leu Gln
65                  70                  75                  80

Thr Gly Asp Glu Ala Asp Tyr Tyr Cys Gly Thr Pro Asp Arg Ser Leu
                85                  90                  95

```
Ser Val Val Phe Gly Gly Gly Thr Lys Val Thr Val Leu
            100                 105
```

<210> SEQ ID NO 133
<211> LENGTH: 13
<212> TYPE: PRT
<213> ORGANISM: Homo sapiens

<400> SEQUENCE: 133

```
Ser Gly Ser Ser Ser Asn Ile Gly Lys Asn Tyr Val Ser
1               5                   10
```

<210> SEQ ID NO 134
<211> LENGTH: 7
<212> TYPE: PRT
<213> ORGANISM: Homo sapiens

<400> SEQUENCE: 134

```
Asp Asn Asn Lys Arg Pro Ser
1               5
```

<210> SEQ ID NO 135
<211> LENGTH: 10
<212> TYPE: PRT
<213> ORGANISM: Homo sapiens

<400> SEQUENCE: 135

```
Gly Thr Pro Asp Arg Ser Leu Ser Val Val
1               5                   10
```

<210> SEQ ID NO 136
<211> LENGTH: 328
<212> TYPE: DNA
<213> ORGANISM: Homo sapiens

<400> SEQUENCE: 136

```
cagtctgtgt tgacgcagcc gccctcagtg tccgcggccc caggacagag ggtcaccatc    60
tcctgctctg gaagcagatc caacattggg aagaattatg tatcctggta ccagcaactc   120
ccaggtacag cccccaaact cctcattttt gacaataata gcgaccctc agggattcct    180 gaccgattct ctggctccaa gtctggcacg tcagccaccc tggccatctc cggactccag   240
gctgcggacg aggccgatta ctactgcgga acatgggata gcagcctgag tgtggtattc   300
ggcgggggga ccaaggtcac cgtcctag                                      328
```

<210> SEQ ID NO 137
<211> LENGTH: 109
<212> TYPE: PRT
<213> ORGANISM: Homo sapiens

<400> SEQUENCE: 137

```
Gln Ser Val Leu Thr Gln Pro Pro Ser Val Ser Ala Ala Pro Gly Gln
1               5                   10                  15

Arg Val Thr Ile Ser Cys Ser Gly Ser Arg Ser Asn Ile Gly Lys Asn
            20                  25                  30

Tyr Val Ser Trp Tyr Gln Gln Leu Pro Gly Thr Ala Pro Lys Leu Leu
        35                  40                  45

Ile Phe Asp Asn Asn Lys Arg Pro Ser Gly Ile Pro Asp Arg Phe Ser
    50                  55                  60

Gly Ser Lys Ser Gly Thr Ser Ala Thr Leu Ala Ile Ser Gly Leu Gln
65                  70                  75                  80
```

Ala Ala Asp Glu Ala Asp Tyr Tyr Cys Gly Thr Trp Asp Ser Ser Leu
            85                  90                  95

Ser Val Val Phe Gly Gly Gly Thr Lys Val Thr Val Leu
            100                 105

<210> SEQ ID NO 138
<211> LENGTH: 13
<212> TYPE: PRT
<213> ORGANISM: Homo sapiens

<400> SEQUENCE: 138

Ser Gly Ser Arg Ser Asn Ile Gly Lys Asn Tyr Val Ser
1               5                   10

<210> SEQ ID NO 139
<211> LENGTH: 7
<212> TYPE: PRT
<213> ORGANISM: Homo sapiens

<400> SEQUENCE: 139

Asp Asn Asn Lys Arg Pro Ser
1               5

<210> SEQ ID NO 140
<211> LENGTH: 10
<212> TYPE: PRT
<213> ORGANISM: Homo sapiens

<400> SEQUENCE: 140

Gly Thr Trp Asp Ser Ser Leu Ser Val Val
1               5                   10

<210> SEQ ID NO 141
<211> LENGTH: 328
<212> TYPE: DNA
<213> ORGANISM: Homo sapiens

<400> SEQUENCE: 141
cagtctgtgt tgacgcagcc gccctcagtg tctgcggccc caggacagat ggtcaccatc      60
tcctgctctg gaagcagctc caacattggg aagaattatg tgtcctggta ccagcaactc     120
ccaggtgcag cccccaaact cctcatcttt gacaataata agcgaccctc agggactcct     180
gaccgattct ctggctccaa gtctggcacg tcagccaccc tggtcatcac cggactccag     240
acaggggacg aggccgatta ttactgcgga acaccggata agcctgag tgtggtattc      300 ggcggaggga ccaaggtcac cgtcctag                                        328

<210> SEQ ID NO 142
<211> LENGTH: 109
<212> TYPE: PRT
<213> ORGANISM: Homo sapiens

<400> SEQUENCE: 142

Gln Ser Val Leu Thr Gln Pro Pro Ser Val Ser Ala Ala Pro Gly Gln
1               5                   10                  15

Met Val Thr Ile Ser Cys Ser Gly Ser Ser Ser Asn Ile Gly Lys Asn
            20                  25                  30

Tyr Val Ser Trp Tyr Gln Gln Leu Pro Gly Ala Ala Pro Lys Leu Leu
        35                  40                  45

Ile Phe Asp Asn Asn Lys Arg Pro Ser Gly Thr Pro Arg Phe Ser
    50                  55                  60

```
Gly Ser Lys Ser Gly Thr Ser Ala Thr Leu Val Ile Thr Gly Leu Gln
65                  70                  75                  80

Thr Gly Asp Glu Ala Asp Tyr Tyr Cys Gly Thr Pro Asp Arg Ser Leu
                85                  90                  95

Ser Val Val Phe Gly Gly Gly Thr Lys Val Thr Val Leu
            100                 105
```

<210> SEQ ID NO 143
<211> LENGTH: 13
<212> TYPE: PRT
<213> ORGANISM: Homo sapiens

<400> SEQUENCE: 143

```
Ser Gly Ser Ser Ser Asn Ile Gly Lys Asn Tyr Val Ser
1               5                   10
```

<210> SEQ ID NO 144
<211> LENGTH: 7
<212> TYPE: PRT
<213> ORGANISM: Homo sapiens

<400> SEQUENCE: 144

```
Asp Asn Asn Lys Arg Pro Ser
1               5
```

<210> SEQ ID NO 145
<211> LENGTH: 10
<212> TYPE: PRT
<213> ORGANISM: Homo sapiens

<400> SEQUENCE: 145

```
Gly Thr Pro Asp Arg Ser Leu Ser Val Val
1               5                   10
```

<210> SEQ ID NO 146
<211> LENGTH: 328
<212> TYPE: DNA
<213> ORGANISM: Homo sapiens

<400> SEQUENCE: 146

```
cagtctgtgt tgacgcagcc gccctcagtg tctgcggccc caggacagaa ggtcaccatc      60
tcctgctctg gaagcagctc aacattggga aaaattatg tatcctggta ccagcactcc     120
ccaggaacag ccccaaaact cctcatttat gacaataata gcgaccccc aggattcct     180 gaccgattct ctggttccaa gtctggcacg tcagccaccc tgggcatcac cggactccag     240
actggggacg aggccgatta ttactgcgca acatgggata aagcctgag tgtggtattc     300 ggcggaggga ccaaggtcac cgtcctag                                       328
```

<210> SEQ ID NO 147
<211> LENGTH: 109
<212> TYPE: PRT
<213> ORGANISM: Homo sapiens

<400> SEQUENCE: 147

```
Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Lys Asn
            20                  25                  30

Tyr Val Ser Trp Tyr Gln His Ser Pro Gly Thr Ala Pro Lys Leu Leu
        35                  40                  45
```

Ile Tyr Asp Asn Asn Lys Arg Pro Gly Ile Pro Asp Arg Phe Ser
        50                  55                  60

Gly Ser Lys Ser Gly Thr Ser Ala Thr Leu Gly Ile Thr Gly Leu Gln
 65                  70                  75                  80

Thr Gly Asp Glu Ala Asp Tyr Tyr Cys Ala Thr Trp Asp Arg Ser Leu
                 85                  90                  95

Ser Val Val Phe Gly Gly Gly Thr Lys Val Thr Val Leu
            100                 105

<210> SEQ ID NO 148
<211> LENGTH: 13
<212> TYPE: PRT
<213> ORGANISM: Homo sapiens

<400> SEQUENCE: 148

Ser Gly Ser Ser Ser Asn Ile Gly Lys Asn Tyr Val Ser
 1               5                  10

<210> SEQ ID NO 149
<211> LENGTH: 7
<212> TYPE: PRT
<213> ORGANISM: Homo sapiens

<400> SEQUENCE: 149

Asp Asn Asn Lys Arg Pro Pro
 1               5

<210> SEQ ID NO 150
<211> LENGTH: 10
<212> TYPE: PRT
<213> ORGANISM: Homo sapiens

<400> SEQUENCE: 150

Ala Thr Trp Asp Arg Ser Leu Ser Val Val
 1               5                  10

<210> SEQ ID NO 151
<211> LENGTH: 328
<212> TYPE: DNA
<213> ORGANISM: Homo sapiens

<400> SEQUENCE: 151
cagtctgtgt tgacgcagcc gccctcagtg tctgcggccc caggacagaa ggtcaccatc    60
tcctgctctg gaagcagctc caacattggg aaaaattatg tatcctgta ccagcacttc   120 ccaggaacag ccccaaaact cctcatttat gacaataata gcgaccctc agggattcct   180 gaccgattct ctggttccaa gtctggcacg tcagccaccc tgggcatcac cggactccag   240
actggggacg aggccgatta ttactgcgca acatgggata gaagcctgag tgtggtattc   300
ggcggaggga ccaaggtcac cgtcctag                                      328

<210> SEQ ID NO 152
<211> LENGTH: 109
<212> TYPE: PRT
<213> ORGANISM: Homo sapiens

<400> SEQUENCE: 152

Gln Ser Val Leu Thr Gln Pro Pro Ser Val Ser Ala Ala Pro Gly Gln
 1               5                  10                  15

Lys Val Thr Ile Ser Cys Ser Gly Ser Ser Ser Asn Ile Gly Lys Asn
             20                  25                  30

```
Tyr Val Ser Trp Tyr Gln His Phe Pro Gly Thr Ala Pro Lys Leu Leu
            35                  40                  45

Ile Tyr Asp Asn Asn Lys Arg Pro Ser Gly Ile Pro Asp Arg Phe Ser
 50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Ala Thr Trp Asp Arg Ser Leu
                85                  90                  95

Ser Val Val Phe Gly Gly Gly Thr Lys Val Thr Val Leu
            100                 105

<210> SEQ ID NO 153
<211> LENGTH: 13
<212> TYPE: PRT
<213> ORGANISM: Homo sapiens

<400> SEQUENCE: 153

Ser Gly Ser Ser Ser Asn Ile Gly Lys Asn Tyr Val Ser
1               5                   10

<210> SEQ ID NO 154
<211> LENGTH: 7
<212> TYPE: PRT
<213> ORGANISM: Homo sapiens

<400> SEQUENCE: 154

Asp Asn Asn Lys Arg Pro Ser
1               5

<210> SEQ ID NO 155
<211> LENGTH: 10
<212> TYPE: PRT
<213> ORGANISM: Homo sapiens

<400> SEQUENCE: 155

Ala Thr Trp Asp Arg Ser Leu Ser Val Val
1               5                   10

<210> SEQ ID NO 156
<211> LENGTH: 328
<212> TYPE: DNA
<213> ORGANISM: Homo sapiens

<400> SEQUENCE: 156
cagtctgtgt tgacgcagcc gccctcagtg tctgcggccc caggacagag ggtcaccatc      60
tcctgctctg gaagcagatc caacattggg aagaattatg tatcctggta ccagcaactc     120
ccaggtacag cccccaaact cctcattttt gacaataata gcgaccctca gggggttcct     180
gaccgattct ctggctccaa gtctggcacg tcagccaccc tggccatctc cggactccag     240
gctgcggacg aggccgatta ctactgcgga acatgggata gcagcctgag tgtggtattc     300 ggcggggga ccaaggtcac cgtcctag                                          328

<210> SEQ ID NO 157
<211> LENGTH: 109
<212> TYPE: PRT
<213> ORGANISM: Homo sapiens

<400> SEQUENCE: 157

Gln Ser Val Leu Thr Gln Pro Pro Ser Val Ser Ala Ala Pro Gly Gln
1               5                   10                  15
```

```
Arg Val Thr Ile Ser Cys Ser Gly Ser Arg Ser Asn Ile Gly Lys Asn
            20                  25                  30

Tyr Val Ser Trp Tyr Gln Gln Leu Pro Gly Thr Ala Pro Lys Leu Leu
        35                  40                  45

Ile Phe Asp Asn Asn Lys Arg Pro Ser Gly Val Pro Asp Arg Phe Ser
    50                  55                  60

Gly Ser Lys Ser Gly Thr Ser Ala Thr Leu Ala Ile Ser Gly Leu Gln
65                  70                  75                  80

Ala Ala Asp Glu Ala Asp Tyr Tyr Cys Gly Thr Trp Asp Ser Ser Leu
                85                  90                  95

Ser Val Val Phe Gly Gly Gly Thr Lys Val Thr Val Leu
            100                 105

<210> SEQ ID NO 158
<211> LENGTH: 13
<212> TYPE: PRT
<213> ORGANISM: Homo sapiens

<400> SEQUENCE: 158

Ser Gly Ser Arg Ser Asn Ile Gly Lys Asn Tyr Val Ser
1               5                   10

<210> SEQ ID NO 159
<211> LENGTH: 7
<212> TYPE: PRT
<213> ORGANISM: Homo sapiens

<400> SEQUENCE: 159

Asp Asn Asn Lys Arg Pro Ser
1               5

<210> SEQ ID NO 160
<211> LENGTH: 10
<212> TYPE: PRT
<213> ORGANISM: Homo sapiens

<400> SEQUENCE: 160

Gly Thr Trp Asp Ser Ser Leu Ser Val Val
1               5                   10

<210> SEQ ID NO 161
<211> LENGTH: 331
<212> TYPE: DNA
<213> ORGANISM: Homo sapiens

<400> SEQUENCE: 161
cagtctgtgt tgacgcagcc gccctcagtg tctgcggccc caggacagag ggtcaccatc      60
tcctgctctg gaagcagatc caacattggg aagaattatg tatcctggta ccagcaactc     120
ccaggtacag cccccaaact cctcattttt gacaataata agcgaccctc agggattcct     180
gaccgattct ctggctccaa gtctggcacg tcagccaccc tggccatctc cggactccag     240
gctgcggacg aggccgatta ctactgcgga acatgggata gtgacctgag tgcttatgtc     300
ttcggaactg ggaccaaggt caccgtccta g                                     331

<210> SEQ ID NO 162
<211> LENGTH: 110
<212> TYPE: PRT
<213> ORGANISM: Homo sapiens

<400> SEQUENCE: 162
```

```
Gln Ser Val Leu Thr Gln Pro Pro Ser Val Ser Ala Ala Pro Gly Gln
1               5                   10                  15

Arg Val Thr Ile Ser Cys Ser Gly Ser Arg Ser Asn Ile Gly Lys Asn
            20                  25                  30

Tyr Val Ser Trp Tyr Gln Gln Leu Pro Gly Thr Ala Pro Lys Leu Leu
        35                  40                  45

Ile Phe Asp Asn Asn Lys Arg Pro Ser Gly Ile Pro Asp Arg Phe Ser
    50                  55                  60

Gly Ser Lys Ser Gly Thr Ser Ala Thr Leu Ala Ile Ser Gly Leu Gln
65                  70                  75                  80

Ala Ala Asp Glu Ala Asp Tyr Tyr Cys Gly Thr Trp Asp Ser Asp Leu
                85                  90                  95

Ser Ala Tyr Val Phe Gly Thr Gly Thr Lys Val Thr Val Leu
            100                 105                 110

<210> SEQ ID NO 163
<211> LENGTH: 13
<212> TYPE: PRT
<213> ORGANISM: Homo sapiens

<400> SEQUENCE: 163

Ser Gly Ser Arg Ser Asn Ile Gly Lys Asn Tyr Val Ser
1               5                   10

<210> SEQ ID NO 164
<211> LENGTH: 7
<212> TYPE: PRT
<213> ORGANISM: Homo sapiens

<400> SEQUENCE: 164

Asp Asn Asn Lys Arg Pro Ser
1               5

<210> SEQ ID NO 165
<211> LENGTH: 11
<212> TYPE: PRT
<213> ORGANISM: Homo sapiens

<400> SEQUENCE: 165

Gly Thr Trp Asp Ser Asp Leu Ser Ala Tyr Val
1               5                   10

<210> SEQ ID NO 166
<211> LENGTH: 328
<212> TYPE: DNA
<213> ORGANISM: Homo sapiens

<400> SEQUENCE: 166
cagtctgtgt tgacgcagcc gccctcagtg tctgcggccc caggacagag ggtcaccatc      60
tcctgctctg gaagcagatc caacattggg aagaattatg tatcctgta ccagcaactc     120 ccaggtacag cccccaaact cctcattttt gacaataata agcgaccctc agggattcct     180
gaccgattct ctggctccaa gtctggcacg tcagccaccc tggccatctc cggactccag     240
gctgcggacg aggccgatta ctactgcgga acatgggata gcagcctgag tgtggtattc     300
ggcgggggga ccaaggtcac cgtcctag                                        328

<210> SEQ ID NO 167
<211> LENGTH: 109
<212> TYPE: PRT
```

<213> ORGANISM: Homo sapiens

<400> SEQUENCE: 167

Gln Ser Val Leu Thr Gln Pro Pro Ser Val Ser Ala Ala Pro Gly Gln
1               5                   10                  15

Arg Val Thr Ile Ser Cys Ser Gly Ser Arg Ser Asn Ile Gly Lys Asn
            20                  25                  30

Tyr Val Ser Trp Tyr Gln Gln Leu Pro Gly Thr Ala Pro Lys Leu Leu
        35                  40                  45

Ile Phe Asp Asn Asn Lys Arg Pro Ser Gly Ile Pro Asp Arg Phe Ser
    50                  55                  60

Gly Ser Lys Ser Gly Thr Ser Ala Thr Leu Ala Ile Ser Gly Leu Gln
65                  70                  75                  80

Ala Ala Asp Glu Ala Asp Tyr Tyr Cys Gly Thr Trp Asp Ser Ser Leu
                85                  90                  95

Ser Val Val Phe Gly Gly Gly Thr Lys Val Thr Val Leu
                100                 105

<210> SEQ ID NO 168
<211> LENGTH: 13
<212> TYPE: PRT
<213> ORGANISM: Homo sapiens

<400> SEQUENCE: 168

Ser Gly Ser Arg Ser Asn Ile Gly Lys Asn Tyr Val Ser
1               5                   10

<210> SEQ ID NO 169
<211> LENGTH: 7
<212> TYPE: PRT
<213> ORGANISM: Homo sapiens

<400> SEQUENCE: 169

Asp Asn Asn Lys Arg Pro Ser
1               5

<210> SEQ ID NO 170
<211> LENGTH: 10
<212> TYPE: PRT
<213> ORGANISM: Homo sapiens

<400> SEQUENCE: 170

Gly Thr Trp Asp Ser Ser Leu Ser Val Val
1               5                   10

<210> SEQ ID NO 171
<211> LENGTH: 328
<212> TYPE: DNA
<213> ORGANISM: Homo sapiens

<400> SEQUENCE: 171
cagtctgtgt tgacgcagcc gccctcagtg tctgcggccc caggacagaa ggtcaccatc      60
tcctgctctg gaaacagctc aacattggga agaattatg tatcctggta ccagcagctc     120
ccaggaacag ccccaaaact cctcattgat gacaataata gcgaccctc agggattcct     180 gaccgattct ctggctccaa gtctggcacg tcagccaccc tgggcatcac cggactccag     240
actggggacg aggccgatta ttactgcgca acatgggata gcagcctggg tgtggtcttc     300
ggcggaggga ccaaggtcac cgtcctag                                        328

<210> SEQ ID NO 172
<211> LENGTH: 109
<212> TYPE: PRT
<213> ORGANISM: Homo sapiens

<400> SEQUENCE: 172

Gln Ser Val Leu Thr Gln Pro Pro Ser Val Ser Ala Ala Pro Gly Gln
1               5                   10                  15

Lys Val Thr Ile Ser Cys Ser Gly Asn Ser Ser Asn Ile Gly Lys Asn
            20                  25                  30

Tyr Val Ser Trp Tyr Gln Gln Leu Pro Gly Thr Ala Pro Lys Leu Leu
        35                  40                  45

Ile Asp Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Ala Thr Trp Asp Ser Ser Leu
                85                  90                  95

Gly Val Val Phe Gly Gly Gly Thr Lys Val Thr Val Leu
            100                 105

<210> SEQ ID NO 173
<211> LENGTH: 13
<212> TYPE: PRT
<213> ORGANISM: Homo sapiens

<400> SEQUENCE: 173

Ser Gly Asn Ser Ser Asn Ile Gly Lys Asn Tyr Val Ser
1               5                   10

<210> SEQ ID NO 174
<211> LENGTH: 7
<212> TYPE: PRT
<213> ORGANISM: Homo sapiens

<400> SEQUENCE: 174

Asp Asn Asn Lys Arg Pro Ser
1               5

<210> SEQ ID NO 175
<211> LENGTH: 10
<212> TYPE: PRT
<213> ORGANISM: Homo sapiens

<400> SEQUENCE: 175

Ala Thr Trp Asp Ser Ser Leu Gly Val Val
1               5                   10

<210> SEQ ID NO 176
<211> LENGTH: 328
<212> TYPE: DNA
<213> ORGANISM: Homo sapiens

<400> SEQUENCE: 176
cagtctgtgt tgacgcagcc gccctcagtg tctgcggccc caggacagag ggtcaccatc      60
tcctgctctg gaagcagctc caacattggg aagaattatg tatcctggta ccagcagctc     120
ccaggaacag ccccaaaact cctcattgat gacaataata gcgaccctc agggattcct      180 gaccgattct ctggctccaa gtctggcacg tcagccaccc tgggcatcac cggactccag     240
actggggacg aggccgatta ttactgcgca acatgggata gcagcctggg tgtggtcttc     300
ggcggaggaa cccagctgat catcctag                                                328

<210> SEQ ID NO 177
<211> LENGTH: 109
<212> TYPE: PRT
<213> ORGANISM: Homo sapiens

<400> SEQUENCE: 177

Gln Ser Val Leu Thr Gln Pro Pro Ser Val Ala Ala Pro Gly Gln
1               5                   10                  15

Arg Val Thr Ile Ser Cys Ser Gly Ser Ser Asn Ile Gly Lys Asn
            20                  25                  30

Tyr Val Ser Trp Tyr Gln Leu Pro Gly Thr Ala Pro Lys Leu Leu
        35                  40                  45

Ile Asp Asp Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Ala Thr Trp Asp Ser Ser Leu
                85                  90                  95

Gly Val Val Phe Gly Gly Gly Thr Gln Leu Ile Ile Leu
            100                 105

<210> SEQ ID NO 178
<211> LENGTH: 13
<212> TYPE: PRT
<213> ORGANISM: Homo sapiens

<400> SEQUENCE: 178

Ser Gly Ser Ser Ser Asn Ile Gly Lys Asn Tyr Val Ser
1               5                   10

<210> SEQ ID NO 179
<211> LENGTH: 7
<212> TYPE: PRT
<213> ORGANISM: Homo sapiens

<400> SEQUENCE: 179

Asp Asn Asn Lys Arg Pro Ser
1               5

<210> SEQ ID NO 180
<211> LENGTH: 10
<212> TYPE: PRT
<213> ORGANISM: Homo sapiens

<400> SEQUENCE: 180

Ala Thr Trp Asp Ser Ser Leu Gly Val Val
1               5                   10

<210> SEQ ID NO 181
<211> LENGTH: 30
<212> TYPE: PRT
<213> ORGANISM: Homo sapiens

<400> SEQUENCE: 181

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30

<210> SEQ ID NO 182
<211> LENGTH: 14
<212> TYPE: PRT
<213> ORGANISM: Homo sapiens

<400> SEQUENCE: 182

Trp Val Arg Gln Ala Pro Gly Gln Gly Leu Glu Trp Met Gly
1               5                   10

<210> SEQ ID NO 183
<211> LENGTH: 32
<212> TYPE: PRT
<213> ORGANISM: Homo sapiens

<400> SEQUENCE: 183

Arg Val Thr Met Thr Arg Asp Thr Ser Ile Ser Thr Ala Tyr Met Glu
1               5                   10                  15

Leu Ser Arg Leu Arg Ser Asp Asp Thr Ala Val Tyr Tyr Cys Ala Arg
                20                  25                  30

<210> SEQ ID NO 184
<211> LENGTH: 32
<212> TYPE: PRT
<213> ORGANISM: Homo sapiens

<400> SEQUENCE: 184

Arg Val Thr Ser Thr Arg Asp Thr Ser Ile Ser Thr Ala Tyr Met Glu
1               5                   10                  15

Leu Ser Arg Leu Arg Ser Asp Asp Thr Val Val Tyr Tyr Cys Ala Arg
                20                  25                  30

<210> SEQ ID NO 185
<211> LENGTH: 22
<212> TYPE: PRT
<213> ORGANISM: Homo sapiens

<400> SEQUENCE: 185

Gln Ser Val Leu Thr Gln Pro Pro Ser Val Ser Ala Ala Pro Gly Gln
1               5                   10                  15

Lys Val Thr Ile Ser Cys
                20

<210> SEQ ID NO 186
<211> LENGTH: 15
<212> TYPE: PRT
<213> ORGANISM: Homo sapiens

<400> SEQUENCE: 186

Trp Tyr Gln Gln Leu Pro Gly Thr Ala Pro Lys Leu Leu Ile Tyr
1               5                   10                  15

<210> SEQ ID NO 187
<211> LENGTH: 32
<212> TYPE: PRT
<213> ORGANISM: Homo sapiens

<400> SEQUENCE: 187

Gly Ile Pro Asp Arg Phe Ser Gly Ser Lys Ser Gly Thr Ser Ala Thr
1               5                   10                  15

Leu Gly Ile Thr Gly Leu Gln Thr Gly Asp Glu Ala Asp Tyr Tyr Cys
                20                  25                  30

<210> SEQ ID NO 188

```
<211> LENGTH: 20
<212> TYPE: PRT
<213> ORGANISM: Homo sapiens

<400> SEQUENCE: 188

Tyr Tyr Tyr Tyr Tyr Gly Met Asp Val Trp Gly Gln Gly Thr Thr Val
1               5                   10                  15

Thr Val Ser Ser
            20

<210> SEQ ID NO 189
<211> LENGTH: 16
<212> TYPE: PRT
<213> ORGANISM: Homo sapiens

<400> SEQUENCE: 189

Asp Ala Phe Asp Ile Trp Gly Gln Gly Thr Met Val Thr Val Ser Ser
1               5                   10                  15

<210> SEQ ID NO 190
<211> LENGTH: 16
<212> TYPE: PRT
<213> ORGANISM: Homo sapiens

<400> SEQUENCE: 190

Asn Trp Phe Asp Ser Trp Gly Gln Gly Thr Leu Val Thr Val Ser Ser
1               5                   10                  15

<210> SEQ ID NO 191
<211> LENGTH: 16
<212> TYPE: PRT
<213> ORGANISM: Homo sapiens

<400> SEQUENCE: 191

Asn Trp Phe Asp Pro Trp Gly Gln Gly Thr Leu Val Thr Val Ser Ser
1               5                   10                  15

<210> SEQ ID NO 192
<211> LENGTH: 12
<212> TYPE: PRT
<213> ORGANISM: Homo sapiens

<400> SEQUENCE: 192

Tyr Val Phe Gly Thr Gly Thr Lys Val Thr Val Leu
1               5                   10

<210> SEQ ID NO 193
<211> LENGTH: 12
<212> TYPE: PRT
<213> ORGANISM: Homo sapiens

<400> SEQUENCE: 193

Val Val Phe Gly Gly Gly Thr Lys Leu Thr Val Leu
1               5                   10

<210> SEQ ID NO 194
<211> LENGTH: 12
<212> TYPE: PRT
<213> ORGANISM: Homo sapiens

<400> SEQUENCE: 194

Val Val Phe Gly Gly Gly Thr Lys Leu Thr Val Leu
1               5                   10
```

```
<210> SEQ ID NO 195
<211> LENGTH: 12
<212> TYPE: PRT
<213> ORGANISM: Homo sapiens

<400> SEQUENCE: 195

Trp Val Phe Gly Gly Gly Thr Lys Leu Thr Val Leu
1               5                   10

<210> SEQ ID NO 196
<211> LENGTH: 20
<212> TYPE: DNA
<213> ORGANISM: Artificial Sequence
<220> FEATURE:
<223> OTHER INFORMATION: Primer 179-Je

<400> SEQUENCE: 196
agagaaccca ctgcttactg                                              20

<210> SEQ ID NO 197
<211> LENGTH: 17
<212> TYPE: PRT
<213> ORGANISM: Artificial Sequence
<220> FEATURE:
<223> OTHER INFORMATION: Synthetic peptide

<400> SEQUENCE: 197

Asn Glu Thr Ile Tyr Asn Thr Thr Leu Lys Tyr Gly Asp Val Val Gly
1               5                   10                  15
Val

<210> SEQ ID NO 198
<211> LENGTH: 23
<212> TYPE: DNA
<213> ORGANISM: Artificial Sequence
<220> FEATURE:
<223> OTHER INFORMATION: Primer 074-Je

<400> SEQUENCE: 198
gtcagwccca gtcaggacac agc                                          23

<210> SEQ ID NO 199
<211> LENGTH: 23
<212> TYPE: DNA
<213> ORGANISM: Artificial Sequence
<220> FEATURE:
<223> OTHER INFORMATION: Primer 075-Je

<400> SEQUENCE: 199
actcctcagt tcaccttctc acm                                          23

<210> SEQ ID NO 200
<211> LENGTH: 21
<212> TYPE: DNA
<213> ORGANISM: Artificial Sequence
<220> FEATURE:
<223> OTHER INFORMATION: Primer 076-Je

<400> SEQUENCE: 200
tcagttagga cccagasgga a                                            21

<210> SEQ ID NO 201
<211> LENGTH: 24
<212> TYPE: DNA
<213> ORGANISM: Artificial Sequence
<220> FEATURE:
```

```
<223> OTHER INFORMATION: Primer 150-Je

<400> SEQUENCE: 201
caacaggcag gcagggggcag caag                                            24

<210> SEQ ID NO 202
<211> LENGTH: 24
<212> TYPE: DNA
<213> ORGANISM: Artificial Sequence
<220> FEATURE:
<223> OTHER INFORMATION: Primer 151-Je

<400> SEQUENCE: 202
cacctgcagg tcagggccaa ggtt                                             24

<210> SEQ ID NO 203
<211> LENGTH: 39
<212> TYPE: DNA
<213> ORGANISM: Artificial Sequence
<220> FEATURE:
<223> OTHER INFORMATION: Primer 077-Je

<400> SEQUENCE: 203
ctgaagcttc catggacatg agggtccccg ctcagctcc                             39

<210> SEQ ID NO 204
<211> LENGTH: 41
<212> TYPE: DNA
<213> ORGANISM: Artificial Sequence
<220> FEATURE:
<223> OTHER INFORMATION: Primer 078-Je

<400> SEQUENCE: 204
ctgaggcttc catgaggctc cctgctcagc tcctggggct g                          41

<210> SEQ ID NO 205
<211> LENGTH: 41
<212> TYPE: DNA
<213> ORGANISM: Artificial Sequence
<220> FEATURE:
<223> OTHER INFORMATION: Primer 007-Je

<400> SEQUENCE: 205
ctgaagcttc catggaagcc ccagcgcagc ttctcttcct c                          41

<210> SEQ ID NO 206
<211> LENGTH: 42
<212> TYPE: DNA
<213> ORGANISM: Artificial Sequence
<220> FEATURE:
<223> OTHER INFORMATION: Primer 152-Je

<400> SEQUENCE: 206
ctgaagcttc catggtgttg cagacccagg tcttcatttc tc                         42

<210> SEQ ID NO 207
<211> LENGTH: 42
<212> TYPE: DNA
<213> ORGANISM: Artificial Sequence
<220> FEATURE:
<223> OTHER INFORMATION: Primer 153-Je

<400> SEQUENCE: 207
ctgaagcttc catggggtcc caggttcacc tcctcagctt cc                         42
```

```
<210> SEQ ID NO 208
<211> LENGTH: 32
<212> TYPE: DNA
<213> ORGANISM: Artificial Sequence
<220> FEATURE:
<223> OTHER INFORMATION: Primer 066-Je

<400> SEQUENCE: 208
tagagcgctt gatttccacc ttggtccctt gg                                   32

<210> SEQ ID NO 209
<211> LENGTH: 32
<212> TYPE: DNA
<213> ORGANISM: Artificial Sequence
<220> FEATURE:
<223> OTHER INFORMATION: Primer 067-Je

<400> SEQUENCE: 209
tagagcgctt gatctccagc ttggtcccct gg                                   32

<210> SEQ ID NO 210
<211> LENGTH: 32
<212> TYPE: DNA
<213> ORGANISM: Artificial Sequence
<220> FEATURE:
<223> OTHER INFORMATION: Primer 068-Je

<400> SEQUENCE: 210
tagagcgctt gatatccact ttggtcccag gg                                   32

<210> SEQ ID NO 211
<211> LENGTH: 32
<212> TYPE: DNA
<213> ORGANISM: Artificial Sequence
<220> FEATURE:
<223> OTHER INFORMATION: Primer 069-Je

<400> SEQUENCE: 211
tagagcgctt gatctccacc ttggtccctc cg                                   32

<210> SEQ ID NO 212
<211> LENGTH: 32
<212> TYPE: DNA
<213> ORGANISM: Artificial Sequence
<220> FEATURE:
<223> OTHER INFORMATION: Primer 070-Je

<400> SEQUENCE: 212
tagagcgctt aatctccagt cgtgtccctt gg                                   32

<210> SEQ ID NO 213
<211> LENGTH: 23
<212> TYPE: DNA
<213> ORGANISM: Artificial Sequence
<220> FEATURE:
<223> OTHER INFORMATION: Primer 258-Je

<400> SEQUENCE: 213
caggactcag gacaatctcc agc                                             23

<210> SEQ ID NO 214
<211> LENGTH: 18
<212> TYPE: DNA
<213> ORGANISM: Artificial Sequence
<220> FEATURE:
<223> OTHER INFORMATION: Primer 259-Je
```

<400> SEQUENCE: 214
yyycsggacg tcyycacc                                                18

<210> SEQ ID NO 215
<211> LENGTH: 18
<212> TYPE: DNA
<213> ORGANISM: Artificial Sequence
<220> FEATURE:
<223> OTHER INFORMATION: Primer 260-Je

<400> SEQUENCE: 215
atctgggggk ctyycrcc                                                18

<210> SEQ ID NO 216
<211> LENGTH: 37
<212> TYPE: DNA
<213> ORGANISM: Artificial Sequence
<220> FEATURE:
<223> OTHER INFORMATION: Primer 261-Je

<400> SEQUENCE: 216
gataagcttc catggcctgs tccctctcc tcctcac                            37

<210> SEQ ID NO 217
<211> LENGTH: 35
<212> TYPE: DNA
<213> ORGANISM: Artificial Sequence
<220> FEATURE:
<223> OTHER INFORMATION: Primer 262-Je

<400> SEQUENCE: 217
gataagcttc catggcctgg gctctgctcc tcctc                             35

<210> SEQ ID NO 218
<211> LENGTH: 35
<212> TYPE: DNA
<213> ORGANISM: Artificial Sequence
<220> FEATURE:
<223> OTHER INFORMATION: Primer 263-Je

<400> SEQUENCE: 218
gataagcttc catggcctgg acccctctcc tsctc                             35

<210> SEQ ID NO 219
<211> LENGTH: 26
<212> TYPE: DNA
<213> ORGANISM: Artificial Sequence
<220> FEATURE:
<223> OTHER INFORMATION: Primer 264-Je

<400> SEQUENCE: 219
gagcctagga cggtgacctt ggtccc                                       26

<210> SEQ ID NO 220
<211> LENGTH: 29
<212> TYPE: DNA
<213> ORGANISM: Artificial Sequence
<220> FEATURE:
<223> OTHER INFORMATION: Primer 265-Je

<400> SEQUENCE: 220
gagcctagga tgatcagctg ggttcctcc                                    29

<210> SEQ ID NO 221
<211> LENGTH: 29

```
<212> TYPE: DNA
<213> ORGANISM: Artificial Sequence
<220> FEATURE:
<223> OTHER INFORMATION: Primer 266-Je

<400> SEQUENCE: 221
gagcctagga cggtcagctc gctcccctc                                29

<210> SEQ ID NO 222
<211> LENGTH: 29
<212> TYPE: DNA
<213> ORGANISM: Artificial Sequence
<220> FEATURE:
<223> OTHER INFORMATION: Primer 267-Je

<400> SEQUENCE: 222
gagcctaggg cggtcagctg ggtgcctcc                                29

<210> SEQ ID NO 223
<211> LENGTH: 23
<212> TYPE: DNA
<213> ORGANISM: Artificial Sequence
<220> FEATURE:
<223> OTHER INFORMATION: Primer 84-B

<400> SEQUENCE: 223
ccctgagagc acagytcctc acc                                      23

<210> SEQ ID NO 224
<211> LENGTH: 20
<212> TYPE: DNA
<213> ORGANISM: Artificial Sequence
<220> FEATURE:
<223> OTHER INFORMATION: Primer 155-Je

<400> SEQUENCE: 224
agtgactcct gtgcmccacc                                          20

<210> SEQ ID NO 225
<211> LENGTH: 21
<212> TYPE: DNA
<213> ORGANISM: Artificial Sequence
<220> FEATURE:
<223> OTHER INFORMATION: Primer 85-B

<400> SEQUENCE: 225
gcactgaaca cagaggcatc a                                        21

<210> SEQ ID NO 226
<211> LENGTH: 22
<212> TYPE: DNA
<213> ORGANISM: Artificial Sequence
<220> FEATURE:
<223> OTHER INFORMATION: Primer 161-Je

<400> SEQUENCE: 226
cmtggayctc mtgyrcraga ac                                       22

<210> SEQ ID NO 227
<211> LENGTH: 28
<212> TYPE: DNA
<213> ORGANISM: Artificial Sequence
<220> FEATURE:
<223> OTHER INFORMATION: Primer 162-Je

<400> SEQUENCE: 227
```

```
agggcttcat tttctgtcct ccaccatc                                            28
```

<210> SEQ ID NO 228
<211> LENGTH: 24
<212> TYPE: DNA
<213> ORGANISM: Artificial Sequence
<220> FEATURE:
<223> OTHER INFORMATION: Primer 154-Je

<400> SEQUENCE: 228

```
gggcagtcac cagagctcca gaca                                                24
```

<210> SEQ ID NO 229
<211> LENGTH: 41
<212> TYPE: DNA
<213> ORGANISM: Artificial Sequence
<220> FEATURE:
<223> OTHER INFORMATION: Primer 001-Je

<400> SEQUENCE: 229

```
ctgaagcttc catggactgg acctggagga tcctcttctt g                             41
```

<210> SEQ ID NO 230
<211> LENGTH: 38
<212> TYPE: DNA
<213> ORGANISM: Artificial Sequence
<220> FEATURE:
<223> OTHER INFORMATION: Primer 158-Je

<400> SEQUENCE: 230

```
ctgaagcttc catggacaca ctttgctcca cgctcctg                                 38
```

<210> SEQ ID NO 231
<211> LENGTH: 42
<212> TYPE: DNA
<213> ORGANISM: Artificial Sequence
<220> FEATURE:
<223> OTHER INFORMATION: Primer 003-Je

<400> SEQUENCE: 231

```
ctgaagcttc catggagttt gggctgagct gggttttcct tg                            42
```

<210> SEQ ID NO 232
<211> LENGTH: 42
<212> TYPE: DNA
<213> ORGANISM: Artificial Sequence
<220> FEATURE:
<223> OTHER INFORMATION: Primer 159-Je

<400> SEQUENCE: 232

```
ctgaagcttc catgaaacac ctgtggttct tcctcctsct gg                            42
```

<210> SEQ ID NO 233
<211> LENGTH: 42
<212> TYPE: DNA
<213> ORGANISM: Artificial Sequence
<220> FEATURE:
<223> OTHER INFORMATION: Primer 156-Je

<400> SEQUENCE: 233

```
ctgaagcttc catggggtca accgccatcc tcgccctcct cc                            42
```

<210> SEQ ID NO 234
<211> LENGTH: 42
<212> TYPE: DNA
<213> ORGANISM: Artificial Sequence

```
<220> FEATURE:
<223> OTHER INFORMATION: Primer 157-Je

<400> SEQUENCE: 234
ctgaagcttc catgtctgtc tccttcctca tcttcctgcc cg                           42

<210> SEQ ID NO 235
<211> LENGTH: 34
<212> TYPE: DNA
<213> ORGANISM: Artificial Sequence
<220> FEATURE:
<223> OTHER INFORMATION: Primer 062-Je

<400> SEQUENCE: 235
tagagcgctg gagacggtga ccagggttcc ctgg                                    34

<210> SEQ ID NO 236
<211> LENGTH: 33
<212> TYPE: DNA
<213> ORGANISM: Artificial Sequence
<220> FEATURE:
<223> OTHER INFORMATION: Primer 063-Je

<400> SEQUENCE: 236
tagagcgctg gagacagtga ccagggtgcc acg                                     33

<210> SEQ ID NO 237
<211> LENGTH: 34
<212> TYPE: DNA
<213> ORGANISM: Artificial Sequence
<220> FEATURE:
<223> OTHER INFORMATION: Primer 065-Je

<400> SEQUENCE: 237
tagagcgcta gagacggtga ccattgtccc ttgg                                    34

<210> SEQ ID NO 238
<211> LENGTH: 35
<212> TYPE: DNA
<213> ORGANISM: Artificial Sequence
<220> FEATURE:
<223> OTHER INFORMATION: Primer 064-Je

<400> SEQUENCE: 238
tagagcgctg gagacggtga ccgtggtgcc ttttt                                   35

<210> SEQ ID NO 239
<211> LENGTH: 906
<212> TYPE: PRT
<213> ORGANISM: Homo sapiens

<400> SEQUENCE: 239
```

Met Glu Ser Arg Ile Trp Cys Leu Val Val Cys Val Asn Leu Cys Ile
1               5                   10                  15

Val Cys Leu Gly Ala Ala Val Ser Ser Ser Thr Ser His Ala Thr
            20                  25                  30

Ser Ser Thr His Asn Gly Ser His Thr Ser Arg Thr Thr Ser Ala Gln
        35                  40                  45

Thr Arg Ser Val Tyr Ser Gln His Val Thr Ser Ser Glu Ala Val Ser
    50                  55                  60

His Arg Ala Asn Glu Thr Ile Tyr Asn Thr Thr Leu Lys Tyr Gly Asp
65                  70                  75                  80

Val Val Gly Val Asn Thr Thr Lys Tyr Pro Tyr Arg Val Cys Ser Met

-continued

```
                85                  90                  95
Ala Gln Gly Thr Asp Leu Ile Arg Phe Glu Arg Asn Ile Ile Cys Thr
                    100                 105                 110

Ser Met Lys Pro Ile Asn Glu Asp Leu Asp Glu Gly Ile Met Val Val
            115                 120                 125

Tyr Lys Arg Asn Ile Val Ala His Thr Phe Lys Val Arg Val Tyr Gln
        130                 135                 140

Lys Val Leu Thr Phe Arg Arg Ser Tyr Ala Tyr Ile Tyr Thr Thr Tyr
145                 150                 155                 160

Leu Leu Gly Ser Asn Thr Glu Tyr Val Ala Pro Pro Met Trp Glu Ile
                165                 170                 175

His His Ile Asn Lys Phe Ala Gln Cys Tyr Ser Ser Tyr Ser Arg Val
            180                 185                 190

Ile Gly Gly Thr Val Phe Val Ala Tyr His Arg Asp Ser Tyr Glu Asn
        195                 200                 205

Lys Thr Met Gln Leu Ile Pro Asp Asp Tyr Ser Asn Thr His Ser Thr
    210                 215                 220

Arg Tyr Val Thr Val Lys Asp Gln Trp His Ser Arg Gly Ser Thr Trp
225                 230                 235                 240

Leu Tyr Arg Glu Thr Cys Asn Leu Asn Cys Met Leu Thr Ile Thr Thr
                245                 250                 255

Ala Arg Ser Lys Tyr Pro Tyr His Phe Phe Ala Thr Ser Thr Gly Asp
            260                 265                 270

Val Val Tyr Ile Ser Pro Phe Tyr Asn Gly Thr Asn Arg Asn Ala Ser
        275                 280                 285

Tyr Phe Gly Glu Asn Ala Asp Lys Phe Phe Ile Phe Pro Asn Tyr Thr
    290                 295                 300

Ile Val Ser Asp Phe Gly Arg Pro Asn Ala Ala Pro Glu Thr His Arg
305                 310                 315                 320

Leu Val Ala Phe Leu Glu Arg Ala Asp Ser Val Ile Ser Trp Asp Ile
                325                 330                 335

Gln Asp Glu Lys Asn Val Thr Cys Gln Leu Thr Phe Trp Glu Ala Ser
            340                 345                 350

Glu Arg Thr Ile Arg Ser Glu Ala Glu Asp Ser Tyr His Phe Ser Ser
        355                 360                 365

Ala Lys Met Thr Ala Thr Phe Leu Ser Lys Lys Gln Glu Val Asn Met
    370                 375                 380

Ser Asp Ser Ala Leu Asp Cys Val Arg Asp Glu Ala Ile Asn Lys Leu
385                 390                 395                 400

Gln Gln Ile Phe Asn Thr Ser Tyr Asn Gln Thr Tyr Glu Lys Tyr Gly
                405                 410                 415

Asn Val Ser Val Phe Glu Thr Ser Gly Gly Leu Val Val Phe Trp Gln
            420                 425                 430

Gly Ile Lys Gln Lys Ser Leu Val Glu Leu Glu Arg Leu Ala Asn Arg
        435                 440                 445

Ser Ser Leu Asn Ile Thr His Arg Thr Arg Ser Thr Ser Asp Asn
    450                 455                 460

Asn Thr Thr His Leu Ser Ser Met Glu Ser Val His Asn Leu Val Tyr
465                 470                 475                 480

Ala Gln Leu Gln Phe Thr Tyr Asp Thr Leu Arg Gly Tyr Ile Asn Arg
                485                 490                 495

Ala Leu Ala Gln Ile Ala Glu Ala Trp Cys Val Asp Gln Arg Arg Thr
            500                 505                 510
```

```
Leu Glu Val Phe Lys Glu Leu Ser Lys Ile Asn Pro Ser Ala Ile Leu
            515                 520                 525

Ser Ala Ile Tyr Asn Lys Pro Ile Ala Arg Phe Met Gly Asp Val
        530                 535                 540

Leu Gly Leu Ala Ser Cys Val Thr Ile Asn Gln Thr Ser Val Lys Val
545                 550                 555                 560

Leu Arg Asp Met Asn Val Lys Glu Ser Pro Gly Arg Cys Tyr Ser Arg
                565                 570                 575

Pro Val Val Ile Phe Asn Phe Ala Asn Ser Ser Tyr Val Gln Tyr Gly
                580                 585                 590

Gln Leu Gly Glu Asp Asn Glu Ile Leu Leu Gly Asn His Arg Thr Glu
            595                 600                 605

Glu Cys Gln Leu Pro Ser Leu Lys Ile Phe Ile Ala Gly Asn Ser Ala
        610                 615                 620

Tyr Glu Tyr Val Asp Tyr Leu Phe Lys Arg Met Ile Asp Leu Ser Ser
625                 630                 635                 640

Ile Ser Thr Val Asp Ser Met Ile Ala Leu Asp Ile Asp Pro Leu Glu
                645                 650                 655

Asn Thr Asp Phe Arg Val Leu Glu Leu Tyr Ser Gln Lys Glu Leu Arg
                660                 665                 670

Ser Ser Asn Val Phe Asp Leu Glu Glu Ile Met Arg Glu Phe Asn Ser
            675                 680                 685

Tyr Lys Gln Arg Val Lys Tyr Val Glu Asp Lys Val Val Asp Pro Leu
        690                 695                 700

Pro Pro Tyr Leu Lys Gly Leu Asp Asp Leu Met Ser Gly Leu Gly Ala
705                 710                 715                 720

Ala Gly Lys Ala Val Gly Val Ala Ile Gly Ala Val Gly Gly Ala Val
                725                 730                 735

Ala Ser Val Val Glu Gly Val Ala Thr Phe Leu Lys Asn Pro Phe Gly
            740                 745                 750

Ala Phe Thr Ile Ile Leu Val Ala Ile Ala Val Val Ile Ile Thr Tyr
        755                 760                 765

Leu Ile Tyr Thr Arg Gln Arg Arg Leu Cys Thr Gln Pro Leu Gln Asn
770                 775                 780

Leu Phe Pro Tyr Leu Val Ser Ala Asp Gly Thr Thr Val Thr Ser Gly
785                 790                 795                 800

Ser Thr Lys Asp Thr Ser Leu Gln Ala Pro Pro Ser Tyr Glu Glu Ser
                805                 810                 815

Val Tyr Asn Ser Gly Arg Lys Gly Pro Gly Pro Pro Ser Ser Asp Ala
            820                 825                 830

Ser Thr Ala Ala Pro Pro Tyr Thr Asn Glu Gln Ala Tyr Gln Met Leu
        835                 840                 845

Leu Ala Leu Ala Arg Leu Asp Ala Glu Gln Arg Ala Gln Gln Asn Gly
850                 855                 860

Thr Asp Ser Leu Asp Gly Gln Thr Gly Thr Gln Asp Lys Gly Gln Lys
865                 870                 875                 880

Pro Asn Leu Leu Asp Arg Leu Arg His Arg Lys Asn Gly Tyr Arg His
                885                 890                 895

Leu Lys Asp Ser Asp Glu Glu Asn Val
                900                 905

<210> SEQ ID NO 240
<211> LENGTH: 907
```

<212> TYPE: PRT
<213> ORGANISM: Homo sapiens

<400> SEQUENCE: 240

Met Glu Ser Arg Ile Trp Cys Leu Val Val Cys Val Asn Leu Cys Ile
1               5                   10                  15

Val Cys Leu Gly Ala Ala Val Ser Ser Ser Thr Arg Gly Thr Ser
            20                  25                  30

Ala Thr His Ser His His Ser Ser His Thr Thr Ser Ala Ala His Ser
        35                  40                  45

Arg Ser Gly Ser Val Ser Gln Arg Val Thr Ser Ser Gln Thr Val Ser
    50                  55                  60

His Gly Val Asn Glu Thr Ile Tyr Asn Thr Thr Leu Lys Tyr Gly Asp
65                  70                  75                  80

Val Val Gly Val Asn Thr Thr Lys Tyr Pro Tyr Arg Val Cys Ser Met
                85                  90                  95

Ala Gln Gly Thr Asp Leu Ile Arg Phe Glu Arg Asn Ile Val Cys Thr
            100                 105                 110

Ser Met Lys Pro Ile Asn Glu Asp Leu Asp Glu Gly Ile Met Val Val
        115                 120                 125

Tyr Lys Arg Asn Ile Val Ala His Thr Phe Lys Val Arg Val Tyr Gln
    130                 135                 140

Lys Val Leu Thr Phe Arg Arg Ser Tyr Ala Tyr Ile His Thr Thr Tyr
145                 150                 155                 160

Leu Leu Gly Ser Asn Thr Glu Tyr Val Ala Pro Pro Met Trp Glu Ile
                165                 170                 175

His His Ile Asn Ser His Ser Gln Cys Tyr Ser Ser Tyr Ser Arg Val
            180                 185                 190

Ile Ala Gly Thr Val Phe Val Ala Tyr His Arg Asp Ser Tyr Glu Asn
        195                 200                 205

Lys Thr Met Gln Leu Met Pro Asp Asp Tyr Ser Asn Thr His Ser Thr
    210                 215                 220

Arg Tyr Val Thr Val Lys Asp Gln Trp His Ser Arg Gly Ser Thr Trp
225                 230                 235                 240

Leu Tyr Arg Glu Thr Cys Asn Leu Asn Cys Met Val Thr Ile Thr Thr
                245                 250                 255

Ala Arg Ser Lys Tyr Pro Tyr His Phe Phe Ala Thr Ser Thr Gly Asp
            260                 265                 270

Val Val Asp Ile Ser Pro Phe Tyr Asn Gly Thr Asn Arg Asn Ala Ser
        275                 280                 285

Tyr Phe Gly Glu Asn Ala Asp Lys Phe Phe Ile Phe Pro Asn Tyr Thr
    290                 295                 300

Ile Val Ser Asp Phe Gly Arg Pro Asn Ser Ala Leu Glu Thr His Arg
305                 310                 315                 320

Leu Val Ala Phe Leu Glu Arg Ala Asp Ser Val Ile Ser Trp Asp Ile
                325                 330                 335

Gln Asp Glu Lys Asn Val Thr Cys Gln Leu Thr Phe Trp Glu Ala Ser
            340                 345                 350

Glu Arg Thr Ile Arg Ser Glu Ala Glu Asp Ser Tyr His Phe Ser Ser
        355                 360                 365

Ala Lys Met Thr Ala Thr Phe Leu Ser Lys Lys Gln Glu Val Asn Met
    370                 375                 380

Ser Asp Ser Ala Leu Asp Cys Val Arg Asp Glu Ala Ile Asn Lys Leu
385                 390                 395                 400

```
Gln Gln Ile Phe Asn Thr Ser Tyr Asn Gln Thr Tyr Glu Lys Tyr Gly
            405                 410                 415
Asn Val Ser Val Phe Glu Thr Thr Gly Gly Leu Val Val Phe Trp Gln
        420                 425                 430
Gly Ile Lys Gln Lys Ser Leu Val Glu Leu Glu Arg Leu Ala Asn Arg
            435                 440                 445
Ser Ser Leu Asn Leu Thr His Asn Arg Thr Lys Arg Ser Thr Asp Gly
        450                 455                 460
Asn Asn Ala Thr His Leu Ser Asn Met Glu Ser Val His Asn Leu Val
465                 470                 475                 480
Tyr Ala Gln Leu Gln Phe Thr Tyr Asp Thr Leu Arg Gly Tyr Ile Asn
            485                 490                 495
Arg Ala Leu Ala Gln Ile Ala Glu Ala Trp Cys Val Asp Gln Arg Arg
        500                 505                 510
Thr Leu Glu Val Phe Lys Glu Leu Ser Lys Ile Asn Pro Ser Ala Ile
        515                 520                 525
Leu Ser Ala Ile Tyr Asn Lys Pro Ile Ala Arg Phe Met Gly Asp
        530                 535                 540
Val Leu Gly Leu Ala Ser Cys Val Thr Ile Asn Gln Thr Ser Val Lys
545                 550                 555                 560
Val Leu Arg Asp Met Asn Val Lys Glu Ser Pro Gly Arg Cys Tyr Ser
            565                 570                 575
Arg Pro Val Val Ile Phe Asn Phe Ala Asn Ser Ser Tyr Val Gln Tyr
            580                 585                 590
Gly Gln Leu Gly Glu Asp Asn Glu Ile Leu Leu Gly Asn His Arg Thr
        595                 600                 605
Glu Glu Cys Gln Leu Pro Ser Leu Lys Ile Phe Ile Ala Gly Asn Ser
        610                 615                 620
Ala Tyr Glu Tyr Val Asp Tyr Leu Phe Lys Arg Met Ile Asp Leu Ser
625                 630                 635                 640
Ser Ile Ser Thr Val Asp Ser Met Ile Ala Leu Asp Ile Asp Pro Leu
            645                 650                 655
Glu Asn Thr Asp Phe Arg Val Leu Glu Leu Tyr Ser Gln Lys Glu Leu
            660                 665                 670
Arg Ser Ser Asn Val Phe Asp Leu Glu Glu Ile Met Arg Glu Phe Asn
        675                 680                 685
Ser Tyr Lys Gln Arg Val Lys Tyr Val Glu Asp Lys Val Val Asp Pro
        690                 695                 700
Leu Pro Pro Tyr Leu Lys Gly Leu Asp Asp Leu Met Ser Gly Leu Gly
705                 710                 715                 720
Ala Ala Gly Lys Ala Val Gly Val Ala Ile Gly Ala Val Gly Gly Ala
            725                 730                 735
Val Ala Ser Val Val Glu Gly Val Ala Thr Phe Leu Lys Asn Pro Phe
        740                 745                 750
Gly Ala Phe Thr Ile Ile Leu Val Ala Ile Ala Val Val Ile Ile Ile
        755                 760                 765
Tyr Leu Ile Tyr Thr Arg Gln Arg Arg Leu Cys Met Gln Pro Leu Gln
        770                 775                 780
Asn Leu Phe Pro Tyr Leu Val Ser Ala Asp Gly Thr Thr Val Thr Ser
785                 790                 795                 800
Gly Asn Thr Lys Asp Thr Ser Leu Gln Ala Pro Pro Ser Tyr Glu Glu
            805                 810                 815
```

Ser Val Tyr Asn Ser Gly Arg Lys Gly Pro Pro Ser Ser Asp
                820                 825                 830

Ala Ser Thr Ala Ala Pro Pro Tyr Thr Asn Glu Gln Ala Tyr Gln Met
            835                 840                 845

Leu Leu Ala Leu Val Arg Leu Asp Ala Glu Gln Arg Ala Gln Gln Asn
        850                 855                 860

Gly Thr Asp Ser Leu Asp Gly Gln Thr Gly Thr Gln Asp Lys Gly Gln
865                 870                 875                 880

Lys Pro Asn Leu Leu Asp Arg Leu Arg His Arg Lys Asn Gly Tyr Arg
                885                 890                 895

His Leu Lys Asp Ser Asp Glu Glu Asn Val
            900                 905

<210> SEQ ID NO 241
<211> LENGTH: 375
<212> TYPE: DNA
<213> ORGANISM: Homo sapiens

<400> SEQUENCE: 241
caggtgcagc tgcaggagtc gggcccagga ctggtgaagc cttcggagac cctgtccctc    60
acctgcactg tctctggtgg ctccatcggc gttggtgact cctactgggg ctggctccgc   120
cagtccccag ggaagggact ggagtcgatt gggagtatat attttactgg gaccaccctc   180
tacaacccgt ccttcaagag tcgagtcacc atatccgtag accgcccaa gaagcagttc    240 tccctgaacc tgaagtctgt gaccgccgca gacacggcta tttactattg cgccagacac   300
gcctatgact tttgggttcg tggggtgtcc tggatcgccc cctggggccc gggaattttg   360
gtcaccgtct cctca                                                    375

<210> SEQ ID NO 242
<211> LENGTH: 125
<212> TYPE: PRT
<213> ORGANISM: Homo sapiens

<400> SEQUENCE: 242

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Gly Val Gly
            20                  25                  30

Asp Ser Tyr Trp Gly Trp Leu Arg Gln Ser Pro Gly Lys Gly Leu Glu
        35                  40                  45

Ser Ile Gly Ser Ile Tyr Phe Thr Gly Thr Thr Leu Tyr Asn Pro Ser
    50                  55                  60

Phe Lys Ser Arg Val Thr Ile Ser Val Asp Pro Pro Lys Lys Gln Phe
65                  70                  75                  80

Ser Leu Asn Leu Lys Ser Val Thr Ala Ala Asp Thr Ala Ile Tyr Tyr
                85                  90                  95

Cys Ala Arg His Ala Tyr Asp Phe Trp Val Arg Gly Val Ser Trp Ile
            100                 105                 110

Ala Pro Trp Gly Pro Gly Ile Leu Val Thr Val Ser Ser
        115                 120                 125

<210> SEQ ID NO 243
<211> LENGTH: 7
<212> TYPE: PRT
<213> ORGANISM: Homo sapiens

<400> SEQUENCE: 243

Val Gly Asp Ser Tyr Trp Gly
1               5

<210> SEQ ID NO 244
<211> LENGTH: 16
<212> TYPE: PRT
<213> ORGANISM: Homo sapiens

<400> SEQUENCE: 244

Ser Ile Tyr Phe Thr Gly Thr Thr Leu Tyr Asn Pro Ser Phe Lys Ser
1               5                   10                  15

<210> SEQ ID NO 245
<211> LENGTH: 15
<212> TYPE: PRT
<213> ORGANISM: Homo sapiens

<400> SEQUENCE: 245

His Ala Tyr Asp Phe Trp Val Arg Gly Val Ser Trp Ile Ala Pro
1               5                   10                  15

<210> SEQ ID NO 246
<211> LENGTH: 375
<212> TYPE: DNA
<213> ORGANISM: Homo sapiens

<400> SEQUENCE: 246
caggtgcagc tgcaggagtc gggcccagga ctggtgaagc cttcggagac cctgtccctc      60
acctgcactg tctctggtgg ctccatgagt agttactact ggagctggat ccggcagccc     120
ccagggaagg gactggagtg gattggatat atctattaca gtgggagcac caactacaac     180
ccctccctca gagtcgagt caccatatca gtagacacgt ccaagaacca gttctccctg     240
aagctgagct ctgtgaccgc tgcggacacg gccgtgtatt actgtgcgag agacgtgcgt     300
agcagcagcc ctccagtcta ctactactac ggtatggacg tctggggcca agggaccacg     360
gtcaccgtct cctca                                                      375

<210> SEQ ID NO 247
<211> LENGTH: 125
<212> TYPE: PRT
<213> ORGANISM: Homo sapiens

<400> SEQUENCE: 247

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Met Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Val Arg Ser Ser Ser Pro Val Tyr Tyr Tyr Tyr Gly Met
            100                 105                 110

Asp Val Trp Gly Gln Gly Thr Thr Val Thr Val Ser Ser
        115                 120                 125

<210> SEQ ID NO 248
<211> LENGTH: 5
<212> TYPE: PRT
<213> ORGANISM: Homo sapiens

<400> SEQUENCE: 248

Ser Tyr Tyr Trp Ser
1               5

<210> SEQ ID NO 249
<211> LENGTH: 16
<212> TYPE: PRT
<213> ORGANISM: Homo sapiens

<400> SEQUENCE: 249

Tyr Ile Tyr Tyr Ser Gly Ser Thr Asn Tyr Asn Pro Ser Leu Lys Ser
1               5                   10                  15

<210> SEQ ID NO 250
<211> LENGTH: 17
<212> TYPE: PRT
<213> ORGANISM: Homo sapiens

<400> SEQUENCE: 250

Asp Val Arg Ser Ser Pro Pro Val Tyr Tyr Tyr Gly Met Asp
1               5                   10                  15

Val

<210> SEQ ID NO 251
<211> LENGTH: 390
<212> TYPE: DNA
<213> ORGANISM: Homo sapiens

<400> SEQUENCE: 251
caggtgcagc tgcaggagtc gggcccggga ctggtgaagc cttcggagac cctgtccctc        60
atctgcactg tctctggtgc ccccattagg agttactact ggagctggat ccggcagtcc       120
ccaggaaggg gactggagta cattgggtgt atcaacacca tgggaggtc  caactacaac       180
ccctccctca ggggtcgagt caccatatca gtggactcgt cccagaatca gttctccctg       240
acggtcagct ctctgaccgc agcggacacg gccgtgtatt actgtgcgac tgcaagccaa       300
caccgctacg attctttgac tggctcttat cgctattatc cctatgtaat ggacgtctgg       360
ggccgcggga ccacggtcac cgtttcctca                                        390

<210> SEQ ID NO 252
<211> LENGTH: 130
<212> TYPE: PRT
<213> ORGANISM: Homo sapiens

<400> SEQUENCE: 252

Gln Val Gln Leu Gln Glu Ser Gly Pro Gly Leu Val Lys Pro Ser Glu
1               5                   10                  15

Thr Leu Ser Leu Ile Cys Thr Val Ser Gly Ala Pro Ile Arg Ser Tyr
            20                  25                  30

Tyr Trp Ser Trp Ile Arg Gln Ser Pro Gly Arg Gly Leu Glu Tyr Ile
        35                  40                  45

Gly Cys Ile Asn Thr Asn Gly Arg Ser Asn Tyr Asn Pro Ser Leu Arg
    50                  55                  60

Gly Arg Val Thr Ile Ser Val Asp Ser Ser Gln Asn Gln Phe Ser Leu 65                  70                  75                  80
Thr Val Ser Ser Leu Thr Ala Ala Asp Thr Ala Val Tyr Tyr Cys Ala
                    85                  90                  95

Thr Ala Ser Gln His Arg Tyr Asp Ser Leu Thr Gly Ser Tyr Arg Tyr
                100                 105                 110

Tyr Pro Tyr Val Met Asp Val Trp Gly Arg Gly Thr Thr Val Thr Val
        115                 120                 125

Ser Ser
    130

<210> SEQ ID NO 253
<211> LENGTH: 5
<212> TYPE: PRT
<213> ORGANISM: Homo sapiens

<400> SEQUENCE: 253

Ser Tyr Tyr Trp Ser
1               5

<210> SEQ ID NO 254
<211> LENGTH: 16
<212> TYPE: PRT
<213> ORGANISM: Homo sapiens

<400> SEQUENCE: 254

Cys Ile Asn Thr Asn Gly Arg Ser Asn Tyr Asn Pro Ser Leu Arg Gly
1               5                   10                  15

<210> SEQ ID NO 255
<211> LENGTH: 22
<212> TYPE: PRT
<213> ORGANISM: Homo sapiens

<400> SEQUENCE: 255

Ala Ser Gln His Arg Tyr Asp Ser Leu Thr Gly Ser Tyr Arg Tyr Tyr
1               5                   10                  15

Pro Tyr Val Met Asp Val
            20

<210> SEQ ID NO 256
<211> LENGTH: 360
<212> TYPE: DNA
<213> ORGANISM: Homo sapiens

<400> SEQUENCE: 256
cagctgcagc tgcaggagtc gggcccagga ctggtgaagc cttcggagac cctgtccctc      60
acctgcactg tgtctggtgc ctccatcgac aggagtactt actactgggg ctggatccgc     120
cagcccccag ggaagggcct ggaatggatt gcaaatatct attataatgg agggccgtc      180 tacagcccgt ccctcaagag tcgagtcacc atatcagtag acacgtccaa gaatcagttc     240
tccctgaagg tgaggtctct gaccgccgca gacacggctg tgtattattg cgcgacccgg     300
tggaattatt tcttcgactt tgactattgg ggccggggaa ccctggtcac cgtctcctca     360

<210> SEQ ID NO 257
<211> LENGTH: 120
<212> TYPE: PRT
<213> ORGANISM: Homo sapiens

<400> SEQUENCE: 257

Gln Leu Gln Leu Gln Glu Ser Gly Pro Gly Leu Val Lys Pro Ser Glu

```
              1               5                  10                 15
Thr Leu Ser Leu Thr Cys Thr Val Ser Gly Ala Ser Ile Asp Arg Ser
            20                  25                 30

Thr Tyr Tyr Trp Gly Trp Ile Arg Gln Pro Pro Gly Lys Gly Leu Glu
          35                  40                 45

Trp Ile Ala Asn Ile Tyr Tyr Asn Gly Arg Ala Val Tyr Ser Pro Ser
        50                  55                 60

Leu Lys Ser Arg Val Thr Ile Ser Val Asp Thr Ser Lys Asn Gln Phe
65                  70                  75                  80

Ser Leu Lys Val Arg Ser Leu Thr Ala Ala Asp Thr Ala Val Tyr Tyr
              85                  90                  95

Cys Ala Thr Arg Trp Asn Tyr Phe Phe Asp Phe Asp Tyr Trp Gly Arg
              100                 105                110

Gly Thr Leu Val Thr Val Ser Ser
          115                 120

<210> SEQ ID NO 258
<211> LENGTH: 7
<212> TYPE: PRT
<213> ORGANISM: Homo sapiens

<400> SEQUENCE: 258

Arg Ser Thr Tyr Tyr Trp Gly
1               5

<210> SEQ ID NO 259
<211> LENGTH: 16
<212> TYPE: PRT
<213> ORGANISM: Homo sapiens

<400> SEQUENCE: 259

Asn Ile Tyr Tyr Asn Gly Arg Ala Val Tyr Ser Pro Ser Leu Lys Ser
1               5                   10                  15

<210> SEQ ID NO 260
<211> LENGTH: 10
<212> TYPE: PRT
<213> ORGANISM: Homo sapiens

<400> SEQUENCE: 260

Arg Trp Asn Tyr Phe Phe Asp Phe Asp Tyr
1               5                   10

<210> SEQ ID NO 261
<211> LENGTH: 336
<212> TYPE: DNA
<213> ORGANISM: Homo sapiens

<400> SEQUENCE: 261
gatattgtga tgacccaatc tccactctcc ctgcccgtca cccctggaga gccggcctcc        60
atctcctgca ggtctagtca gaccctcctg catagtaatg gaaacaatta tttggattgg       120
tacctacaga agccagggca gtctccgcaa ctcctgatct attatgcttc taatcgggcc       180
tccggggtcc ctgacaggtt cagtggcagt ggttcaggca catctttcac actgaaaatc       240
agcagagtgg gggctgaaga tgttggggtt tattactgca tgcaagctct acaatctccg       300
ctcactttcg gcggagggac caagctggag atcaaa                                 336

<210> SEQ ID NO 262
<211> LENGTH: 112
```

```
<212> TYPE: PRT
<213> ORGANISM: Homo sapiens

<400> SEQUENCE: 262

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Thr Leu Leu His Ser
            20                  25                  30

Asn Gly Asn Asn Tyr Leu Asp Trp Tyr Leu Gln Lys Pro Gly Gln Ser
        35                  40                  45

Pro Gln Leu Leu Ile Tyr Tyr Ala Ser Asn Arg Ala Ser Gly Val Pro
    50                  55                  60

Asp Arg Phe Ser Gly Ser Gly Ser Gly Thr Ser Phe Thr Leu Lys Ile
65                  70                  75                  80

Ser Arg Val Gly Ala Glu Asp Val Gly Val Tyr Tyr Cys Met Gln Ala
                85                  90                  95

Leu Gln Ser Pro Leu Thr Phe Gly Gly Gly Thr Lys Leu Glu Ile Lys
            100                 105                 110

<210> SEQ ID NO 263
<211> LENGTH: 16
<212> TYPE: PRT
<213> ORGANISM: Homo sapiens

<400> SEQUENCE: 263

Arg Ser Ser Gln Thr Leu Leu His Ser Asn Gly Asn Asn Tyr Leu Asp
1               5                   10                  15

<210> SEQ ID NO 264
<211> LENGTH: 7
<212> TYPE: PRT
<213> ORGANISM: Homo sapiens

<400> SEQUENCE: 264

Tyr Ala Ser Asn Arg Ala Ser
1               5

<210> SEQ ID NO 265
<211> LENGTH: 9
<212> TYPE: PRT
<213> ORGANISM: Homo sapiens

<400> SEQUENCE: 265

Met Gln Ala Leu Gln Ser Pro Leu Thr
1               5

<210> SEQ ID NO 266
<211> LENGTH: 336
<212> TYPE: DNA
<213> ORGANISM: Homo sapiens

<400> SEQUENCE: 266
gatattgtga tgactcagtc tccactctcc ctgcccgtca cccctggaga gccggcctcc      60
atctcctgca ggtctagtca gagcctcctg catagtaatg gatacaacta tttggattgg     120
tacctgcaga agccagggca gtctccacag ctcctgatct atttgggttc taatcgggcc     180
tccggggtcc ctgacaggtt cagtggcagt ggattaggca cagatttac  actgaaaatc     240 agcagagtgg aggctgagga tgttggggtt tattactgca tgcaagctct acaaactcct     300 cggactttg  gccaggggac caagctggag atcaaa                               336
```

<210> SEQ ID NO 267
<211> LENGTH: 112
<212> TYPE: PRT
<213> ORGANISM: Homo sapiens

<400> SEQUENCE: 267

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Leu Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Arg Thr Phe Gly Gln Gly Thr Lys Leu Glu Ile Lys
            100                 105                 110

<210> SEQ ID NO 268
<211> LENGTH: 16
<212> TYPE: PRT
<213> ORGANISM: Homo sapiens

<400> SEQUENCE: 268

Arg Ser Ser Gln Ser Leu Leu His Ser Asn Gly Tyr Asn Tyr Leu Asp
1               5                   10                  15

<210> SEQ ID NO 269
<211> LENGTH: 7
<212> TYPE: PRT
<213> ORGANISM: Homo sapiens

<400> SEQUENCE: 269

Leu Gly Ser Asn Arg Ala Ser
1               5

<210> SEQ ID NO 270
<211> LENGTH: 9
<212> TYPE: PRT
<213> ORGANISM: Homo sapiens

<400> SEQUENCE: 270

Met Gln Ala Leu Gln Thr Pro Arg Thr
1               5

<210> SEQ ID NO 271
<211> LENGTH: 321
<212> TYPE: DNA
<213> ORGANISM: Homo sapiens

<400> SEQUENCE: 271
gacatccaga tgacccagtc tccatcctcc ctgtatgcat ctgtaggaga cagagtcacc        60
atcacttgcc aggcgagtca ggacattagg aagtctttaa attggtatca gaagaaagta       120
gggatagccc ctaaagtcct gatctacgac gcatccaatt tggaaacagg cgtcccatca       180
aggttcagtg aagtggatc tgggacacat tttaccttca ccatcggcag cctgcagcct       240
gaagattttg caacatatta ctgtcaacat tacgataatt ttccgcccac tttcggcgga       300
gggaccaagg tggagatcaa a                                                  321

<210> SEQ ID NO 272
<211> LENGTH: 107
<212> TYPE: PRT
<213> ORGANISM: Homo sapiens

<400> SEQUENCE: 272

Asp Ile Gln Met Thr Gln Ser Pro Ser Ser Leu Tyr Ala Ser Val Gly
1               5                   10                  15

Asp Arg Val Thr Ile Thr Cys Gln Ala Ser Gln Asp Ile Arg Lys Ser
            20                  25                  30

Leu Asn Trp Tyr Gln Lys Lys Val Gly Ile Ala Pro Lys Val Leu Ile
        35                  40                  45

Tyr Asp Ala Ser Asn Leu Glu Thr Gly Val Pro Ser Arg Phe Ser Gly
    50                  55                  60

Ser Gly Ser Gly Thr His Phe Thr Phe Thr Ile Gly Ser Leu Gln Pro
65                  70                  75                  80

Glu Asp Phe Ala Thr Tyr Tyr Cys Gln His Tyr Asp Asn Phe Pro Pro
                85                  90                  95

Thr Phe Gly Gly Gly Thr Lys Val Glu Ile Lys
            100                 105

<210> SEQ ID NO 273
<211> LENGTH: 11
<212> TYPE: PRT
<213> ORGANISM: Homo sapiens

<400> SEQUENCE: 273

Gln Ala Ser Gln Asp Ile Arg Lys Ser Leu Asn
1               5                   10

<210> SEQ ID NO 274
<211> LENGTH: 7
<212> TYPE: PRT
<213> ORGANISM: Homo sapiens

<400> SEQUENCE: 274

Asp Ala Ser Asn Leu Glu Thr
1               5

<210> SEQ ID NO 275
<211> LENGTH: 9
<212> TYPE: PRT
<213> ORGANISM: Homo sapiens

<400> SEQUENCE: 275

Gln His Tyr Asp Asn Phe Pro Pro Thr
1               5

<210> SEQ ID NO 276
<211> LENGTH: 324
<212> TYPE: DNA
<213> ORGANISM: Homo sapiens

<400> SEQUENCE: 276
cagtctgtgc tgactcagcc accctcagcg tctgggaccc ccgggcagag ggtcaccatc    60
tcttgttctg gaagcagttc caacatcgaa actaattatg tatcctggta ccagcagttc   120
ccaggaacgg cccccaagct cctcatctat aggaataatc agcggccctc aggggtccct   180

```
gaccgattct ctggctccaa gtctggcacc tcagcctccc tggccatcag tgggctccgg    240
tccgaggatg aggctgagta ttactgtgga acgtgggatg acaattcctg ggtgttcggc    300
ggagggacca agctgaccgt ccta                                            324
```

<210> SEQ ID NO 277
<211> LENGTH: 108
<212> TYPE: PRT
<213> ORGANISM: Homo sapiens

<400> SEQUENCE: 277

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Glu Thr Asn
            20                  25                  30

Tyr Val Ser Trp Tyr Gln Phe Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Glu Tyr Tyr Cys Gly Thr Trp Asp Asp Asn Ser
                85                  90                  95

Trp Val Phe Gly Gly Gly Thr Lys Leu Thr Val Leu
            100                 105
```

<210> SEQ ID NO 278
<211> LENGTH: 13
<212> TYPE: PRT
<213> ORGANISM: Homo sapiens

<400> SEQUENCE: 278

```
Ser Gly Ser Ser Ser Asn Ile Glu Thr Asn Tyr Val Ser
1               5                   10
```

<210> SEQ ID NO 279
<211> LENGTH: 7
<212> TYPE: PRT
<213> ORGANISM: Homo sapiens

<400> SEQUENCE: 279

```
Arg Asn Asn Gln Arg Pro Ser
1               5
```

<210> SEQ ID NO 280
<211> LENGTH: 9
<212> TYPE: PRT
<213> ORGANISM: Homo sapiens

<400> SEQUENCE: 280

```
Gly Thr Trp Asp Asp Asn Ser Trp Val
1               5
```

<210> SEQ ID NO 281
<211> LENGTH: 30
<212> TYPE: PRT
<213> ORGANISM: Homo sapiens

<400> SEQUENCE: 281

```
Gln Leu Gln Leu Gln Glu Ser Gly Pro Gly Leu Val Lys Pro Ser Glu
1               5                   10                  15
```

```
Thr Leu Ser Leu Thr Cys Thr Val Ser Gly Gly Ser Ile Ser
            20                  25                  30
```

<210> SEQ ID NO 282
<211> LENGTH: 14
<212> TYPE: PRT
<213> ORGANISM: Homo sapiens

<400> SEQUENCE: 282

```
Trp Ile Arg Gln Pro Pro Gly Lys Gly Leu Glu Trp Ile Gly
1               5                   10
```

<210> SEQ ID NO 283
<211> LENGTH: 32
<212> TYPE: PRT
<213> ORGANISM: Homo sapiens

<400> SEQUENCE: 283

```
Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys Ala Arg
            20                  25                  30
```

<210> SEQ ID NO 284
<211> LENGTH: 30
<212> TYPE: PRT
<213> ORGANISM: Homo sapiens

<400> SEQUENCE: 284

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser
            20                  25                  30
```

<210> SEQ ID NO 285
<211> LENGTH: 14
<212> TYPE: PRT
<213> ORGANISM: Homo sapiens

<400> SEQUENCE: 285

```
Trp Ile Arg Gln Pro Pro Gly Lys Gly Leu Glu Trp Ile Gly
1               5                   10
```

<210> SEQ ID NO 286
<211> LENGTH: 32
<212> TYPE: PRT
<213> ORGANISM: Homo sapiens

<400> SEQUENCE: 286

```
Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys Ala Arg
            20                  25                  30
```

<210> SEQ ID NO 287
<211> LENGTH: 23
<212> TYPE: PRT
<213> ORGANISM: Homo sapiens

<400> SEQUENCE: 287

```
Asp Ile Val Met Thr Gln Ser Pro Leu Ser Leu Pro Val Thr Pro Gly
1               5                   10                  15

Glu Pro Ala Ser Ile Ser Cys
```

```
                    20

<210> SEQ ID NO 288
<211> LENGTH: 15
<212> TYPE: PRT
<213> ORGANISM: Homo sapiens

<400> SEQUENCE: 288

Trp Tyr Leu Gln Lys Pro Gly Gln Ser Pro Gln Leu Leu Ile Tyr
1               5                   10                  15

<210> SEQ ID NO 289
<211> LENGTH: 32
<212> TYPE: PRT
<213> ORGANISM: Homo sapiens

<400> SEQUENCE: 289

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 290
<211> LENGTH: 23
<212> TYPE: PRT
<213> ORGANISM: Homo sapiens

<400> SEQUENCE: 290

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 291
<211> LENGTH: 15
<212> TYPE: PRT
<213> ORGANISM: Homo sapiens

<400> SEQUENCE: 291

Trp Tyr Gln Gln Lys Pro Gly Lys Ala Pro Lys Leu Leu Ile Tyr
1               5                   10                  15

<210> SEQ ID NO 292
<211> LENGTH: 32
<212> TYPE: PRT
<213> ORGANISM: Homo sapiens

<400> SEQUENCE: 292

Gly Val Pro Ser Arg Phe Ser Gly Ser Gly Ser Gly Thr Asp Phe Thr
1               5                   10                  15

Phe Thr Ile Ser Ser Leu Gln Pro Glu Asp Ile Ala Thr Tyr Tyr Cys
            20                  25                  30

<210> SEQ ID NO 293
<211> LENGTH: 22
<212> TYPE: PRT
<213> ORGANISM: Homo sapiens

<400> SEQUENCE: 293

Gln Ser Val Leu Thr Gln Pro Pro Ser Ala Ser Gly Thr Pro Gly Gln
1               5                   10                  15

Arg Val Thr Ile Ser Cys
            20
```

```
<210> SEQ ID NO 294
<211> LENGTH: 15
<212> TYPE: PRT
<213> ORGANISM: Homo sapiens

<400> SEQUENCE: 294

Trp Tyr Gln Gln Leu Pro Gly Thr Ala Pro Lys Leu Leu Ile Tyr
1               5                   10                  15

<210> SEQ ID NO 295
<211> LENGTH: 32
<212> TYPE: PRT
<213> ORGANISM: Homo sapiens

<400> SEQUENCE: 295

Gly Val Pro Asp Arg Phe Ser Gly Ser Lys Ser Gly Thr Ser Ala Ser
1               5                   10                  15

Leu Ala Ile Ser Gly Leu Arg Ser Glu Asp Glu Ala Asp Tyr Tyr Cys
            20                  25                  30

<210> SEQ ID NO 296
<211> LENGTH: 27
<212> TYPE: DNA
<213> ORGANISM: Artificial Sequence
<220> FEATURE:
<223> OTHER INFORMATION: Primer 5'Ig L VH 4/6

<400> SEQUENCE: 296
cccagatggg tcctgtccca ggtgcag                                              27

<210> SEQ ID NO 297
<211> LENGTH: 24
<212> TYPE: DNA
<213> ORGANISM: Artificial Sequence
<220> FEATURE:
<223> OTHER INFORMATION: Primer 5'Ig L V kappa 1/2

<400> SEQUENCE: 297
atgaggstcc cygctcagct gctg                                                 24

<210> SEQ ID NO 298
<211> LENGTH: 23
<212> TYPE: DNA
<213> ORGANISM: Artificial Sequence
<220> FEATURE:
<223> OTHER INFORMATION: Primer 5'Ig L V lambda 3

<400> SEQUENCE: 298
gctctgtgac ctcctatgag ctg                                                  23

<210> SEQ ID NO 299
<211> LENGTH: 23
<212> TYPE: DNA
<213> ORGANISM: Artificial Sequence
<220> FEATURE:
<223> OTHER INFORMATION: Primer 5'Ig L V lambda 1

<400> SEQUENCE: 299
ggtcctgggc ccagtctgtg ctg                                                  23

<210> SEQ ID NO 300
<211> LENGTH: 23
<212> TYPE: DNA
<213> ORGANISM: Artificial Sequence
```

```
<220> FEATURE:
<223> OTHER INFORMATION: Primer 3'Ig C gamma CH 1

<400> SEQUENCE: 300
ggaaggtgtg cacgccgctg gtc                                            23

<210> SEQ ID NO 301
<211> LENGTH: 24
<212> TYPE: DNA
<213> ORGANISM: Artificial Sequence
<220> FEATURE:
<223> OTHER INFORMATION: Primer 3'Ig C kappa 543

<400> SEQUENCE: 301
gtttctcgta gtctgctttg ctca                                           24

<210> SEQ ID NO 302
<211> LENGTH: 24
<212> TYPE: DNA
<213> ORGANISM: Artificial Sequence
<220> FEATURE:
<223> OTHER INFORMATION: Primer 3'Ig C lambda chain

<400> SEQUENCE: 302
caccagtgtg gccttgttgg cttg                                           24

<210> SEQ ID NO 303
<211> LENGTH: 38
<212> TYPE: DNA
<213> ORGANISM: Artificial Sequence
<220> FEATURE:
<223> OTHER INFORMATION: Primer 5'Ig AgeI VH4

<400> SEQUENCE: 303
ctgcaaccgg tgtacattcc caggtgcagc tgcaggag                            38

<210> SEQ ID NO 304
<211> LENGTH: 39
<212> TYPE: DNA
<213> ORGANISM: Artificial Sequence
<220> FEATURE:
<223> OTHER INFORMATION: Primer 5'Ig AgeI V kappa 2-24

<400> SEQUENCE: 304
ctgcaaccgg tgtacatggg gatattgtga tgacccaga                           39

<210> SEQ ID NO 305
<211> LENGTH: 40
<212> TYPE: DNA
<213> ORGANISM: Artificial Sequence
<220> FEATURE:
<223> OTHER INFORMATION: Primer 5'Ig AgeI V kappa 2-28

<400> SEQUENCE: 305
ctgcaaccgg tgtacatggg gatattgtga tgactcagtc                          40

<210> SEQ ID NO 306
<211> LENGTH: 38
<212> TYPE: DNA
<213> ORGANISM: Artificial Sequence
<220> FEATURE:
<223> OTHER INFORMATION: Primer 5'Ig AgeI V lambda 3

<400> SEQUENCE: 306
ctgctaccgg ttctgtgacc tcctatgagc tgacwcag                            38
```

```
<210> SEQ ID NO 307
<211> LENGTH: 40
<212> TYPE: DNA
<213> ORGANISM: Artificial Sequence
<220> FEATURE:
<223> OTHER INFORMATION: Primer 5'Ig AgeI V kappa 1-5

<400> SEQUENCE: 307
ctgcaaccgg tgtacattct gacatccaga tgacccagtc                              40

<210> SEQ ID NO 308
<211> LENGTH: 38
<212> TYPE: DNA
<213> ORGANISM: Artificial Sequence
<220> FEATURE:
<223> OTHER INFORMATION: Primer 5'Ig AgeI VH 4-39

<400> SEQUENCE: 308
ctgcaaccgg tgtacattcc cagctgcagc tgcaggag                                38

<210> SEQ ID NO 309
<211> LENGTH: 38
<212> TYPE: DNA
<213> ORGANISM: Artificial Sequence
<220> FEATURE:
<223> OTHER INFORMATION: Primer 5'Ig AgeI V lambda 1

<400> SEQUENCE: 309
ctgctaccgg ttcctgggcc cagtctgtgc tgackcag                                38

<210> SEQ ID NO 310
<211> LENGTH: 32
<212> TYPE: DNA
<213> ORGANISM: Artificial Sequence
<220> FEATURE:
<223> OTHER INFORMATION: Primer 3'Ig SalI JH

<400> SEQUENCE: 310
tgcgaagtcg acgctgagga gacggtgacc ag                                      32

<210> SEQ ID NO 311
<211> LENGTH: 30
<212> TYPE: DNA
<213> ORGANISM: Artificial Sequence
<220> FEATURE:
<223> OTHER INFORMATION: Primer 3'Ig BsiWI J kappa 2

<400> SEQUENCE: 311
gccaccgtac gtttgatctc cagcttggtc                                         30

<210> SEQ ID NO 312
<211> LENGTH: 33
<212> TYPE: DNA
<213> ORGANISM: Artificial Sequence
<220> FEATURE:
<223> OTHER INFORMATION: Primer 3'Ig SalI JH 6

<400> SEQUENCE: 312
tgcgaagtcg acgctgagga gacggtgacc gtg                                     33

<210> SEQ ID NO 313
<211> LENGTH: 30
<212> TYPE: DNA
<213> ORGANISM: Artificial Sequence
<220> FEATURE:
<223> OTHER INFORMATION: Primer 3'Ig Bsi WIJ kappa 1/4
```

```
<400> SEQUENCE: 313
gccaccgtac gtttgatytc caccttggtc                                          30

<210> SEQ ID NO 314
<211> LENGTH: 28
<212> TYPE: DNA
<213> ORGANISM: Artificial Sequence
<220> FEATURE:
<223> OTHER INFORMATION: Primer 3'Ig XhoI C lambda

<400> SEQUENCE: 314
ctcctcactc gagggyggga acagagtg                                            28

<210> SEQ ID NO 315
<211> LENGTH: 21
<212> TYPE: DNA
<213> ORGANISM: Artificial Sequence
<220> FEATURE:
<223> OTHER INFORMATION: Primer 5'Absense

<400> SEQUENCE: 315
gcttcgttag aacgcggcta c                                                   21

<210> SEQ ID NO 316
<211> LENGTH: 22
<212> TYPE: DNA
<213> ORGANISM: Artificial Sequence
<220> FEATURE:
<223> OTHER INFORMATION: Primer 3'IgG internal

<400> SEQUENCE: 316
gttcggggaa gtagtccttg ac                                                  22

<210> SEQ ID NO 317
<211> LENGTH: 22
<212> TYPE: DNA
<213> ORGANISM: Artificial Sequence
<220> FEATURE:
<223> OTHER INFORMATION: Primer 3'C kappa 494

<400> SEQUENCE: 317
gtgctgtcct tgctgtcctg ct                                                  22

<210> SEQ ID NO 318
<211> LENGTH: 24
<212> TYPE: DNA
<213> ORGANISM: Artificial Sequence
<220> FEATURE:
<223> OTHER INFORMATION: Primer 3'C lambda

<400> SEQUENCE: 318
caccagtgtg gccttgttgg cttg                                                24

<210> SEQ ID NO 319
<211> LENGTH: 5
<212> TYPE: PRT
<213> ORGANISM: Artificial Sequence
<220> FEATURE:
<223> OTHER INFORMATION: Linker sequence

<400> SEQUENCE: 319

Ile Ala Gly Ser Gly
1               5
```

```
<210> SEQ ID NO 320
<211> LENGTH: 27
<212> TYPE: PRT
<213> ORGANISM: Homo sapiens

<400> SEQUENCE: 320

Met Pro Ala Pro Arg Gly Leu Leu Arg Ala Thr Phe Leu Val Leu Val
1               5                   10                  15

Ala Phe Gly Leu Leu Leu His Ile Asp Phe Ser
            20                  25

<210> SEQ ID NO 321
<211> LENGTH: 9
<212> TYPE: PRT
<213> ORGANISM: Artificial Sequence
<220> FEATURE:
<223> OTHER INFORMATION: HA tag

<400> SEQUENCE: 321

Tyr Pro Tyr Asp Val Pro Asp Tyr Ala
1               5
```